United States Patent
Ahrens et al.

(10) Patent No.: US 12,325,715 B2
(45) Date of Patent: Jun. 10, 2025

(54) FLUOROUS METAL CHELATES COMPOSITIONS

(71) Applicant: The Regents of the University of California, Oakland, CA (US)

(72) Inventors: Eric T. Ahrens, Encinitas, CA (US); Stephen Adams, Poway, CA (US); Chao Wang, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 826 days.

(21) Appl. No.: 17/311,299

(22) PCT Filed: Dec. 9, 2019

(86) PCT No.: PCT/US2019/065279
§ 371 (c)(1),
(2) Date: Jun. 4, 2021

(87) PCT Pub. No.: WO2020/118307
PCT Pub. Date: Jun. 11, 2020

(65) Prior Publication Data
US 2022/0033424 A1  Feb. 3, 2022

Related U.S. Application Data

(60) Provisional application No. 62/777,008, filed on Dec. 7, 2018.

(51) Int. Cl.
| | | |
|---|---|---|
| C07F 11/00 | (2006.01) |
| A61K 49/10 | (2006.01) |
| A61K 49/18 | (2006.01) |
| C07F 15/02 | (2006.01) |

(52) U.S. Cl.
CPC .......... C07F 11/005 (2013.01); A61K 49/106 (2013.01); A61K 49/1806 (2013.01); C07F 15/025 (2013.01)

(58) Field of Classification Search
CPC .... C07F 15/025; C07F 11/005; A61K 49/106; A61K 31/295; A61K 31/28; A61K 49/1806; C07C 251/24
See application file for complete search history.

(56) References Cited

U.S. PATENT DOCUMENTS

| | | | |
|---|---|---|---|
| 4,188,373 | A | 2/1980 | Krezanoski et al. |
| 4,866,096 | A | 9/1989 | Schweighardt et al. |
| 4,897,355 | A | 1/1990 | Eppstein et al. |
| 4,990,283 | A | 2/1991 | Visca et al. |
| 5,071,965 | A * | 12/1991 | Dunn ............... C07C 251/24 534/14 |
| 5,279,833 | A | 1/1994 | Rose et al. |
| 5,283,185 | A | 2/1994 | Epand et al. |
| 5,330,681 | A | 7/1994 | Brunetta et al. |
| 5,334,761 | A | 8/1994 | Gebeyehu et al. |
| 5,527,928 | A | 6/1996 | Nantz et al. |
| 5,552,155 | A | 9/1996 | Bailey et al. |
| 5,578,475 | A | 11/1996 | Jessee et al. |
| 6,676,963 | B1 | 1/2004 | Lanza et al. |
| 9,352,057 | B2 | 5/2016 | Ahrens et al. |
| 2003/0215392 | A1 | 3/2003 | Lanza et al. |
| 2003/0086867 | A1 | 5/2003 | Lanza et al. |
| 2004/0248856 | A1 | 1/2004 | Lanza et al. |
| 2004/0115192 | A1 | 6/2004 | Lanza et al. |
| 2006/0079705 | A1 | 4/2006 | Bachmann et al. |
| 2007/0258886 | A1 | 4/2007 | Ahrens et al. |
| 2011/0166372 | A1 | 7/2011 | Masumoto et al. |
| 2012/0149906 | A1 | 6/2012 | Pereira et al. |
| 2013/0343999 | A1 | 5/2013 | Ahrens et al. |
| 2014/0011032 | A1 | 1/2014 | Ishikawa et al. |

FOREIGN PATENT DOCUMENTS

| | | |
|---|---|---|
| EP | 231091 | 8/1987 |
| WO | WO 1989/010118 | 12/1989 |
| WO | WO 2005/072780 | 8/2005 |

OTHER PUBLICATIONS

Yamaguchi et al., Inorganic Chemistry, 2008, 47(13), p. 5736. (Year: 2008).*
Bollinger et al., Nuclear Medicine & Biology, 1996, 23, p. 645-652. (Year: 1996).*
Chiyaya et al., WO 2011083845, 2011, abstract translation. (Year: 2011).*
Jahromi et al. (2018) "Fluorous-soluble metal chelate for sensitive fluorine-19 magnetic resonance imaging nanoemulsion probe," ACS nano. 13(1):143-151.
International Search Report with Written Opinion corresponding to International Patent Application No. PCT/US19/65279, dated Mar. 31, 2020, 12 pages.
U.S. Appl. No. 61/062,710, filed Jan. 28, 2008, Janjic et al.
Ahrens, E. T., et al. "In Vivo Imaging Platform for Tracking Immunotherapeutic Cells." Nat Biotechnol 2005, 23, 983.
Ahrens, E. T., et al. "In Vivo MRI Cell Tracking Using Perfluorocarbon Probes and Fluorine-19 Detection." NMR Biomed 2013, 26, 860.
Ahrens, E. T., et al. "Clinical Cell Therapy Imaging Using a Perfluorocarbon Tracer and Fluorine-19 MRI." Magn Reson Med 2014, 72, 1696.
Bansal et al., "Novel [89]Zr cell labeling approach for PET-based cell trafficking studies" EJNMMI Res. Mar. 28, 2015, 5:19.
Betzer et al., "Nanoparticle-Based CT Imaging Technique for Longitudinal and Quantitative Stem Cell Tracking within the Brain: Application in Neuropsychiatric Disorders", ACS Nano, Sep. 23, 2014, 8(9):9274-85.
Bloembergen, N.; Morgan, L. O. "Proton Relaxation Times in Paramagnetic Solutions. Effects of Electron Spin Relaxation." J Chem Phys 1961, 34, 842.

(Continued)

Primary Examiner — Michael G. Hartley
Assistant Examiner — Leah H Schlientz
(74) Attorney, Agent, or Firm — Morgan, Lewis & Bockius, LLP

(57) ABSTRACT

This disclosure provides compositions of SALTAME core containing compounds and associated methods for use in tracking cells by magnetic resonance imaging (MRI), computed tomography (CT), positron emission tomography (PET), and related methods.

19 Claims, 64 Drawing Sheets

(56) References Cited

OTHER PUBLICATIONS

Bonner, F., et al. "Monocyte Imaging After Myocardial Infarction with 19F MRI at 3 T: A Pilot Study in Explanted Porcine Hearts." Eur Heart J-Card Img 2015, 16, 612.

Bouchlaka, M. N.; Ludwig, K. D.; Gordon, J. W.; Kutz, M. P.; Bednarz, B. P.; Fain, S. B.; Capitini, C. M. 19F-MRI for Monitoring Human NK Cells In Vivo. OncoImmunology 2016, 5, e1143996.

Chu, et al. "Bulk Magnetic-Susceptibility Shifts in NMR Studies of Compartmentalized Samples—Use of Paramagnetic Reagents." Magn Reson Med 1990, 13, 239.

Colotti, R.; et al., "Characterization of Perfluorocarbon Relaxation Times and Their Influence on the Optimization of Fluorine-19 MRI at 3 Tesla." Magn Reson Med 2016 77(6), 2263.

Cormode et al., "Nanoparticle Contrast Agents for Computed Tomography: A Focus on Micelles", Contrast Media Mol Imaging, Jan.-Feb. 2014, 9(1):37-52.

Deluca, E.; et al., "Characterisation and Evaluation of Paramagnetic Fluorine Labelled Glycol Chitosan Conjugates for (19)F and (1)H Magnetic Resonance Imaging.", J Biol Inorg Chem 2014, 19, 215.

Derossi et al., "The Third Helix of the Antennapedia Homeodomain Translocates through Biological Membranes" (1994) J Biol Chem 269:10444-10450.

Derossi et al., "Cell Internalization of the Third Helix of the Antennapedia Homeodomain Is Receptor-independent", (1996) J Biol Chem 271:18188-18193.

Felgner et al., "Lipofection: A highly efficient, lipid-mediated DNA-transfection procedure" 1987, PNAS 84.

Filippini, G., et al. "Photochemical Direct Perfluoroalkylation of Phenols." Tetrahedron 2015, 71, 4535.

Flaim, S. F. "Pharmacokinetics and Side Effects of Perfluorocarbon-Based Blood Substitutes." Artif Cell Blood Sub 1994, 22, 1043.

Funk, A. M., et al. "Experimental Measurement and Theoretical Assessment of Fast Lanthanide Electronic Relaxation in Solution with Four Series of Isostructural Complexes." J Phys Chem A 2013, 117, 905.

Giraudeau, C. et al., A New Paradigm for High-Sensitivity 19F Magnetic Resonance Imaging of Perfluorooctylbromide. Magn Reson Med 2010, 63, 1119.

Gottschaldt, et al., "InIII and GaIII Complexes of Sugar-Substituted Tripodal Trisalicylidene Imines: The First 68Ga-Labelled Sugar Derivative." Eur. J. Inorg. Chem., 2009: 4298-4307.

Graves et al., "Novel Preparation Methods of $^{52}$Mn for ImmunoPET Imaging," Bioconjugate Chemistry, 2015, 26(10)_2118-2124.

Green MA, et al. "Potential gallium-68 tracers for imaging the heart with PET: evaluation of four gallium complexes with functionalized tripodal tris(salicylaldimine) ligands." J Nucl Med. Feb. 1993;34(2) 228-233. PMID: 8429341.

Griessinger et al., "64Cu antibody-targeting of the T-cell receptor and subsequent internalization enables in vivo tracking of lymphocytes by PET" Proc Natl Acad Sci USA, Jan. 27, 2015, 112(4):1161-6.

Harvey, P., et al. "Lanthanide Complexes as Paramagnetic Probes for 19F Magnetic Resonance." Eur J Inorg Chem 2012, 2015.

Helfer, B. M., et al. "Functional Assessment of Human Dendritic Cells Labeled for In Vivo F-19 Magnetic Resonance Imaging Cell Tracking." Cytotherapy 2010, 12, 238.

Jacoby, C., et al. "Probing Different Perfluorocarbons for In Vivo Inflammation Imaging by 19F MRI: Image Reconstruction, Biological Half-Lives and Sensitivity." NMR Biomed 2014, 27, 261.

Janjic, J. M., et al. "Self-Delivering Nanoemulsions for Dual Fluorine-19 MRI and Fluorescence Detection." J Am Chem Soc 2008, 130, 2832.

Janjic, J. M et al., "Fluorine-Containing Nanoemulsions for MRI Cell Tracking." Wiley Interdiscip Rev Nanomed Nanobiotechnol 2009, 1, 492.

Kim et al., "Simple Methods for Tracking Stem Cells with 64Cu-Labeled DOTA-hexadecyl-benzoate", ACS Med Chem Lett, Apr. 7, 2015, 6(5):528-30.

Kislukhin, A. A., et al. "Paramagnetic Fluorinated Nanoemulsions for Sensitive Cellular Fluorine-19 Magnetic Resonance Imaging." Nat Mater 2016, 15, 662.

Klein, D. H., et al. "Intravascular Behavior of Perflubron Emulsions." Colloid Surface A 1994, 84, 89.

Kok, M. B., et al. "Quantitative (1)H MRI, (19)F MRI, and (19)F MRS of Cell-Internalized Perfluorocarbon Paramagnetic Nanoparticles." Contrast Media Mol I 2011, 6, 19.

Lusic, et al. "X-Ray Computed Tomography Contrast Agents" Chem Rev, Mar. 13, 2013, 113(3):1641-66.

Marmion, et al. "Synthesis and characterization of novel N3O3-Schiff base complexes of 99gTc, and in vivo imaging studies with analogous 99mTc complexes", Nuclear Medicine and Biology, vol. 23, Issue 5, 1996, pp. 567-584.

Matsugi, M., et al., "Direct Perfluoroalkylation of Non-Activated Aromatic C—H Bonds of Phenols." Tetrahedron Lett 2008, 49, 4189.

Mattrey, R. F., et al. "Perfluorochemicals as Gastrointestinal Contrast Agents for MR Imaging: Preliminary Studies in Rats and Humans." Am J Roentgen 1987, 148, 1259.

Means et al. "Chemical Modifications of Proteins: History and Applications", (1990) Bioconjugate Chemistry 1:2-12.

Mumper, et al. "Formation and Stability of Lanthanide Complexes and Their Encapsulation Into Polymeric Microspheres." J. Phys. Chem. 1992, 96, 8626.

Neubauer, A. M., et al. "Gadolinium-Modulated 19F Signals from Perfluorocarbon Nanoparticles as a New Strategy for Molecular Imaging." Magn Reson Med 2008, 60, 1066.

Normandin et al., "Heat Induced Radiolabeled Nanoparticles Allow PET-derived Monocyte Tracking" Angew Chem Int Ed Engl, Oct. 26, 2015, 54(44):13002-6.

Perez et al. "Antennapedia homeobox as a signal for the cellular internalization and nuclear addressing of a small exogenous peptide", (1992) J Cell Sci 102:717-722.

Qie et al., "Self-assembled gold coating enhances X-ray imaging of alcinate microcapsules" Nanoscale, Feb. 14, 2015, 7(6):2480-8.

Ratner, A. V., et al., "19F Magnetic Resonance Imaging of the Reticuloendothelial System." Magn Reson Med 1987, 5, 548.

Rose, L. C., et al. "Fluorine-19 Labeling of Stromal Vascular Fraction Cells for Clinical Imaging Applications." Stem Cells Transl Med 2015, 4, 1472.

Ruben et al., "Structural and Functional Characterization of Human Immunodeficiency Virus tat Protein" (1989) J. Virol 63:1-8.

Sanchez et al., "Highly concentrated 1,2-bis(perfluoroalkyl) iodoethene emulsions for use as contrast agents for diagnosis," Journal of Fluorine Chemistry, Aug. 1995, 73(2):259-264.

Sato et al., "89 Zr-Oxine Complex PET Cell Imaging in Monitoring Cell-based Therapies" Radiology. May 2015, 275(2):490-500.

Schirra, C. O., et al. "Toward True 3D Visualization of Active Catheters Using Compressed Sensing." Magn Reson Med 2009, 62, 341.

Schmid, F. et al., "Boosting (19) F MRI-SNR Efficient Detection of Paramagnetic Contrast Agents Using Ultrafast Sequences.", Magn Reson Med 2013, 69, 1056.

Shannon R.D., "Revised Effective Ionic Radil and Systematic Studies of Interatomic Distances in Halides and Chalcogenides" Acta Crystallographica. (1976), A32, p. 751-767.

Srinivas, M., et al. "In Vivo Cytometry of Antigen-Specific T Cells Using 19F MRI." Magn Reson Med 2009, 62.

Tavare et al., "An Effective Immuno-PET Imaging Method to Monitor CD8-Dependent Responses to Immunotherapy" Cancer Res, Jan. 1, 2016;76(1):73-82.

Temme, S., et al. "19F Magnetic Resonance Imaging of Endogenous Macrophages in Inflammation." Wiley Interdiscip Rev Nanomed Nanobiotechnol 2012, 4, 329.

Temme, S., et al. "Technical Advance: Monitoring the Trafficking of Neutrophil Granulocytes and Monocytes During the Course of Tissue Inflammation by Noninvasive 19F MRI." J Leukoc Biol 2014, 95, 689.

Toscano, et al. "Synthesis and Characterization of Polyfluorinated β-Diketonate Transition Metal Complexes" Journal of Coordination Chemistry, 38:4, 319-335.

(56) References Cited

OTHER PUBLICATIONS

Weizenecker, J. et al. "Three-dimensional real-time in vivo magnetic particle imaging" 2009 Physics in Medicine and Biology, vol. 54, Issue 5, pp. L1-L10.
Yang et al., "Tracking and Therapeutic Value of Human Adipose Tissue-derived Mesenchymal Stem Cell Transplantation in Reducing Venous Neointimal Hyperplasia Associated with Arteriovenous Fistula" Radiology, May 2016, 279(2):513-22.
Yi et al., "High quality polyacrylic acid modified multifunction luminescent nanorods for tri-modality bioimaging in vivo long-lasting tracking and biodistribution", Nanoscale, Jan. 14, 2015;7(2):542-50.

* cited by examiner

190X81mm (300 X 300 DPI)

127x53mm (300 x 300 DPI)

Reagents and conditions: (i) $Cs_2CO_3$, DMF, 100 degree Celcius; (ii) 1 atm $H_2$, Pd-C, NaOAc.

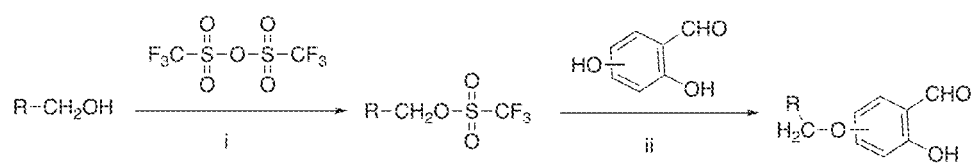
Where R represents:
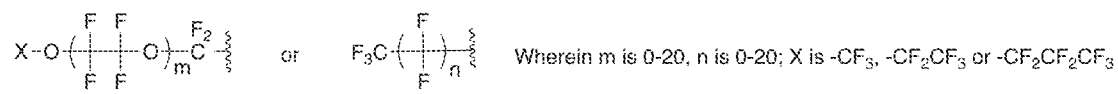  Wherein m is 0-20, n is 0-20; X is -CF$_3$, -CF$_2$CF$_3$ or -CF$_2$CF$_2$CF$_3$
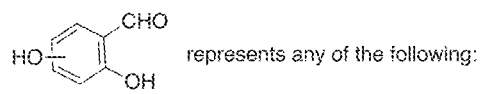 represents any of the following:
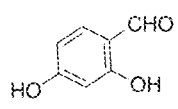 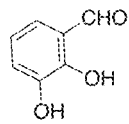 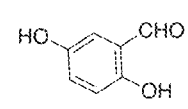 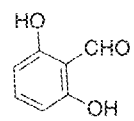
Reagents and conditions: (i) Pyridine, CH$_2$Cl$_2$, overnight (ii) CH$_3$CN, KHCO$_3$, 60 degree Celcius, overnight.
Figure 20.

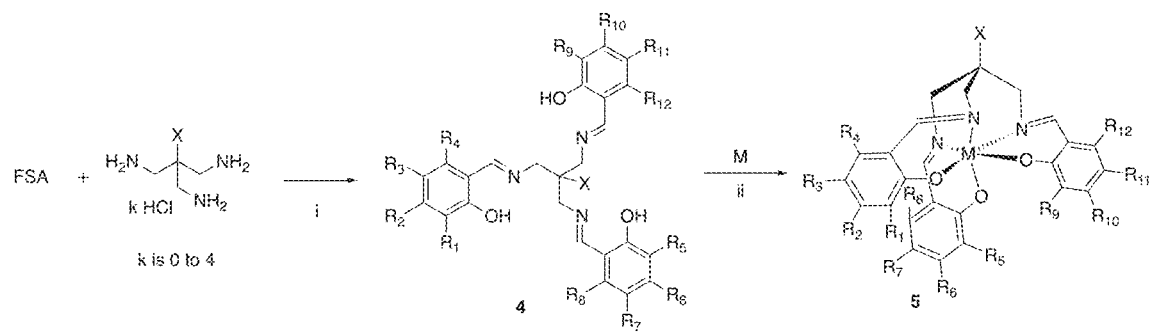

Where

FSA represents any single compound or a mixture of two compounds from compounds 2, 4, 5, 6, 7, 8, 9 as shown in previous drawings.

X represents

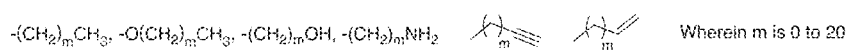

Wherein m is 0 to 20

For compound 10 with $R_1, R_2, R_3, R_4, R_5, R_6, R_7, R_8, R_9, R_{10}, R_{11}, R_{12}$, at least three of them represent:

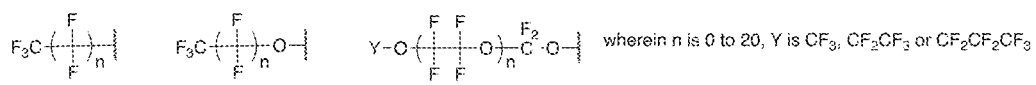

wherein n is 0 to 20, Y is $CF_3$, $CF_2CF_3$ or $CF_2CF_2CF_3$

While the others represent H or $CH_3$

M represents $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, $Cr^{3+}$ Reagents and conditions: (i) triethylamine, anhydrous ethanol, reflux, 6h (ii) sodium acetate, anhydrous ethanol, 10min.

Figure 21.

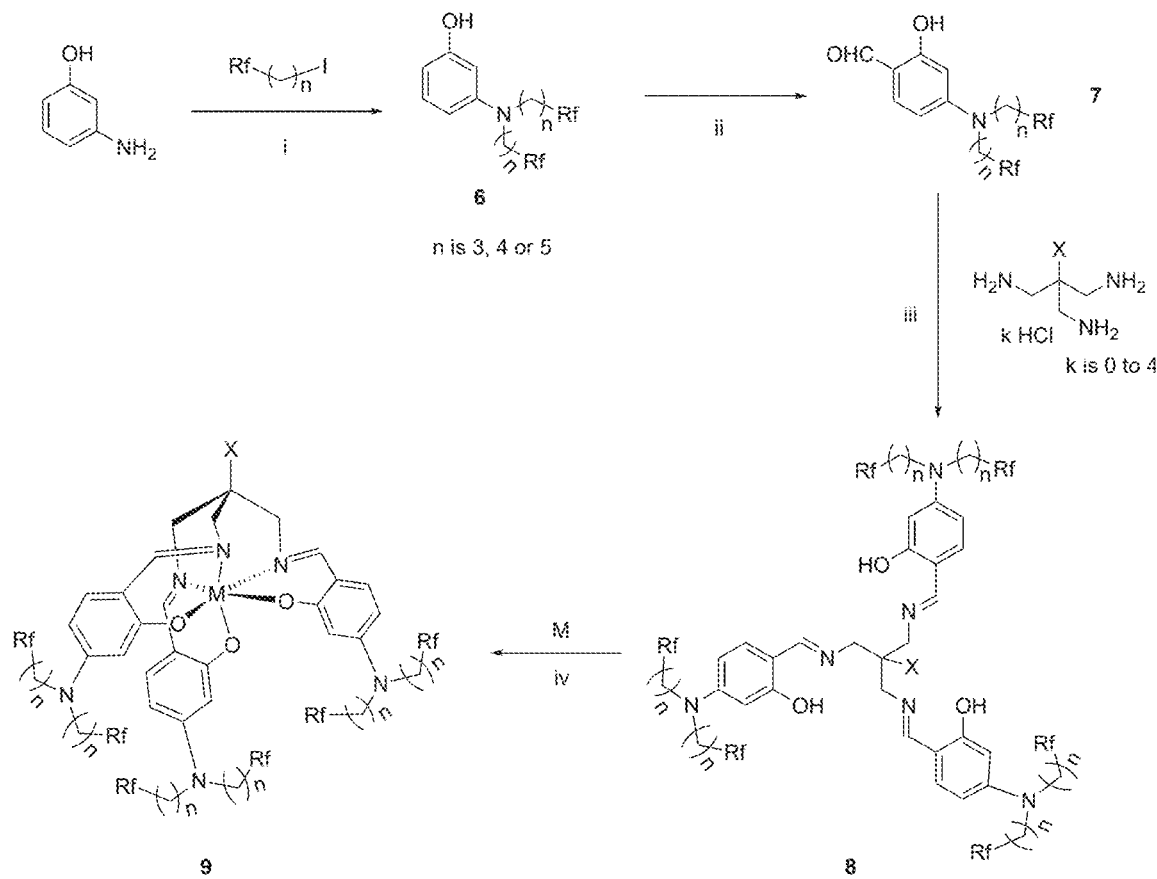

Where

Rf represents

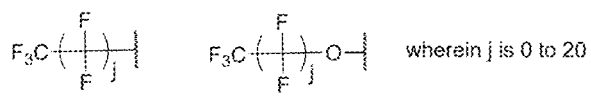 wherein j is 0 to 20

X represents:

-(CH$_2$)$_m$CH$_3$, -O(CH$_2$)$_m$CH$_3$, -(CH$_2$)$_m$OH, -(CH$_2$)$_m$NH$_2$ 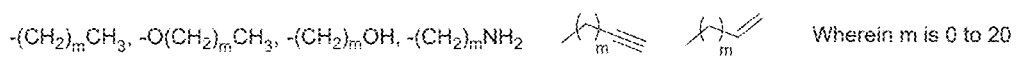 Wherein m is 0 to 20

M represents

Fe$^{3+}$, Fe$^{2+}$, Ga$^{3+}$, Mn$^{2+}$, Mn$^{3+}$, Mn$^{4+}$, Ni$^{2+}$, Cu$^{2+}$, Zn$^{2+}$, Co$^{3+}$, Cr$^{3+}$

Reagents and conditions:
(i) N,N-Diisopropylethylamine, DMF, 100 degree Celcius, overnight.
(ii) POCl$_3$, DMF, 80 degree Celcius, 2h, then NaHCO$_3$.
(iii) triethylamine, anhydrous ethanol, reflux, 6h (iv) sodium acetate, anhydrous ethanol, 10min.

Figure 22.

Figure 23A (top):
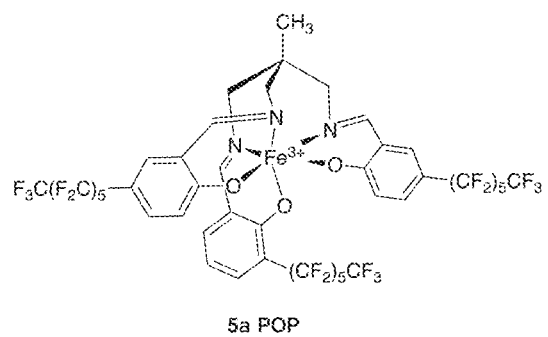
5a POP
Figure 23B (bottom):
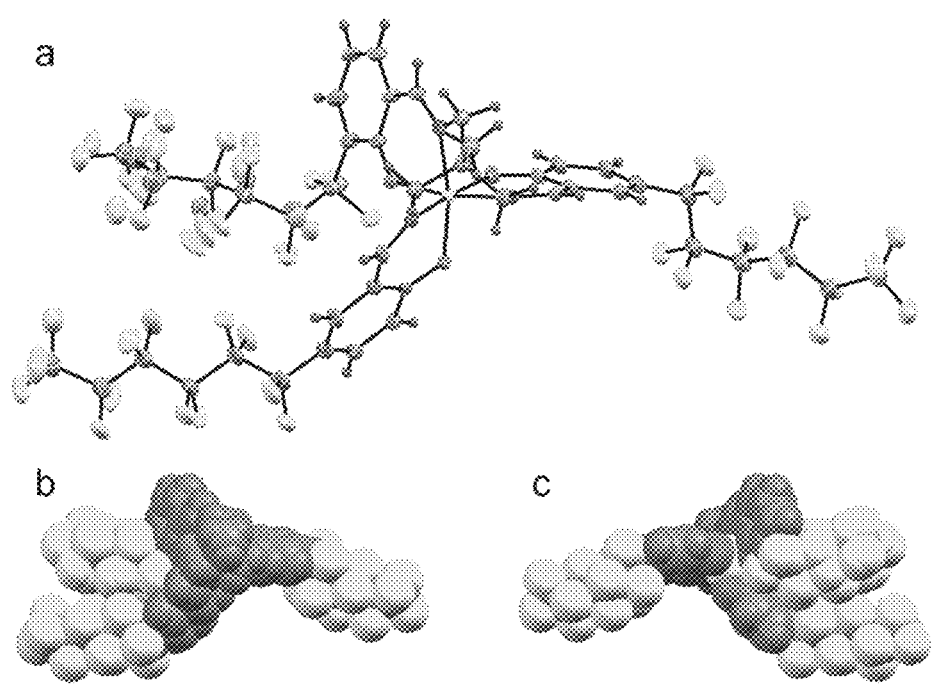
Figure 23.

Figure 24A (Top):
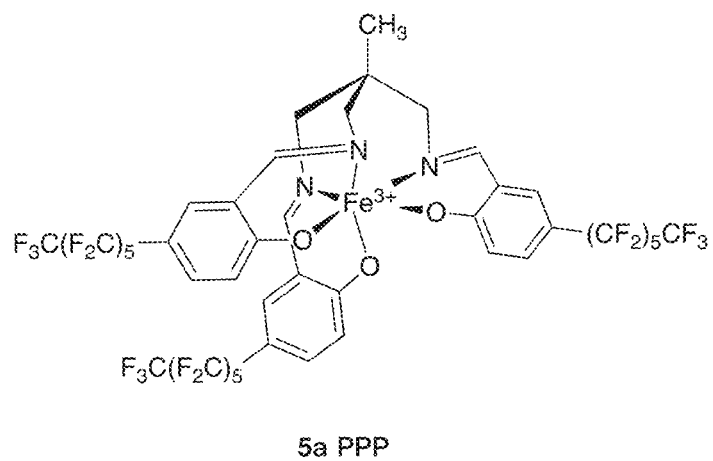
5a PPP
Figure 24B (Bottom):
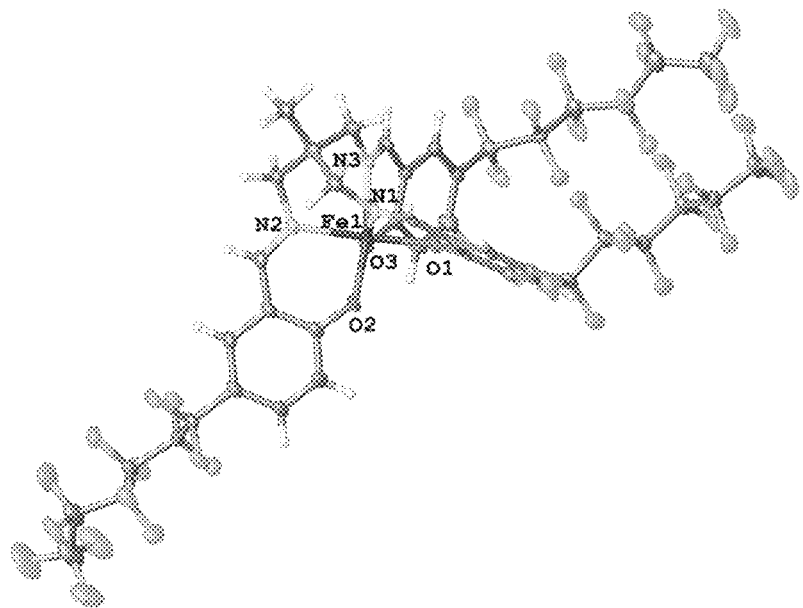
Figure 24.

Figure 25A (Top):
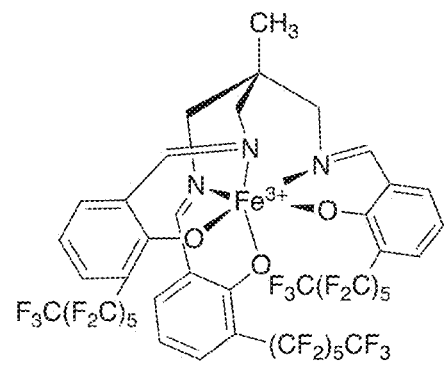
5a OOO
Figure 25B (Bottom):
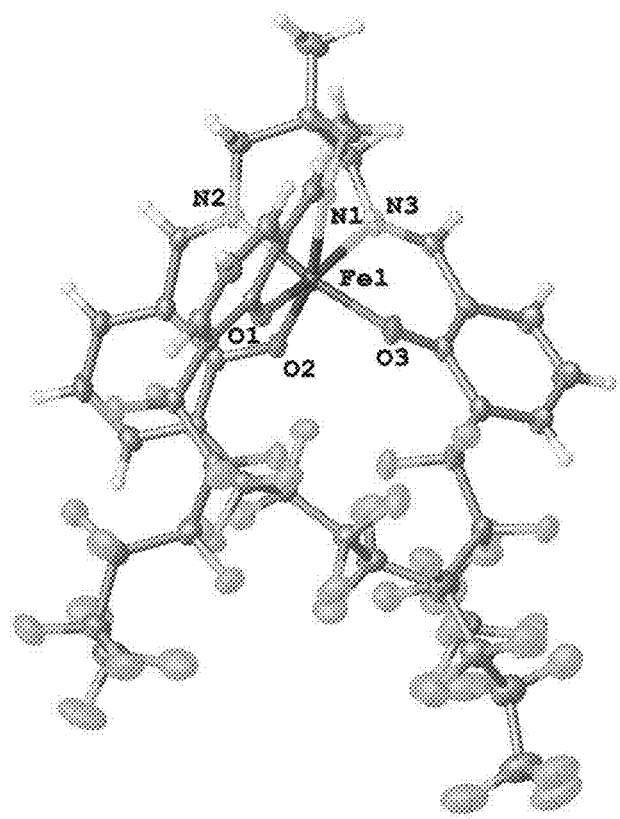
Figure 25.

Fig. 27A. 3-Bromo-5-perfluorohexyl-salicylaldehyde (2a)

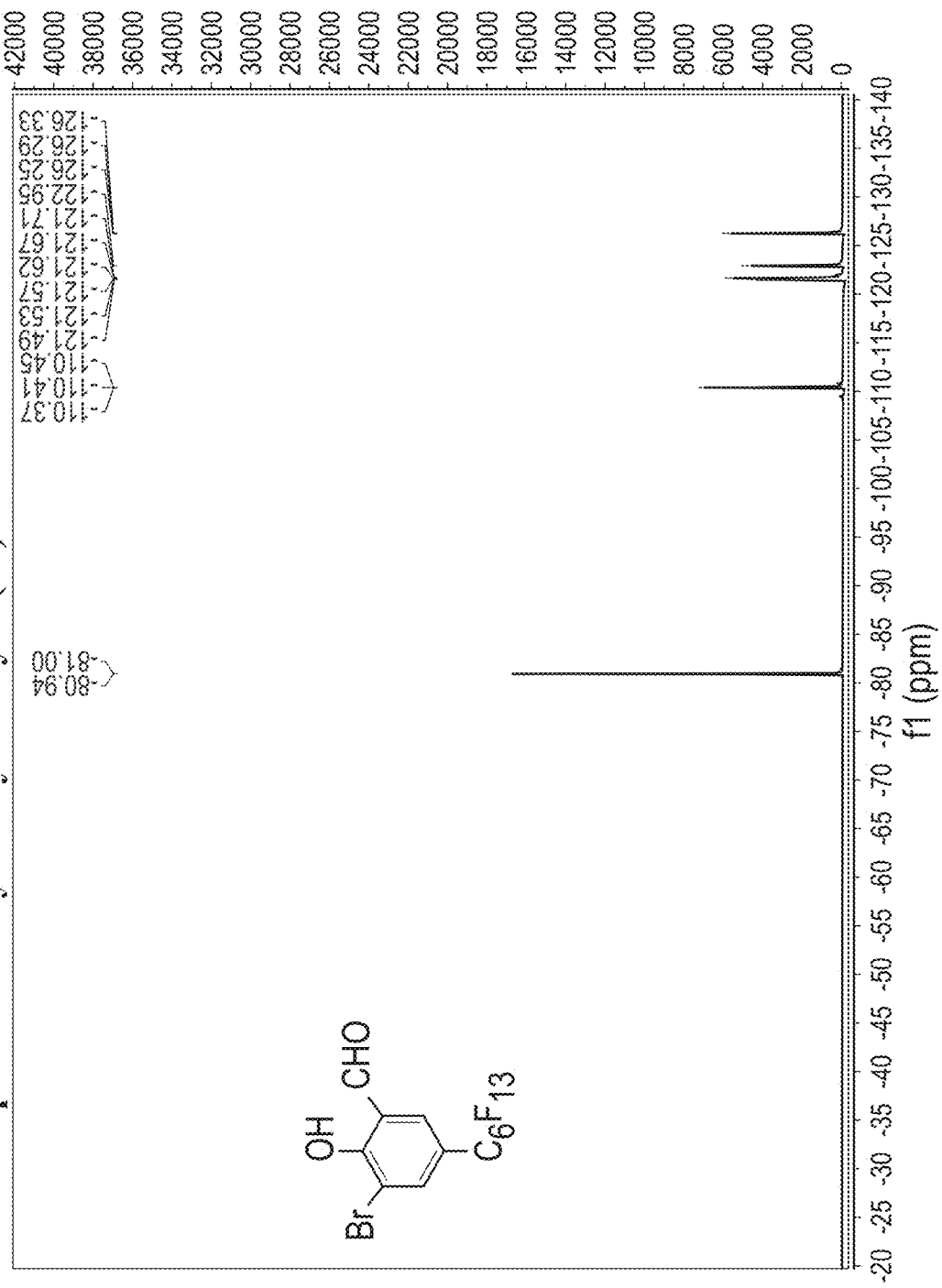
Fig. 27B. 3-Bromo-5-perfluorohexyl-salicylaldehyde (2a)

Fig. 27C. 3-Bromo-5-perfluorohexyl-salicylaldehyde (2a)
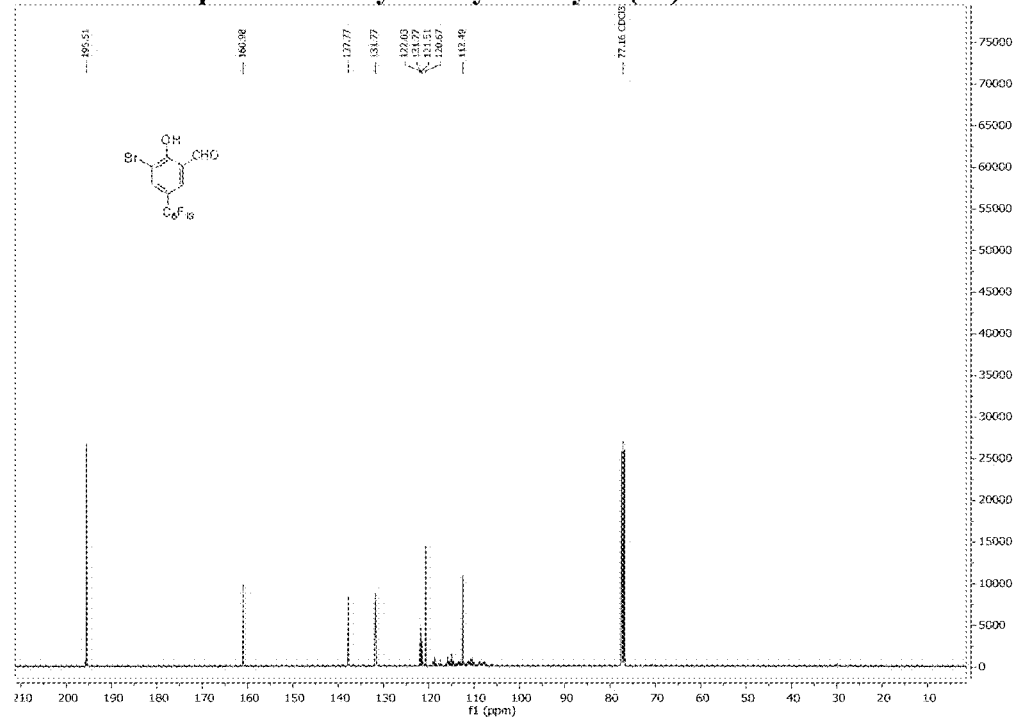
Fig. 27D. 5-Bromo-3-perfluorohexyl-salicylaldehyde (2b)
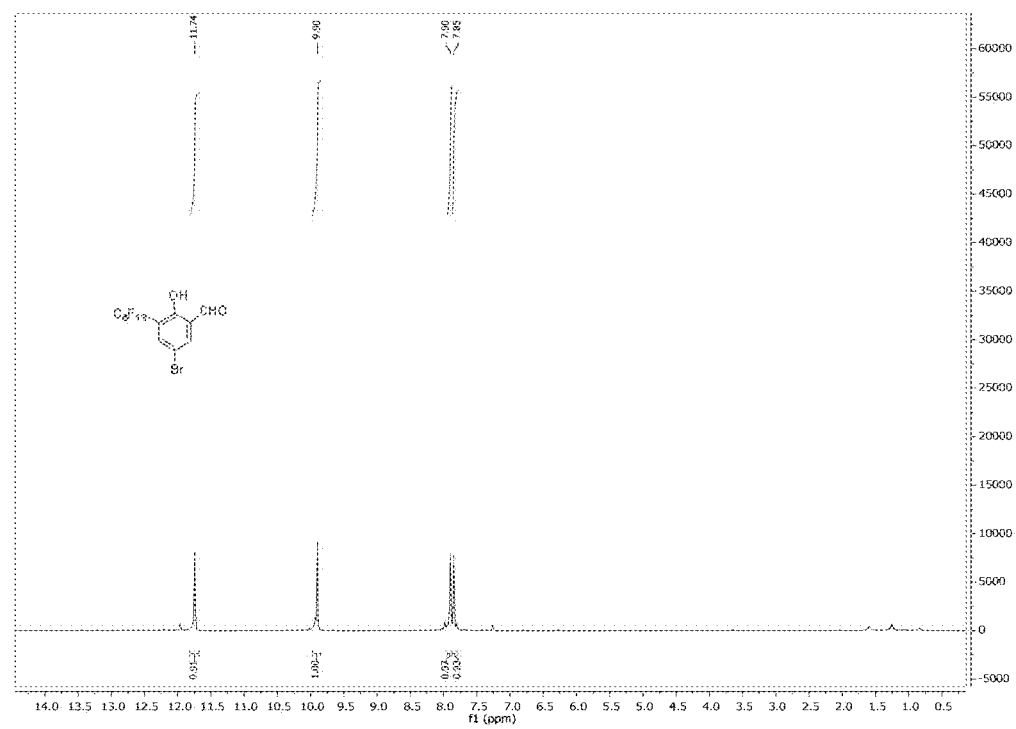

Fig. 27E. 5-Bromo-3-perfluorohexyl-salicylaldehyde (2b)
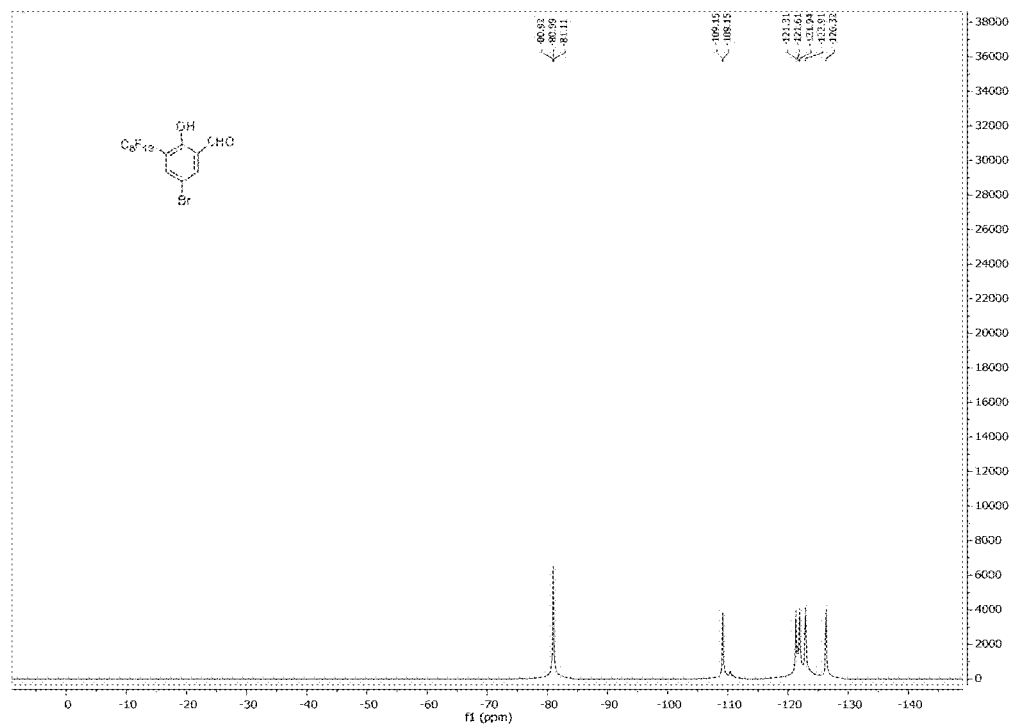
Fig. 27F. 5-Bromo-3-perfluorohexyl-salicylaldehyde (2b)
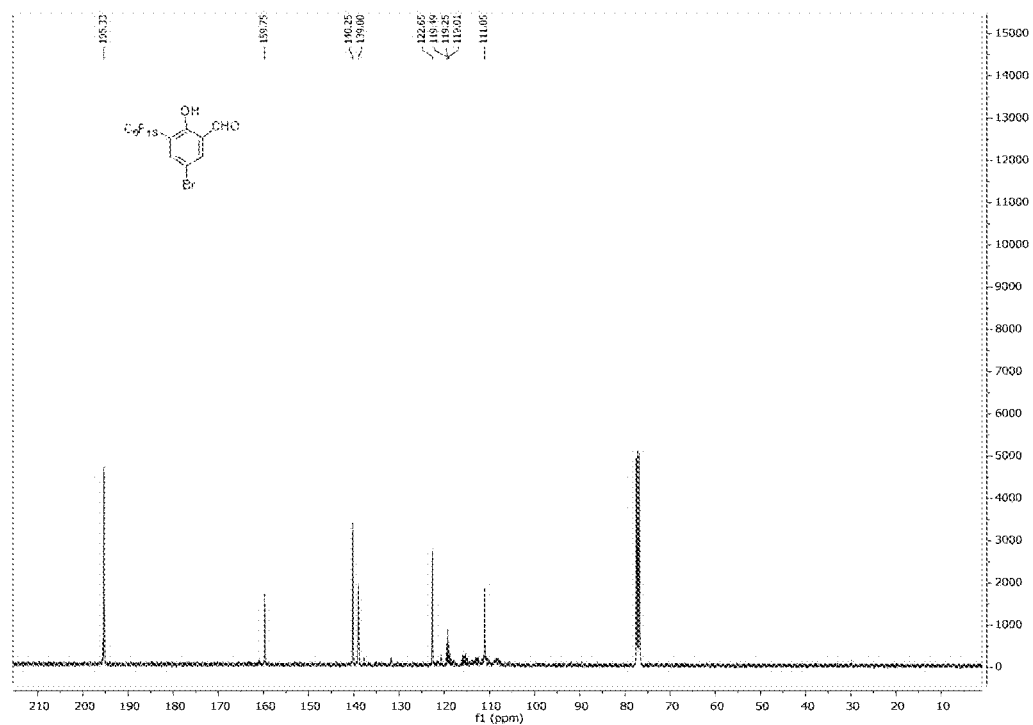

Fig. 27G. 5-Perfluorohexyl-salicylaldehyde (3a)
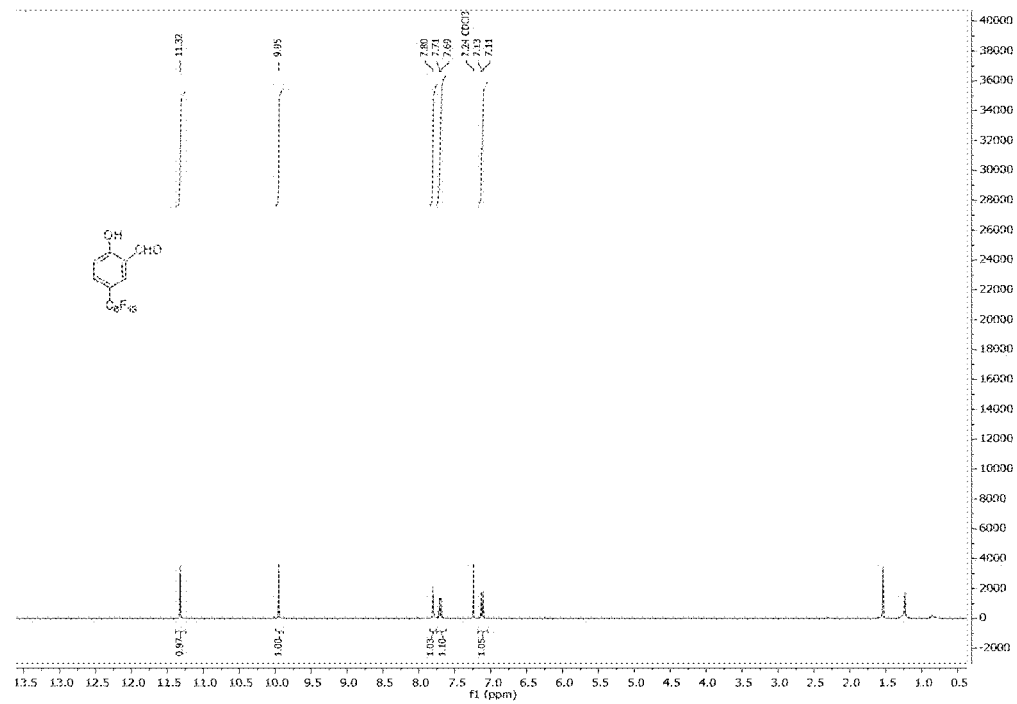
Fig. 27H. 5-Perfluorohexyl-salicylaldehyde (3a)
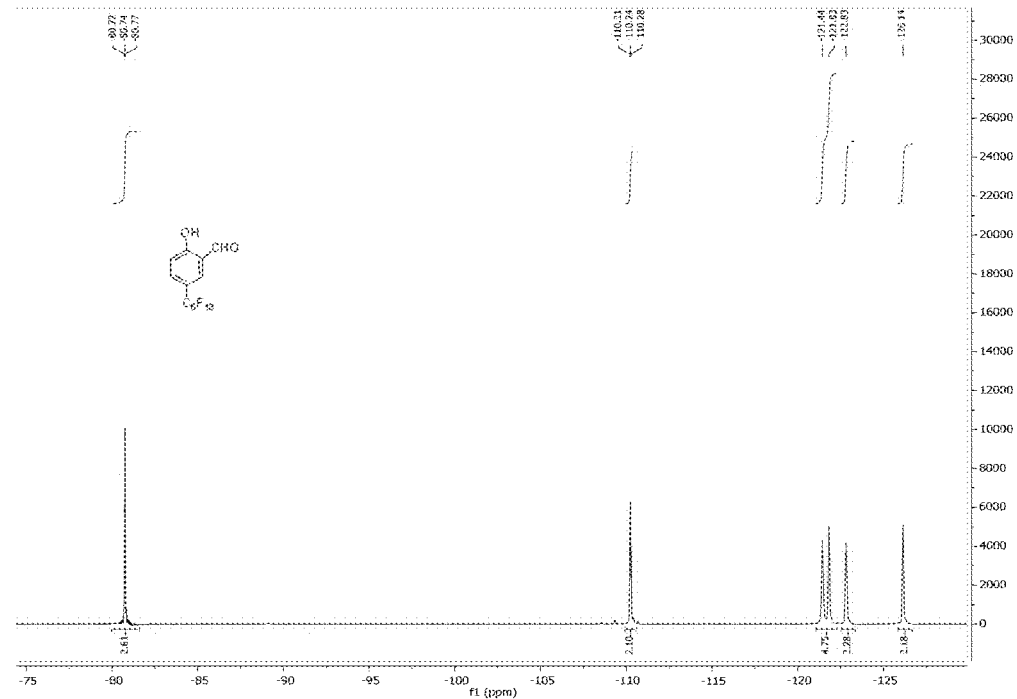

Fig. 27I. 5-Perfluorohexyl-salicylaldehyde (3a)
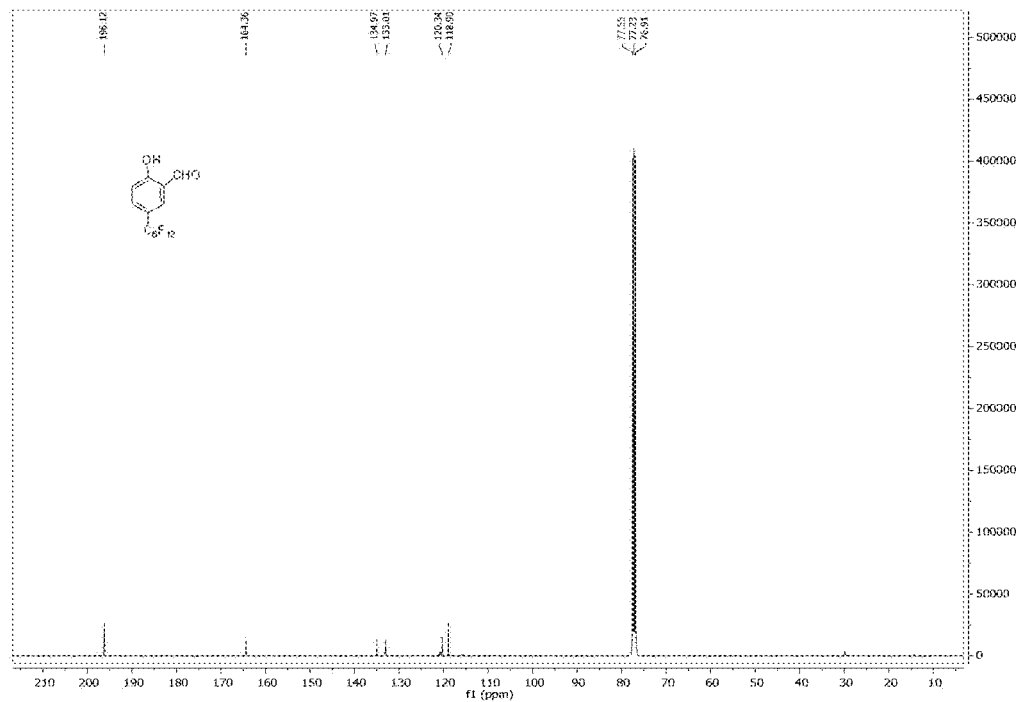
Fig. 27J. 3-Perfluorohexyl-salicylaldehyde (3b)
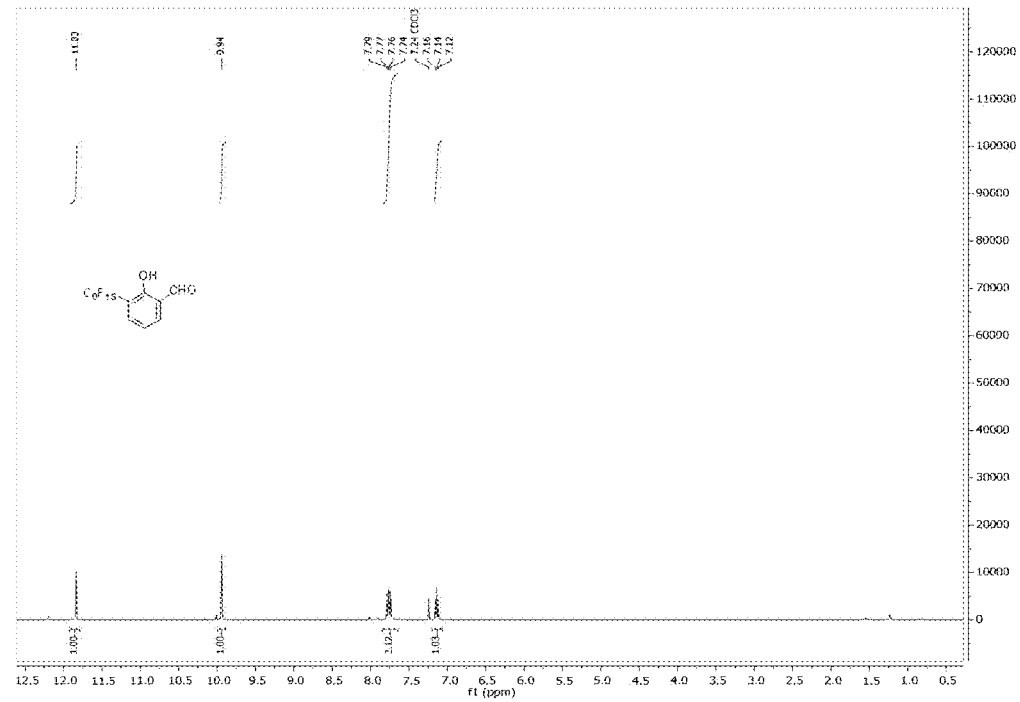

Fig. 27K. 3-Perfluorohexyl-salicylaldehyde (3b)
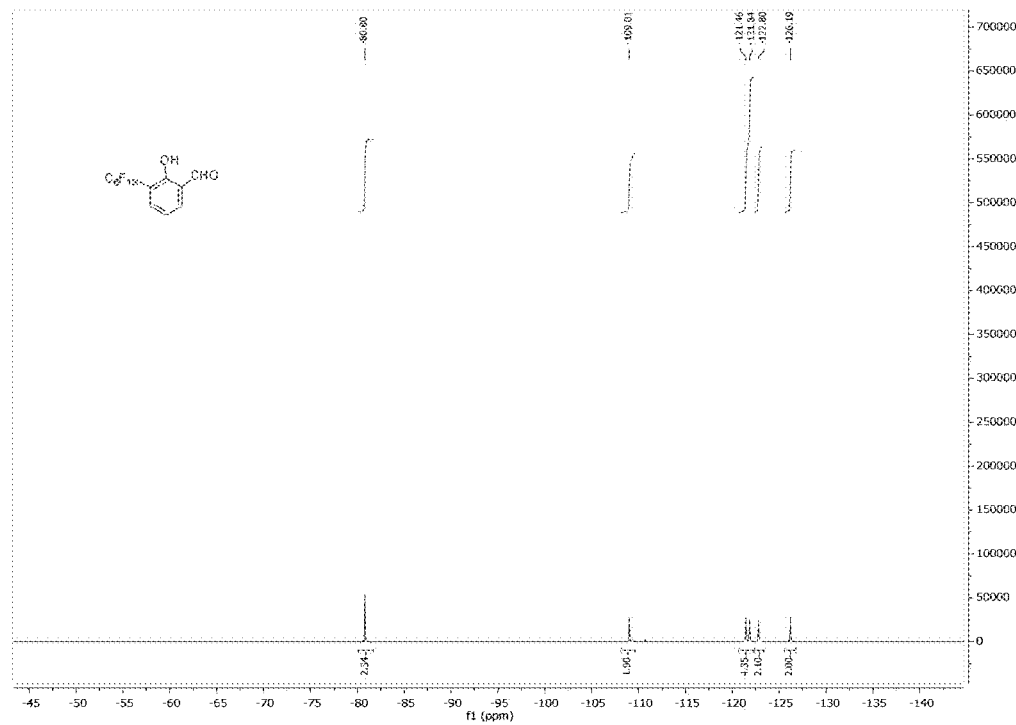
Fig. 27L. 3-Perfluorohexyl-salicylaldehyde (3b)
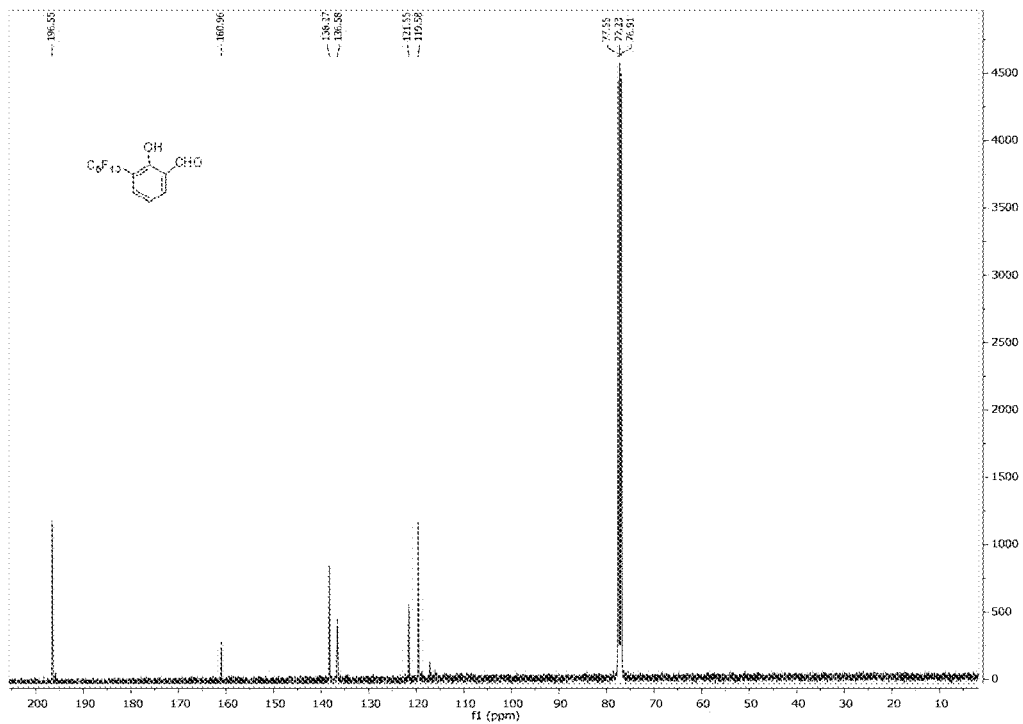

Fig. 27M. 3, 5-di-perfluorohexyl-salicylaldehyde (3c)
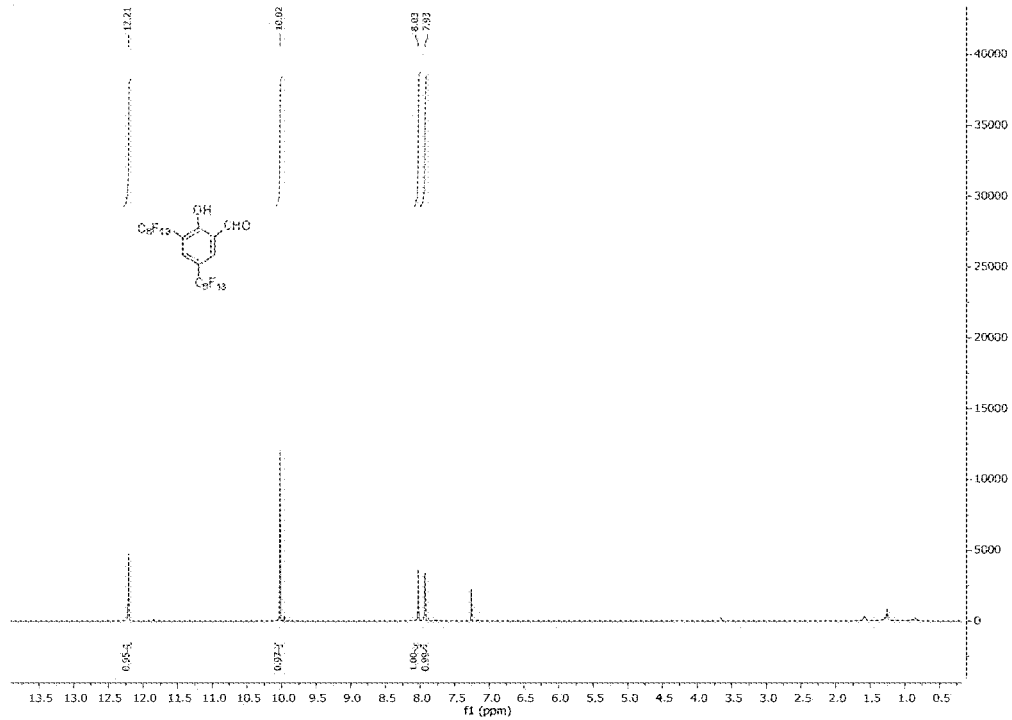
Fig. 27N. 3, 5-di-perfluorohexyl-salicylaldehyde (3c)
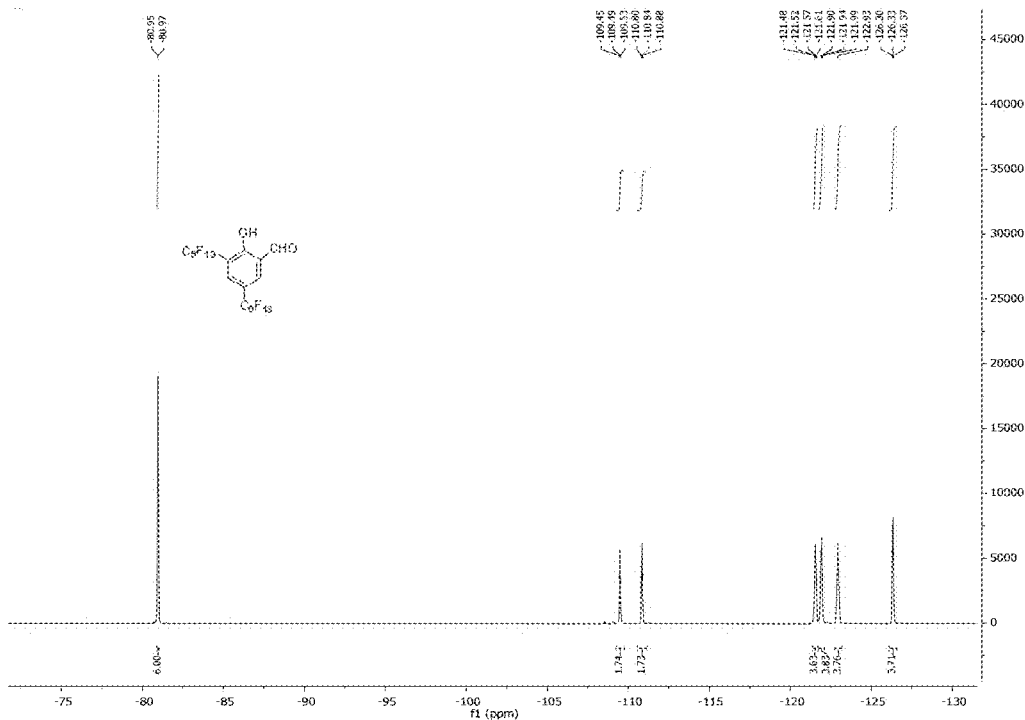

Fig. 27O. 3, 5-di-perfluorohexyl-salicylaldehyde (3c)
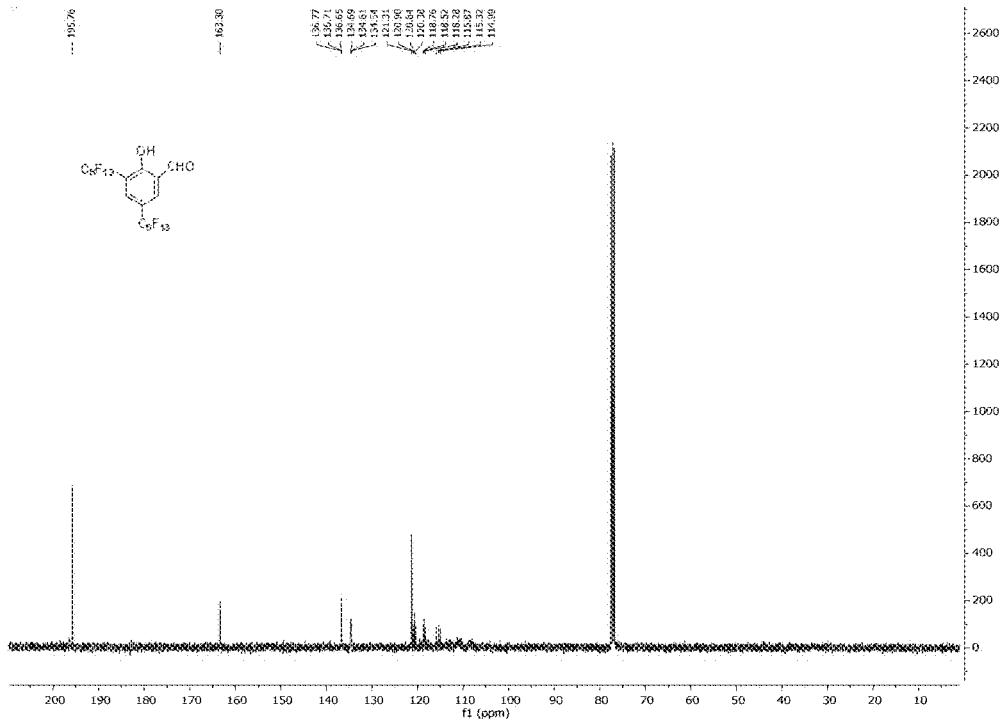
Fig. 27P. 5-methyl-3-perfluohexyl-salicylaldehyde (3d)
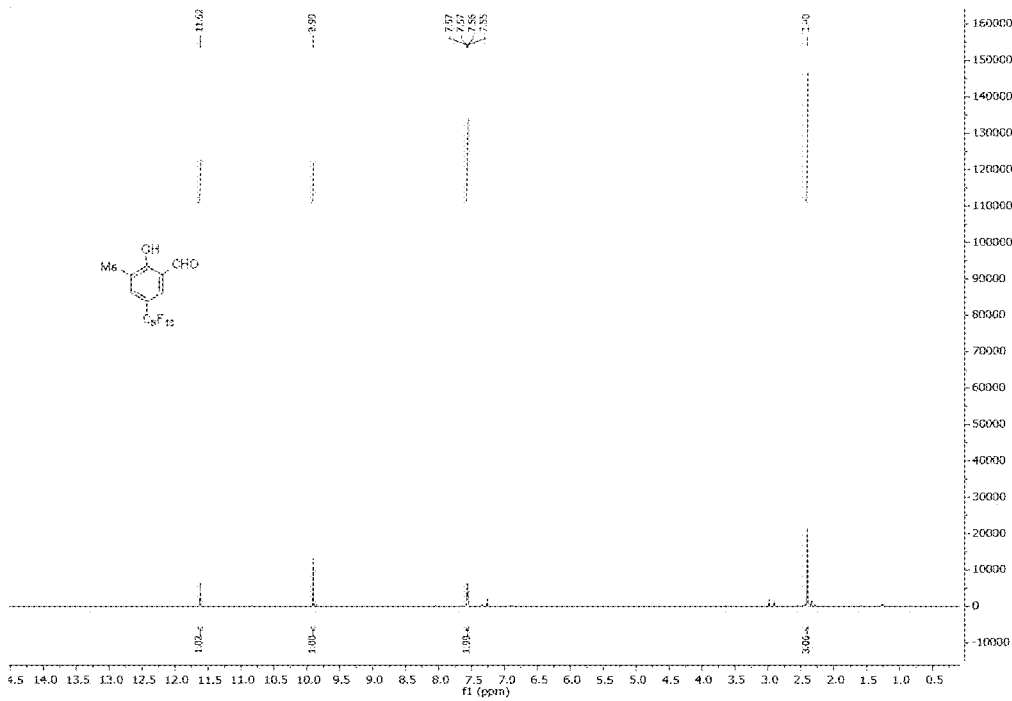

Fig. 27Q. 5-methyl-3-perfluohexyl-salicylaldehyde (3d)
Fig. 27R. 5-methyl-3-perfluohexyl-salicylaldehyde (3d)
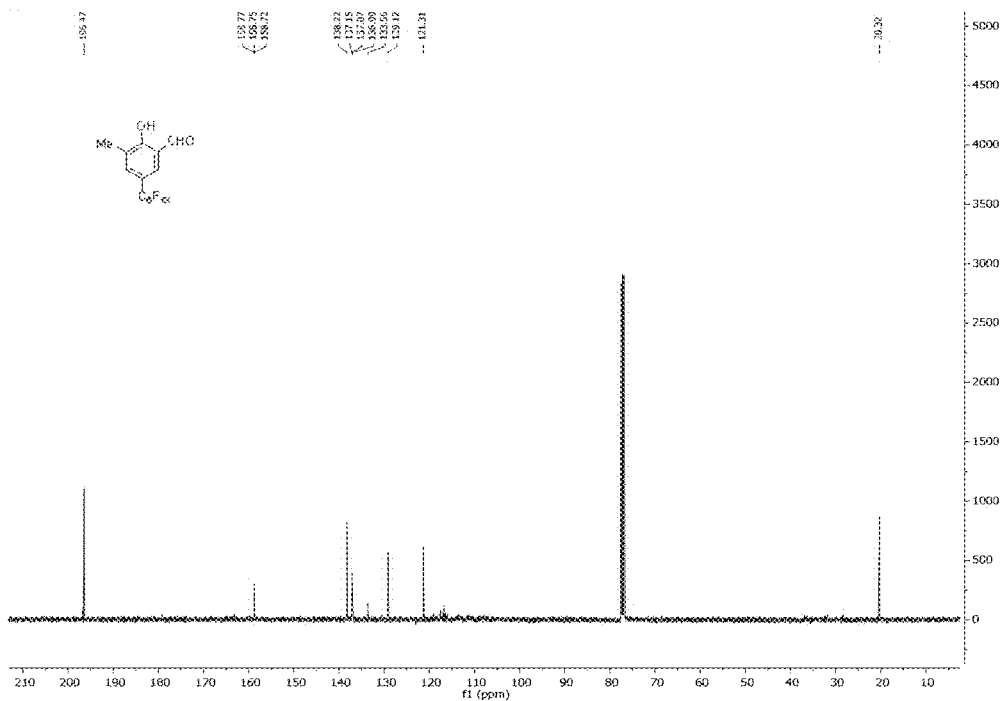

Fig. 27S. 3-methyl-5-perfluorooctyl-salicylaldehyde (3f)
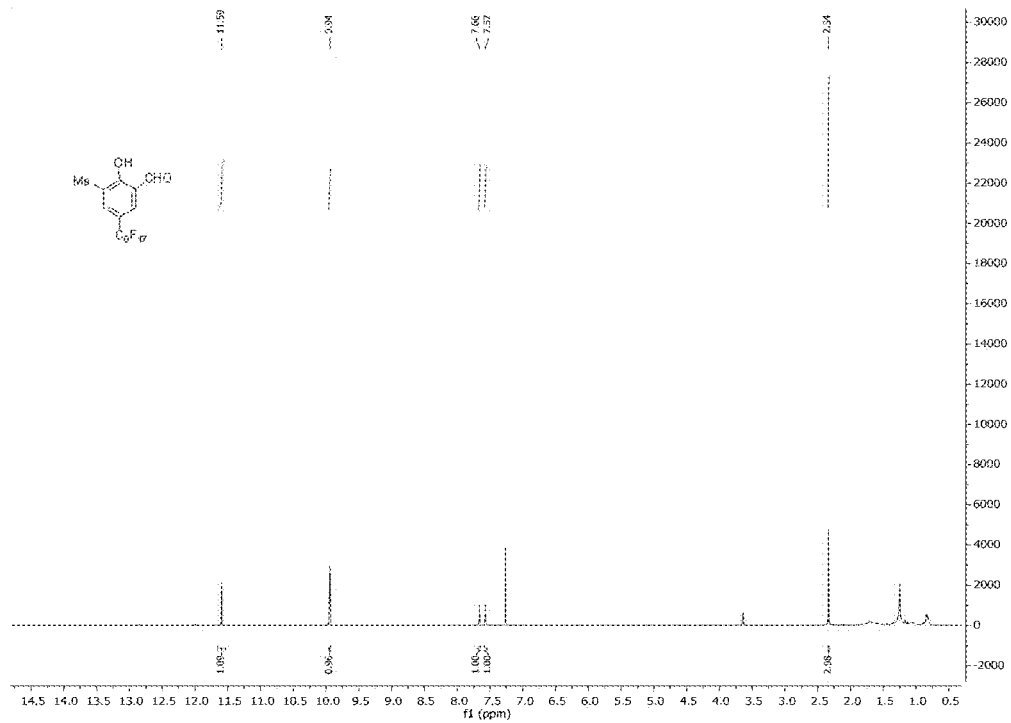
Fig. 27T. 3-methyl-5-perfluorooctyl-salicylaldehyde (3f)
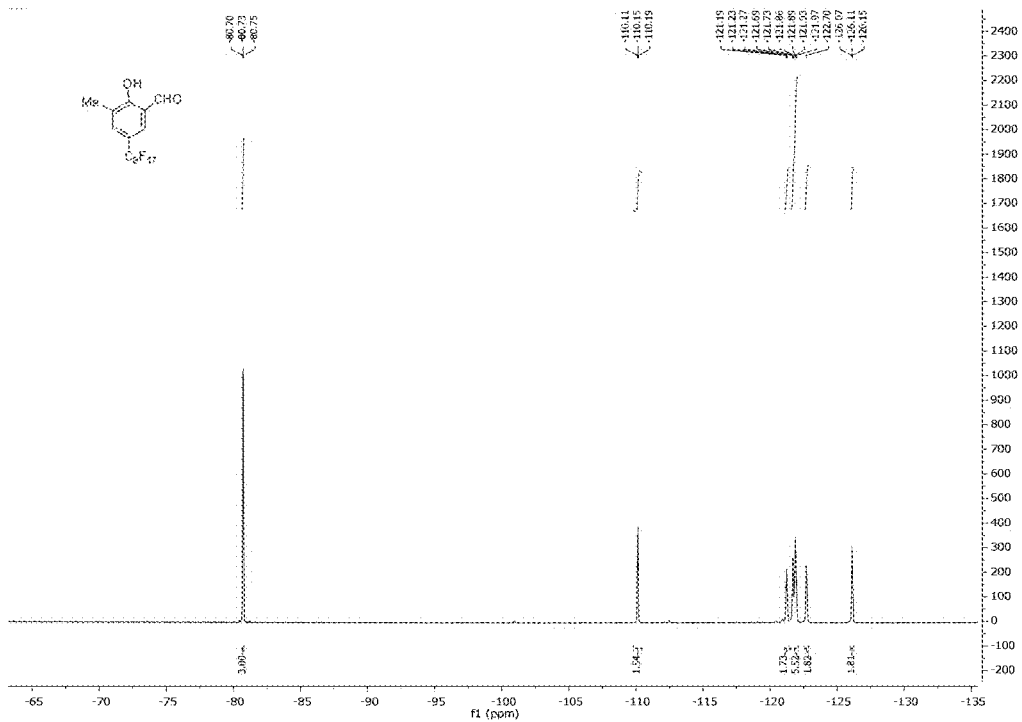

Fig. 27U. 3-methyl-5-perfluorooctyl-salicylaldehyde (3f)
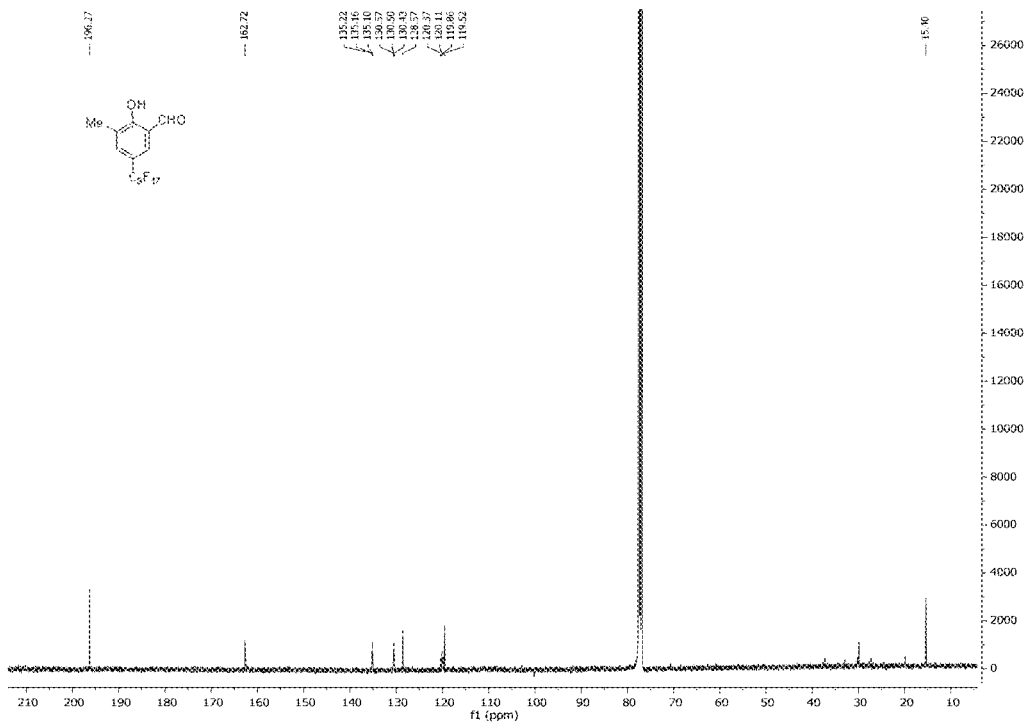
Fig. 27V. 4a OOO
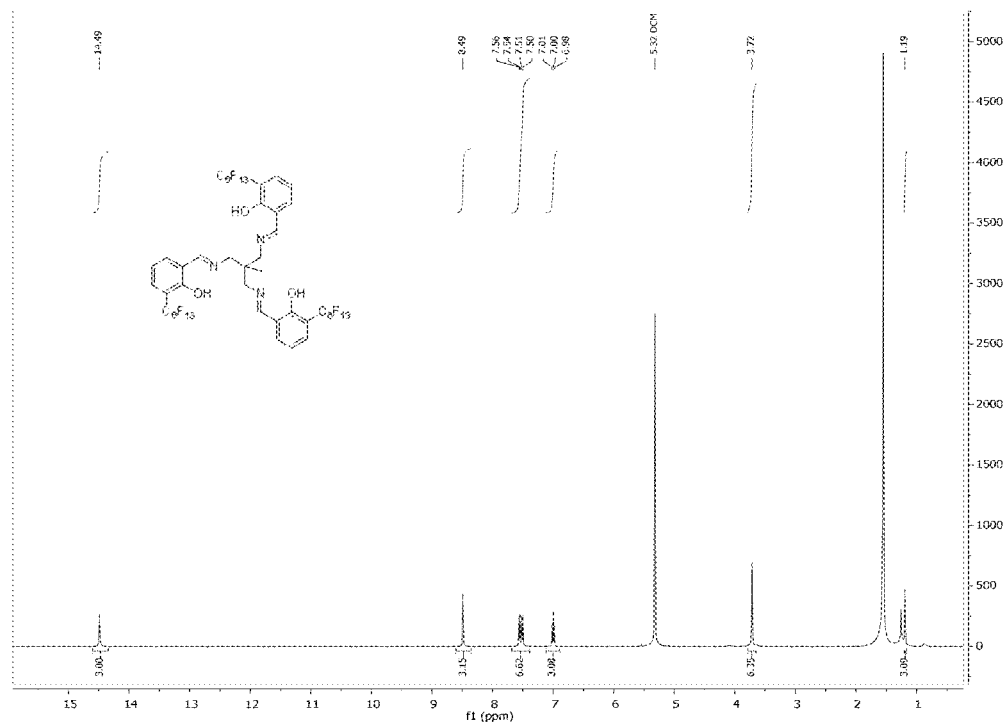

Fig. 27W. 4a OOO
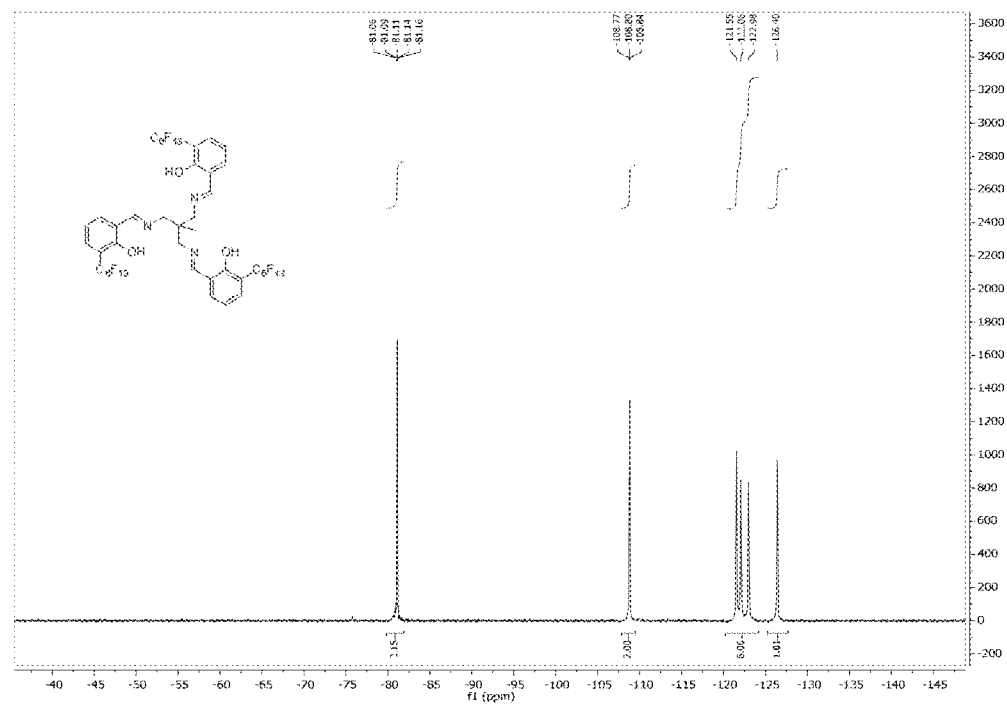
Fig. 27X. 4a OOP
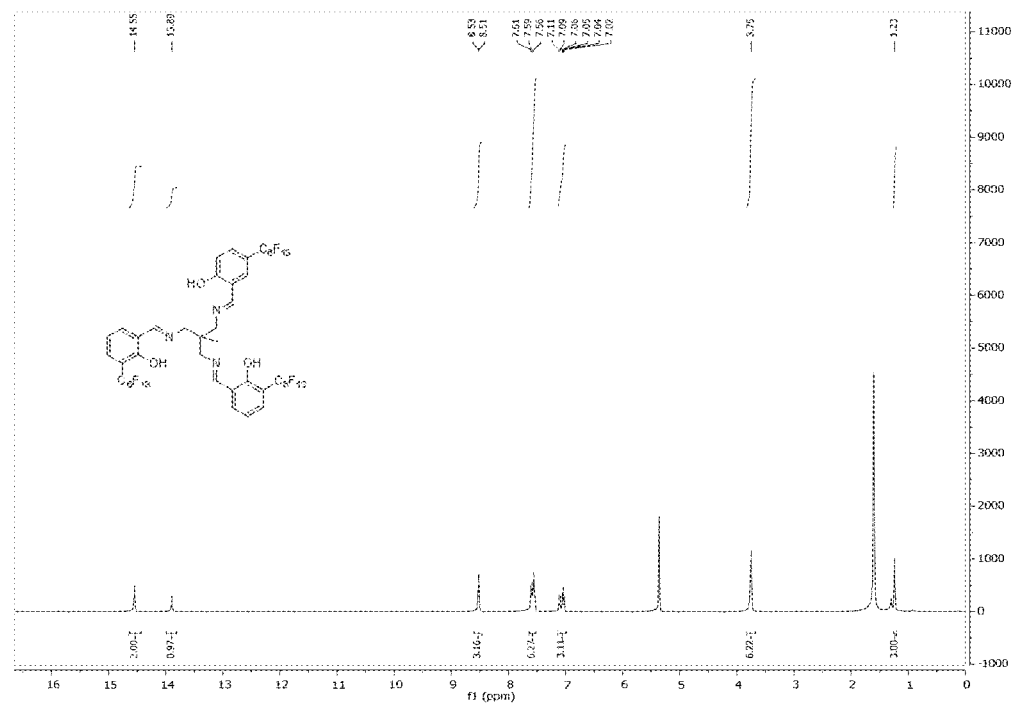

Fig. 27Y. 4a OOP
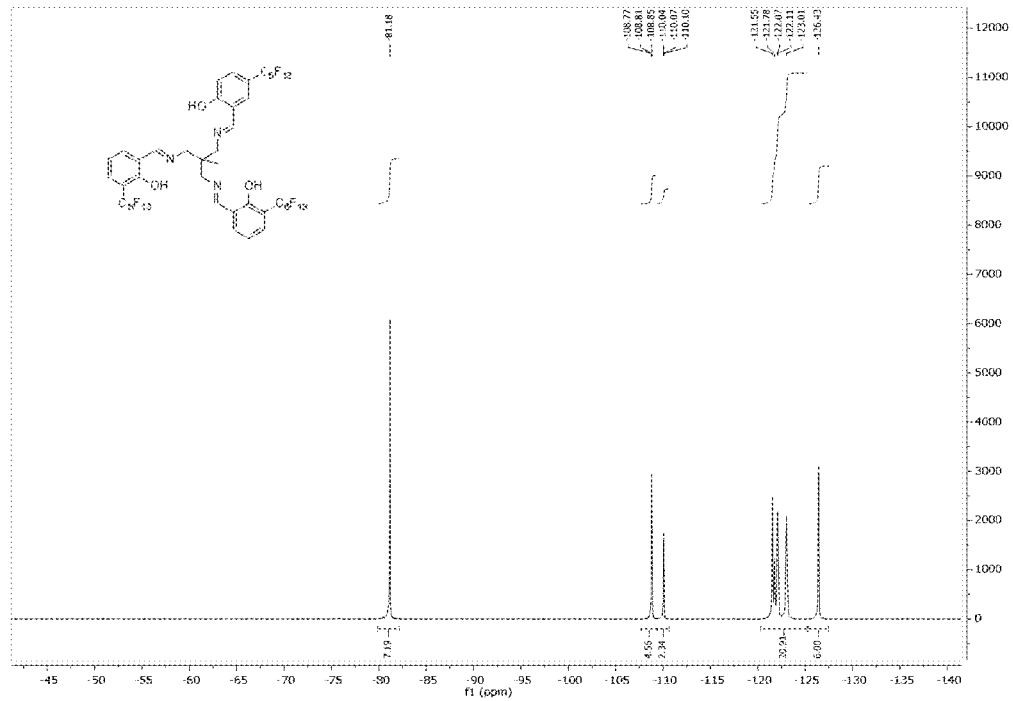
Fig. 27Z. 4a POP
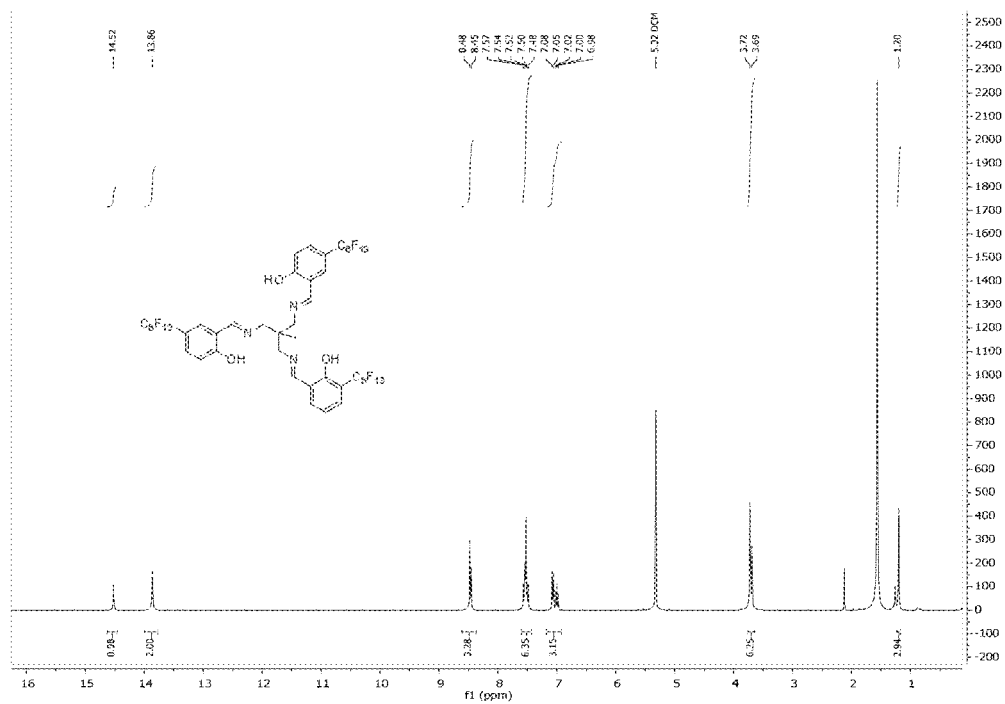

Fig. 27AA. 4a POP
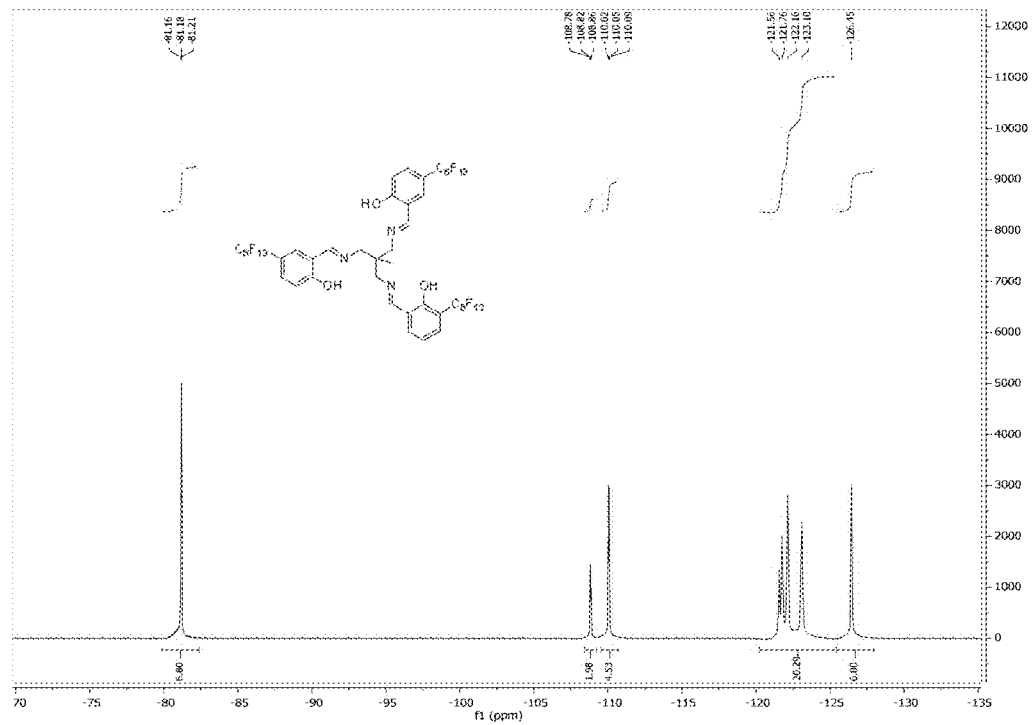
Fig. 27AB. 4a PPP
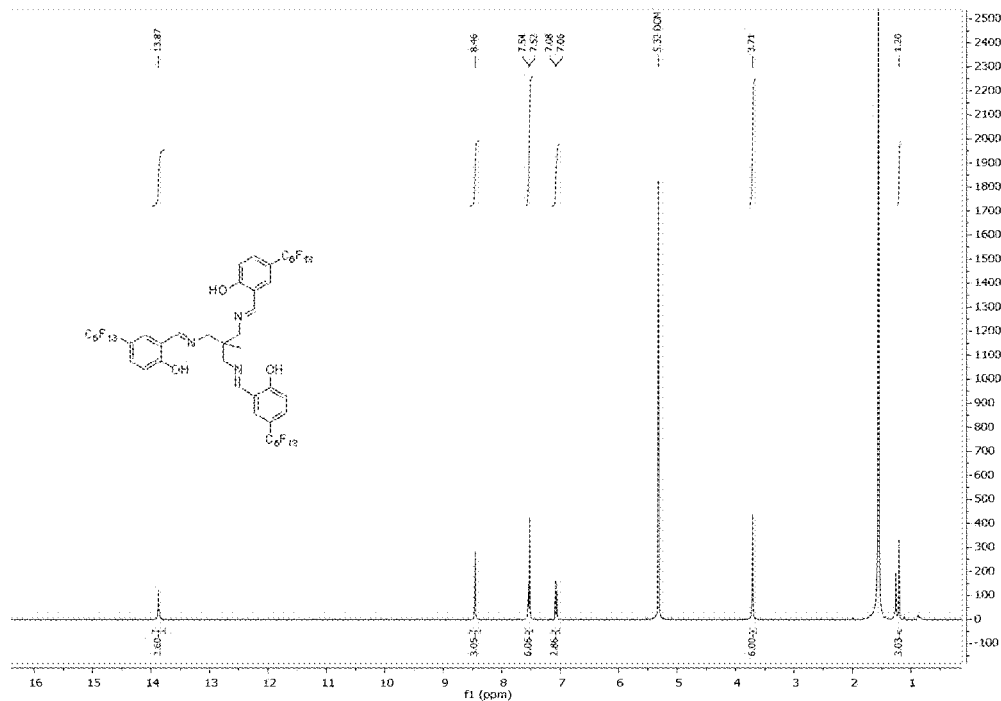

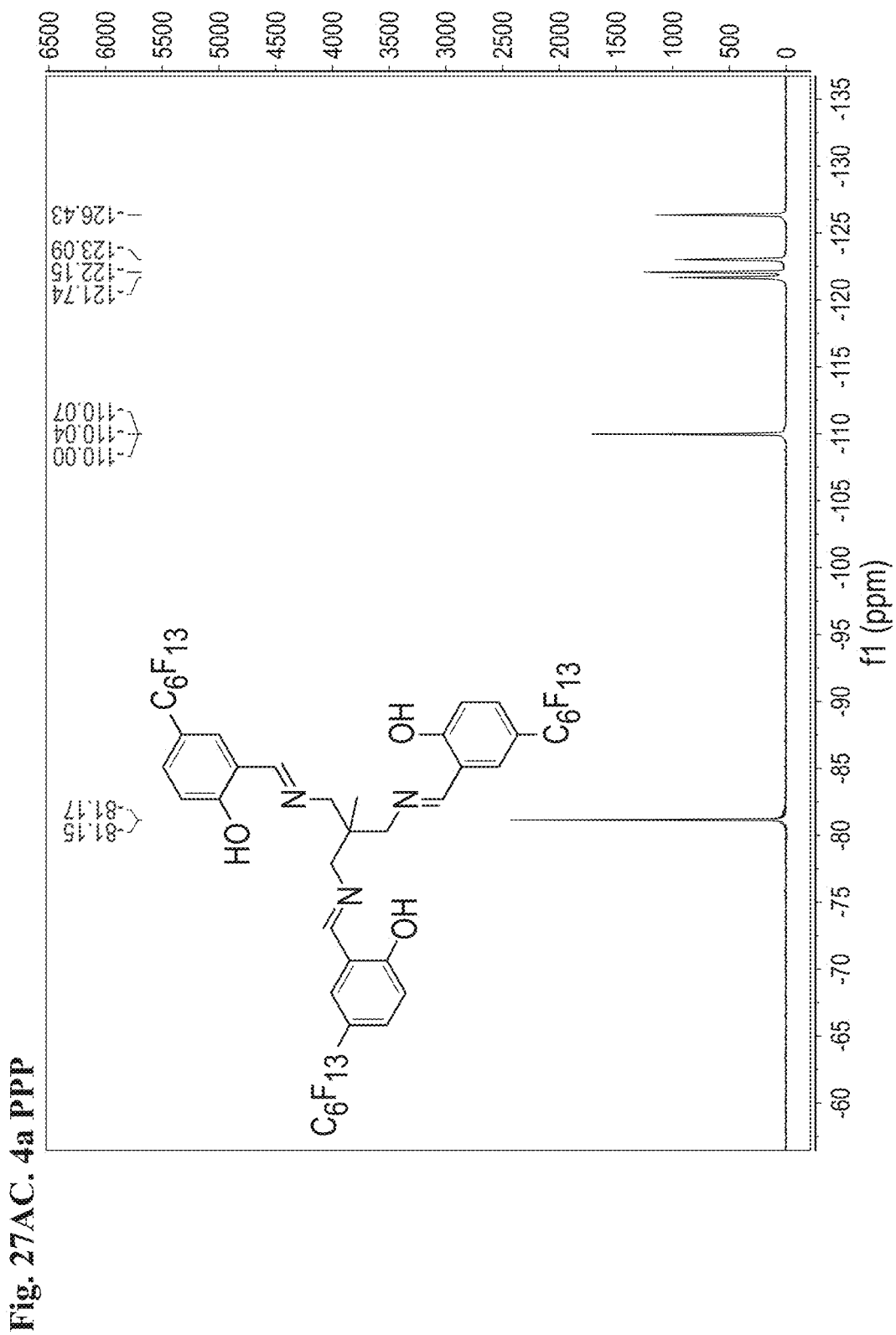
Fig. 27AC. 4a PPP

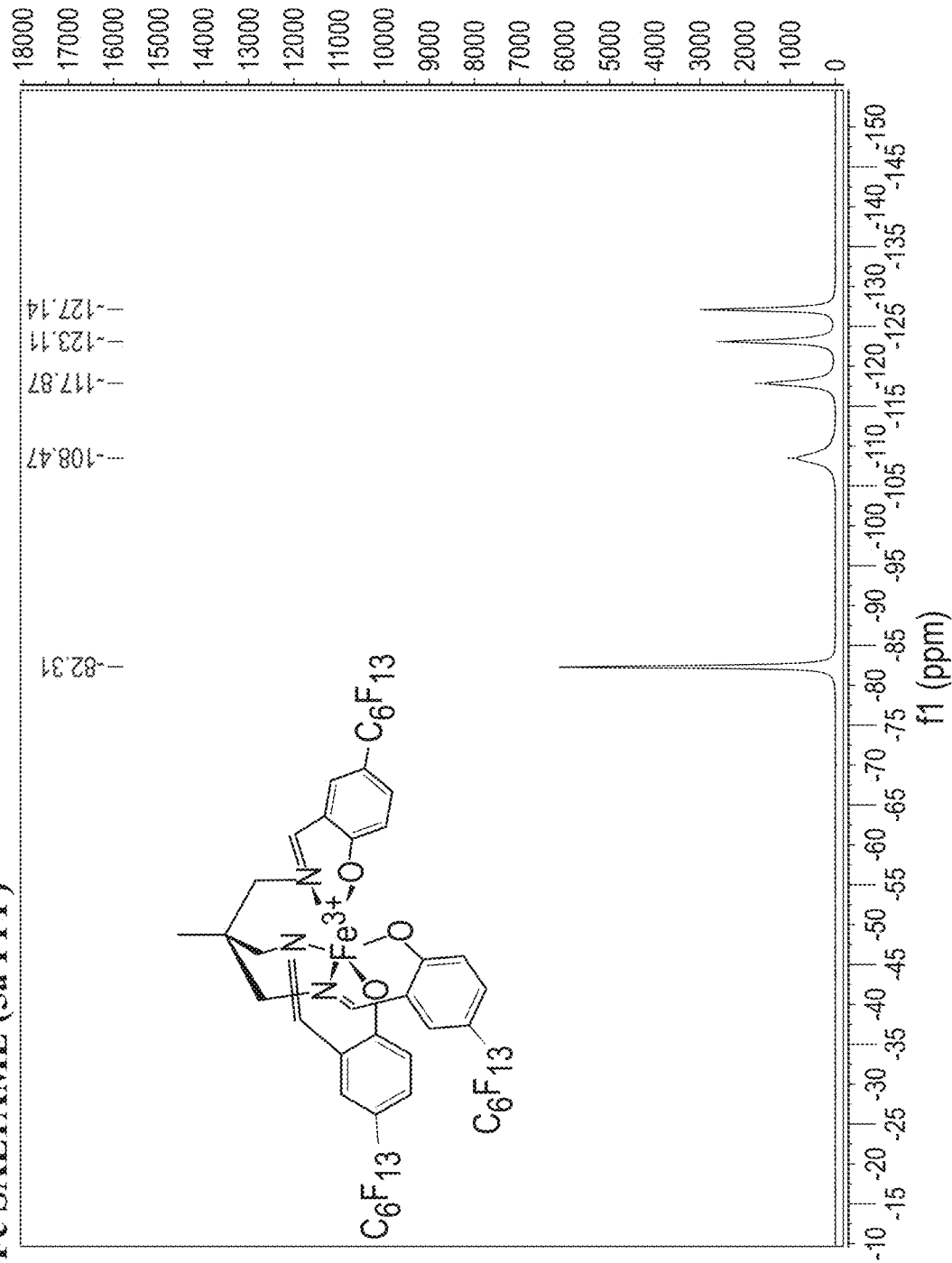
Fig. 27AD. Fe SALTAME (5a PPP)

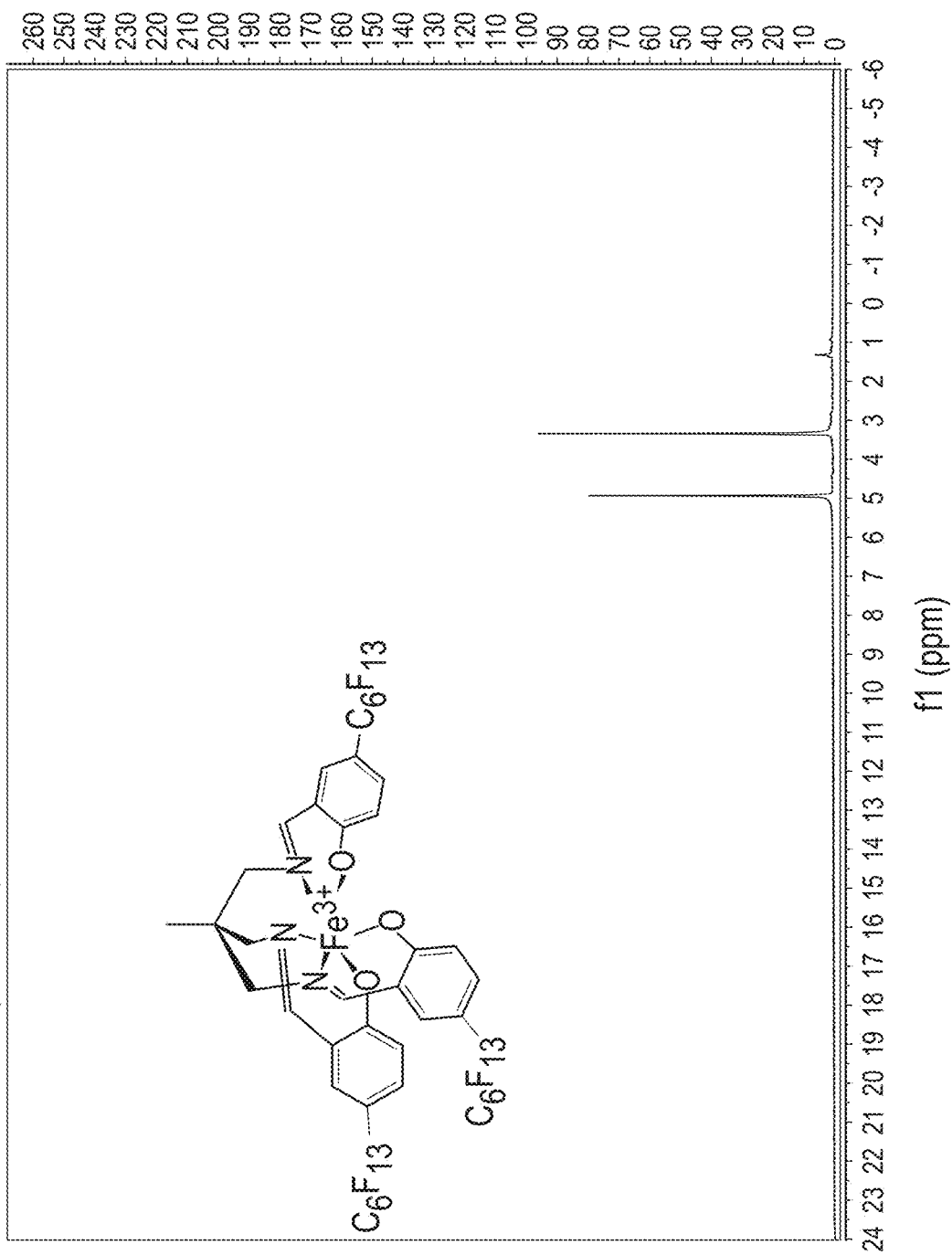
Fig. 27AE. Fe SALTAME (5a PPP)

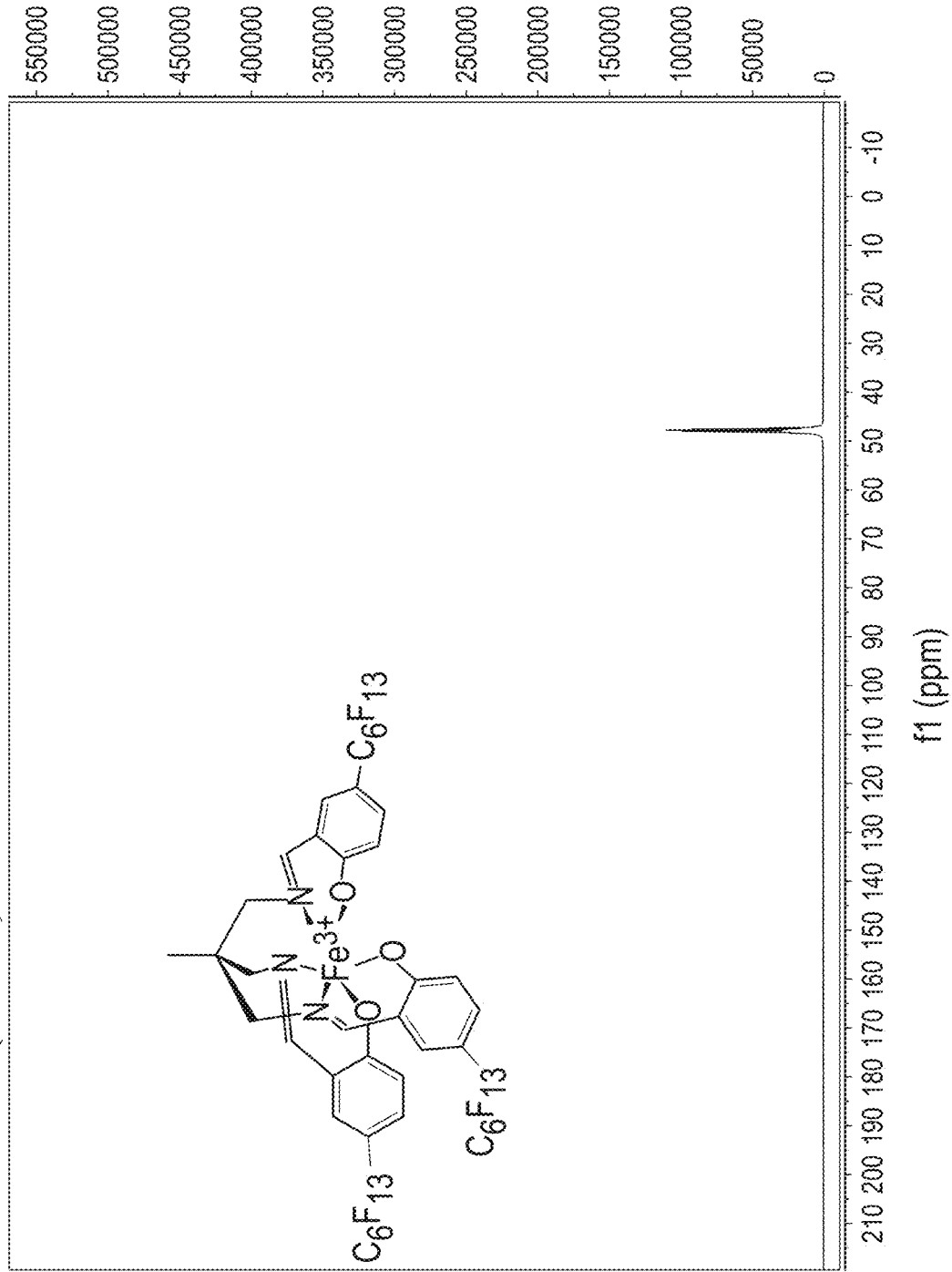
Fig. 27AF. Fe SALTAME (5a PPP)

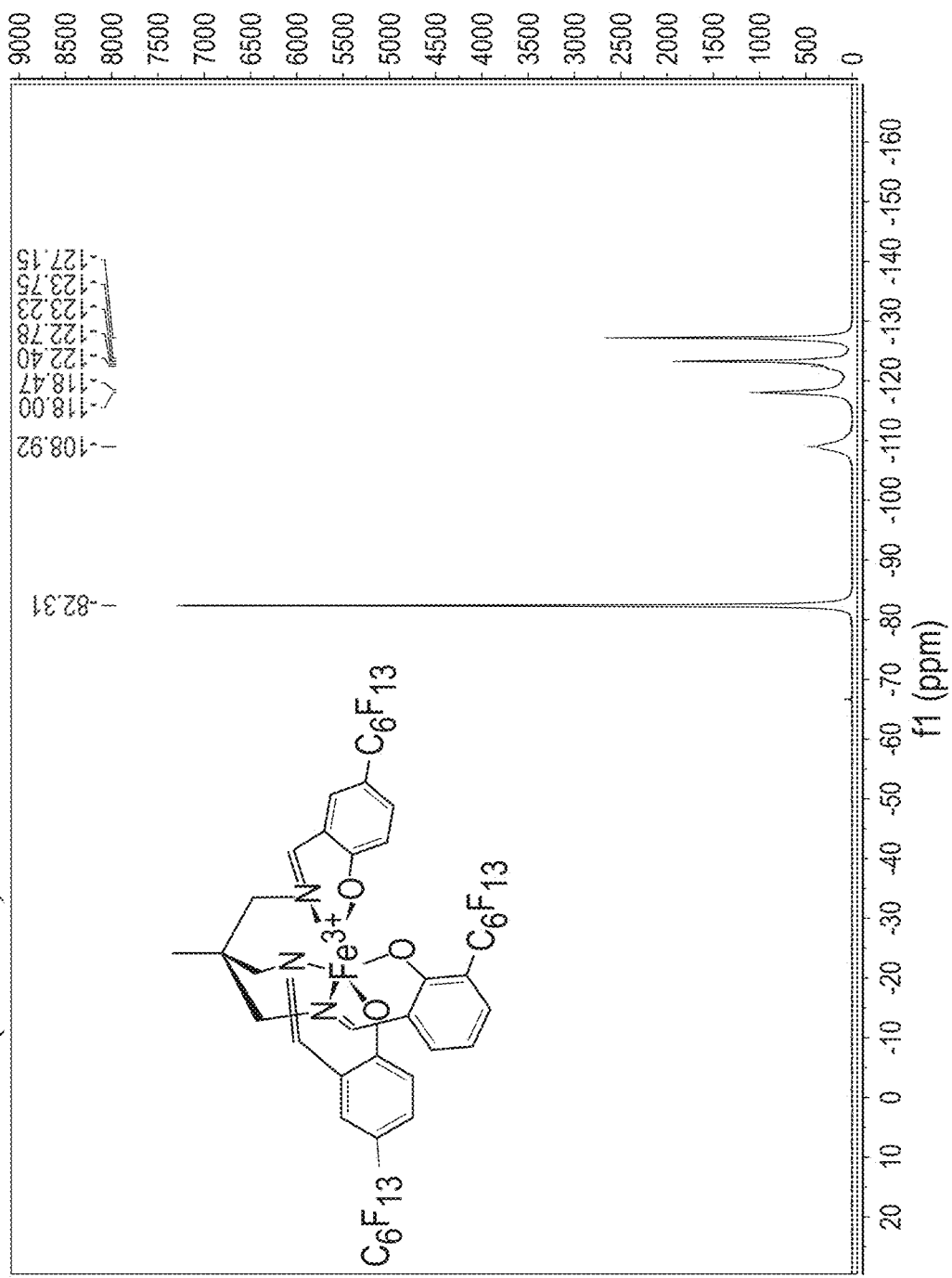
Fig. 27AG. Fe SALTAME (5a POP)

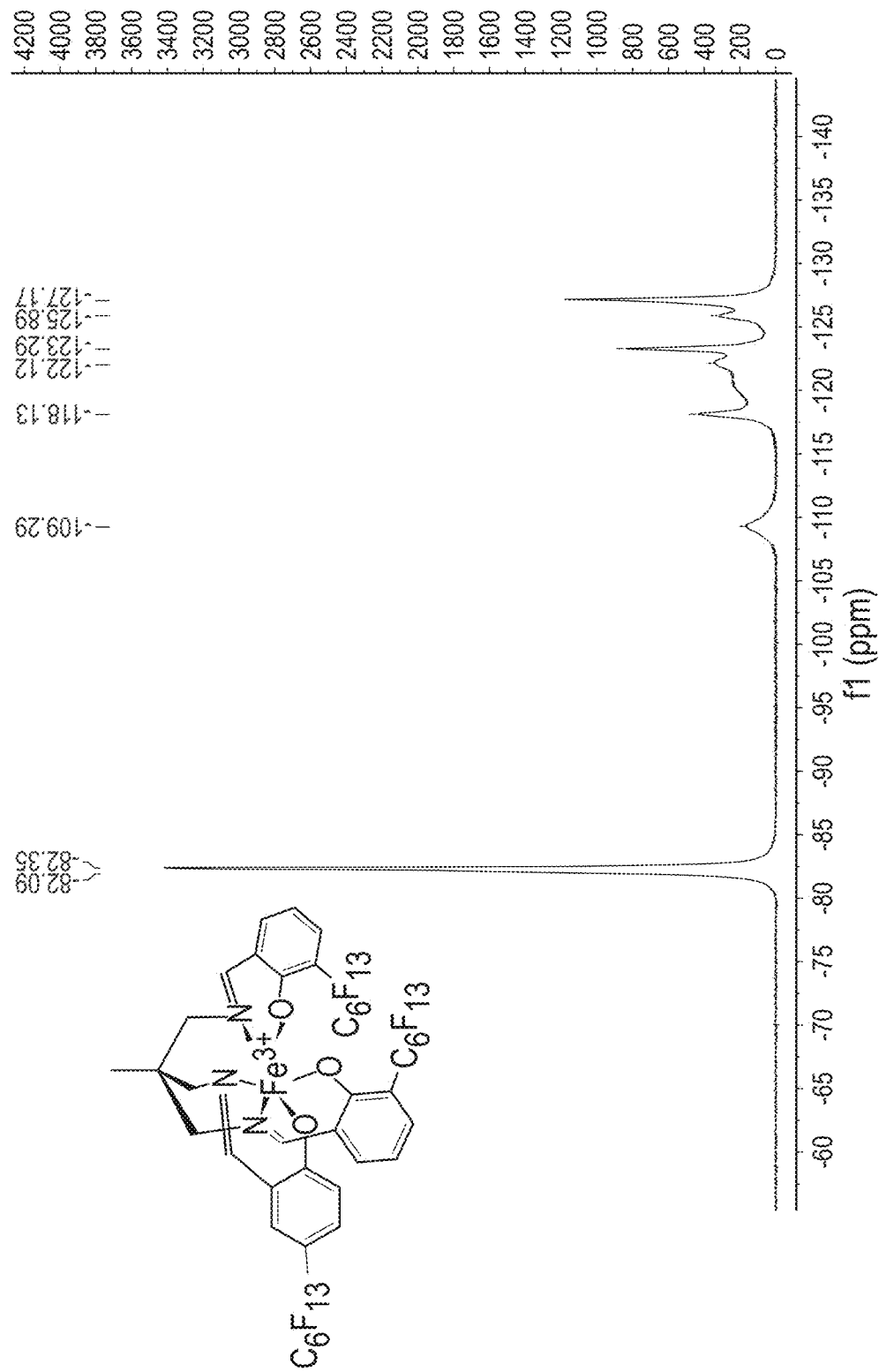
Fig. 27AH. Fe SALTAME (5a OOP)

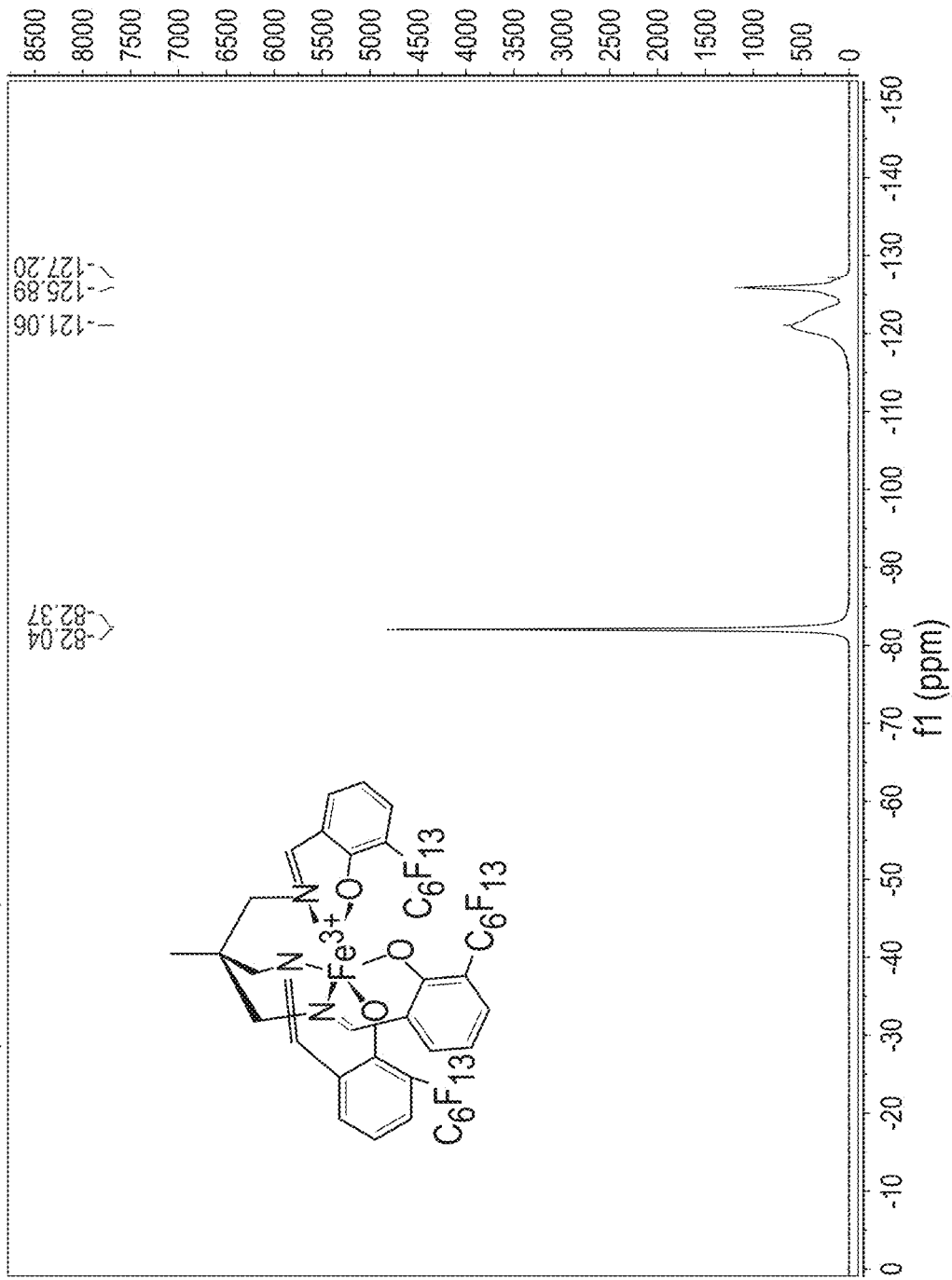
Fig. 27A1. Fe SALTAME (5a OOO)

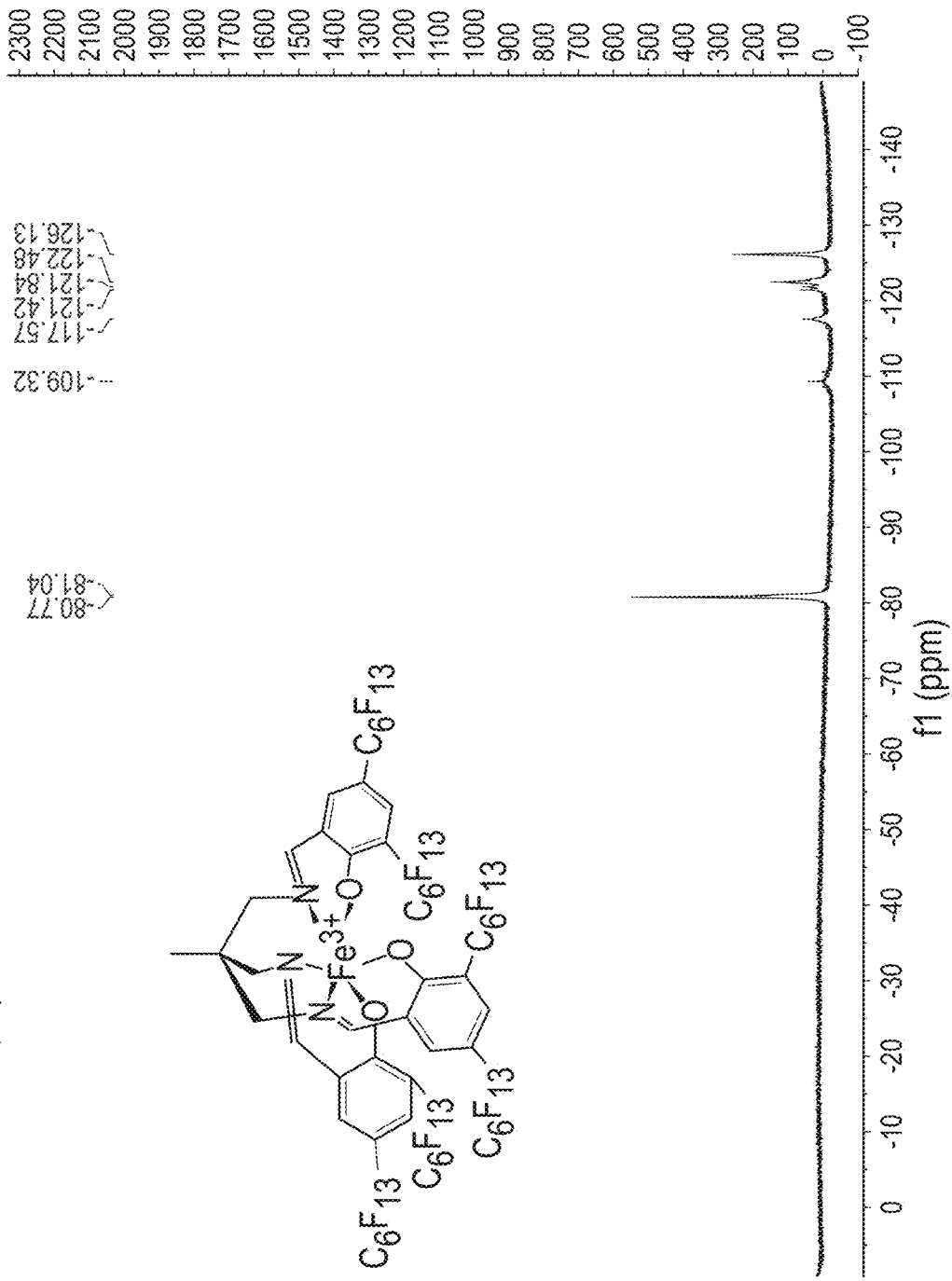
Fig. 27AJ. Fe SALTAME (5c)

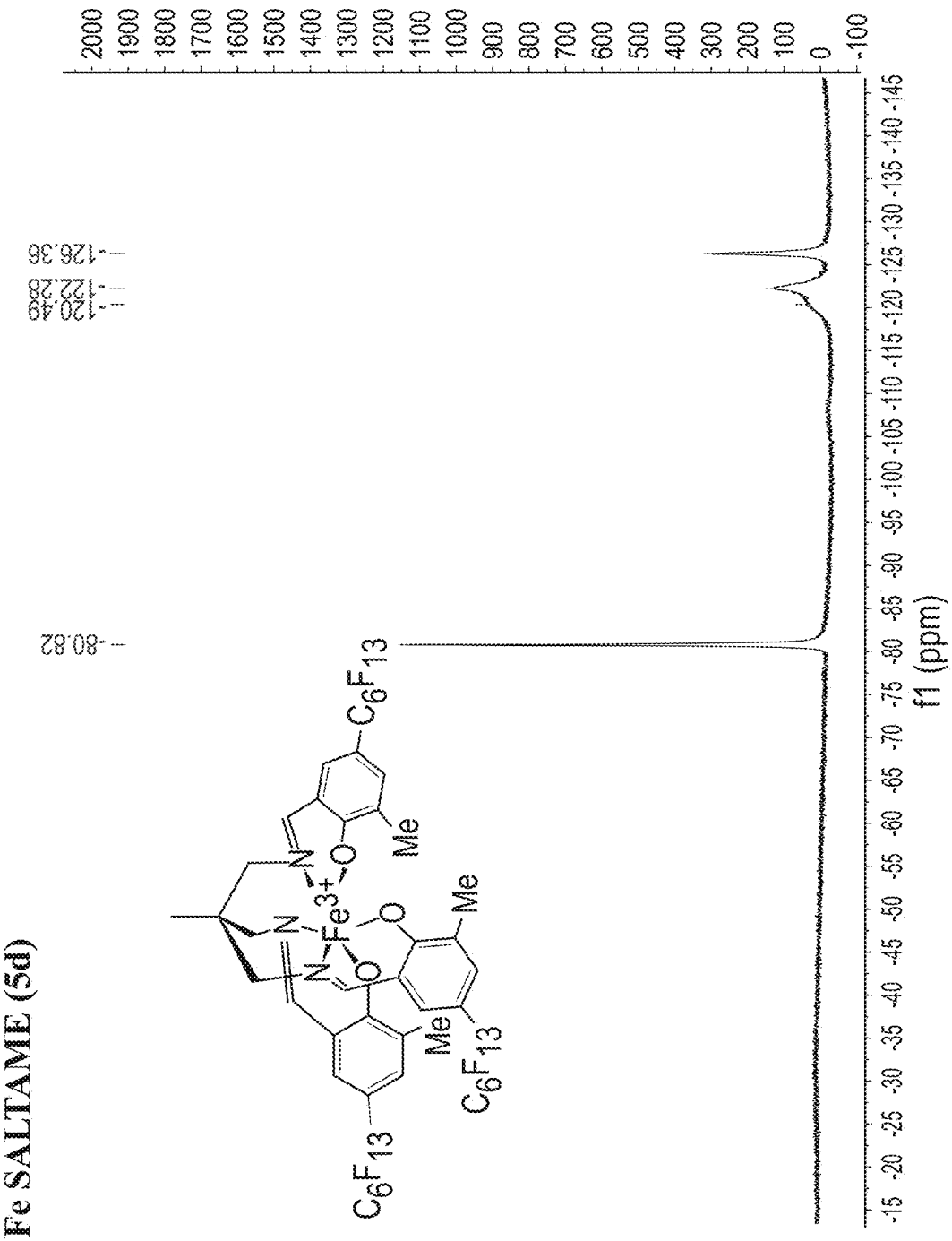
Fig. 27AK. Fe SALTAME (5d)

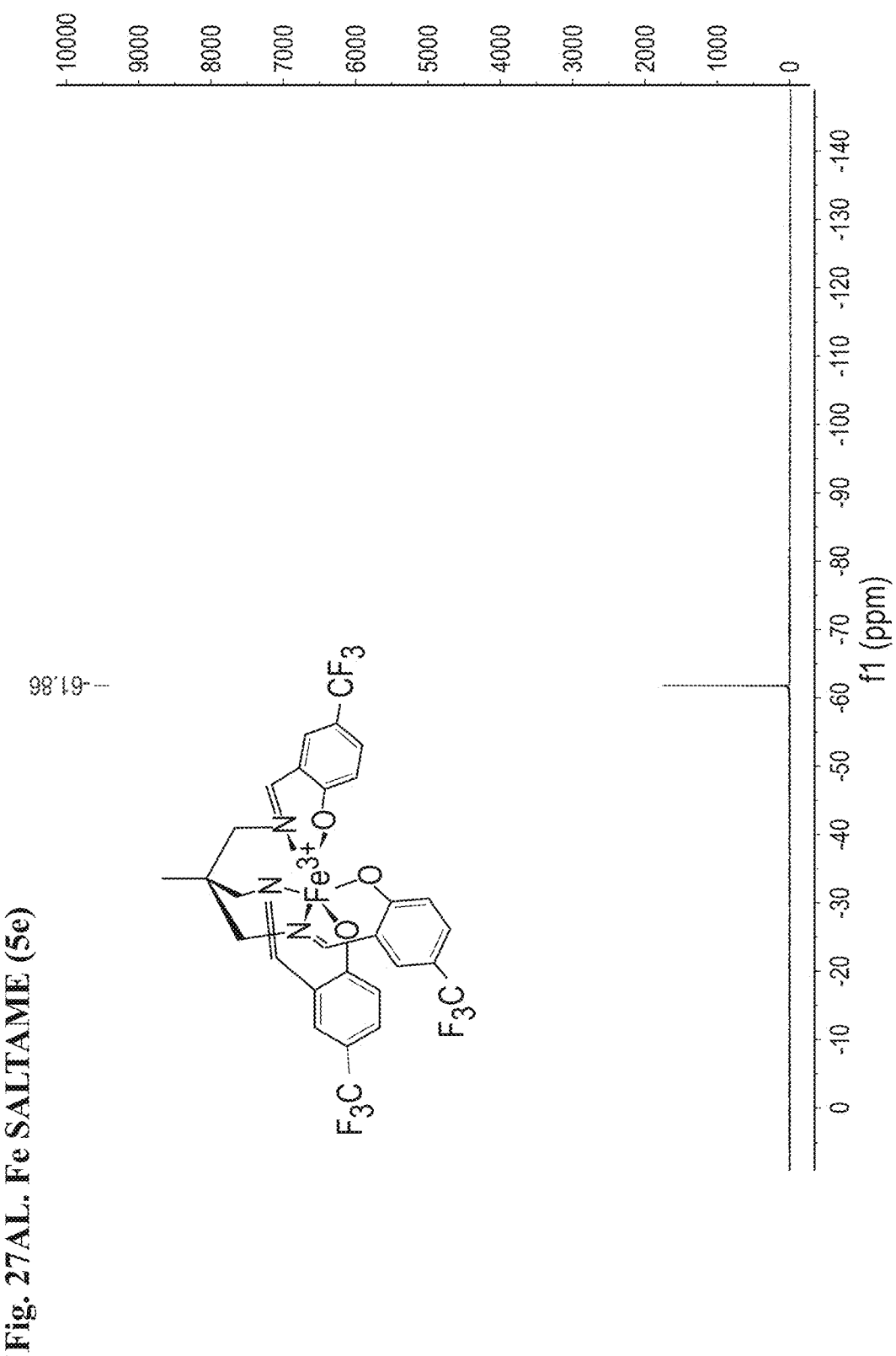
Fig. 27AL. Fe SALTAME (5e)

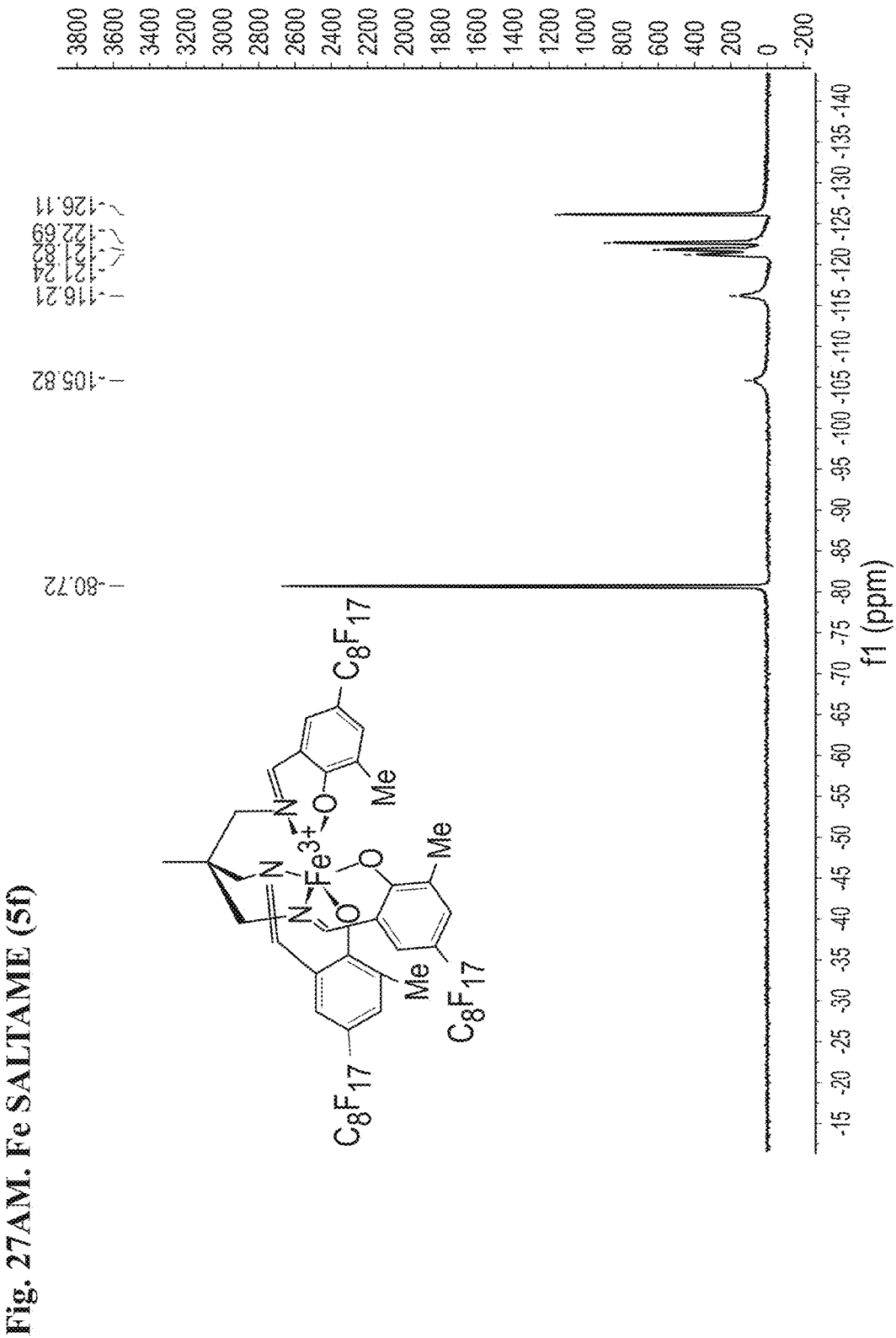
Fig. 27AM. Fe SALTAME (5f)

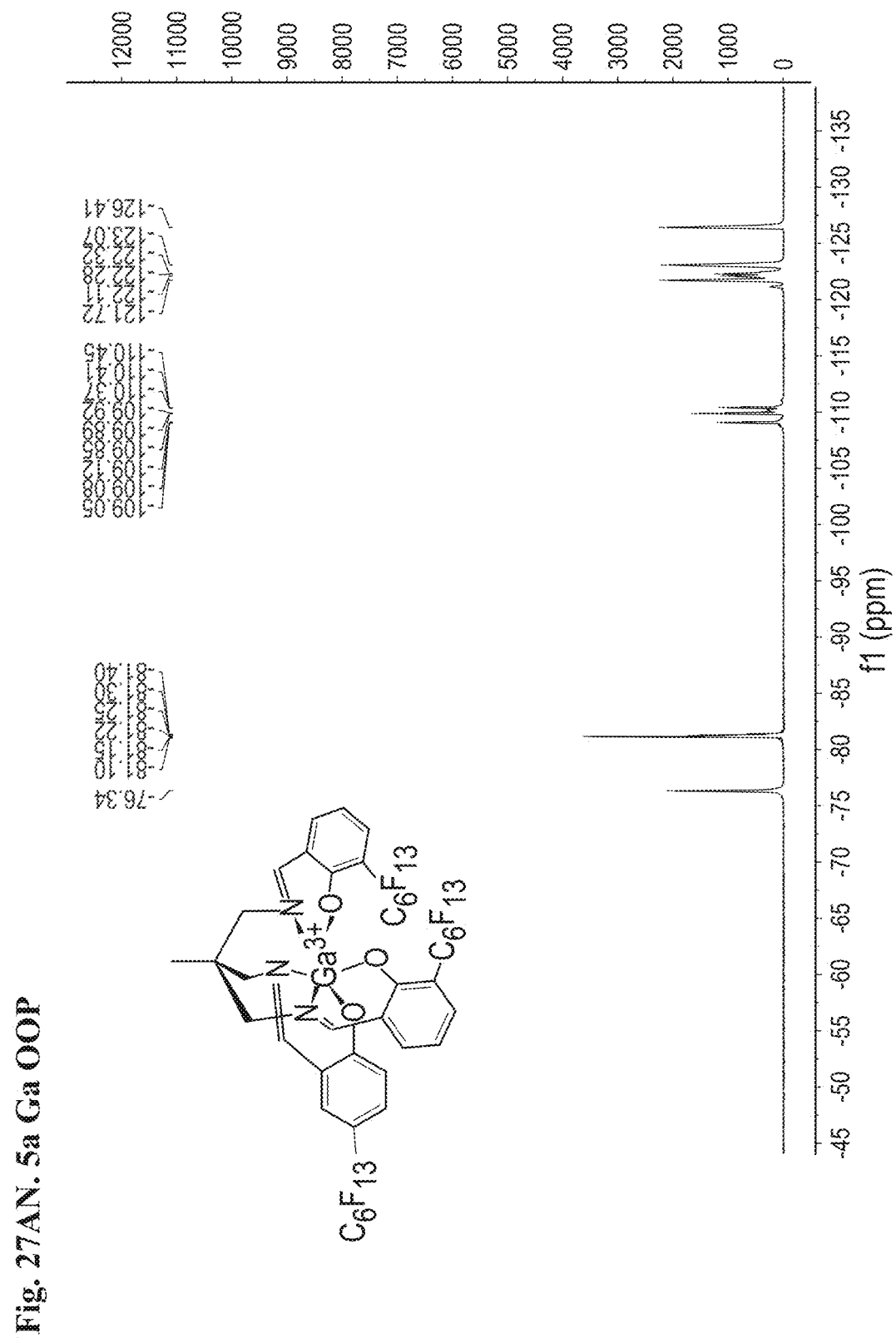
Fig. 27AN. 5a Ga OOP

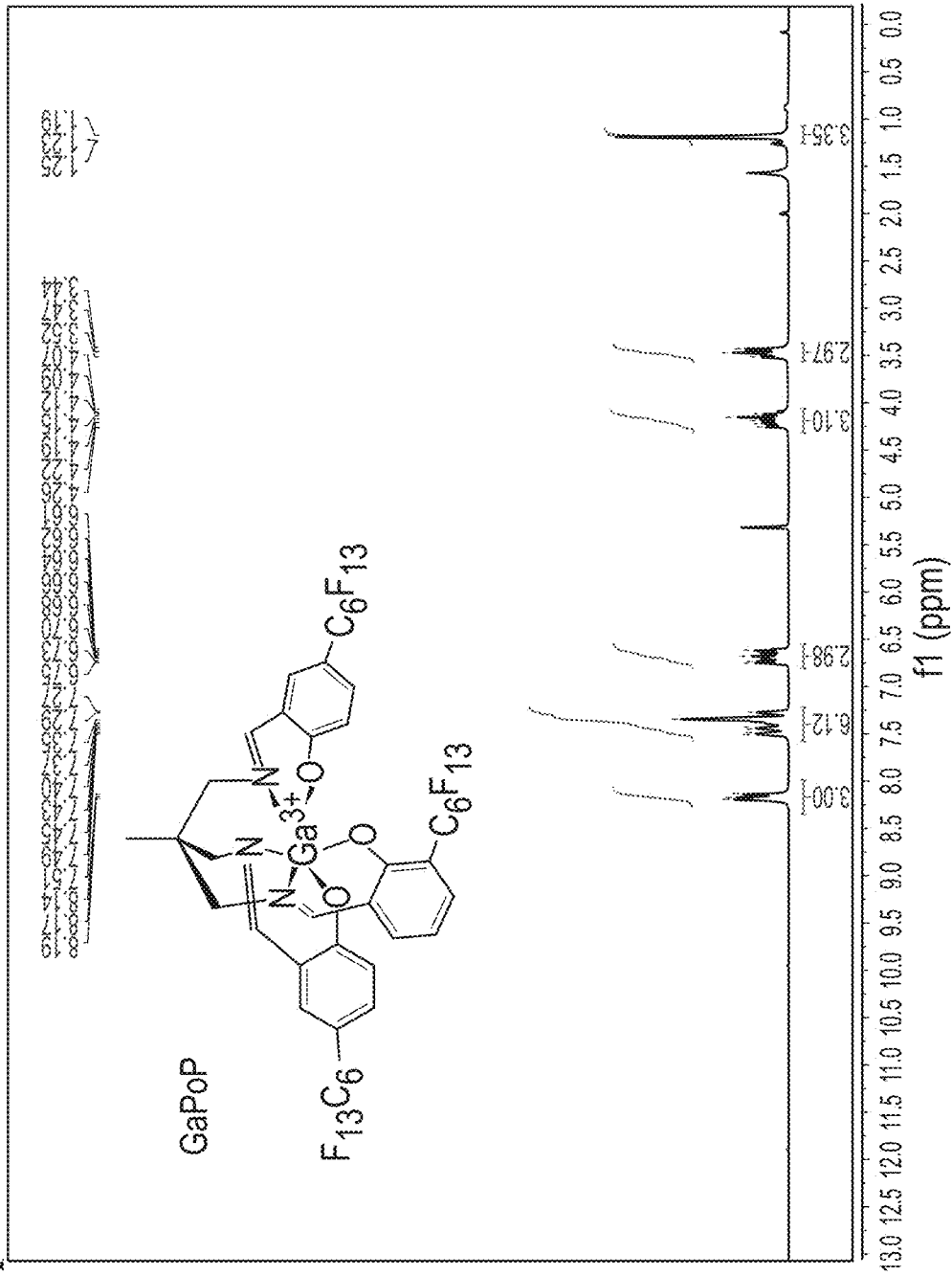
Fig. 27AO. 5a Ga POP
5a Ga POP

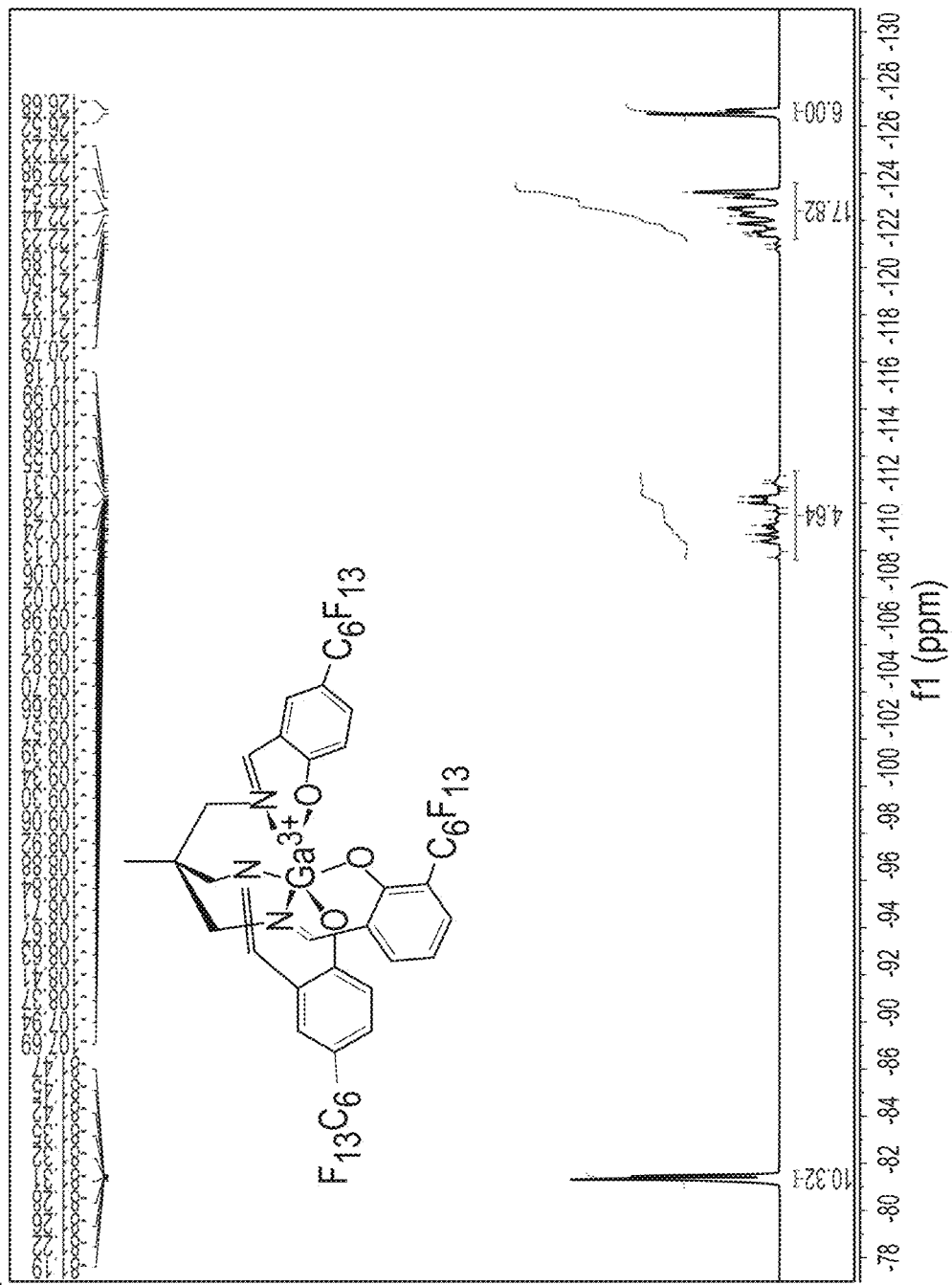
Fig. 27AP. 5a Ga POP
5a Ga POP

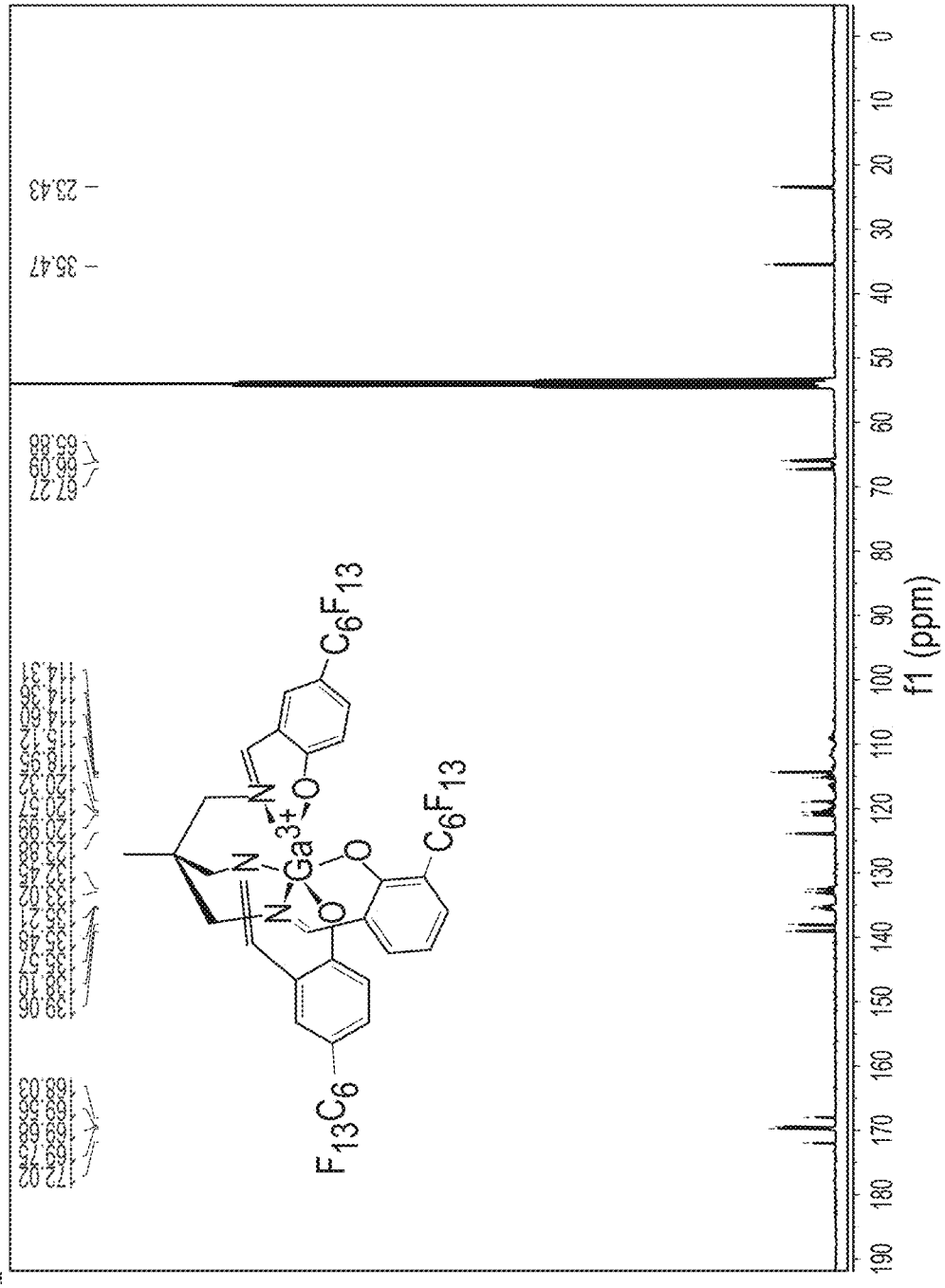
Fig. 27AQ. 5a Ga POP
5a Ga POP

|  | PCE | | | | PFOB | | |
|---|---|---|---|---|---|---|---|
| Fe-PFHA (mM) | 0 | 13.79 | 20.00 | 27.58 | 6.37 | 15.81 | 28.15 |
| R1(s$^{-1}$) | 1.24 | 6.36 | 8.93 | 12.3 | 7.56 | 17.3 | 29.6 |
| R2(s$^{-1}$) | 1.51 | 16.34 | 21.92 | 32.05 | 8.95 | 22.2 | 42.7 |
| R1/R2 | 0.82 | 0.39 | 0.38 | 0.38 | 0.84 | 0.78 | 0.69 |
| Relaxivity (s$^{-1}$ mM$^{-1}$) | r1 = 0.40; r2=1.09 | | | | r1 = 1.01; r2=1.56 | | |

Figure 30.

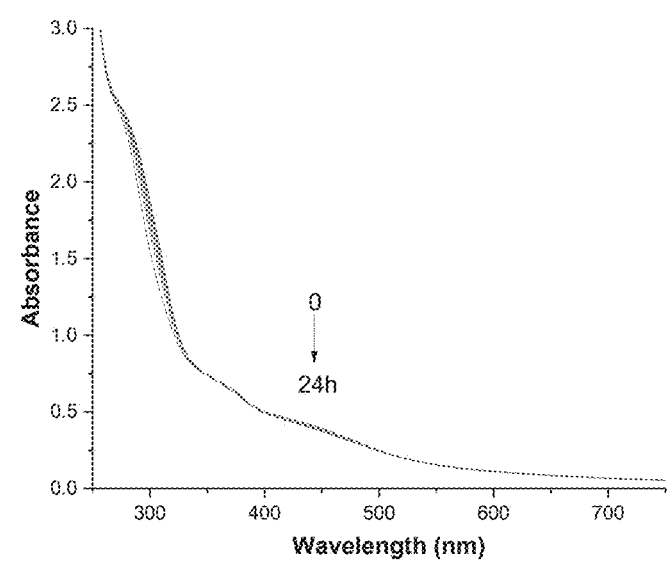
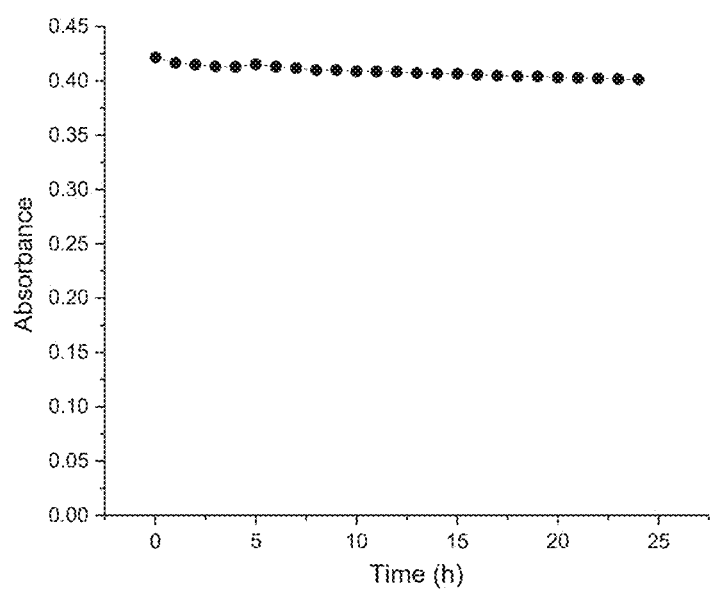
Figure 31.

| | r1 (/mM/s) | r2(/mM/s) | r1/r2 |
|---|---|---|---|
| Fe(III) | 0.4200 | 1.3130 | 0.3199 |
| Gd(III) | 0.2637 | 3.3467 | 0.0788 |
| Mn(II) | 0.0667 | 0.8683 | 0.0768 |
| Ni(II) | 0.0175 | 0.0275 | 0.6364 |
| Cr(III) | 0.0017 | 0.0042 | 0.4000 |
| Er(III) | 0.0077 | 0.3447 | 0.0222 |
| Ho(III) | 0.0121 | 0.6671 | 0.0181 |
| Dy(III) | 0.0147 | 0.6504 | 0.0225 |

FLUOROUS METAL CHELATES COMPOSITIONS

CROSS-REFERENCE TO RELATED APPLICATION

The present application is a U.S. National Stage Patent Application of International Patent Application No. PCT/US2019/065279, filed on Dec. 9, 2019, which claims priority to U.S. Provisional Patent Application No. 62/777,008, filed on Dec. 7, 2018, entitled "Fluorous Metal Chelates Compositions," each of which applications is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under CA139579, EB017271, and EB024015 awarded by the National Institutes of Health. The government has certain rights in the invention.

BACKGROUND OF THE INVENTION

Clinical non-invasive imaging techniques are widely used as diagnostics and to track medical procedures. Magnetic resonance imaging (MRI) is a widely used clinical diagnostic tool because it is non-invasive, allows views into optically opaque subjects, and provides contrast among soft tissues at reasonably high spatial resolution. Conventional MRI mostly focuses on visualizing anatomy and lesions and has no specificity for any particular cell type. The 'probe' used by conventional MRI is the ubiquitous proton (H) in mobile water molecules. Cells are the fundamental building blocks of any organ system. An exogenous MRI probe or reagent to specifically tag cells is needed to facilitate cell-specific imaging in living subjects. For small animal studies, there are many options available for tracking cells in their native environment, especially using various fluorescent and bioluminescent probes and reporters. However, there remains a great unmet need for cell tracking technologies that have the potential for clinical translation. There are several non-invasive diagnostic imaging modalities that are routinely used in humans including various radioisotope methods, MRI, computed tomography, and ultrasound. Adopting existing diagnostic imaging modalities to visualize cells in the body is a complex problem. Non-invasive imaging of the dynamic trafficking patterns of populations of immune cells can play an important role in elucidating the basic pathogenesis of major diseases such as cancer and autoimmune disorders. Other cell populations, such as tumor or stem cells, can be tracked using MRI to provide insight into metastatic processes, cell engraftment and differentiation, and tissue renewal. Moreover, cells are increasingly being used as therapeutic agents to treat genetic and neurological disorders, as well as chronic conditions such as autoimmunity and cancer. A common need for virtually all cell therapies, particularly at the development stage, is a non-invasive way to detect and quantify the cell biodistribution (e.g, the distribution or location of the cell in the body) following injection. Non-invasive imaging of cell trafficking is capable of providing critical feedback regarding modes of action of the cells, optimal routes of delivery and therapeutic doses for individuals. On the regulatory side, emerging new therapies, such as those using immunotherapeutic and stem cells, are slow to gain regulatory approvals partly because clinical researchers are challenged to verify where the cells go immediately after inoculation and where they migrate to days and weeks later. Cell tracking can potentially provide this information and may help in lowering regulatory approval barriers.

Intimately related to cell trafficking is inflammation and the inflammatory response. Prevalent inflammatory diseases include, for example, arthritis, asthma, atherosclerosis, cancer, diabetes, chronic obstructive pulmonary disease (COPD), inflammatory bowel disease (IBD), infection, multiple sclerosis, and organ transplant rejection. The progression of these diseases can often be slow, and the effectiveness of treatment can be observed only after days, weeks or months. Thus, there is a strong unmet need for inflammation-specific diagnostics, as well as inflammation surrogate biomarkers that permit therapeutic developers to determine efficacy quickly, quantitatively, and in a longitudinal fashion. A related need entails pharmacological safety profiling to detect 'off target' inflammatory side effects in pre/clinical drug trials. A non-invasive, image-based biomarker could potentially fill these unmet needs. Vital imaging can accelerate the 'go/no go' decision making process at the preclinical and clinical trial stages, and can facilitate smaller, less costly trials by enrolling fewer patients. Imaging can potentially yield quantitative data about inflammation severity and time course in the anatomical context. The highest value imaging biomarker would have broad utility for multiple diseases and be applicable from mouse-to-man, thereby minimizing validation studies.

Fluorine-19 ($^{19}F$) 'tracer' agents are an emerging approach to intracellularly label cells of interest, either ex vivo or in situ, to enable cell detection via $^{19}F$ MRI (Ahrens, 2013). The $^{19}F$ label yields positive-signal 'hot-spot' images, with no background signal due to negligible fluorine concentration in tissues. Images can be quantified to measure fluorine content in regions of interest yielding a measure of cell numbers at sites of accumulation. Tracer agent compositions have mostly focused on nontoxic perfluorocarbons (PFC). Fluorine-19 is an alternate nucleus that can be imaged using many of today's MRI installations, and this ability is well known in the art.

Often a key limitation of $^{19}F$ MRI using various types of probes is sensitivity. Improving the sensitivity of $^{19}F$ cell detection could lower the barriers for using these technologies in a much wider range of biomedical applications. Unlike conventional $^1H$ MRI, where the probe (water) concentration (>100 Molar $^1H$) and thus sensitivity is high, $^{19}F$ MRI is limited by the total amount and distribution of fluorine atoms introduced into the subject's tissue. In cell tracking and inflammation imaging applications, most often the amount of $^{19}F$ in a region of interest is limited by the amount of tracer agent that can be safely internalized into cells of interest. Thus, to improve sensitivity and overall detectability of sparse cell numbers in tissue, one must somehow improve the intrinsic MRI sensitivity of the PFC molecule (or other type of $^{19}F$ probe molecule).

A key approach for boosting intrinsic sensitivity of PFC is by decreasing the intrinsically-high $^{19}F$ spin-lattice relaxation time ($T_1$) of PFC molecules. The $T_1$ parameterizes the characteristic time constant for the time that it takes for $^{19}F$ nuclei to align along the field direction of the MRI magnet, i.e., the equilibrium alignment direction or longitudinal direction, or alternatively $T_1$ is the time constant for the nuclei to align along the field direction after it has been knocked out of equilibrium. The $T_1$ value ultimately limits the rate of $^{19}F$ MRI data acquisitions. Generally, $^{19}F$ images require summation of multiple acquisitions (i.e., signal averaging) to generate a sufficient signal-to-noise ratio (SNR) for confident interpretation. High $^{19}$F $T_1$ values require a long repetition time (TR) to allow for longitudinal signal recovery, thus limiting the number of signal acquisitions attainable during a fixed total imaging time ($t_i$). As $t_i$ is constrained when scanning patients, the key parameter to maximize is SNR/$t_i$. Shortening $T_1$ can increase SNR/$t_i$, sensitivity, and decrease the minimum number of detectable cells per voxel. Overall, the creation of stable and cytocompatible $^{19}$F agents with 'ultra-fast' $T_1$, as well as a high 19F density on the molecule, has been an open challenge that can greatly impact the MRI field, enabling accelerated MRI acquisitions and the detection of sparser cell populations in vivo.

The relaxation times $T_1$ and $T_2$ can be profoundly altered by high-spin paramagnetic metal ions (e.g., $Mn^{2+}$, $Fe^{3+}$, $Gd^{3+}$). Prior studies have attached $Gd^{3+}$ to the outer surface of the PFC nanoemulsion droplet resulting in modest reductions in $T_1$. With increasing distance (r), the steep fall-off ($\sim r^{-6}$) of paramagnetic relaxation rate enhancement from paramagnetic centers limit the efficacy of relaxation agents bound to the surface of PFC nanoparticles. Thus, effective relaxation enhancement necessitates introduction of metal ions into the fluorous phase, i.e., within the nanoemulsion droplets, to achieve a short $T_1$ using a minimum amount of a paramagnetic additive. This presents a significant challenge due to very disparate properties of fluorocarbons (extremely hydrophobic) and common MRI contrast agents (hydrophilic, multidentate chelates). A key innovation of the present disclosure was achieved by devising a material that permits combining metal ions with bulk fluorocarbons, while retaining the high fluorination and sensitivity as well as biological inertness typical of fluorocarbons.

It should be noted that fluorinated lanthanide chelates have been proposed for MRI cell tracking applications, but these have not been shown to be particularly useful for this purpose. Most importantly, these molecules would not provide any improvement in sensitivity for cell tracking applications over previous perfluorocarbon emulsions that have been used in the past, and in fact they would have inferior sensitivity in these applications. This is due to the fact that it is infeasible to get sufficiently high levels of fluorinated lanthanide complexes into cells, where even under the best loading conditions, the cellular loading level is at least 10 times smaller than what is widely reported with PFC nanoemulsions, which achieve up to $10^{12}$ $^{19}$F/cell for "normal" cell and $10^{13}$ $^{19}$F/cell for larger cells (e.g., antigen presenting cells). Importantly, minimum cell detectability scales linearly with intracellular loading. Thus, far greater intracellular loadings of $^{19}$F can be achieved by labeling with emulsified liquid fluorocarbons than with osmotically active hydrophilic chelates with relatively low fluorine content. See, U.S. Pat. No. 9,352,057 which is incorporated by reference herein in its entirety.

The present invention meets this need by providing such compounds.

BRIEF SUMMARY OF THE INVENTION

The present invention provides compositions of SALTAMEs as well as imaging methods using the described compounds.

In some embodiments, the present invention provides a compound comprising an salicylidene-tris(aminomethyl)ethane (SALTAME) core as described herein.

In some embodiments, the present invention provides a composition comprising a compound comprising a SAL-TAME core, wherein the compound is selected from the group consisting of the following compounds:

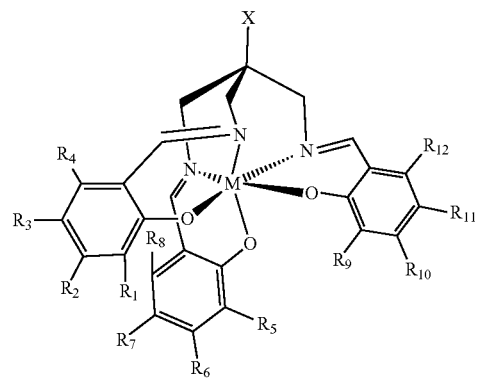

wherein X is selected from the group consisting of $^{11}$C, $^{13}$N, $^{15}$O or $^{18}$F, and $R_1$ to $R_{12}$ are selected from the group consisting of: H, $CH_3$, perfluorohexyl (PFH), perfluorooctyl (PFO), Me, $CF_3$, O—$(CF_2)_n$—$CF_3$, $(CF_2)_n$—$CF_3$, and O—$CF_2$—$(OCF_2CF_2)_n$—O—Y, wherein n is 0 to 20, and Y is $CF_3$, $CF_2$—$CF_3$ or $CF_2$—$CF_2$—$CF_3$;

or

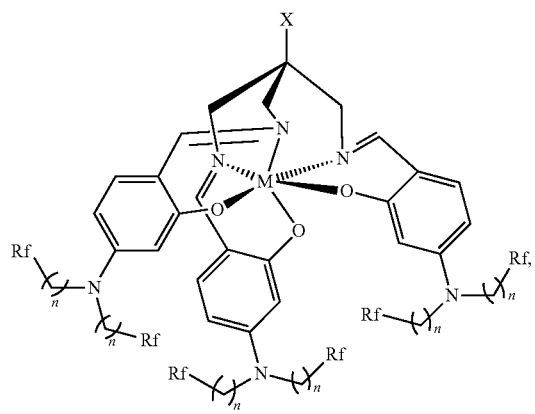

wherein X is selected from the group consisting of $^{11}$C, $^{13}$N, $^{15}$O or $^{18}$F, and Rf is $(CF_2)_j$—$CF_3$ or O—$(CF_2)_j$—$CF_3$, and j is 0 to 20.

In some embodiments, the present invention provides a compound comprising a SALTAME core, wherein the compound is selected from the group consisting of 5a POP (Fe SALTAME), 5a OOP (Fe SALTAME), 5a OOO(Fe SALTAME), 5c (Fe SALTAME), 5d (Fe SALTAME), 5e (Fe SALTAME), 5f (Fe SALTAME), 5g (Fe SALTAME), GA OOP, and GA POP.

In some embodiments, the present invention provides a compound comprising a SALTAME core, wherein the compound is selected from the following compounds:

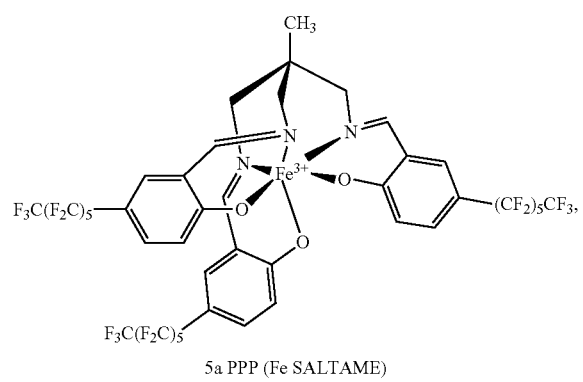
5a PPP (Fe SALTAME)
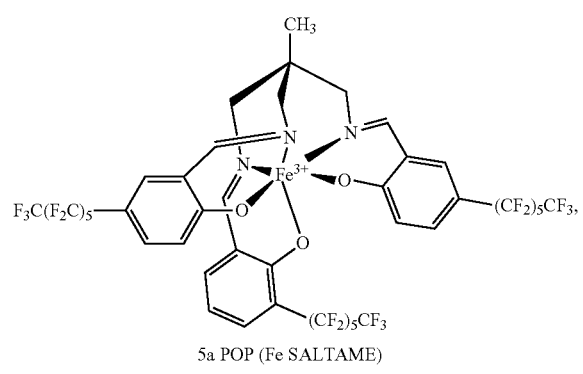
5a POP (Fe SALTAME)
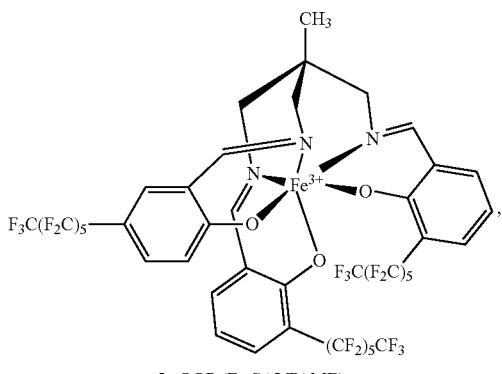
5a OOP (Fe SALTAME)
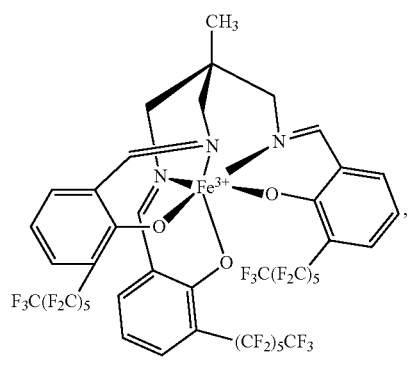
5a OOO (Fe SALTAME)
-continued
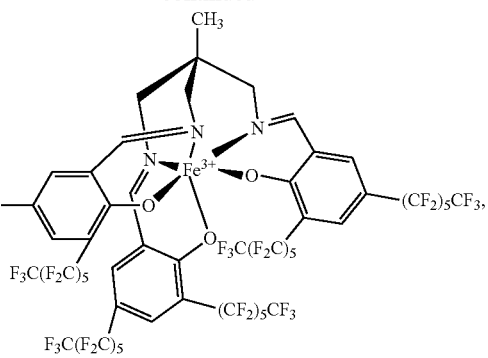
5c (Fe SALTAME)
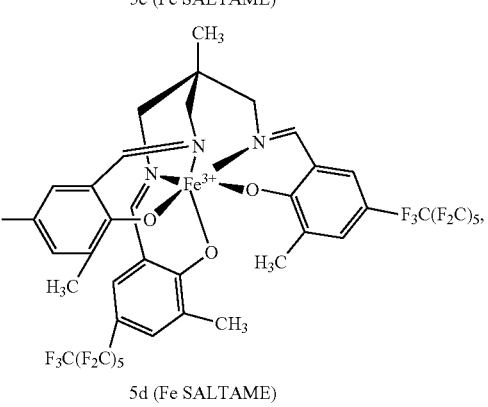
5d (Fe SALTAME)
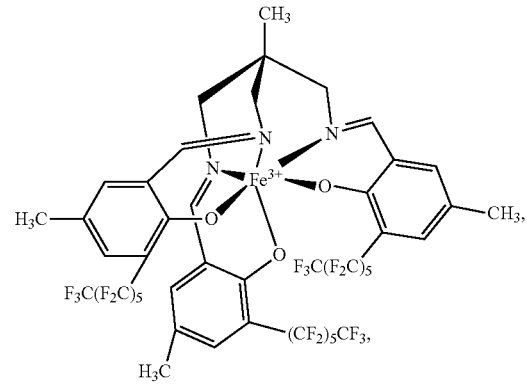
5d (Fe SALTAME)
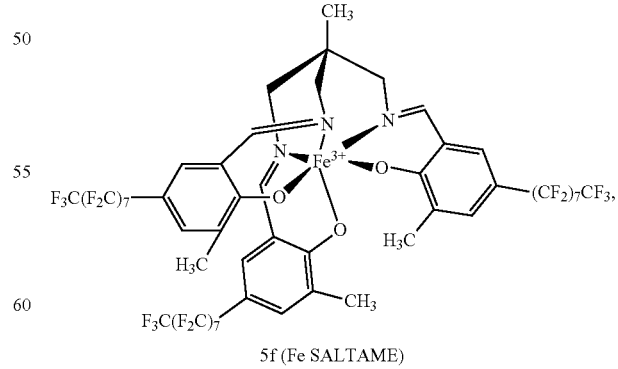
5f (Fe SALTAME)

-continued

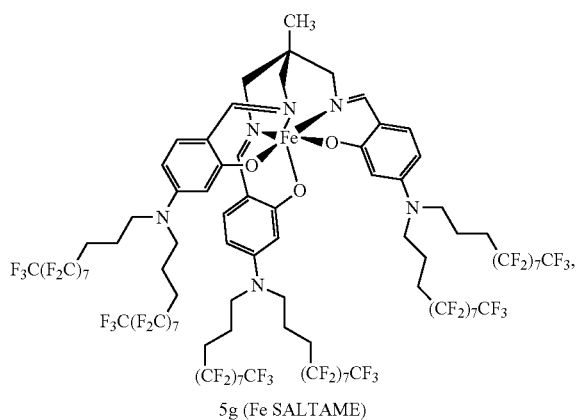

5g (Fe SALTAME)

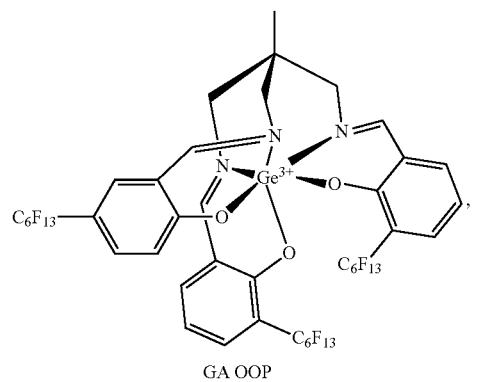

GA OOP

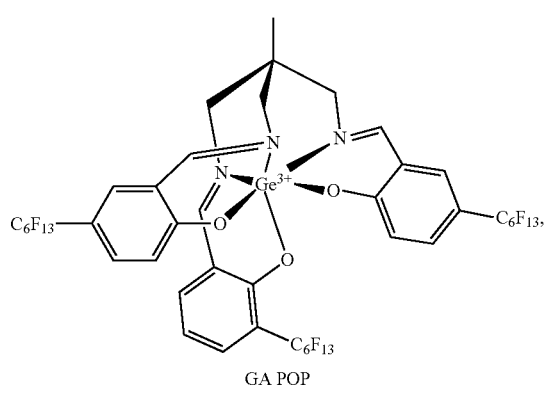

GA POP and

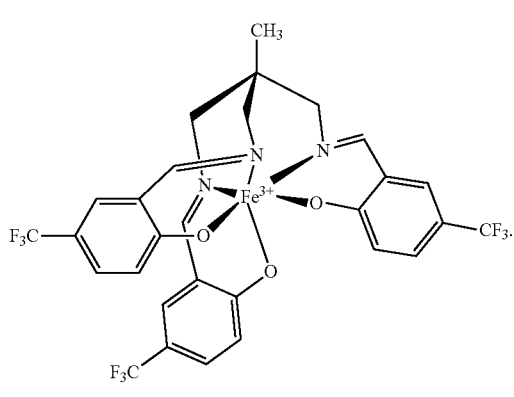

5e (Fe SALTAME)

In some embodiments, the present invention provides a composition comprising a compound comprising an salicylidene-tris(aminomethyl)ethane (SALTAME) core as described herein.

In some embodiments, the present invention provides a composition comprising a compound comprising a SALTAME core, wherein the compound is selected from the group consisting of 5a POP (Fe SALTAME), 5a OOP (Fe SALTAME), 5a OOO(Fe SALTAME), 5c (Fe SALTAME), 5d (Fe SALTAME), 5e (Fe SALTAME), 5f (Fe SALTAME), 5g (Fe SALTAME), GA OOP, and GA POP.

In some embodiments, compound comprises fluorine-19 ($^{19}F$) comprises a perfluorinated compound.

In some embodiments, compound comprises compound comprising fluorine-19 ($^{19}F$) comprises a metalated perfluorinated compound.

In some embodiments, compound comprises compound comprises a metal-binding moiety capable of binding metal ions.

In some embodiments, the metal ions are selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$, and $^{177}Lu^{3+}$.

In some embodiments, the metal ions are selected from the group consisting of $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, and $Cr^{3+}$.

In some embodiments, the metal ions are selected from the group consisting of $Mn^{4+}$, $Fe^{3+}$, $Co^{3+}$, and $Ga^{3+}$.

In some embodiments, the metal ion is $Fe^{3+}$.

In some embodiments, the compound has a solubility greater than 0.005 mol/L in perfluorocarbons selected from the group consisting of perfluorooctylbromide (PFOB), perfluoro-15-crown-5-ether (PFCE), and perfluoro (polyethylene glycol) (PFPE).

In some embodiments, the compound is stable in pH from 1 to 14.

In some embodiments, the binding of one or more of the metal ions to the metal-binding moiety of the SALTAME core in the compound changes the chemical shift of the SALTAME core in 19F nuclear magnetic resonance (19F-NMR).

In some embodiments, the binding of one or more of the metal ions to the metal-binding moiety of the SALTAME core in the compound reduces the T1 relaxivity of fluorine-19 ($^{19}F$) in the SALTAME core.

In some embodiments, the compound is formulated as a nanoemulsion.

In some embodiments, the nanoemulsion further comprises a perfluorocarbon.

The present invention also provides a composition comprising at least two or more compounds as described in any of the preceding paragraphs.

In some embodiments, the present invention provides a composition comprising a compound comprising a SALTAME core, wherein the compound is selected from the following compounds:

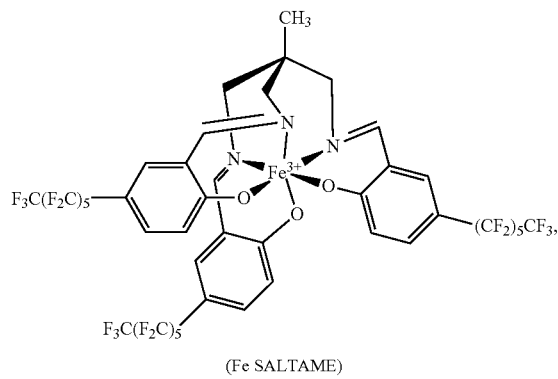
5a PPP
(Fe SALTAME)
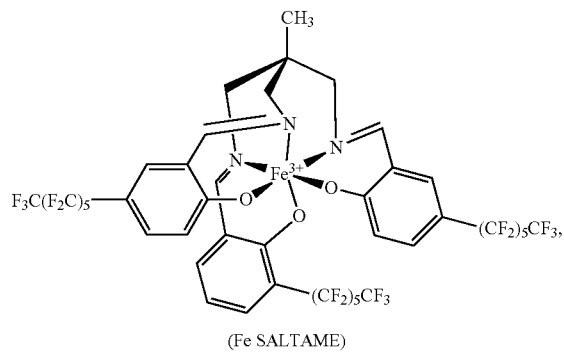
5a POP
(Fe SALTAME)
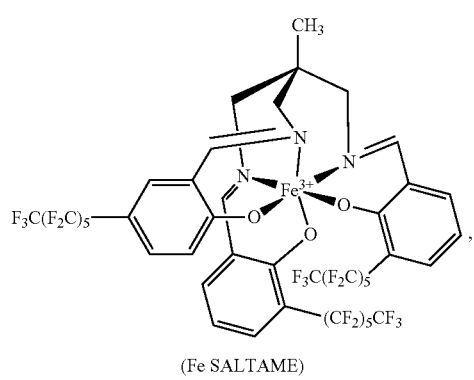
5a OOP
(Fe SALTAME)
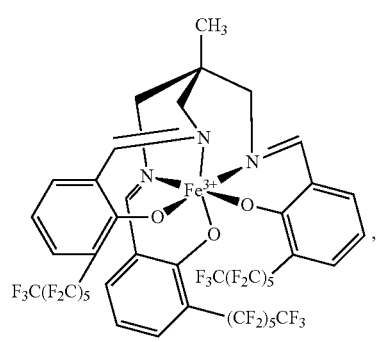
5a OOO
(Fe SALTAME)
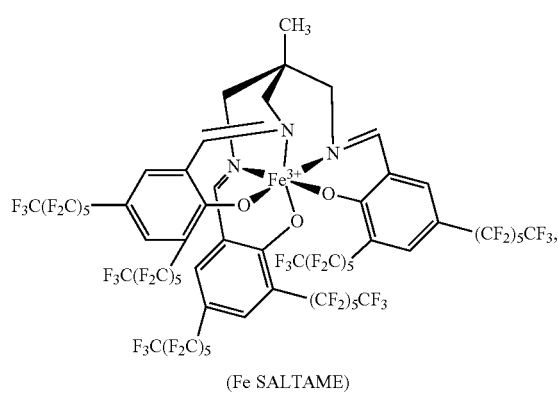
5c
(Fe SALTAME)
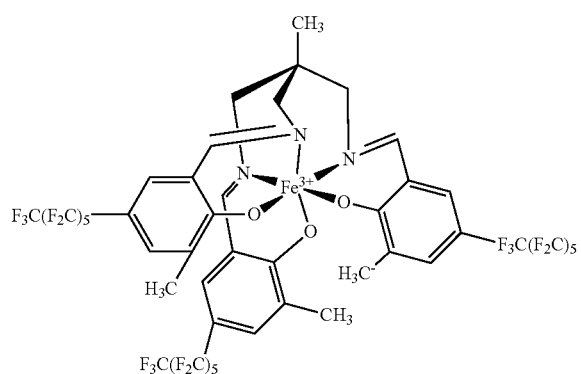
5d
(Fe SALTAME)
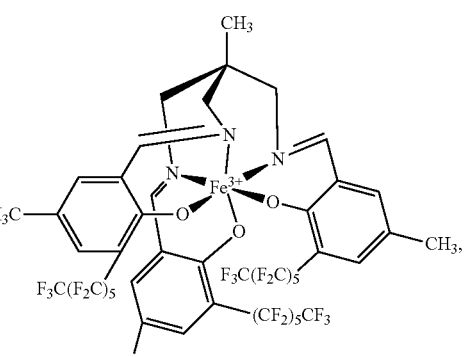
5d -continued

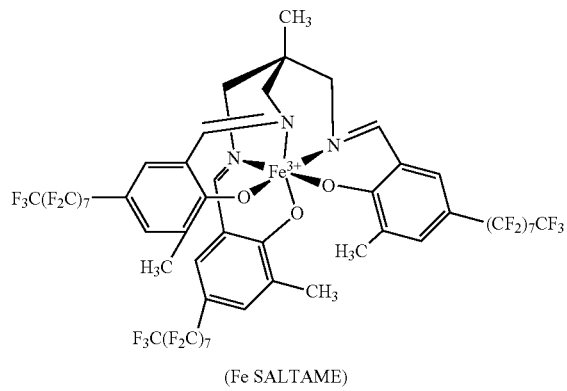

5f
(Fe SALTAME)

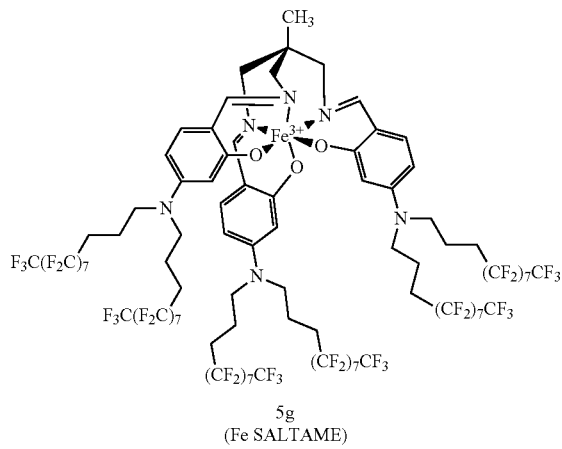

5g 5g
(Fe SALTAME)

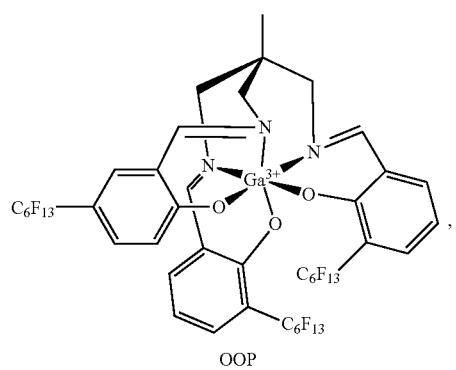

GA
OOP

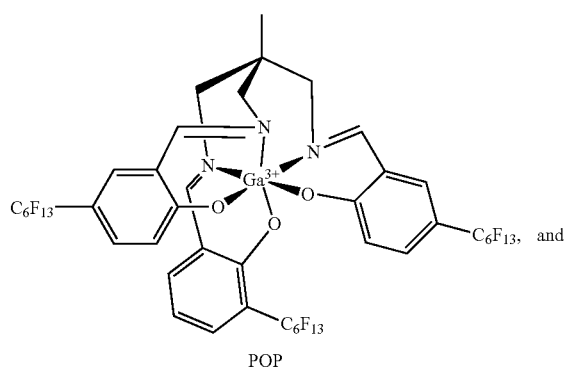

GA
POP, and

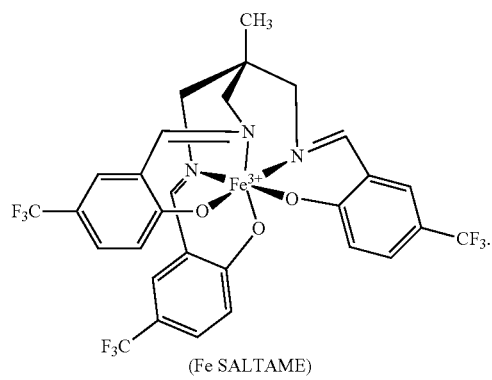

5e
(Fe SALTAME)

In some embodiments, the compound comprising fluorine-19 ($^{19}F$) comprises a perfluorinated compound.

In some embodiments, the compound comprising fluorine-19 ($^{19}F$) comprises a metalated perfluorinated compound.

In some embodiments, the compound comprises a metal-binding moiety capable of binding metal ions.

In some embodiments, the metal ions are selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$, and $^{177}Lu^{3+}$.

In some embodiments, the metal ions are selected from the group consisting of $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, and $Cr^{3+}$.

In some embodiments, the metal ions are selected from the group consisting of $Mn^{4+}$, $Fe^{3+}$, $Co^{3+}$, and $Ga^{3+}$.

In some embodiments, the metal ion is $Fe^{3+}$.

In some embodiments, the compound is formulated as a nanoemulsion.

In some embodiments, the nanoemulsion further comprises a perfluorocarbon.

In some embodiments, the present invention provides a non-invasive imaging method comprising:

a) administering to a subject a cellular labelling composition comprising a compound comprising fluorine-19 ($^{19}F$), wherein the compound comprises a salicylidene-tris(aminomethyl)ethane (SALTAME) core comprising fluorine-19 ($^{19}F$) associates with one or more cells, wherein the compound is a compound comprising an salicylidene-tris(aminomethyl)ethane (SALTAME) core as described herein; and b) detecting the association using an imaging modality, wherein the association can include cellular binding and/or cellular uptake.

In some embodiments, the present invention provides a non-invasive imaging method comprising:

a) administering to a subject a cellular labelling composition comprising a compound comprising fluorine-19 ($^{19}F$), wherein the compound comprising fluorine-19 ($^{19}F$) associates with one or more cells and the compound is selected from the following compounds:

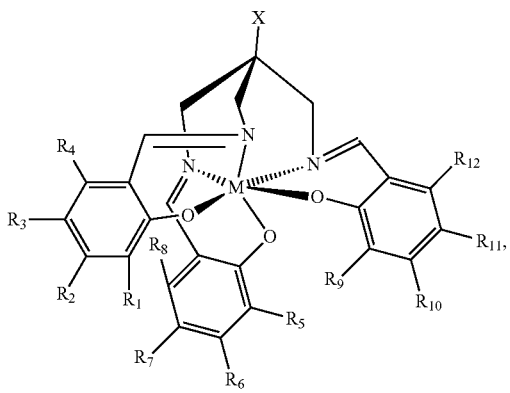

wherein X is selected from the group consisting of $^{11}C$, $^{13}N$, $^{15}O$ or $^{18}F$, and $R_1$ to $R_{12}$ are selected from the group consisting of: H, $CH_3$, perfluorohexyl (PFH), perfluorooctyl (PFO), Me, $CF_3$, O—$(CF_2)_n$—$CF_3$, $(CF_2)_n$—$CF_3$, and O—$CF_2$—$(OCF_2CF_2)_n$—O—Y, wherein n is 0 to 20, and Y is $CF_3$, $CF_2$—$CF_3$ or $CF_2$—$CF_2$—$CF_3$;

or

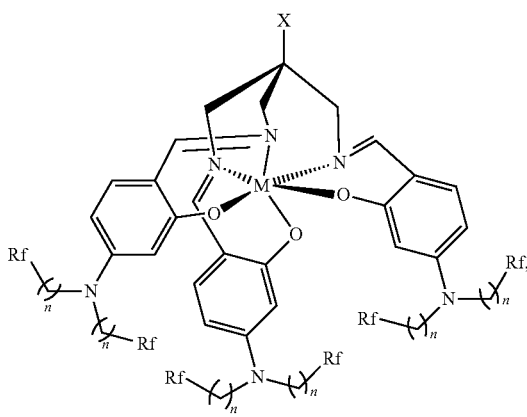

wherein X is selected from the group consisting of $^{11}C$, $^{13}N$, $^{15}O$ or $^{18}F$, and Rf is $(CF_2)_j$—$CF_3$ or O—$(CF_2)_j$—$CF_3$, wherein j is 0 to 20; and b) detecting the association using an imaging modality, wherein the association can include cellular binding and/or cellular uptake.

In some embodiments, the present invention provides a non-invasive imaging method comprising:

a) administering to a subject a cellular labelling composition comprising a compound comprising fluorine-19 ($^{19}F$), wherein the compound comprises a salicylidene-tris(aminomethyl)ethane (SALTAME) core comprising fluorine-19 ($^{19}F$) associates with one or more cells, wherein the compound is a compound selected from the group consisting of 5a POP (Fe SALTAME), 5a OOP (Fe SALTAME), 5a OOO(Fe SALTAME), 5c (Fe SALTAME), 5d (Fe SALTAME), 5e (Fe SALTAME), 5f (Fe SALTAME), 5g (Fe SALTAME), GA OOP, and GA POP; and b) detecting the association using an imaging modality, wherein the association can include cellular binding and/or cellular uptake.

In some embodiments, the present invention provides a non-invasive imaging method comprising:

a) administering to a subject a cellular labelling composition comprising a compound comprising fluorine-19 ($^{19}F$), wherein the compound comprises a salicylidene-tris(aminomethyl)ethane (SALTAME) core comprising fluorine-19 ($^{19}F$) associates with one or more cells, wherein the compound is one of the following compounds:

5a PPP

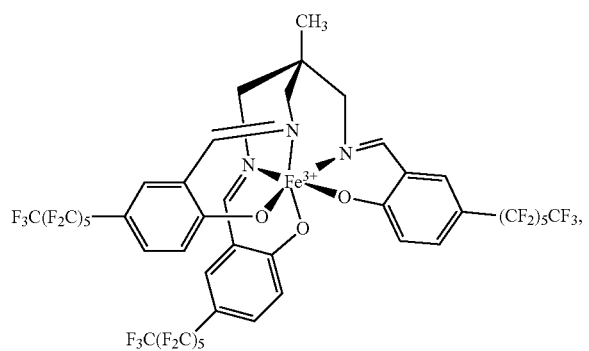

(Fe SALTAME)

5a POP

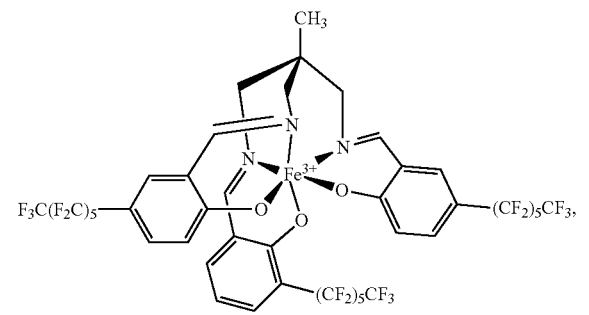

(Fe SALTAME)

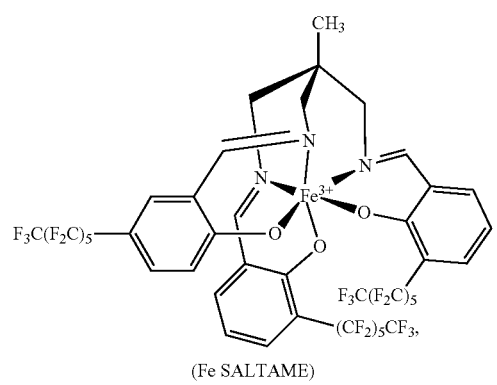
(Fe SALTAME) 5a OOP
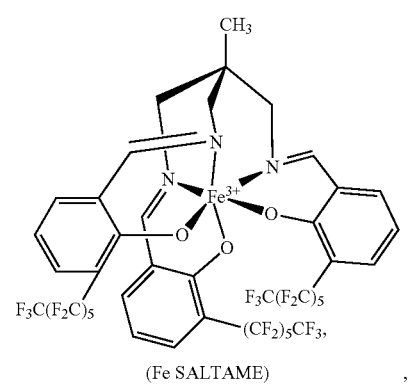
(Fe SALTAME) 5a OOO
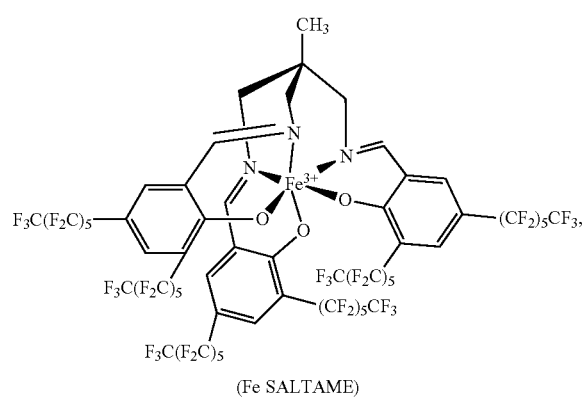
(Fe SALTAME) 5c
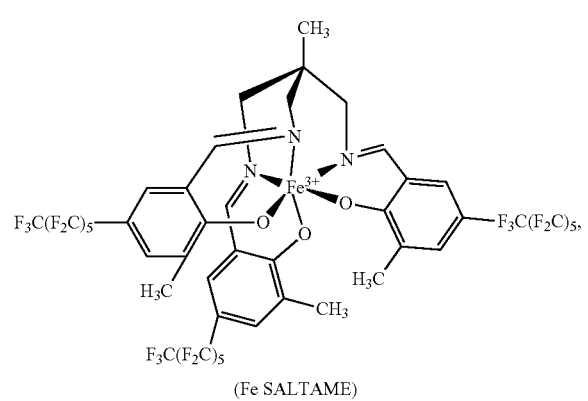
(Fe SALTAME) 5d
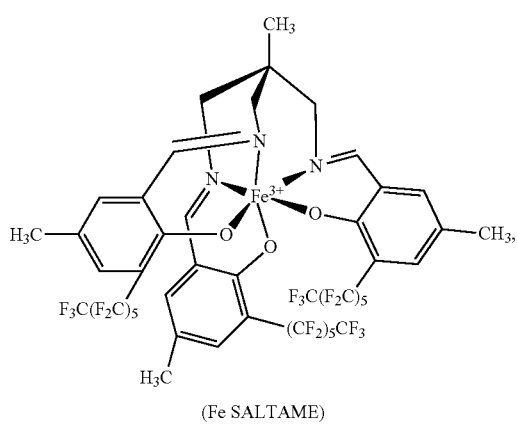
(Fe SALTAME) 5d
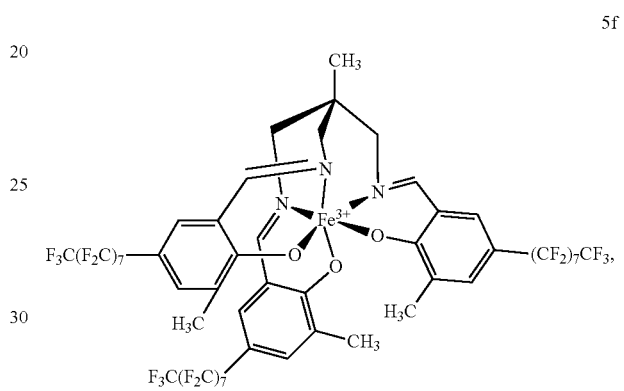
(Fe SALTAME) 5f
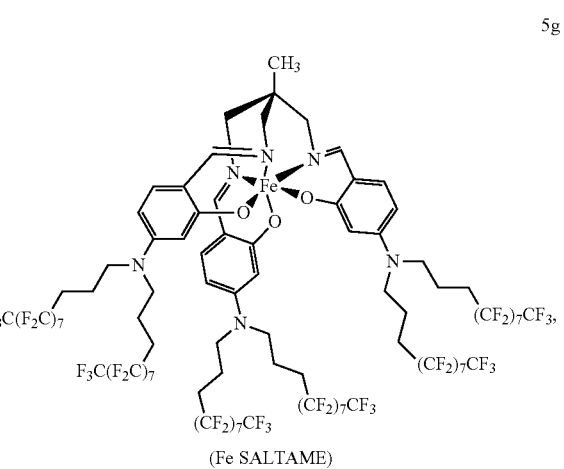
(Fe SALTAME) 5g
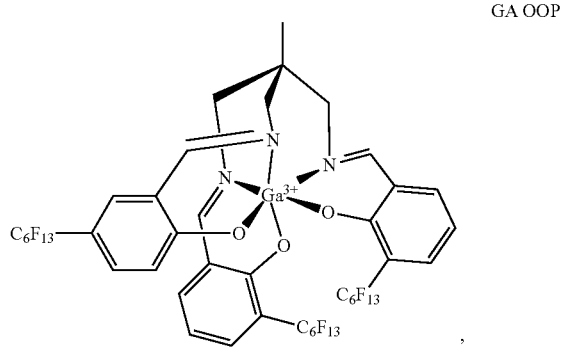
GA OOP -continued

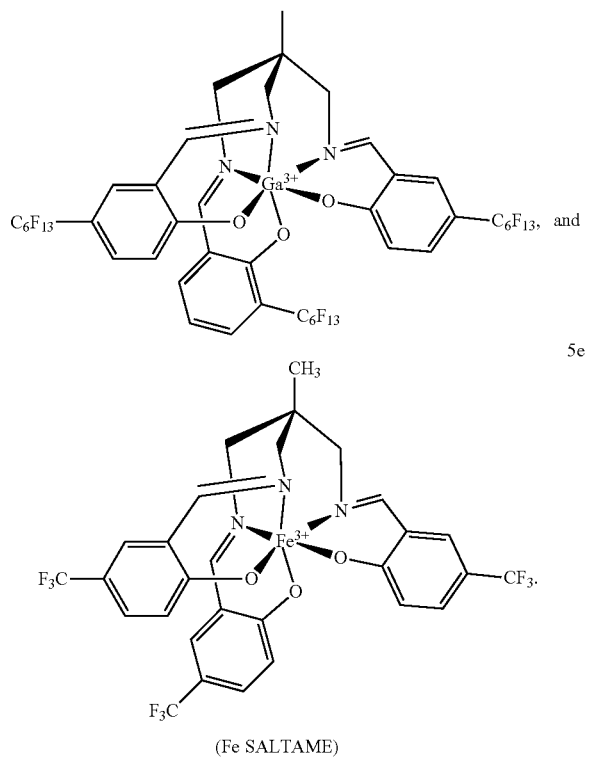

(Fe SALTAME)

b) detecting the association using an imaging modality, wherein the association can include cellular binding and/or cellular uptake.

In some embodiments, the imaging modality is selected from the group consisting of magnetic resonance imaging (MRI), positron emission tomography (PET), single-photon emission coherent tomography (SPECT), ultrasonography (US), and computed tomography (CT).

In some embodiments, the compound comprising fluorine-19 ($^{19}$F) comprises a perfluorinated compound.

In some embodiments, the compound comprising fluorine-19 ($^{19}$F) comprises a metalated perfluorinated compound.

In some embodiments, the compound comprises a metal-binding moiety capable of binding metal ions.

In some embodiments, the metal ions are selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$, and $^{177}Lu^{3+}$.

In some embodiments, the metal ions are selected from the group consisting of $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, and $Cr^{3+}$.

In some embodiments, the metal ions are selected from the group consisting of $Mn^{4+}$, $Fe^{3+}$, $Co^{3+}$, and $Ga^{3+}$.

In some embodiments, the metal ion is $Fe^{3+}$.

In some embodiments, the compound has a solubility greater than 0.005 mol/L in perfluorocarbons selected from the group consisting of perfluorooctylbromide (PFOB), perfluoro-15-crown-5-ether (PFCE), and perfluoro (polyethylene glycol) (PFPE).

In some embodiments, the compound is stable in pH from 1 to 14.

In some embodiments, the binding of one or more of the metal ions to the metal-binding moiety of the SALTAME core in the compound changes the chemical shift of the SALTAME core in 19F nuclear magnetic resonance (19F-NMR).

In some embodiments, the binding of one or more of the metal ions to the metal-binding moiety of the SALTAME core in the compound reduces the T1 relaxivity of fluorine-19 ($^{19}$F) in the SALTAME core.

In some embodiments, the compound is formulated as a nanoemulsion.

In some embodiments, the nanoemulsion further comprises a perfluorocarbon.

In some embodiments, the nanoemulsion further comprises one or more targeting moieties, wherein the targeting moieties are selected from the group consisting of peptides, binding proteins, antibodies, antibody fragment thereof, and aptamers.

In some embodiments, the composition allows tracking cells by MRI, wherein the method comprises detecting the cells associated with at least one component of the composition comprising fluorine-19 ($^{19}$F).

In some embodiments, the one or more cells are immune cells that accumulate at tissue sites as part of an inflammatory response.

In some embodiments, the composition allows tracking cells by MRI, wherein the method comprises detecting the cells associated with at least one component of the composition comprising fluorine-19 ($^{19}$F).

In some embodiments, the one or more cells are immune cells that accumulate at tissue sites as part of an inflammatory response.

In some embodiments, the method is a diagnostic detection method.

In some embodiments, the one or more cells are cells that are grafted into the body in order to treat a disease or condition.

In some embodiments, the method is cytotherapy.

In some embodiments, the one or more cells are endogenous cells in body of the subject.

In some embodiments, the one or more cells are selected from the group consisting of T cells, B cells, macrophages, natural killer (NK) cells, dendritic cells (DCs), stem cells, progenitor cells, and cancer cells.

In some embodiments, the one or more cells comprise engineered cells.

In some embodiments, the compound comprising fluorine-19 ($^{19}$F) is a dual-mode agent and is capable of being detected by more than one imaging modality.

In some embodiments, the compound comprising fluorine-19 ($^{19}$F) is a dual-mode agent and is capable of being detected by two or more imaging modalities.

In some embodiments, the present invention provides an in vivo imaging method, comprising:
a) ex vivo labeling cells with a cellular labelling composition comprising a compound comprising fluorine-19 ($^{19}$F) under such conditions that the compound comprising fluorine-19 ($^{19}$F) as described herein is internalized by the cells;
b) administering the labeled cells to a subject;
c) detecting the labeled cells in the subject using an imaging modality, and
d) assaying for the degree of cell accumulation in one or more tissues in the subject.

In some embodiments, the assaying comprises quantitating the average total intracellular probe mass at sites of accumulation of the labeled cells.

In some embodiments, the cells are autologous cells.

In some embodiments, the cells are allogeneic cells.

In some embodiments, the imaging modality is selected from the group consisting of magnetic resonance imaging (MRI), positron emission tomography (PET), single-photon emission coherent tomography (SPECT), ultrasonography (US), and computed tomography (CT).

In some embodiments, the imaging modality is magnetic resonance imaging (MRI).

In some embodiments, the cells are selected from the group consisting of T cells, B cells, macrophages, natural killer (NK) cells, dendritic cells (DCs), stem cells, progenitor cells, and cancer cells.

In some embodiments, the cells are engineered cells.

In some embodiments, the compound comprising fluorine-19 ($^{19}F$) comprises a perfluorinated compound.

In some embodiments, the compound comprises a metal-binding moiety capable of binding metal ions.

In some embodiments, the metal ions are selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$, and $^{177}Lu^{3+}$.

In some embodiments, the metal ions are selected from the group consisting of $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, and $Cr^{3+}$.

In some embodiments, the metal ions are selected from the group consisting of $Mn^{4+}$, $Fe^{3+}$, $Co^{3+}$, and $Ga^{3+}$.

In some embodiments, the metal ion is $Fe^{3+}$.

In some embodiments, the compound has a solubility greater than 0.005 mol/L in perfluorocarbons selected from the group consisting of perfluorooctylbromide (PFOB), perfluoro-15-crown-5-ether (PFCE), and perfluoro (polyethylene glycol) (PFPE).

In some embodiments, the compound is stable in pH from 1 to 14.

In some embodiments, the binding of one or more of the metal ions to the metal-binding moiety of the SALTAME core in the compound changes the chemical shift of the SALTAME core in 19F nuclear magnetic resonance (19F-NMR).

In some embodiments, the binding of one or more of the metal ions to the metal-binding moiety of the SALTAME core in the compound reduces the T1 relaxivity of fluorine-19 ($^{19}F$) in the SALTAME core.

In some embodiments, the compound is formulated as a nanoemulsion.

In some embodiments, the nanoemulsion further comprises a perfluorocarbon.

In some embodiments, the present invention provides a nanoemulsion formulation comprising any of the compounds disclosed herein in an oil-in-water colloidal suspension or emulsion.

In some embodiments, the present invention provides a pharmaceutical and/or diagnostic composition comprising a nanoemulsion formulation comprising a compound comprising fluorine-19 ($^{19}F$), wherein the compound comprising fluorine-19 ($^{19}F$) associates with one or more cells and the association is capable of being detected using an imaging modality.

In some embodiments, the present invention provides a pharmaceutical and/or diagnostic composition comprising a compound comprising an salicylidene-tris(aminomethyl) ethane (SALTAME) core as described herein.

In some embodiments, the present invention provides a pharmaceutical and/or diagnostic composition comprising a compound comprising a SALTAME core, wherein the compound is selected from the following compounds:

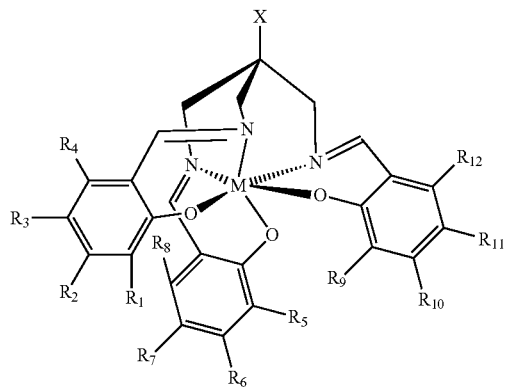

wherein X is selected from the group consisting of $^{11}C$, $^{13}N$, $^{15}O$ or $^{18}F$, and $R_1$ to $R_{12}$ are selected from the group consisting of: H, $CH_3$, perfluorohexyl (PFH), perfluorooctyl (PFO), Me, $CF_3$, O—$(CF_2)_n$—$CF_3$, $(CF_2)_n$—$CF_3$, and O—$CF_2$—$(OCF_2CF_2)_n$—O—Y, wherein n is 0 to 20, and Y is $CF_3$, $CF_2$—$CF_3$ or $CF_2$—$CF_2$—$CF_3$;

or

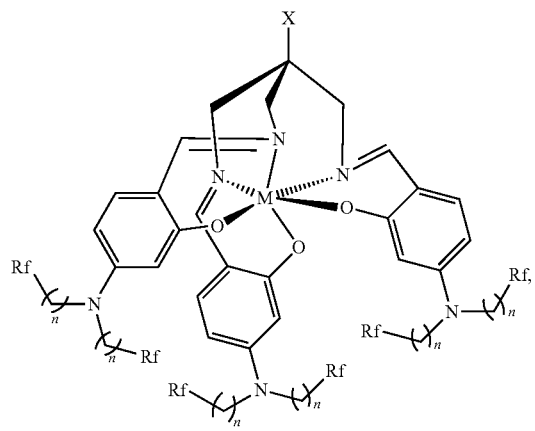

wherein X is selected from the group consisting of $^{11}C$, $^{13}N$, $^{15}O$ or $^{18}F$, and Rf is $(CF_2)_j$ $CF_3$ or O—$(CF_2)_j$—$CF_3$, wherein j is 0 to 20.

In some embodiments, the present invention provides a pharmaceutical and/or diagnostic composition comprising a compound comprising a SALTAME core, wherein the compound is selected from the group consisting of 5a POP (Fe SALTAME), 5a OOP (Fe SALTAME), 5a OOO(Fe SALTAME), 5c (Fe SALTAME), 5d (Fe SALTAME), 5e (Fe SALTAME), 5f (Fe SALTAME), 5g (Fe SALTAME), GA OOP, and GA POP.

In some embodiments, the present invention provides a pharmaceutical and/or diagnostic composition comprising a compound comprising a SALTAME core, wherein the compound is selected from the following compounds:

-continued
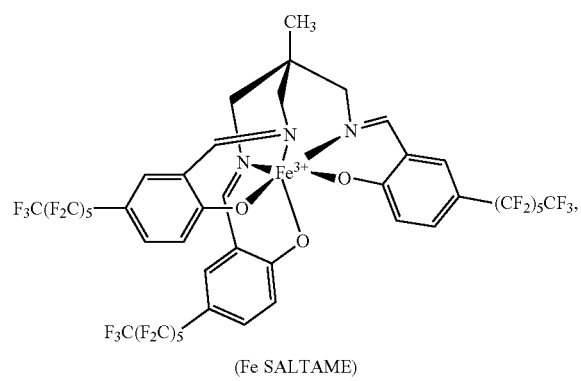
5a PPP
(Fe SALTAME)
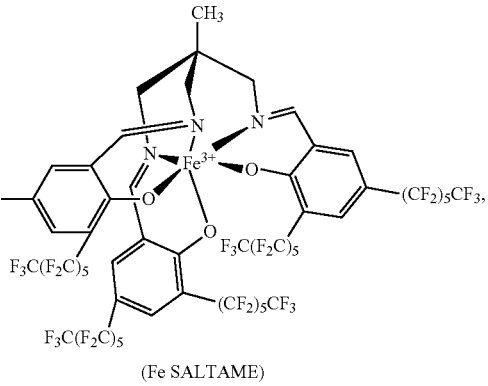
5c
(Fe SALTAME)
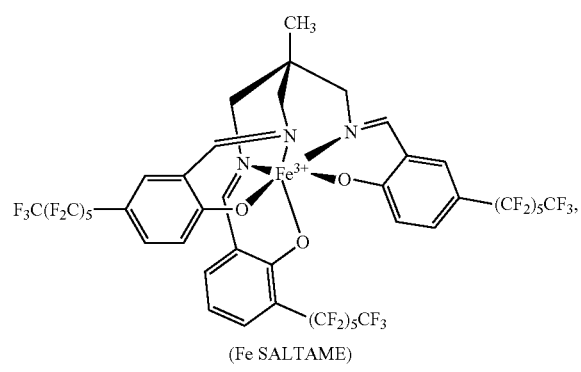
5a POP
(Fe SALTAME)
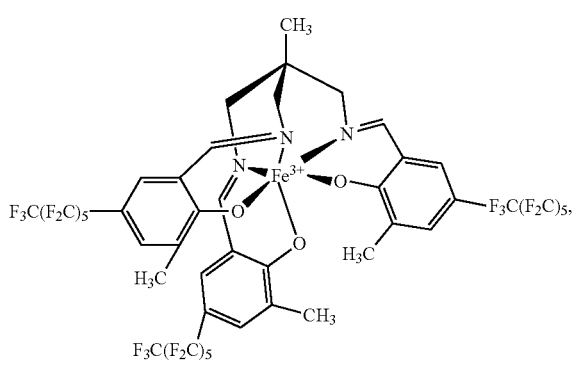
5d
(Fe SALTAME)
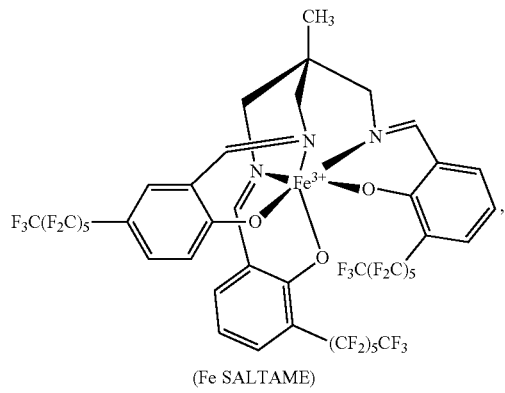
5a OOP
(Fe SALTAME)
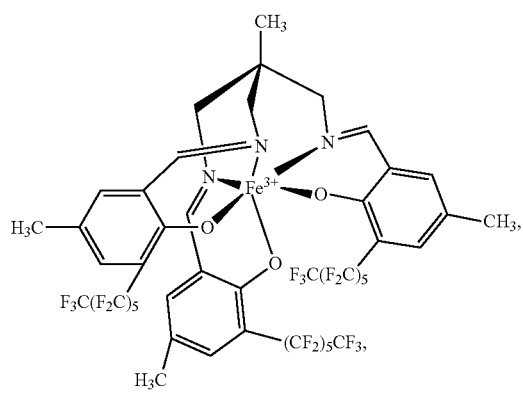
5d
(Fe SALTAME)
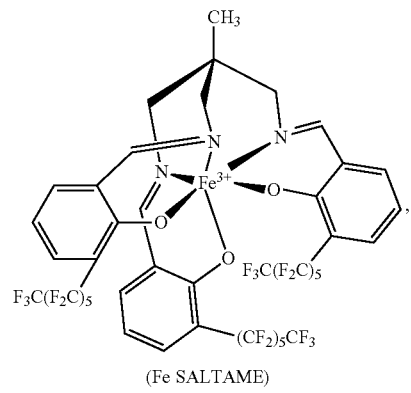
5a OOO
(Fe SALTAME)
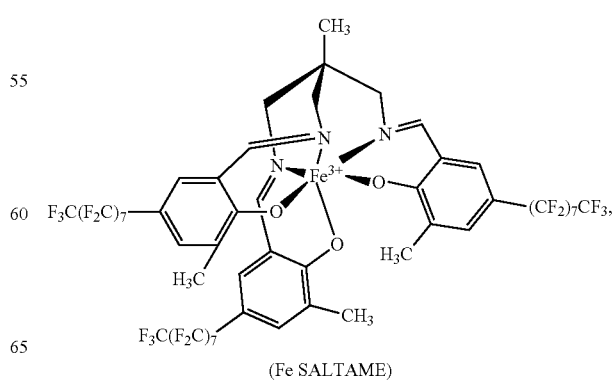
5f
(Fe SALTAME)

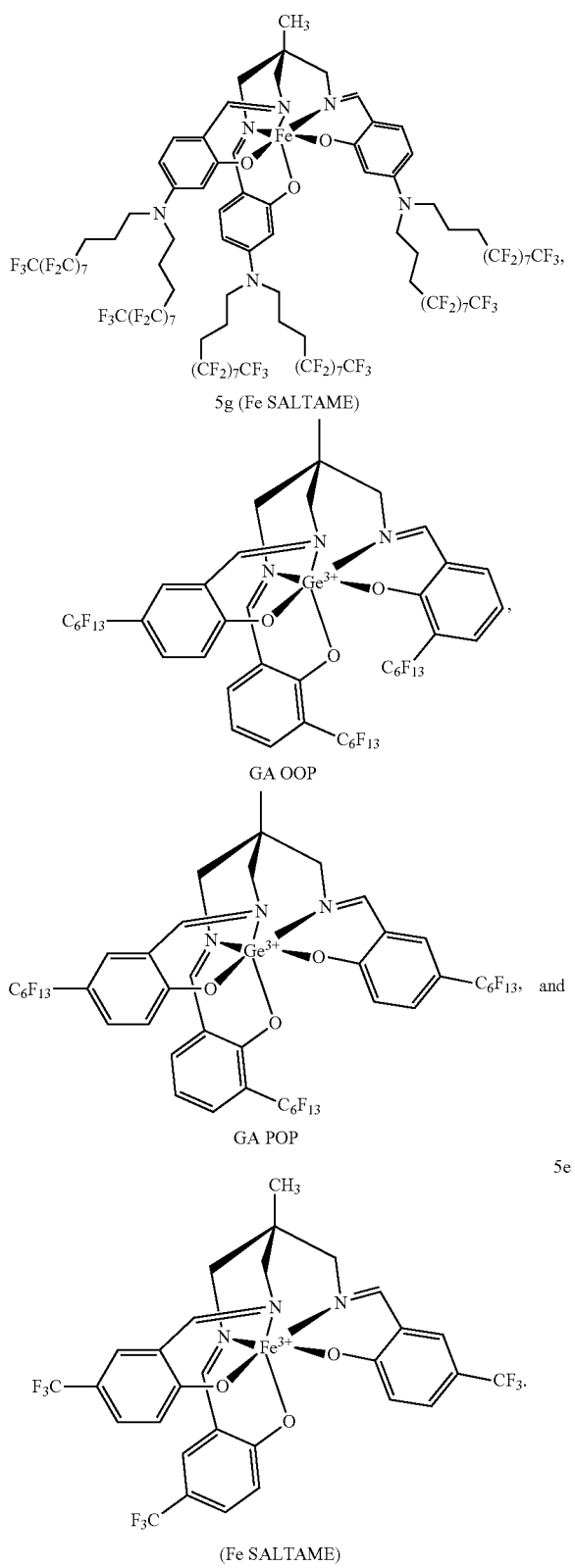

5g (Fe SALTAME)

GA OOP

GA POP, and 5e (Fe SALTAME)

In some embodiments, of the pharmaceutical and/or diagnostic composition the compound comprises fluorine-19 ($^{19}$F) comprises a perfluorinated compound.

In some embodiments, of the pharmaceutical and/or diagnostic composition the compound comprises fluorine-19 ($^{19}$F) comprises a metalated perfluorinated compound.

In some embodiments, of the pharmaceutical and/or diagnostic composition the compound comprises a metal-binding moiety capable of binding metal ions.

In some embodiments, of the pharmaceutical and/or diagnostic composition the metal ions are selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4}$, $^{67}Ga^{3+}$, $^{99m}Tc^{4+}$, $^{111}In^{3+}$, and $^{177}Lu^{3+}$.

In some embodiments, of the pharmaceutical and/or diagnostic composition the metal ions are selected from the group consisting of $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, and $Cr^{3+}$.

In some embodiments, of the pharmaceutical and/or diagnostic composition the metal ions are selected from the group consisting of $Mn^{4+}$, $Fe^{3+}$, $Co^{3+}$, and $Ga^{3+}$.

In some embodiments, of the pharmaceutical and/or diagnostic composition the metal ion is $Fe^{3+}$.

In some embodiments, of the pharmaceutical and/or diagnostic composition, the compound has a solubility greater than 0.005 mol/L in perfluorocarbons selected from the group consisting of perfluorooctylbromide (PFOB), perfluoro-15-crown-5-ether (PFCE), and perfluoro (polyethylene glycol) (PFPE).

In some embodiments, of the pharmaceutical and/or diagnostic composition, the compound is stable in pH from 1 to 14.

In some embodiments, of the pharmaceutical and/or diagnostic composition, the binding of one or more of said metal ions to the metal-binding moiety of said SALTAME core in said compound changes the chemical shift of the SALTAME core in 19F nuclear magnetic resonance (19F-NMR).

In some embodiments, of the pharmaceutical and/or diagnostic composition, the binding of one or more of said metal ions to the metal-binding moiety of said SALTAME core in said compound reduces the T1 relaxivity of fluorine-19 ($^{19}$F) in the SALTAME core.

In some embodiments, of the pharmaceutical and/or diagnostic composition, the compound is formulated as a nanoemulsion.

In some embodiments, of the pharmaceutical and/or diagnostic composition, the nanoemulsion further comprises a perfluorocarbon.

In some embodiments, of the pharmaceutical and/or diagnostic composition, the composition comprises at least two or more of any of the compounds described herein.

In some embodiments, the present invention provides a compound as described herein, including as described in any of the preceding paragraphs.

BRIEF DESCRIPTION OF THE DRAWINGS

FIG. 20. Synthesis of fluorinated salicylaldehyde derivatives 3g containing at least one ether bond FIG. 21. Synthesis of fluorinated imine compounds r and metal chelates 5

FIG. 22. Synthesis of N, N-alkylated imine compounds 14 and metal chelates 15.

FIG. 23A-FIG. 23B. Top (FIG. 23A): the structure of a fluorinated iron complex 5a POP. Bottom: (FIG. 23B): X-ray crystal structure of 5a POP. (a) Crystal structure of 5a POP confirms the hexadentate structure of the Fe$^{3+}$ coordination chelate, (b) is a space-filling rendering of the same view and (c) is a space-filling view after 180 degree rotation to reveal the more solvent-exposed face of the bound ferric ion. Color code: Grey, carbon; Dark green, hydrogen; Light green, fluorine; Blue, nitrogen; Red, oxygen; Cyan, iron.

FIG. 24A-FIG. 24B. Top (FIG. 24A): Structure of fluorinated iron complex 5a PPP. Bottom: (FIG. 24B): X-ray crystal structure of 5a PPP. Color code: Grey, carbon; White, hydrogen; Green, fluorine; Cyan, nitrogen, Red, oxygen; Blue, iron.

FIG. 25A-FIG. 25B. Top (FIG. 25A): Structure of a fluorinated iron complex 5a OOO. Bottom (FIG. 25A): X-ray crystal structure of 5a OOO. Color code: Grey, carbon; White, hydrogen; Green, fluorine; Cyan, nitrogen; Red, oxygen; Blue, iron.

FIG. 30. Effect of Fe-PFHA concentration to the fluorine relaxation rates in the emulsion comprising PCE (NE-A) and emulsion comprising PFOB (NE-B).

FIG. 31. UV-Vis spectra of 50 μL of NE-A in 2.5 mL water containing 10 mM EDTA over a range of 24 hours (top), and absorbances at 438 nm was plotted against time (bottom). A very slow decrease in the absorbance overtime was observed.

DETAILED DESCRIPTION OF THE INVENTION

Introduction

Figure 1:
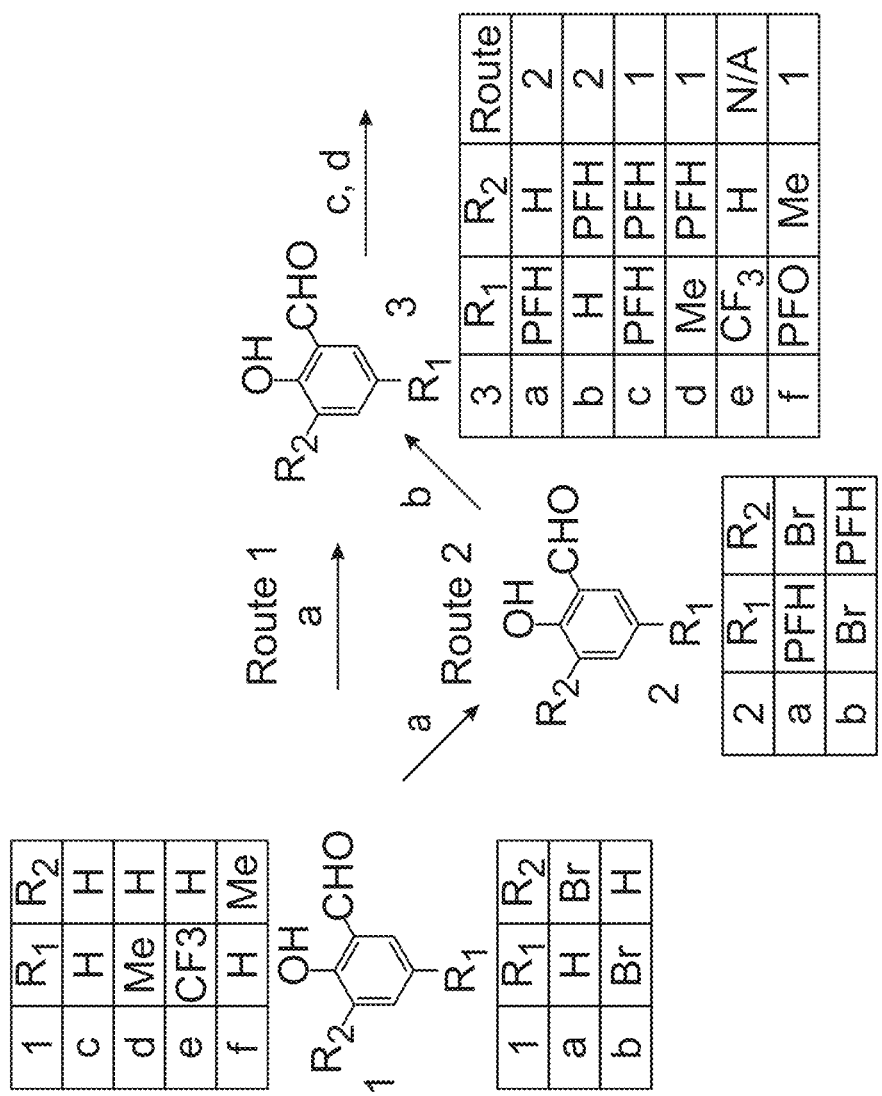
FIG. 1. Synthetic scheme for chelating agents. Fe3+-SALTAME chelate 5a POP is used to form P-PFOB. Reagents: a: perfluoroalkyl iodide, CsCO3, DMF, 100° C.; b: 1 atm H2, Pd—C, NaOAc, MeOH; c: TAME, NEt3, EtOH, 80° C.; d: FeCl3, NaOAc, EtOAc-EtOH.
Figure 1:
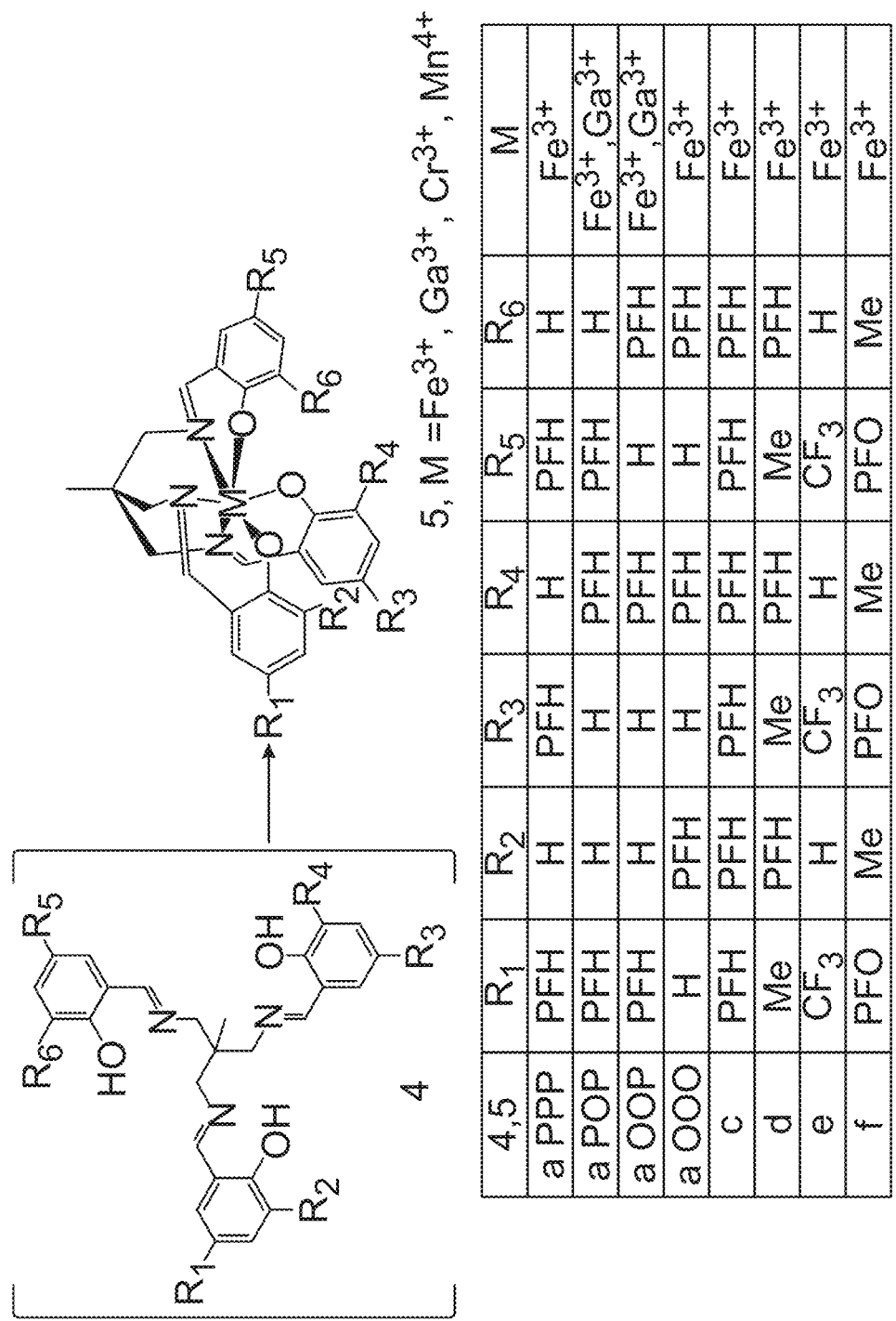
Figure 2:
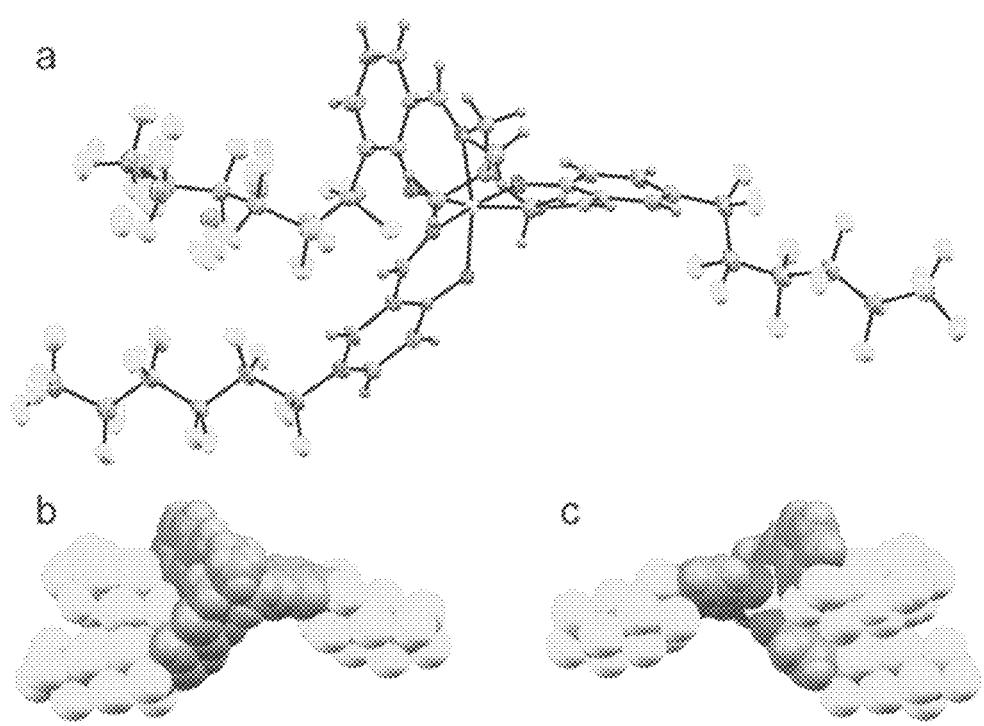
FIG. 2A-FIG. 2C. Crystal structure of 5a POP using x-ray crystallography. (a) Structure confirms the hexadentate coordination the chelated Fe3+; (b) displays a space-filling rendering of the same view, and (c) is after a 180 degree rotation to reveal the solvent-exposed face of the bound ferric ion. Iron is colored cyan for clarity.

The present invention provides clinical non-invasive imaging methods, particularly magnetic resonance imaging (MRI), to visualize cells and cells targets in the body. For instance, cells (e.g., target cells) labelled with the fluorine-19 containing compositions provided herein can be visualized (imaged, tracked, tracked, and the like) in a subject, e.g., a human subject, and quantitated. The invention also describes novel compositions of perfluorinated compounds that can bind and tightly retain metal ions in the fluorous phase to enable sensitive detection using MRI and other imaging modalities. Provided herein are new nanoemulsion materials containing metal-binding β-diketones conjugated to linear perfluoropolyether (PFPE). The compositions described herein are useful for MRI as they can provide a single sharp resonance, provide desirable signal intensity and signal-to-noise ratio (SNR) efficient, eliminate any chemical shift artifact, maximize the SNR, are thermodynamically stable, and allow clear identification of the perfluorinated compound.

A key use of this technology is the production of sensitive cellular labels for tracking cells by fluorine-19 ($^{19}$F) MRI. Some applications include the diagnostic detection of immune cells that accumulate at tissue sites as part of an inflammatory response and cells that are grafted into the body in order to treat a disease or condition, i.e., cytotherapy. Cells can be endogenous cells in the body, for example, various immune cells (T cells, B cells, macrophages, NK cells, DCs, etc.), various stem cells and progenitor cells, cancer cells, as well as engineered cells, which are often used in cytotherapy in its various forms. Non-invasive imaging of immune cells in the body is useful because it can aid in the diagnosis and monitoring of inflammation. In the field of cytotherapy, the ability to image the cell graft provides valuable feedback about the persistence of the graft, potential cell migration, and improves safety surveillance. Many experimental cell therapies that are in clinical trials, e.g., stem cells and immunotherapeutic cells, could benefit from the use of this technology.

Other embodiments of the invention are metalated perfluorinated probes that can be detected by positron emission tomography (PET), single-photon emission coherent tomography (SPECT), ultrasonography (US), or computed tomography (CT), all of which are commonly used medical imaging modalities. The invention provides novel uses for these imaging modalities by providing a means to detect inflammatory cells and track cytotherapies non-invasively. Also, so called "dual-mode" agents are envisioned, which can be detected by more than one imaging modality (e.g., MRI-PET), thereby maximizing the utility of new generations of clinical imaging apparatus that integrate two (or more) detection modalities.

The invention also describes multiple nanoemulsion formulations of metalated perfluorinated compounds (i.e., "imaging probes") to render the molecules compatible for in vivo applications, and to tailor the biodistribution of the labeled cells and the cell uptake of the nanoemulsion.

Additionally, ex vivo or in vivo targeted imaging and theranostic agents are described using the molecular platform that provide imaging of cells, tissues, and/or lesions having selected and prevalent molecular epitopes. For example targeting moieties can include antibodies (or fragments thereof), peptides, arginine-rich domains, cationic lipids, aptamers, etc.

Moreover, formulations of metalated fluorocarbons are envisioned that have a distinct signatures in MRI that can be used to image multiple cell types, the same cell type at different time points, or multiple molecular epitopes (e.g., multiple cell surface epitopes) within a subject. The molecular epitope can correspond to a diseased region or tissue in the subject, or a protein epitope associated with a disease or condition in the subject.

Other variants of the invention composition of matter include so called "theranostic" agents. Such theranostic agents may serve both as a therapeutic (or drug delivery vehicle) agent and an imaging probe (or diagnostic agent) that can help visualize the accurate delivery and dose of the therapy within the body. The pharmaceutical and/or diagnostic composition disclosed herein can be administered to a subject, the delivery of the composition (or cells labelled with the composition), and the dose/amount of the composition can be detected, monitored, tracked, and/or measured in the subject.

The invention also describes novel methods to assay the degree of cell labeling with the imaging probe, for example, as represented by the average total intracellular probe mass following labeling. Methods for quantitating labeled cells include methods known by those skilled in the art and used in MRI, PET, SPECT, US, and CT imaging.

In some embodiments, the compositions or formulations includes a first compound comprising $^{19}$F have a first $^{19}$F spectral frequency and a second compound comprising $^{19}$F have a second $^{19}$F spectral frequency that is different than the first $^{19}$F spectral frequency. In some instances, the first compound includes a first metal ion and the second compound includes a second metal ion, such that the first and second metal ions are different. The first compound and the second compound can provide two separate, different spectral frequencies (i.e., two distinct imaging signatures) when detected simultaneously. In other cases, the first and second compounds are detected sequentially. The compounds can be detected using one imaging modality, e.g., MRI. In some cases, the compounds are detected using two different imaging modalities, such as, but not limited to, MRI and PET, MRI and SPECT, and PET and SPECT.

In some instances, the first $^{19}$F-containing compound labels a first cell type, and the second $^{19}$F-containing compound labels a second cell type. In certain cases, the first $^{19}$F-containing compound labels a cell type at a first time point, and the second $^{19}$F-containing compound labels the same cell type at a second time point (i.e., a later time point). In other cases, the first $^{19}$F-containing compound comprises a first targeting moiety that specifically binds to a first cell type, and the second $^{19}$F-containing compound comprises a second targeting moiety that specifically binds to a second cell type. The first and second cell types can be introduced into the subject. Optionally, the first and second cell types can be two different endogenous cell types located in the subject. In some embodiments, two, three or four different cell types can be introduced.

Fluorinated Metal Chelates for Non-Invasive Imaging

Described herein are composition of matter and synthesis schemes for novel fluorinated metal chelates with broad applications, particularly in the areas of medical and diagnostic imaging. The compounds described herein can also be employed for nuclear imaging. The present invention also provides for the use of metal chelate paramagnetic emulsion for MPI imaging in vivo.

The present invention discloses the preparation of novel fluorinated metal chelates, the formulation of metal chelates into emulsions, and the application in cell tracking and inflammation diagnosis using imaging tools like magnetic resonance imaging (MRI), fluorescence imaging, nuclear imaging, and magnetic particle imaging (MPI), either in vitro or in vivo.

MRI has widespread application in clinics since it has good anatomical resolution and is non-invasive. It relies on the use of magnetic field, instead of invasive X-ray, ionizing radiation or radioisotopes in other modalities. MRI also has good sensitivity and deep tissue penetration, which makes it suitable for whole body imaging. To improve the visibility of MRI when low sensitivity or poor tissue contrast incurs, a variety of paramagnetic metal chelates have been developed successfully. Currently, a majority of the commercialized MRI contrast agents (CAs) are gadolinium-based (Gd) complexes, either cyclic or acyclic. In United States, there are nine Gd-chelated CAs that have been approved by FDA. While chelated $Gd^{3+}$ is regarded safe, the free solubilized $Ga^{3+}$ is more toxic and the toxicity is comparable to iodinated X-ray contrast compounds. The use of gadolinium CAs usually comes with a concern of possible metal leakage. Moreover, gadolinium CAs have been linked to nephrogenic systemic fibrosis, a rare but serious disease, especially in patients with renal malfunctions. FDA has suggested health care professionals to limit the use of gadolinium CAs, and reassess the necessity of repetitive use.

Conventional MRI is used for diagnosis by mapping the distribution of water and fats that have most abundant proton atoms. Improved tissue contrast can sometimes be achieved by using optimized pulse sequence to modify the relaxation property of protons. However, MRI methods based on proton signals are incapable of establishing contrast between different cell types, since the proton content and relaxation is not cell specific. The rising of cell-based therapies, however, demands a non-invasive method to track the distribution and destination of the administered cells in vivo. A quantitative tracking method should also be able to monitor cell accumulation at site of interest and guide the dosage use in the treatment.

To solve the various challenges faced with conventional MRI and meet the needs in cell therapy, a compelling new direction is the use of novel metal chelates in non-proton imaging approaches such as fluorine-19 MRI. $^{19}$F MRI has the advantage of having no background signal enabling lucid "hot-spot" imaging and quantification of spin density images. $^{19}$F MRI using perfluorocarbon (PFC) emulsion (NE) probes has been used to detect cell therapy products in vivo (e.g., stem cells and immune cells) that were labeled ex vivo prior to delivery to the subject; these methods have recently been translated to the clinic. In other uses, PFC probes have been used effectively for imaging leukocyte infiltrates associated with multiple inflammatory diseases; in this approach, following intravenous injection, the NE droplets are taken up by monocytes and macrophages in situ, and these cells accumulate at sites of inflammation yielding $^{19}$F MRI hot-spots. The utility of this nascent technology could be expanded by improving the sensitivity of $^{19}$F detection via molecular design. $^{19}$F MRI is limited by the total amount and distribution of fluorine atoms introduced into the subject's tissue, as well as the amount of PFC that can be safely internalized into cells of interest thus one must improve the intrinsic sensitivity of the PFC molecules. A key parameter for boosting sensitivity is decreasing the high $^{19}$F longitudinal relaxation time ($T_1$) of PFC molecules. $T_1$ relaxation is the process by which the net magnetization of fluorine atoms recovers to its initial maximum value parallel to the external magnetic field after being knocked out of equilibrium. The $T_1$ value ultimately limits the rate of $^{19}$F MRI data acquisition. Generally, $^{19}$F imaging requires summation of multiple acquisitions (i.e., signal averaging) to yield a sufficient signal-to-noise ratio (SNR) to gain statistical confidence. A high $^{19}$F $T_1$ value requires a longer wait time between acquisitions thus limiting the amount of signal averaging attainable during a fixed total imaging time. Shortening $T_1$ allows more signal averages and thus increases SNR, sensitivity, and decreases the minimum number of detectable cells per voxel in the same total imaging time. The paramagnetic relaxation enhancement (PRE) mechanism can be used to decrease $T_1$ by incorporating paramagnetic centers such as $Gd^{3+}$, $Fe^{3+}$, $Mn^{2+}$ into or near the fluorous phase. The strength of the PRE dipole-dipole interaction is inversely proportional to the sixth power ($1/r^6$) of the fluorine-metal distance. Thus, relaxation agents bound to the NE surface can be inefficient, due to the long distance between the relaxation agent and the bulk PFC molecules inside the NE droplet. To yield the optimal $T_1$ and $T_2$ (spin-spin relaxation time) with minimal metal added, the paramagnetic center should be dissolved in PFC. However, dissolving the paramagnetic center is challenging due to the highly hydrophobic and lipophobic nature of PFC. Free paramagnetic cations are insoluble in PFC. They must be bound to a fluorous-soluble chelate to be soluble in PFC. In terms of the choose of paramagnetic metals, iron is preferred than others like gadolinium for its low toxicity and abundance in human body.

Luminescence Imaging

In some embodiments, rare-earth fluorescence imaging can be employed.

Metal Chelates and Nuclear Imaging

Commonly used nuclear imaging methods include positron emission tomography (PET) and single-photon emission computerized tomography (SPECT). The diketonate metal chelates described are strong bindings sites for transition and lanthanide metals, and saltame chelates bind transition metals for example when they are mixed in the fluorous phase of a perfluorocarbon emulsion, including but not limited to Fe, Co, Ni, Cr, Cu, Zn, Pd and all lanthanide metal ions. The chelate-emulsion is capable of extracting metal ions in the aqueous phase to the core of the perfluorocarbon phase. When a positron-emitting or gamma-emitting radionuclide capable of binding to chelate is used, the emulsion can be used as a PET or SPECT imaging tracer, respectively. Suitable radionuclides include, for example, $^{52}$Mn, $^{60}$ or $^{64}$Cu, $^{68}$Ga, $^{89}$Zr for PET and $^{99}$Tc and $^{111}$In for SPECT.

Magnetic Particle Imaging (MPI)

MPI is an emerging non-invasive imaging technique that directly detects and localizes paramagnetic nanoparticle tracers agents throughout a 3D subject, with diagnostic imaging and material science applications (Three-dimensional real-time in vivo magnetic particle imaging By: Weizenecker, J.; Gleich, B.; Rahmer, J.; et al. 2009 PHYSICS IN MEDICINE AND BIOLOGY Volume: 54 Issue: 5 Pages: L1-L10). Use of MPI relies on the injection of paramagnetic tracer agents into the subject prior to imaging, often nanoparticles or micrometer-sized particles. Alternatively, cells labeled with paramagnetic nanoparticle agents ex vivo are delivered to the subject. Paramagnetic PFC emulsions incorporating metal chelates, for example incorporating metal ions with high electronic magnetic moments such as $Gd^{3+}$, $Fe^{3+}$ or $Mn^{2+}$, can be used as an effective, MPI-enabling tracer agents.

This invention provides compositions for a colloidal medium comprising perfluorocarbons and fluorinated metal chelates. The use of novel fluorinated metal chelates increases the imaging sensitivity and reduces scanning time by decreasing the 19F T1 of the fluorine-19 nuclei associated with the perfluorcarbon. This imaging method is non-invasive and is useful for in vivo cell tracking of stem cells, immune cells, and other cell types that are used for immunotherapy or cell replacement therapy. This imaging method is also useful in the visualization of cellular inflammation in vivo that is associated with injury or disease.

In some embodiments, the fluorinated metal chelates named SALTAME have the formula of compound 5 or compound 9:

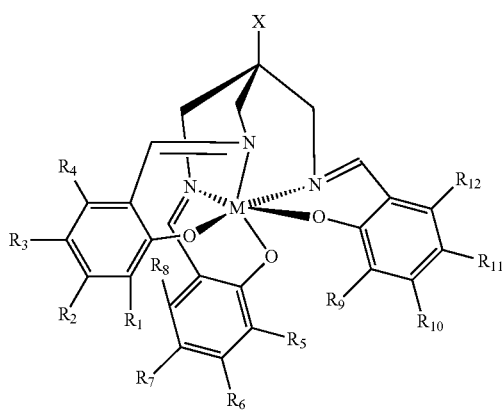

Compound 5

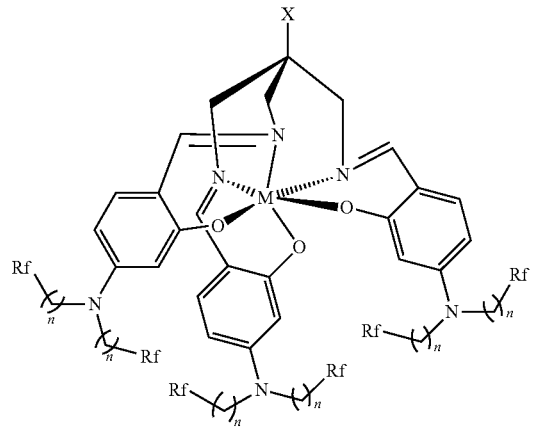

Compound 9

See the drawing part for a complete description of compound 5 and compound 9.

In some embodiments, the metal center of compound 5 or compound 9 can be selected from the following cations: $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, $Cr^{3+}$. In certain embodiments, the metal center is $Fe^{3+}$.

In some embodiments, the metal chelates have a solubility greater than 0.005 mol/L in perfluorocarbons including perfluorooctylbromide (PFOB), perfluoro-15-crown-5-ether (PFCE); perfluoro(polyethylene glycol) (PFPE), and other perfluorcarbons used in biomedicine, blood substitutes, etc.

In some embodiments, the metal chelates are stable enough to be purified by silica-gel column chromatography or high-performance liquid chromatography (HPLC) using reverse phase columns or fluorous columns.

In some embodiments, the purity of the metal chelates SALTAME is determined by thin-layer chromatography (TLC), high-performance liquid chromatography (HPLC) or liquid chromatography-mass spectrometry (LC-MS), or nuclear magnetic resonance (NMR).

In some embodiments, the metal chelates SALTAME are stable in a wide pH range from pH=1 to pH=14. The metal chelates are also stable in the existence of other chelators like ethylenediaminetetraacetic acid (EDTA).

In some embodiments, the metal center forms an octahedral or distorted octahedral structure with the chelator, which has one of the following structures:

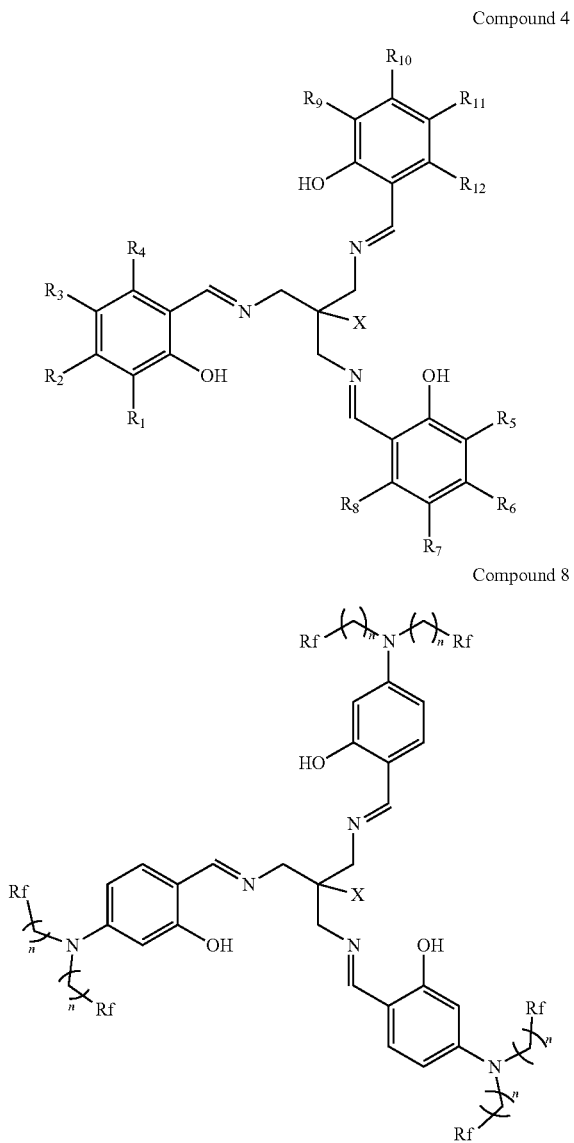

Compound 4

Compound 8

In some embodiments, the colloidal medium an emulsion comprising perfluorocarbons comprising at least one metal chelates. Emulsion droplet sizes range from 5 to 5,000 nm.

In some embodiments, a mixture of one or more metal chelates is used to prepare the colloidal medium.

In some embodiments, the metal cations are added to the preformed colloidal medium comprising compound 4 or compound 8 to form the metal chelates.

In some embodiments, the emulsion is composed of the following materials: water, PFOB, metal chelates, egg yolk phospholipids (other names: egg lecithin, L-α-Lecithin, L-α-Phosphatidylcholine, 1,2-Diacyl-sn-glycero-3-phosphocholine, 3-sn-Phosphatidylcholine), Cremophor EL (Polyoxyl 35 hydrogenated castor oil), mannitol, $CH_3$—$(CH_2)_5$—$(CF_2)_5$—$CF_3$.

In some embodiments, the formulation process of emulsion involves the use of ultrasound or microfluidics.

In some embodiments, metal chelate in perfluorocarbon oil changes the chemical shift of perfluorocarbons in 19F nuclear magnetic resonance (19F-NMR). In certain embodiments, metal chelate in the emulsion does not change the chemical shift of perfluorocarbons in 19F-NMR.

In some embodiments, metal chelates in the core of emulsion reduces the T1 relaxivity of fluorine atoms significantly. In some embodiments, the molar concentration of metal chelates in emulsion is determined by T1 relaxivity.

In some embodiments, emulsion comprising metal chelates show higher signal-to-noise ratio (SNR) per acquisition time compared with metal-free emulsions.

In some embodiments 19F T1 relaxivity of emulsion comprising metal chelates is not affected by the addition of competing chelators like EDTA into the suspension media.

In some embodiments, the emulsion droplets have a mean particle diameter 5-5,000 nm, but preferable below 200 nm, with a shelf-life longer than one week, and preferably greater than one year.

In some embodiments, the emulsion comprising fluorine atoms is incubated with cells and is internalized by cells during incubation.

In some embodiments, cells treated with emulsion contain emulsion droplets inside the cell membrane and show strong signal in 19F-NMR in a cell ensemble.

In some embodiments, the cells treated by emulsion are selected from the following mammalian cell types: Monocytes, macrophages, dendritic cells, stem cells, NK cells, T cells, B cells, tumor cells, mesenchymal stem cells, neural progenitor cells, liver cells, genetically transformed cells, and various stable cell lines, such as RAW 264.7 cells.

In some embodiments, the uptake level of emulsion by cells is accurately quantified by 19F-NMR.

In some embodiments, the uptake level of emulsion by cells is affected by one or more of the following factors: cell type, incubation condition, emulsion dosage, emulsion composition.

In some embodiments, cells treated by emulsion show no significant change in viability and phenotype.

In some embodiments, the emulsion comprising perfluorocarbon comprising metal chelates is used as an inflammation imaging tool in vivo.

In some embodiments, targeting moieties, such as peptides, antibodies, antibody fragments, aptamers, are incorporated into the emulsion surface surfactant to provide phenotypic cell specificity to emulsion uptake either in vitro or in vivo or to impart other desirable properties such as altering emulsion droplet's surface charge or hydro/lipophilicity for example.

Applications of Exemplary Embodiment

Cell Tracking

Cell tracking is important in the development of cell therapy products by providing information on the delivery, destination and fate of cells. Therapeutic cells of interest can be co-incubated with imaging probe thereby labeling the cells prior to infusion into a subject. Subject can be imaged non-invasively or in excised tissues or cells at any time post transfer. This invention provides an efficient way to track cell in vivo using imaging modalities including, for example, 19F MRI. The fluorine atoms of perfluorocarbons provide cell specific signals in 19F MRI without background. The combination of metal chelates with perfluorocarbons in the colloidal medium increases the sensitivity of imaging and/or reduces acquisition time. The notion of using colloidal suspensions comprising perfluorocarbons for labeling of macrophages using 19F MRI to visualize site of inflammation has been used preclinically in a wide range of disease models. The invention describes a synthetic chemistry means to increase sensitivity by the addition of chelates for inflammatory cell scans which, overall, improves the precision of inflammation diagnosis and monitoring. In some embodiments, these compounds find use in fluorescence imaging.

Nuclear Imaging

Nuclear imaging uses sub-atomic particle emitting radionuclides to form images to evaluate the function of tissues in vivo. In some embodiments, radionuclides used in PET scanning are chosen from the list: $^{11}$C, $^{13}$N, $^{15}$O, $^{18}$F, $^{52}$Mn, $^{61\ or\ 64}$Cu, $^{68}$Ga, $^{89}$Zr, $^{82}$Rb. In some embodiments, compound 5 or 9 can be used as radiotracers by using $^{52}$Mn, $^{61\ or\ 64}$Cu, $^{68}$Ga, $^{89}$Zr, $^{82}$Rb as metal cations. In some embodiments, the X group in compound 5 or 9 can be chosen from the list: $^{11}$C, $^{13}$N, $^{15}$O or $^{18}$F. In some embodiments, groups $R_1$, $R_2$, $R_3$, $R_4$, $R_5$, $R_6$, $R_7$, $R_8$, $R_9$, $R_{10}$, $R_{11}$, $R_{12}$ or Rf contains radionuclides. SPECT isotopes often use $^{111}$In and $^{99}$Tc isotopes.

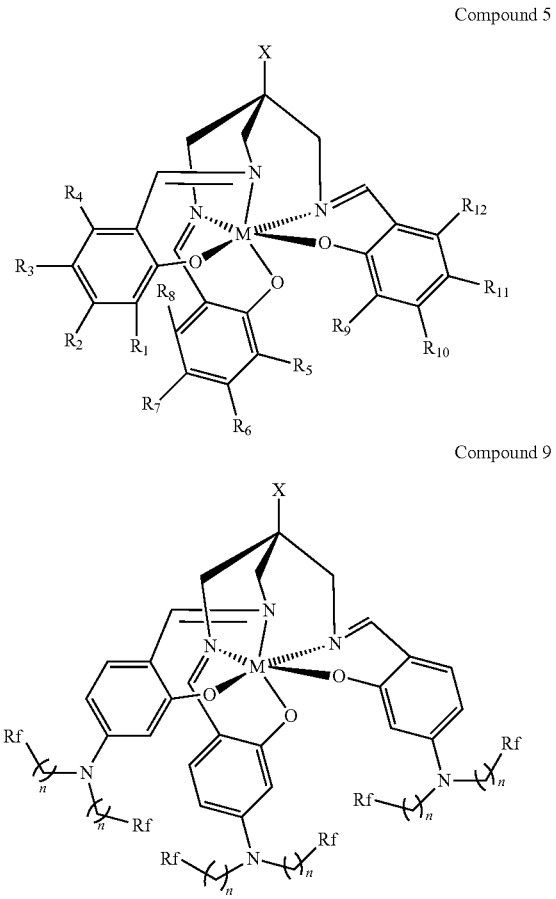

Compound 5

Compound 9

Detailed descriptions can be found in, e.g., Gottschaldt, M.5g, Bohlender, C., Pospiech, A., Gorls, H., Walther, M., Müller, D., Klette, I., Baum, R. P. and Schubert, U. S. (2009), In$^{III}$ and Ga$^{III}$ Complexes of Sugar-Substituted Tripodal Trisalicylidene Imines: The First $^{68}$Ga-Labelled Sugar Derivative. Eur. J. Inorg. Chem., 2009: 4298-4307. Green M A, Mathias C J, Neumann W L, Fanwick P E, Janik M, Deutsch E A. Potential gallium-68 tracers for imaging the heart with PET: evaluation of four gallium complexes with functionalized tripodal tris(salicylaldimine) ligands. J Nucl Med. 1993 February; 34(2) 228-233. PMID: 8429341. Mary E. Marmion, Steven R. Woulfe, William L. Newmann, Gary Pilcher, Dennis L. Nosco, Synthesis and characterization of novel N3O3-Schiff base complexes of 99gTc, and in vivo imaging studies with analogous 99mTc complexes, Nuclear Medicine and Biology, Volume 23, Issue 5, 1996, Pages 567-584.

Multi-Chromic Imaging

The 19F NMR shifts of perfluorocarbons are dependent on the molar concentration of paramagnetic metal chelates dissolved in neat perfluorocarbon oil. The invention provides a way to perform multi-chromic MRI by using perfluorocarbons comprising different concentrations of paramagnetic metal chelates. In some embodiments, the 19F shift of the perfluorocarbon oil is dependent on the vessel geometry of sample by the bulk magnetic susceptibility (BMS) mechanism. In one example, perfluorocarbon in a cylindrical NMR tube has a chemical shift different from the same sample in a spherical NMR tube. In some embodiments, the 19F chemical shift of colloidal suspension comprising perfluorocarbons comprising metal chelates is dependent on the particle size of the suspension.

In some embodiments, multi-chromic imaging is achieved by mixing colloidal suspensions that have different particle sizes.

In some embodiments, multi-chromicity by using different PFCs molecules with different chemical shifts. Alternative versions with/without metal chelates added to fluorous phase can be formulated.

Numerous methods are known in the art to image multiple discrete 19F resonances, for example due to the addition of discrete amounts of chelate into an emulsion composition subset, in a subject to enable multispectral imaging. Various MRI pulse sequences are known in the art enabling detection of the shift agents above and producing multi-chromatic images, such as chemical shift imaging (CSI), pulse sequences.

In some embodiments, multi-chromicity by using emulsions with different concentrations of metal binding chelate to tag emulsion by virtue of the specific T1 value of the emulsion. T1-weighted 19F MRI can then be used to identify T1-tagged emulsion, for example present in different labeled cell populations of interest. Often this approach uses differential image analysis where two or more T1-weighted images are acquired of a subject at different T1-weightings to identify T1-tagged emulsions.

Magnetic Particle Imaging (MPI)

Catalyst

Heavily fluorinated chelates containing transition metals, such as palladium, ruthenium, iron, manganese and nickel, have been widely used as catalysts in different kind of reactions. This invention provides an efficient route to prepare heavily fluorinated metal chelates that can be used as catalysts. In some embodiments, liquid-liquid extractions are used to isolate and recycle the metal chelates after the catalytic reaction with the use of perfluorocarbons as solvents. In some embodiment, the partition coefficients of metal chelates between perfluorocarbons and organic solvents are dependent on the temperature. In some embodiments, the catalytic reaction is performed in a homogeneous solution at higher temperatures, while the recycling of the metal chelates is performed in two phases at lower temperatures.

Liquid Crystals

Fluorinated compounds have demonstrated unique properties when used as materials. A combination of small size and large polarity of fluorine atoms often results in significant modifications to the physical properties of liquid crystals, including melting point, mesophase morphology and transitions temperatures (Liquid Crystals: Materials Design and Self-assembly by Carsten Tschierske; Fluorinated liquid crystals-properties and applications by Michael Hirda). The invention provides the preparation of fluorinated compounds that are potentially useful in the fabrication of liquid crystals.

In one aspect of the invention, novel compounds comprising a salicylidene-tris(aminomethyl)ethane core (referred to as SALTAME), are provided.

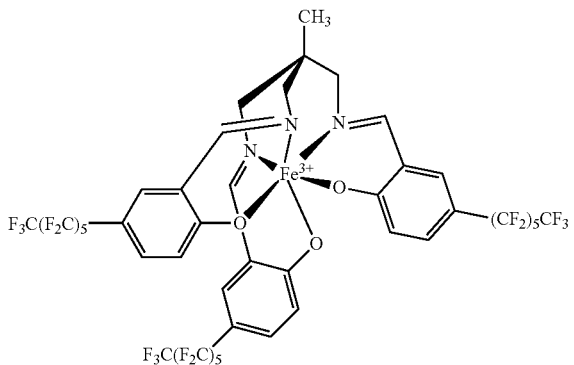
5a PPP (Fe SALTAME)

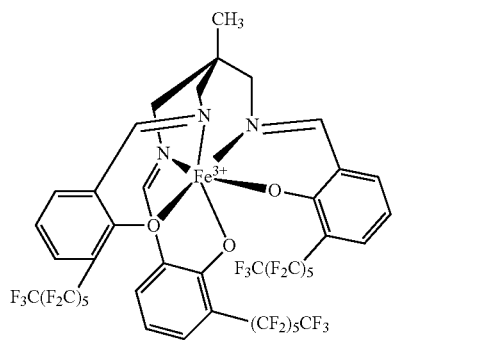
5a OOP (Fe SALTAME)

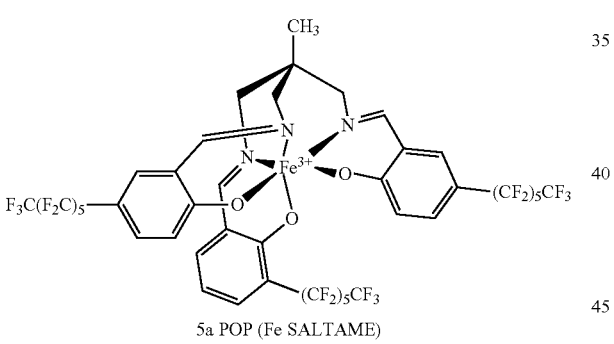
5a POP (Fe SALTAME)

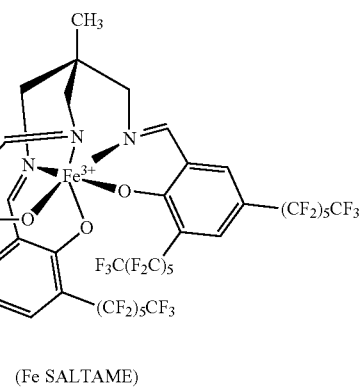
5c (Fe SALTAME)

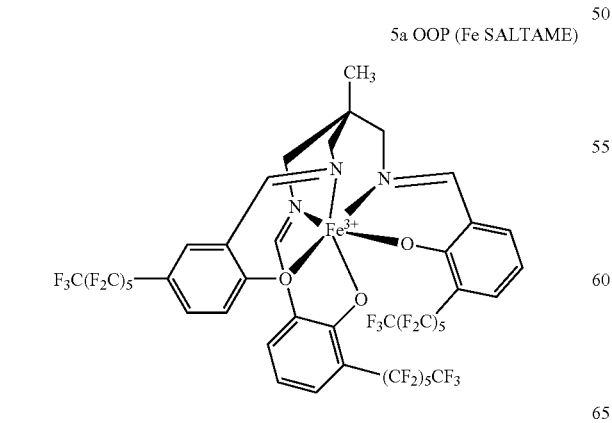
5a OOP (Fe SALTAME)

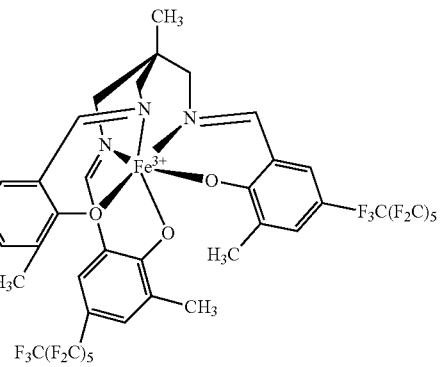
5d (Fe SALTAME)

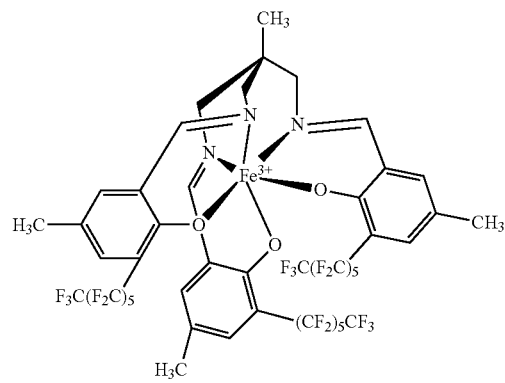

5d

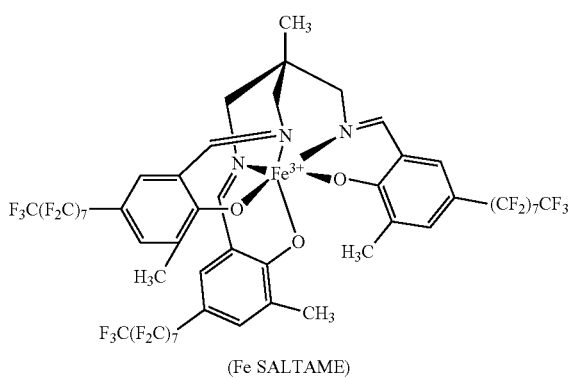

5f (Fe SALTAME)

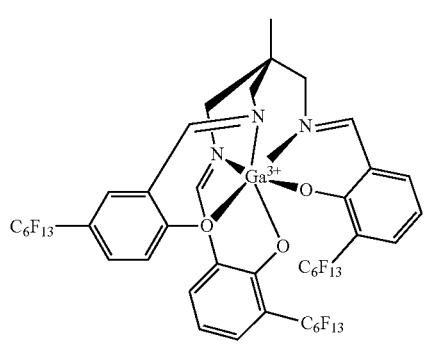

GA OOP

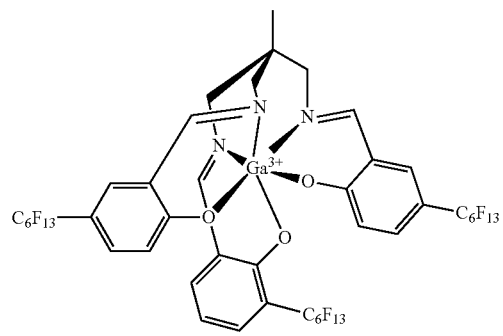

GA POP

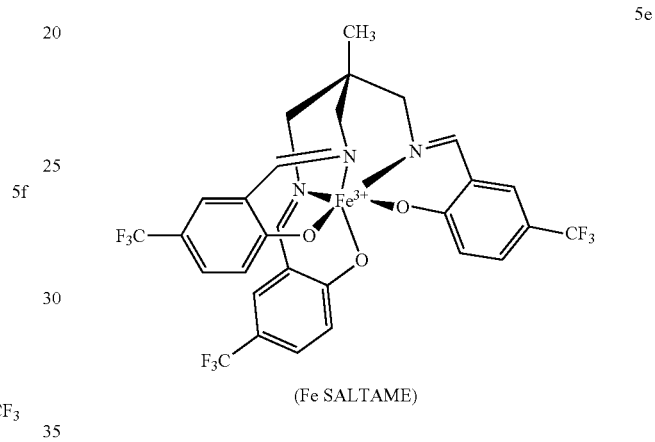

5e (Fe SALTAME)

The fluorinated diketone and/or the perfluorocarbon can be formulated as an aqueous nanoemulsion, such as an oil-in-water colloidal suspension or an oil-in-water colloidal emulsion. Such nanoemulsions can also be formulated to include additional fluorocarbons or fluorocarbon blends (e.g., a mixture of two or more different fluorocarbons). The nanoemulsions can be metalated with a transition metal ion or a lanthanide ion. In some embodiments, the composition of the present invention includes iron(III) tris-β-diketonate and perfluoroether.

Metalation of fluorinated nanoparticles or nanoemulsion can impart contrast in multiple imaging modalities. Introduction of high quantities of metals into the fluorous phase is feasible using metal-binding ligands that are compatible with (soluble in) the fluorous phase. Strong, deleterious effects of high viscosity and high molecular weight on magnetic relaxation properties impose further limitations on the nature of ligands and metal chelates that would be suitable for enhancing magnetic resonance (MR) signals. Because of extremely poor solvent properties of fluorocarbons, conventional multidentate chelates (e.g., DTPA, DOTA) are expected to be poorly soluble in PFCs. However, due to sequestration of the metal into a separate, fluorous phase, it is permissible to use metal chelates formed by relatively weak ligands of low denticity; such complexes would not otherwise be stable in homogenous aqueous solutions containing, under biological conditions, large excess of competing ligands. Previous studies (Mumper and Jay, J. Phys. Chem. 1992, 96, 8626) showed that lanthanides are efficiently extracted into polymeric microspheres by lipophilic diketonate ligands. Reverse extraction of metals from fluorous to aqueous phase (thereafter referred to as metal leakage) can compromise imaging contrast and potentially cause toxicity. It is desirable to use metals known to be bioavailable and non-toxic (e.g. iron). Alternatively, one could use extremely small amount of metals detectable by means of the radioactive decay products (e.g. radioisotopes used in nuclear imaging) to generate contrast. In all cases, it is important to ascertain minimal rates of metal leakage from the fluorous phase of the nanoemulsions, as described herein.

In some embodiments, the fluorinated nanoparticles or nanoemulsion comprises a metalated perfluorocarbon blended (mixed) with a miscible nonmetalated perfluorocarbon. In certain embodiments, the fluorinated nanoparticles or nanoemulsion comprises a conjugated, metalated perfluorocarbon and a miscible unconjugated, nonmetalated perfluorocarbon. The ratio of metalated perfluorocarbon and nonmetalated perfluorocarbon in the nanoemulsion can be selected, adjusted, or tuned. Such a ratio can change (enhance or reduce) one or more properties of the nanoemulsion, including for example, signal intensity, SNR efficiency, detection sensitivity, detection limits, and/or stability, etc. In some embodiments, the signal intensity, SNR efficiency, detection sensitivity, detection limits, and/or stability can be enhanced. In some embodiments, the signal-to-noise ratio can be reduced. In some embodiments, blending and/or mixing can be employed to tune the formulation and increase or decrease potency, as needed, by one of skill in the art. In some embodiments, conjugated, metallated perfluorocarbon can be blended with like (i.e., miscible), unconjugated, nonmetallated perfluorocarbon. In some embodiments, such a blending ratio is tunable to increase/decrease 'potency' of the formulation. In some embodiments, the blending ratio is altered to increase the potency of the formulation. In some embodiments, the blending ratio is altered to decrease the potency of the formulation.

The compounds, compositions, and methods described herein can be used to track or trace cells by an imaging method, such as MRI, by detecting the cells associated (labeled) with the fluorine-19 containing compound or composition.

In some embodiments, the compounds, compositions, and methods are used to diagnose a disease by detecting or tracking the labeled cells, e.g., labeled immune cells. In some cases, the compounds and compositions can be administered to a subject to label a specific cell type. In other cases, cells of interest are labeled with the compounds and compositions in vitro, the labeled cells are administered to a subject, and the cells are detected using an imaging modality, e.g., MRI, PET, SPECT, CT, and ultrasound. The cells can be engineered cells, such as cells that express recombinant DNA encoding one or more recombinant proteins. In some cases, the recombinant protein is a targeting moiety, such as antibodies and fragments thereof, peptides, arginine-rich domains, cationic lipids, and aptamers.

The compounds, compositions, and methods described herein can be used for cytotherapy, e.g., cell-based treatment of a disease or condition. Cytotherapy includes introducing, administering, or grafting therapeutic cells into a tissue in order to treat a disease or condition. In other embodiments, the compounds and compositions are used to treat a disease or condition by administering or grafting cells labeled with the fluorine-19 containing compound or composition to a subject in need thereof. The labeled cells can be autologous or allogeneic cells. The cells can also be engineered cells, such as cells that express recombinant DNA encoding one or more recombinant proteins. In some cases, the recombinant protein is a therapeutic protein, e.g., antibody or a fragment thereof. The recombinant protein can be a targeting moiety, such as antibodies and fragments thereof, peptides, arginine-rich domains, cationic lipids, and aptamers.

The compounds and compositions can be an imaging probe that can be used for in vivo applications (e.g., diagnostic detection methods, cytotherapeutic methods, and the like). For instance, cells labeled with the compounds and compositions can be monitored after administration to a subject to determine the biodistribution of the labeled cells or uptake of the labeled cells in the subject.

Paramagnetic Relaxation Enhancement

In the presence of paramagnetic species in close proximity, the magnetic relaxation rates of atomic nuclei increases. Spin-lattice relaxation rate ($R_1=1/T_1$) and spin-spin relaxation time ($R_2=1/T_2$) are affected. Suitable metal cations for altering magnetic resonance relaxation rates include $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$, and $^{177}Lu^{3+}$. In some embodiments, the metals are $Mn^{2+}$, $Gd^{3+}$, and $Fe^{3+}$. In certain embodiments, the metal is $Fe^{3+}$. Typically, $Fe^{3+}$ is found in negative ($R_2$-enhancing) $^1H$ MRI contrast agents (superparamagnetic iron oxide, SPIO) and not typically considered as a positive ($R_1$-enhancing) agent. Conversely, $Gd^{3+}$ compounds are predominantly used as a positive $^1H$ contrast agents, although high concentrations of $Gd^{3+}$ are known to cause negative contrast. The unexpected discovery we made using metalated fluorocarbons was the superiority of $Fe^{3+}$ as $R_1$ agent, while $Gd^{3+}$ acted as $R_2$ agent, effectively a signal quencher. In some embodiments, a metal atom is attached (binds to) to the fluorinated diketone disclosed herein.

Positron Emission Tomography and Single Photon Computed Tomography

Positron emission tomography (PET) is based on coincidence detection of two 511 keV photons produced upon annihilation of a positron emitted upon the radioactive decay of certain nuclei. Suitable metals cations for preparing radiolabeled emulsions for PET include $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$. Single photon computed tomography (SPECT) and related two-dimensional gamma scintigraphy are based on the detection of gamma-photons emitted upon the radioactive decay of certain nuclei. Suitable metals cations for preparing radiolabeled emulsions for SPECT imaging include $^{67}Ga^{3+}$, $^{99m}Tc^{4+}$, $^{111}In^{3+}$, $^{177}Lu^{3+}$. In some embodiments, long-lived isotopes $^{64}Cu^{2+}$ ($t_{1/2}=12.7$ h) and $^{89}Zr^{4+}$ ($t_{1/2}=78.4$ h) are used.

Detailed descriptions of uses of radioisotopes for cell tracking can be found, for example, in Yang et al., Radiology, 2016 May, 279(2):513-22; Bansal et al., EJNMMI Res. 2015 Mar. 28, 5:19; Normandin et al., Angew Chem Int Ed Engl, 2015 Oct. 26, 54(44):13002-6; Tavare et al., Cancer Res, 2016 Jan. 1; 76(1):73-82; Sato et al., Radiology. 2015 May, 275(2):490-500; Kim et al., ACS Med Chem Lett, 2015 Apr. 7, 6(5):528-30; Greissinger et al., Proc Natl Acad Sci USA, 2015 Jan. 27, 112(4):1161-6; and Graves et al., Bioconjug Chem. 2015 Oct. 21, 26(10):2118-24; all of which are incorporated by reference herein in their entireties.

X-Ray Computed Tomography (CT)

CT contrast agents are radioopaque, electron-dense materials that absorb X-ray radiation stronger than surrounding tissue, due to photoelectric effect. CT contrast agents typically contain high weight percentage of elements with high atomic number (Z) such as iodine (Z=53) or barium (Z=56).

Suitable cations that bind to fluorinated ligands and generate CT contrast include $Ba^{2+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Hf^{4+}$, $Ta^{5+}$, $Pt^{2+}$, $Au^+$, $Bi^{3+}$, as well as metal, metal oxide, or metal sulfide nanoparticles containing elements with Z ranging from 56 to 83. It should be noted that certain fluorocarbons (e.g. PFOB) possess inherent CT contrast due to high density of the fluorinated liquids (typically 1.6-2.0 g/mL) and optional substitution with heavy halogens (Br, I). Metalation of fluorocarbons with high-Z elements will further boost radioopacity, and aid detectability in multispectral (colored) K-edge CT, for which conventional iodinated contrast agents are not suitable.

The perfluorinated compound and/or perfluorocarbon described herein are metalated (e.g., binds and tightly retains metal ions in the fluorous phase) with transition metal ions or lanthanide ions.

Ultrasonography

Ultrasound (US) contrast agents are widely employed to enhance images. These agents impart contrast by locally altering the acoustic impedance seen by the traveling ultrasonic wave in tissue media. The acoustic impendence is defined as the product of the medium density times the sound velocity. Fluorocarbons are intrinsically high-density materials. Moreover, metalated fluorocarbon emulsions, where the metal ion is fully coordinated by fluorophilic ligands, thereby crosslinking the fluorous molecules, will increase bulk modulus of elasticity and sound velocity within the droplet. Thus, the presence of the metalated fluorinated emulsion inside cells, or otherwise, will increase the acoustic impendence locally, thereby enhancing ultrasound contrast. In some compositions for ultrasound applications, diamagnetic metal ions are employed, i.e., ions with no unpaired d- or f-electrons.

Water Remediation

Water remediation, particularly the removal of unwanted heavy metals, is useful in many industrial processes and for environmental clean-up. Toxic metals include, for example, Al, An, Ba, Bi, Cd, Cr, Co, Cu, Au, Fe, Pb, Li, Mg, Hg, Ni, P, Se, Ag, Ti, Sn and Zn. Formulations of emulsions harboring metal binding ligands, but initially devoid of metal ions upon manufacture, can be used for this purpose. Such emulsions can scavenge metals from contaminated aqueous pools upon simple addition and mixing. The emulsion will take up (toxic) metal ions and internalize these inside the fluorous phase of the emulsion droplets thereby encapsulating the metal and rendering it non-reactive. Fluorous emulsions are dense, and they tend to settle and sediment over time, thereby removing the toxic metal from the bulk water. Moreover, emulsion droplets tend to coalesce over time due to the well known process of Ostwald ripening, and the net effect is that the metal-harboring fluorous oil will form macroscopic pools at the water's bottom. Useful references include, but are not limited to, Lusic and Grinstaff, Chem Rev, 2013 Mar. 13, 113(3):1641-66; Comode et al., Contrast Media Mol Imaging, 2014 January-February, 9(1):37-52; Meri et al., ACS Nano, 2015 Jun. 23, 9(6):6363-72; Betzer et al., ACS Nano, 2014 Sep. 23, 8(9):9274-85; Qie et al., Nanoscale, 2015 Feb. 14, 7(6):2480-8; Bonitatibus et al., ACS Nano, 2012 6 (8), 6650-6658; Yi et al., Nanoscale, 2015 Jan. 14; 7(2):542-50; and Sanchez et al., Journal of Fluorine Chemistry, 1995 August, 73(2):259-264; all of which are incorporated by reference herein in their entireties.

Synthesis of Metal-Binding Oils

Unless otherwise noted, all solvents and reagents were obtained from commercial sources (Sigma-Aldrich, St. Louis, MO) and used without further purification. PFPE-OMe (Exfluor Research, Round Rock, TX), a fluorinated derivative of polyethyleneglycol with $M_n$=600 (PEG-600) terminated with reactive ester groups, is a mixture of oligomers represented by a formula $R'O(CF_2CF_2O)_nCF_2CO_2Me$, where n=4-16, $M_n$=1750 g/mol, and R' represents $CF_2CO_2Me$, $CF_3$, or $CF_2CF_3$. The latter two functionalities originate from the cleavage of polymer backbone during fluorination, giving rise to minor peaks at −58, −90, and −93 ppm in $^{19}F$ NMR, and are chemically inert. PFPE-OMe oil was determined to be ca. 80% bifunctional; the balance was considered monofunctional, and contained 1.14 mmol reactive ester groups per gram. Trifluorotoluene, $PhCF_3$ (anhydrous, ≥99%) and methyl t-butyl ether, MTBE, were dried and stored over activated 4 Å molecular sieves.

Kinetic Measurements of Metal Uptake

Strong absorbance of aromatic diketone and its complexes permits facile kinetic investigation of metalation rates. In a typical measurement, emulsion from example 4 was diluted to 70 uM diketone (excess ligand, modeling radiolabeling conditions) into a solution of chosen pH and treated with 10 uM metal cations of relevance to medical imaging, including $Fe^{3+}$ (MRI), $Cu^{2+}$ (PET), $Ga^{3+}$ (PET, SPECT), $Sc^{3+}$ (PET), and $In^{3+}$ (SPECT). In all cases, UV-Vis spectral changes indicative of metal uptake into the fluorous phase were detected, proportional in magnitude to the amount of metal. For some metals, kinetic analysis was performed. The reaction time course fit well to a pseudo-first-order process with rate constant $k_{obs}$ (Table 1).

TABLE 1

Kinetics of emulsion metalation with various metal salts.

| Metal salt | final $[M^{3+}]$, uM | final [ligand], uM | Condition | $k_{obs}$ (min$^{-1}$) |
|---|---|---|---|---|
| $FeCl_3$ | 5 | 70 | pH 2.1 (8 mM HCl) | 0.79 |
| $FeCl_3$ | 10 | 70 | pH 2.1 (8 mM HCl) | 0.70 |
| $GaCl_3$ | 10 | 70 | pH 2.1 (8 mM HCl) | 0.043 |
| $InCl_3$ | 2 | 14 | pH ~5 (unbuffered $H_2O$) | >10 |
| $InCl_3$ | 10 | 70 | pH 7.4 HEPES | 0.0322 |

Purification

In some embodiments, the compounds described herein are purified to improve the product purity and increase the product yield. In some cases, the purification method includes substantially complete or complete removal of one or more reaction side products and/or unreacted starting materials. Such side products and unreacted starting materials include, but not limited to, PFPE methyl ester, p-acetanisole, potassium tert-butoxide, potassium methoxide, potassium acetate, and the like. Useful purification methods can include silica chromatography, neutral aluminum oxide chromatography, and fluorous solid phase extraction (F-SPE). In some embodiments, the purification method comprises F-SPE.

The compounds described herein can be substantially pure or completely pure, such that they are a substantially free or completely free of reaction side products and/or unreacted starting materials.

In some embodiments, the purity of the metal chelates SALTAME is determined by thin-layer chromatography (TLC), high-performance liquid chromatography (HPLC) or liquid chromatography-mass spectrometry (LC-MS), or nuclear magnetic resonance (NMR).

In some embodiments, the metal chelates SALTAME are stable in a wide pH range from pH=1 to pH=14. The metal chelates are also stable in the existence of other chelators including but not limited to ethylenediaminetetraacetic acid (EDTA).

In some embodiments, the metal chelates are stable enough to be purified by silica-gel column chromatography or high-performance liquid chromatography (HPLC) using reverse phase columns or fluorous columns.

The yield of synthesis can be optimized or increase by adding ethanol (instead of hexane) after the reaction is quenched with acetic acid. In some embodiments, a washing step comprising methanol is omitted. In other instances, inorganics of the reaction are removed by Buchner filtration, washing with water and brine, and celite filtration. In some embodiments, the pre-purification yield of the compound is at least about 80%, e.g., about 80%, 81%, 82%, 83%, 84%, 85%, 86%, 87%, 88%, 89%, 90%, 91%, 92%, 93%, 94%, 95%, 96%, 97%, 98%, 99%, or about 100%.

In other embodiments, the synthesis reaction is performed in trifluorotoluene. In other embodiments, the synthesis reaction is performed in methyl-tert-butyl ether (MTBE), instead of trifluorotoluene.

In some embodiments, the metal chelates SALTAME are stable in a wide pH range from pH=1 to pH=14. The metal chelates are also stable in the existence of other chelators like ethylenediaminetetraacetic acid (EDTA).

In some embodiments, condensation between tris-1,1,1-(aminomethyl)ethane (TAME) and salicylaldehyde (SAL) is used to form the tripodal salicylidene-tris(aminomethyl)ethane chelating agent (SALTAME), for three reasons: (i) SALTAME is known to be a high affinity hexadentate chelating agent with three N and three O atoms, capable of binding different paramagnetic cations; (ii) with a maximum of three negative charges, a chelated trivalent paramagnetic center (e.g., Fe3+) gives an overall neutral charge that favors solubility in PFCs; (iii) the geometry of the chelate stabilizes the high spin-state of cations, such as $S=5/2$ for $Fe^{3+}$, which maximizes PRE effect.

In some embodiments, unsubstituted SALTAME chelate (FIG. 1, 5 R1-R6=H) is insoluble in PFCs due to the simultaneous hydrophobic and lipophobic nature of all PFCs. In a specific embodiment, perfluoroalkyl substituents are appended to SALTAME complex to increase fluorophilicity, as PFCs only dissolve highly fluorinated compounds.

In some embodiments, the reported photochemical ring alkylation of SA with perfluoroalkyl iodides are performed under basic conditions to produce a mixture of monoalkylated isomers 3a, 3b and dialkylated isomer 3c (route 1). In other embodiments, alkylation of bromosalicylaldehydes with heating under basic conditions, followed by reductive debromination gave 3a and 3b in much higher yields (route 2). In some embodiments, different isomers of 5a can be obtained by condensation of pure 3a or 3b or their weighed mixtures (1:2 or 2:1 w/w) with TAME and subsequent addition of ferric chloride and separation of the isomers. Though the SALTAME imines tend to dissociate, their iron complexes are very stable and can be readily isolated using chromatographic methods. Confirmation of their structures was achieved by high resolution liquid chromatography-mass spectrometry (LC-MS) of 5a, as well as NMR analysis of the respective SALTAME ligands (see, Figures). As expected, incorporation of paramagnetic Fe3+ into SAL-TAME greatly increases the intrinsic longitudinal and transverse relaxation rates for fluorine NMR of the 5a isomers (see, Tables) and perturb their proton and carbon NMR spectra. Definitive structural assignment of three of the four possible 5a isomers (5a POP, OOO and PPP) is shown by x-ray crystallography (see, Figures). In some embodiments, the four 5a isomers are soluble in various PFC molecules, especially PFOB, and to a lesser extent (<0.5 mM) in perfluoro-15-crown-5-ether (PFCE) and perfluoropolyether (PFPE), which are other PFC compounds previously used for 19F MRI applications. In certain embodiments, the 5a isomers have significantly different solubility in PFOB, with 5a PPP and 5a POP having the highest solubility (26 mM and 102 mM, respectively) among all the isomers (5a OOP and 5a OOO solubilities are 9.4 and 2.0 mM, respectively). Initial studies indicated that more stable PFOB emulsions with 5a POP were formed with concentrations up to 30 mM of the SALTAME incorporated, thus we explored the properties and applications of this isomer. In some embodiments, SALTAME complexes 5c-f show inferior solubility in PFOB.

In some embodiments, the metal chelates have a solubility greater than 0.005 mol/L in perfluorocarbons including perfluorooctylbromide (PFOB), perfluoro-15-crown-5-ether (PFCE); perfluoro(polyethylene glycol) (PFPE); other perfluorocarbons used in biomedicine, blood substitutes, etc.

In some embodiments, solubility of SALTAME compounds in perfluorocarbons are determined by absorption spectroscopy. In certain embodiments, solubility of SALTAME compounds in perfluorocarbons are determined by absorbance at 450 nm following dilution in ethyl acetate using experimentally-determined extinction coefficients of 700 M−1cm−1 for the 5a isomers.

In some embodiments, the metal center forms an octahedral or distorted octahedral structure with the chelator, which has one of the following structures:

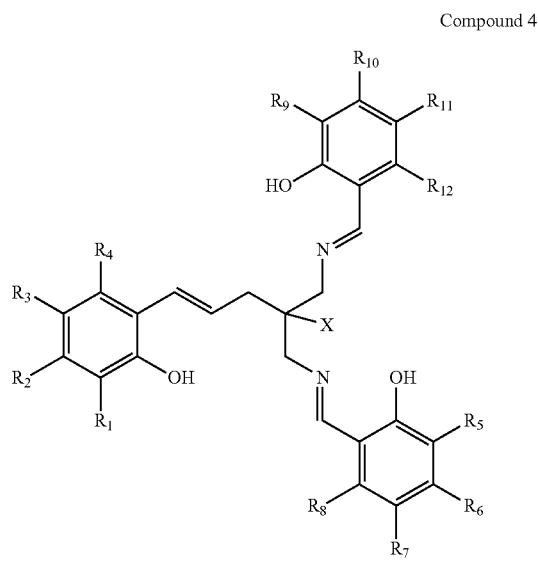

Compound 4

-continued

Compound 8

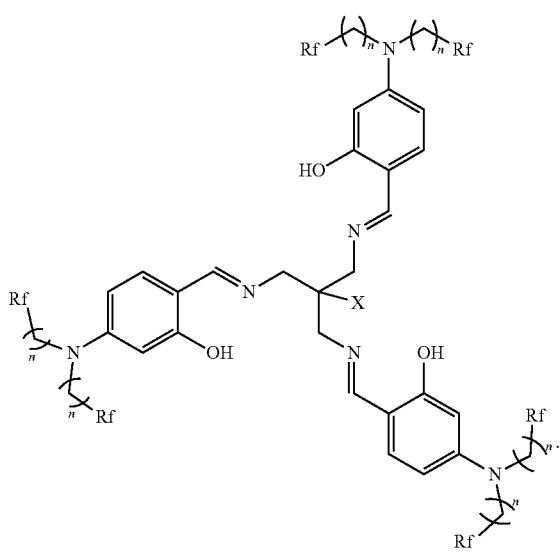

wherein X is selected from the group consisting of $^{11}C$, $^{13}N$, $^{15}O$ or $^{18}F$, $R_1$ to $R_{12}$ are selected from the group consisting of: H, $CH_3$, perfluorohexyl (PFH), perfluorooctyl (PFO), Me, $CF_3$, O—$(CF_2)_n$—$CF_3$, $(CF_2)_n$—$CF_3$, and O—$CF_2$—$(OCF_2CF_2)_n$—O—Y, wherein n is 0 to 20, and Y is $CF_3$, $CF_2$—$CF_3$ or $CF_2$—$CF_2$—$CF_3$; and Rf is $(CF_2)_j$—$CF_3$ or O—$(CF_2)_j$—$CF_3$, wherein j is 0 to 20.

Leakage Assays

Metalated emulsions prepared as described above were incubated with a large excess of strong metal chelator (disodium ethylenediaminetetraacetate, EDTA) to simulate the biological conditions characterized by an abundance of competing ligands. Spectral changes that occurred upon metalation were reverted by the action of EDTA as metal decomplexation and trapping by EDTA proceeded. The rates of metal leakage were inversely correlated with ionic radius of the metal (Shannon R. D., Acta Crystallographica. (1976), A32, page 751-767).

TABLE 2

Kinetics of metal leakage from the emulsion fluorous phase in the presence of 2.5 mM EDTA as determined by UV-Vis spectrophometry at room temperature.

| Metal cation | Ionic radius (pm) for coord. number = 6 | $t_{1/2}$ (min) |
|---|---|---|
| $Ga^{3+}$ | 62 | very slow (>1000) |
| $Fe^{3+}$ | 64.5 | very slow (>1000) |
| $Cu^{2+}$ | 73 | 33 |
| $Sc^{3+}$ | 74.5 | 77 |
| $In^{3+}$ | 80 | 2.1 |
| $Gd^{3+}$ | 93.8 | very fast (<1) |
| $Eu^{3+}$ | 94.7 | very fast (<1) |

Since $Fe^{3+}$-labeled nanoemulsion showed no decrease in characteristic absorbance of the $Fe^{3+}$ chelate even with prolonged exposure to EDTA, the samples were incubated in NMR tubes at 37° C. and measured the changes in relaxation rates over time. Decrease in relaxation rate $^{19}F$ $R_1$ would indicate sequestration of $Fe^{3+}$ to the aqueous phase, where it is too far from fluorine-19 nuclei to have an effect on $^{19}F$ $R_1$. PFPE-based nanoemulsions with compositions detailed in emulsion examples 4 and 8 showed ~20% decrease in $R_1$ over 2 weeks of incubation at 37° C. with 75 mM EDTA. Notably, this test proved more stringent than the conditions encountered during cell labeling; despite rapid leakage of lanthanides from the fluorous phase, $Eu^{3+}$ photoluminescence and elevated $^{19}F$ $R_1$ due to the presence of $Gd^{3+}$ in the fluorous phase were reliably detected in cells labeled with emulsion from an exemplary embodiment and europium or gadolinium, respectively.

Similar studies performed with small fluorinated diketones (H-fod, H-hhd, H-tdd, H-hfp, H-bta, H-tta, H-bda) revealed that they are highly effective at enhancing relaxation, but not stable enough under the conditions of EDTA competition and cell labeling. It may be necessary for sufficient stability to use fluorinated diketones with heavily fluorinated substituents that are well-miscible with other fluorinated agents known in the art to be useful for $^{19}F$ MRI.

In some embodiments, the $t_{1/2}$ is >1000 minutes, less than 100 minutes, less than 90 minutes, less than 80 minutes, less than 70 minutes, less than 60 minutes, less than 50 minutes, less than 40 minutes, less than 30 minutes, less than 20 minutes, less than 10 minutes, less than 5 minutes, less than 2 minutes, or less than 1 minutes. In some embodiments, the $t_1/2$ is less than 90 minutes, less than 80 minutes, less than 70 minutes, less than 60 minutes, less than 50 minutes, less than 40 minutes, or less than 30 minutes.

Emulsions

The imaging reagent used in the subject methods is a fluorocarbon, i.e., a molecule including at least one carbon-fluorine bond. By virtue of the $^{19}F$ atoms, the imaging reagents disclosed herein may be detected by $^{19}F$ MRI and other nuclear magnetic resonance techniques, such as MRS techniques. In certain embodiments, a fluorocarbon imaging reagent will have one or more of the following properties: (1) reduced cytotoxicity; (2) a $^{19}F$ NMR spectrum that is simple, ideally having a single, narrow resonance to minimize chemical shift artifacts; (3) high sensitivity with a large number of NMR-equivalent fluorine atoms in each molecule; and (4) formulated to permit efficient labeling of many cell types and not restricted to phagocytic cells. In some embodiments, the imaging reagent comprises a plurality of fluorines bound to carbon, e.g., greater than 5, greater than 10, greater than 15 or greater than 20 fluorines bound to carbon. In some embodiments, at least 4, at least 8, at least 12 or at least 16 of the fluorines have a roughly equivalent NMR chemical shift.

For labeling cells in culture, the imaging reagents can be employed in one or more of at least three modalities: (1) imaging reagents that are internalized or otherwise absorbed by target cells without the formation of any covalent or other binding association (first type); (2) imaging reagents that covalently attach to target cells (second type); and (3) imaging reagents coupled to molecules, such as antibodies or ligands, that bind to molecules present on the target cells (third type). In some embodiments, the imaging reagents that are internalized or otherwise absorbed by target cells without the formation of any covalent or other binding association (first type). In some embodiments, the imaging reagents that covalently attach to target cells (second type). In some embodiments, the imaging reagents coupled to molecules, such as antibodies or ligands, that bind to molecules present on the target cells (third type). In some embodiments, the imaging agent is a mixture of one or more of first, second, third types.

Imaging reagents of the first type include the perfluoro crown ethers and other perfluoropolyethers (PFPEs) that are taken up by cells and, preferably, are retained in the cell without degradation for a substantial period of time, e.g., having a half-life in the cell of at least 1 hour, at least 4 hours, at least about a day, at least about three days, or even at least about a week. In some embodiments, the imaging reagent does not interfere with ordinary cellular functions or exhibit cytotoxicity at the concentrations employed for labeling. As demonstrated herein, perfluoropolyethers show reduced toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See, for example, Means et al. (1990) Bioconjugate Chemistry 1:2-12, for additional approaches to such coupling.

Imaging reagents of the third type can be prepared by reacting imaging reagents of the second type not with the cells themselves, but with a functional moiety that is cell-targeting ligand or antibody. Suitable ligands and antibodies can be selected for the application of interest. For example, a ligand that selectively targets hematopoietic cells could be labeled with an imaging reagent as described herein and administered to a patient such as by infection. In some embodiments, the ligand can be a ligand that targets an immune cell.

Alternatively, an imaging reagent can be coupled to an indiscriminate internalizing peptide, such as antennapedia protein, HIV transactivating (TAT) protein, mastoparan, melittin, bombolittin, delta hemolysin, pardaxin, *Pseudomonas* exotoxin A, clathrin, Diphtheria toxin, C9 complement protein, or a fragment of any of these. Cells treated with this indiscriminate molecule ex vivo will absorb the imaging reagent. When such labeled cells are implanted into an animal, such as a mammal, the imaging reagent can be used to visualize and/or track the implanted cells by nuclear magnetic resonance techniques.

In one embodiment, the internalizing peptide is derived from the *Drosophila* antepennepadia protein, or homologs thereof. The 60-amino acid-long homeodomain of the homeo-protein antennapedia has been demonstrated to translocate through biological membranes and can facilitate the translocation of heterologous polypeptides to which it is coupled. See, for example, Derossi et al, (1994) J Biol Chem 269:10444-10450; and Perez et al. (1992) J Cell Sci 102: 717-722. It has been demonstrated that fragments as small as 16 amino acids long of this protein are sufficient to drive internalization. See, for example, Derossi et al, (1990) J Biol Chem 271:18188-18193.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol 63:1-8). Peptides or analogs that include a sequence present in the highly basic region can be conjugated to fluorinated imaging reagents to aid in internalization and targeting those reagents to the intracellular milieu.

The present invention provides novel compositions comprising imaging reagents. For example, the present invention provides an aqueous composition comprising perfluoro-15-crown-5 ether or PFPE oxide, an emulsifier, a surfactant co-mixture, and an additive, in certain embodiments, the surfactant co-mixture comprises lecithin (i.e., lipoid egg phosphatidyl choline), cholesterol, and dipalmltoyl phosphatidylethanolamine (DPPE). In certain such embodiments, the surfactant co-mixture comprises 70 mol % of lecithin; 28 mol % of cholesterol; and 2 mol % of DPPE. In certain embodiments, the additive is propylene glycol.

As used herein, the term "PFPE oxide" refers to perfluoropoly(ethylene glycol) Dialkyl Ether (e.g., commercially available and can be purchased from Exfluor Inc., TX).

In certain embodiments, the emulsifier is also a non-ionic solubiliser. In certain embodiments, the emulsifier comprises glycerol polyethylene glycol ricinoleate. In certain such embodiments, the emulsifier further comprises fatty acid esters of polyethylene glycol, free polyethylene glycols, and ethoxylated glycerol. In certain embodiments, the emulsifier is prepared by reacting castor oil and ethylene oxide in a molar ratio of 1:35. Exemplary emulsifiers can be obtained from BASF Corporation and are sold under the trade name of Cremophor EL®.

In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 20% to 50% w/v, such as 25% to 45% w/v, such as 30% to 40% w/v, such as 30%, 31%, 32%, 33%, 34%, 35%, 36%, 37%, 38%, 39% or 40% w/v. In certain such embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 35% to 36% w/v, such as 35.1%, 35.2%, 35.3%, 35.4%, 35.5%, 35.6%, 35.7%, 35.8%, or 35.9% w/v. In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether pr PFPE oxide in 35.6% w/v.

In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL® in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL® in 3% w/v.

In certain embodiments, the aqueous composition comprising perfluoro-15-crown-5 ether or PFPE oxide, Cremophor EL®, a surfactant co-mixture (e.g., comprising lecithin, cholesterol, and DPPE), and propylene glycol comprises propylene glycol in the range of 1% to 10% w/v, such, as 1% to 5% w/v, such as 1%, 2%, 3%, 4%, or 5% w/v. In certain embodiments, the aqueous composition comprising perfluoro-15-crown-5 ether or PFPE oxide), Cremophor EL®, a surfactant co-mixture (e.g., comprising lecithin, cholesterol, and DPPE), and propylene glycol comprises propylene glycol in 2% w/v.

In certain embodiments, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in 2% w/v.

In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) further comprises polyethylamine. In certain such embodiments, the aqueous composition comprises polyethylamine in the range of 0.01% to 5.0% w/w. In certain embodiments, the aqueous composition comprising perfluoro-15-crown-5 ether or PFPE oxide, Cremophor EL®, a surfactant co-mixture (e.g., comprising lecithin, cholesterol, and DPPE), an additive (e.g., propylene glycol), and polyethylamine further comprises protamine sulfate. In certain such embodiments, the aqueous composition protamine-sulfate in the range of 0.01% to 5.0% w/w.

In certain embodiments, the present invention provides an aqueous composition comprising perfluoro-15-crown-5 ether or PFPE oxide in 35.6% w/v, Cremophor EL® in 3.0% w/v, a surfactant co-mixture (e.g., comprising lecithin, cholesterol, and DPPE) in 2.0% w/v, and an additive (e.g., propylene glycol) in 2.0% w/v.

The terms emulsion and nanoemulsion as used in this application are equivalent unless specifically stated otherwise. In certain embodiments, the emulsion may further comprise a block copolymer of polyethylene and polypropylene glycol. In certain embodiments, the emulsion may further comprise a Plutonic™ Nonionic Plutonic™ surfactants, polyethyleneoxide (PEO)/polypropyleneoxide (PPO)/polyethyleneoxide (PEO) block (ABA type), (PEO/PPO/PEO) block copolymers, exhibit a wide range of hydrophilicity/hydrophobicity as a function of the PEO/PPO ratio, so that one can expect to obtain different phase separated morphologies with polymers such as PLA as well as different degrees of hydration of the matrix. In particular, hydration plays an important role in determining polymer degradation via hydrolysis of the ester backbone. These polymeric surfactants exhibited minimal toxicities in vivo and some of them are in clinical use, as described by BASF Corporation in their 1989 Technical Bulletin; Attwood, et al., Int. J. Pharm. 26, 25 (1985); and U.S. Pat. No. 4,188,373 to Krezanoski. These materials can be obtained from BASF Corporation. In certain embodiments, emulsions of the present invention further comprise tri-block copolymer which comprises polyethyleneoxide and polypropyleneoxide.

In certain embodiments, emulsions of the present invention comprise a tri-block copolymer of poly(ethylene oxide)-poly(propylene oxide)-poly(ethylene oxide) (PEO-PPO-PEO) comprising 80% PEO content. In certain such embodiments, the hydrophilic-lipophilic balance (HLB) value of the tri-block copolymer is 29, wherein the HLB value can be calculated from the following equation:

$$HLB = -36\frac{m}{2n+m} + 33$$

where n represents the number of repeat units in the PEO segment of the polymer and m represents the number of repeat units in the PPO segment of the polymer. Exemplary tri-block copolymers can be obtained, from BASF Corporation and are sold under the trade name of Pluronic™ F68.

The present invention further provides an aqueous composition comprising perfluoro-15-crown-5 ether or PFPE oxide and the Pluronic™ F68. In certain embodiments, the aqueous composition comprising perfluoro-15-crown-5 ether or PFPE-oxide and the Pluronic™ F68, comprises perfluoro-15-crown-5 or PFPE oxide ether in the range of 10% to 20% w/w, such as 12% to 1/% w/w, such as 12%, 13%, 14%, 15%, 16%, or 17% w/w. In certain embodiments, the aqueous composition comprising perfluoro-15-crown-5 ether or PFPE oxide and the Pluronic™ F68, comprises-perfluoro-15-crown-5 ether or PFPE oxide in 15% w/w. In certain embodiments, the aqueous composition comprising perfluoro-15-crown-5 ether or PFPE oxide and the Pluronic™ F68, comprises the Pluronic™ F68 in the range of 0.1% to 2.0% w/w, such as 0.1% to 1.0% w/w, such as 0.1%, 0.2%, 0.3%, 0.4%, 0.5%, 0.6%, 0.7%, 0.8%, 0.9% or 1.0% w/w. In certain embodiments, the aqueous composition comprising perfluoro-15-crown-5 ether or PFPE oxide and the Pluronic™ F68, comprises the Pluronic™ F68 in 0.6% w/w.

In certain embodiments, the present invention provides an aqueous composition comprising perfluoro-15-crown-5 ether or PFPE oxide in 15% w/w and the Pluronic™ F68 in 0.6% w/w.

In certain embodiments, the aqueous composition comprising perfluoro-15-crown-5 ether or PFPE oxide and the Pluronic™ F68 further comprises protamine sulfate. In certain such embodiments, the aqueous composition comprising perfluoro-15-crown-5 ether or PFPE oxide, the Pluronic™ F68, and protamine sulfate comprises protamine sulfate in the range of 0.01% to 1.0% w/w, such as 0.01% to 0.5% w/w, such as 0.01% to 0.10% w/w, such as 0.01%, 0.02%, 0.03%, 0.04%, 0.05%, 0.06%, 0.07%, 0.08%, 0.09%, or 0.10% w/w. In certain embodiments, the aqueous composition comprising perfluoro-15-crown-5 ether or PFPE oxide, the Pluronic™ F68, and protamine sulfate comprises protamine sulfate in 0.04% w/w.

In certain embodiments, the aqueous composition comprising perfluoro-15-crown-5 ether or PFPE oxide and the Pluronic™ F68 further comprises polyethylamine. In certain embodiments, the present invention provides an aqueous composition comprising perfluoro-15-crown-5 ether or PFPE oxide in 15% w/w, the Pluronic™ F68 in 0.6% w/w, and protamine sulfate in 0.04% w/w.

The present invention also provides formulations of the compositions of the present invention as described above that are suitable for uptake by cells. For example, the compositions of the present invention may be formulated as an emulsion. As an example, the present invention provides an emulsion comprising an aqueous composition comprising perfluoro-15-crown-5 ether or PFPE oxide. Cremophor EL®, a surfactant co-mixture, and an additive. In certain embodiments, the surfactant co-mixture comprises lecithin, cholesterol, and dipalmitoyl phosphatidyl ethanolamine (DPPE). In certain such embodiments, the surfactant co-mixture comprises 70 mol % of lecithin; 28 mol % of cholesterol; and 2 mol % of DPPI. In certain embodiments, the additive is propylene glycol.

In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 20% to 50% w/v, such as 25% to 45% w/v, such as 30% to 40% w/v, such as 30%, 31%, 32%, 33%, 34%, 35%, 36%, 37%, 38%, 39% or 40% w/v. In certain such embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 35% to 36% w/v, such as 35.1%, 35.2%, 35.3%, 35.4%, 35.5%, 35.6%, 35.7%, 35.8%, or 35.9% w/v. In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in 35.6% w/v.

In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL®, in the range of 1% to 10% w/v, such as 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL® in 3% w/v.

In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and propylene glycol comprises propylene glycol in the range of 1% to 10% w/v, such as 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and propylene glycol comprises propylene glycol in 2% w/v.

In certain embodiments of the foregoing emulsion, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in the range of 1% to 10% w/v, such as, 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, com- prises the surfactant co-mixture, wherein the surfactant co-mixture comprises lecithin, cholesterol, and DPPE, in 2% w/v.

In certain embodiments, the present invention provides an emulsion comprising an aqueous composition comprising perfluoro-15-crown-5 ether or PFPE oxide in 35.6% w/v, Cremophor EL® in 3.0% w/v, a surfactant co-mixture (e.g., comprising lecithin, cholesterol, and DPPE) in 2.0% w/v, and an additive (e.g., propylene glycol) in 2.0% w/v.

The present invention further provides an emulsion comprising an aqueous composition comprising perfluoro-15-crown-5 ether or PFPE oxide and the Pluronic™ F68. In certain embodiments of the foregoing emulsion, the aqueous composition comprising perfluoro-15-crown-5 ether or PFPE oxide and the Pluronic™ F68, comprises perfluoro-15-crown-5 ether or PFPE oxide in the range of 10% to 20% w/w, such as 12% to 17% w/w, such as 12%, 13%, 14%, 15%, 16%, or 17% w/w. In certain embodiments of the foregoing emulsion, the aqueous composition comprising perfluoro-15-crown-5 ether or PFPE oxide and the Pluronic™ F68, comprises perfluoro-15-crown-5 ether or PFPE oxide in 15% w/w. In certain embodiments of the foregoing emulsion, the aqueous composition comprising perfluoro-15-crown-5 ether or PFPE oxide and the Pluronic™ F68, comprises the Pluronic™ F68 in the range of 0.1% to 2.0% w/w, such as 0.1% to 1.0% w/w, such as 0.1%, 0.2%, 0.3%, 0.4%, 0.5%, 0.6%, 0.7%, 0.8%, 0.9% or 1.0% w/w. In certain embodiments of the foregoing emulsion, the aqueous composition comprising perfluoro-15-crown-5 ether or PFPE oxide and the Pluronic™ F68, comprises the Pluronic™ F68 in 0.6% w/w.

In certain embodiments, the present invention provides an emulsion comprising an aqueous composition comprising perfluoro-15-crown-5 ether or PFPE oxide in 15% w/w and the Pluronic™ F68 in 0.6% w/w.

In certain embodiments of the foregoing emulsion, the aqueous composition comprising perfluoro-15-crown-5 ether or PFPE oxide and the Pluronic™ F68 further comprises protamine sulfate. In certain such embodiments of the foregoing emulsion, the aqueous composition comprising perfluoro-15-crown-5 ether or PFPE oxide, the Pluronic™ F68, and protamine sulfate comprises protamine sulfate in the range of 0.01% to 1.0% w/w, such as 0.01% to 0.5% w/w, such as 0.01% to 0.10% w/w, such as 0.01%, 0.02%, 0.03%, 0.04%, 0.05%, 0.06%, 0.07%, 0.08%, 0.09%, or 0.10% w/w. In certain embodiments of the foregoing emulsion, the aqueous composition comprising perfluoro-15-crown-5 ether or PFPE oxide, the Pluronic™ F68, and protamine sulfate comprises protamine sulfate in 0.04% w/w.

In certain embodiments, the present invention provides an emulsion comprising an aqueous composition comprising perfluoro-15-crown-5 ether or PFPE oxide, in 15% w/w, the Pluronic™ F68 in 0.6% w/w, and protamine sulfate in 0.04% w/w.

In certain embodiments, the compositions and emulsions of the present invention comprise Cremophor® EL, a non-ionic solubiliser and emulsifier comprising polyethylene glycol ricinoleate, made by reacting castor oil with ethylene oxide in a molar ratio of 1:35. This material can be obtained from BASF Corporation.

In certain embodiments, the emulsion may further comprise a lipid. In certain embodiments of emulsions of the present invention that further comprise a lipid, the lipid is DMPC. In certain embodiments of emulsions of the present invention that further comprise a lipid, the emulsion further comprises a Pluronic™. In certain embodiments, the Pluronic™ is F68.

In certain embodiments, the emulsion may further comprise polyethylamine.

In certain embodiments, the emulsion may further comprise protamine sulfate. In certain embodiments of emulsions of the present invention that further comprise protamine sulfate, the emulsion further comprises a Pluronic™. In certain embodiments, the Pluronic™ is F68. In certain embodiments, the emulsion of the present invention further comprises protamine sulfate.

Emulsions of the present invention will preferably have a distribution of droplet sizes that allow adequate cellular uptake. In certain embodiments, a uniform droplet size may be advantageous. The desired degree of uniformity of droplet size may vary depending upon the application. In certain embodiments, the emulsion has a mean droplet size less than 500 nm, or less than 400 nm, or less than 300 nm, or less than 200 nm in diameter. Optionally, 25%, or 50%, or 75% or more of the droplets will fall within the selected range. Droplet sizes may be evaluated by, for example, light scattering techniques or by visualizing the emulsion droplets using electron microscopy micrographs. In certain cell types that have a relatively small amount of cytoplasm, such as most stem cells, the emulsions have a mean droplet size of less than 200 nm, or less than 100 nm, or less than 50 nm in diameter. In some embodiments, the nanoemulsion droplets are about 50-300 nm in mean diameter, e.g., about 50-300 nm, 50-250 nm, 50-150 nm, 50-100 nm, 100-300 nm, 100-200 nm, 100-150 nm, 110-200 nm, 120-200 nm, 130-200 nm, 140-200 nm, 150-200 nm, 150-300 nm, 160-300 nm, 170-300 nm, or about 200-300 nm in mean diameter.

In certain embodiments, small droplet size is advantageous. In certain embodiments, small droplet size increases: circulation time in applications where the emulsion is injected intravenously (iv). In certain embodiments, droplets are separable from cells by circulation. In certain embodiments, small droplet size increases ex vivo cell labeling. In certain embodiments, small droplet size increases uniform labeling.

Emulsions for use in cells should preferably be stable at a wide range of temperatures. In certain embodiments, emulsions will be stable at body temperature (37° C. for humans) and at a storage temperature, such as 4° C. or room temperature (20-25° C.). For example, it will often be desirable to store the emulsion at a cool temperature, in the range of 2-10° C., such as 4° C., and then warm the emulsion to room temperature (e.g., 18 to 28° C., and more typically 20 to 25° C.). After labeling of cells, the emulsion will experience a temperature of about 37° C. Accordingly, a emulsion will retain the desired range of droplet sizes at temperatures ranging from refrigeration temperatures up to body temperature. In certain embodiments, the emulsion is stable at temperatures ranging from 4° C. to 37° C.

In certain embodiments, the emulsion has a polydispersity index ranging from 0.1 to 0.2.

The properties of an emulsion may be controlled primarily by the properties of the imaging reagent itself, the nature of surfactants and/or solvents used, and the type of processing device (e.g., sonicator, Microfluidizer, homogenixer, etc.). Methods for forming emulsions with certain PFPE molecules are extensively described in U.S. Pat. Nos. 5,330,681 and 4,990,283; herein incorporated by reference in their entireties. A continuous phase of a polyhydroxylated compound, such as polyalcohols and saccharides in concentrated aqueous solution may be effective. The following polyalcohols and saccharides have proved to be particularly effective; glycerol, xylitol, mannitol, sorbitol, glucose, fructose, saccharose, maltitol, dimer compounds of glycerol (diglycerol or bis(2,3-dihydroxypropyl) ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and non-ionic surfactants. Examples of suitable surfactants include sodium lauryl sulphate, sulphosuccinate (sulphosuccinic hemiester), coco-amphocarboxyglycinate, potassium cetyl phosphate, sodium alkyl-polyoxyethylene-ether carboxylate, potassium benzalconium chloride, alkyl amidopropyl betaine, cetyl-stearilic ethoxylated alcohol, and sorbitan-ethoxylate(20)-mono-oleate Tween-20. While thermodynamic equations may be used to attempt to predict mixtures of imaging reagents that will give emulsions having the desired droplet sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

In the applications involving ex vivo labeling, some emulsions are designed to facilitate uptake of the imaging reagent by the subject cells. A surfactant may be designed to form stable emulsions that carry a large quantity of perfluoro-15-crown-5 ether or PFPE oxide into the aqueous phase. Additionally, it may have properties that increase the intracellular delivery of the emulsion droplets in the shortest possible incubation time. Increasing the perfluoro-15-crown-5 ether or PFPE oxide intracellular loading improves sensitivity to the labeled cells. Furthermore, minimizing the culture time can be important when working with the primary cells cultures. The efficiency of intracellular uptake depends on cell type. For example macrophages and some dendritic cells will endocytose almost any particulate, whereas other cell types of interest may only be weakly phagocytic. In either case the uptake efficiency can be boosted substantially by designing the surfactant so that the surface of the emulsion droplet has properties that promote cellular uptake in culture (i.e., "self-delivering" emulsion droplets) (see Janjie et al, JACS, 2008, 130 (9), 2832-2841 and U.S. Provisional Patent Application 61/062,710, both of which are incorporated by reference in their entirety). The emulsion droplet surface can be made to have lipophilic, or optionally cationic, properties via appropriate surfactant design. For example the surfactant can incorporate lipids, such as cationic or neutral lipids, oil-in-water colloidal emulsions, micelles, mixed micelles, or liposomes, that tend to bind to or fuse with the cell's surface, thereby enhancing emulsion droplet uptake. The emulsion droplet surface may also incorporate cell delivery signals such as polyamines. Examples include emulsions that have polyamines, such as polyethylenimine or protamine sulfate, incorporated into the emulsion droplet's surfactant layer during processing.

In certain embodiments, a colloidal system for use as a delivery vehicle in vitro and in vivo is a liposome (i.e., an artificial membrane vesicle). The preparation and use of such systems is well known in the art. Suitable cationic lipids are described in the following and are herein incorporated in their entirety; Felgner et al., 1987, PNAS 84, 7413-7417; U.S. Pat. Nos. 4,897,355; 5,279,833; 5,283,185; 5,334,761; 5,527,928; Bailey et al., U.S. Pat. Nos. 5,552, 155; and 5,578,475). Other approaches include incorporation into the surfactant peptides (e.g. oligo-Arg9 and TAT-like peptides) that facilitate entry into cells, or antibodies that target specific cell surface molecules. Additionally, in certain embodiments, one can incorporate small cationic proteins into the surfactant, such as protamine sulfate, to enhance cellular uptake. Protamine sulfate is non-toxic to cells and has FDA approval for use in humans as a heparin antagonist. In certain embodiments, colloidal dispersion systems are used, such as macromolecule complexes, nanocapsules, microspheres, and beads. Other approaches for enhancing uptake of the emulsified fluorocarbons, such as by using additional transfection agents or by using electroporation of the cells, is described herein.

In some embodiments, emulsions have "self-delivering" properties without having to add uptake enhancing reagents. Said emulsions are preferably stable and have a shelf-life of a period of months or years. In some embodiments, the stability is 3 months, 6 months, 9 months, 12 months, 24 months, or 48 months. In some embodiments, the stability is at 0° C., 10° C., 15° C., 20° C., 25° C., 30° C., 35° C., 37° C., and/or 40° C.

It is understood that surfactants and uptake enhancing reagents are not meant to be exclusive groups and in some cases they may be overlapping.

Additional descriptions of emulsions can be found, for example, in U.S. Pat. No. 9,352,057, the contents are herein incorporated by reference in its entirety.

Cells and Labeling

Methods described herein may be used with a wide range of cells, including both prokaryotic and eukaryotic cells, and including mammalian cells, such as human cells. In some embodiments, the cells are mammalian cells. In some embodiments, the cells are human cells. Technologies for cell preparation include cell culture, cloning, nuclear transfer, genetic modification and encapsulation. In some embodiments, the cells are engineered cells, such as genetically engineered or genetically modified cells. In some cases, the engineered cells are recombinant human cells, e.g., a human cell expressing recombinant DNA or a recombinant protein.

A partial list of suitable mammalian cells includes: blood cells, myoblasts, bone marrow cells, peripheral blood cells: umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells), stem cells, and diseased cells, such as cancer cells. In certain embodiments, the cells to be used are a fractionated population of immune cells. Recognized subpopulations of immune cells include lymphocytes, such as B lymphocytes (Fc receptors, MHC class II, CD19+, CD21+), hELer T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dentritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (i.e., cells derived from a genetically different individual of the same species) are also contemplated. Xenogeneic (i.e., derived from a different species than the recipient) cells, such as cells from transgenic pigs, may also be administered. When the donor cells are xenogeneic, the cells can be obtained from an individual of a species within the same order, more preferably the same superfamily or family (e.g., when the recipient is a human, the cells can be derived from a primate, more preferably a member of the superfamily Hominoidea).

Cells may, where medically and ethically appropriate, be obtained from any stage of development of a donor individual (e.g., a human donor), including prenatal (e.g., embryonic or fetal), infant (e.g., from birth to approximately three years of age in humans), child (e.g., from about three years of age to about 13 years of age in humans); adolescent (e.g., from about 13 years of age to about 18 years of age in humans), young adult (e.g., front about 18 years of age to about 35 years of age in humans), adult (from about 35 years of age to about 55 years of age in humans) or elderly (e.g., from about 55 years and beyond of age in humans).

A variety of methods may be used to label cells with imaging reagent. In general, cells will be placed in contact with imaging reagent such that the imaging reagent becomes associated with the cell. Conditions will often be standard cell culture conditions designed to maintain, cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety.

In some embodiments, a targeting moiety will be selected to facilitate association of the imaging reagent with the cell to be labeled. A targeting moiety may be designed to cause non-specific insertion of the fibrocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. Examples of the targeting moiety include but are not limited to: a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, the fluorocarbon imaging reagent comprises perfluoro-15-crown ether.

In many embodiments, cells are labeled by contacting the cells with an emulsion of the imaging compound, such that the compound is associated with (e.g., internalized) cells. In some embodiments, cells are labeled ex vivo or in vitro under certain conditions such that the imaging compound is internalized by the cells. Both phagocytic and non-phagocytic cells may be labeled by such a method. For example, as demonstrated in WO2005072780, both dendritic cells (phagocytic) and gliosarcoma cells (non-phagocytic) can be labeled by contacting the cells with an emulsion of the imaging compound.

In certain embodiments, a method of the invention may comprise labeling cells in vivo with a $^{19}$F imaging compound and detecting labeled cells in the subject. The imaging compound can be administered to the subject, e.g., human subject, by administration routes including, but not limited to, parenterally administration, e.g., intravenous administration. The cells to be labeled may be determined by specific properties of the cells such as phagocytic activity. The cells that are labeled may be controlled by the route of administration of the imaging reagent. The types of cells that are labeled may be controlled by the nature of the imaging compound. For example, simple colloidal suspensions of imaging compound will tend to be taken up more quickly by cells with phagocytic activity. As another example, an imaging compound may be formulated with or covalently bound to a targeting moiety that facilitates selective targeting of the imaging reagent to a particular population of cells. In certain embodiments, the imaging compound comprises a metalated fluorinated diketones.

In certain embodiments the cells to be labeled are stem cells. Stem cell therapies are commonly used as part of an ablative regimen for treatment of cancer with high dose radiation and/or chemotherapeutic agents. Ablative regimens generally employ hematopoietic stem cells, or populations of cells containing hematopoietic stem cells, as may be obtained, for example, from peripheral blood, umbilical cord blood or bone marrow. Cells of this type, or a portion thereof, may be labeled and tracked in vivo to monitor survival and engraftment at the appropriate location. Other types of stem cells are increasingly attractive as therapeutic agents for a wide variety of disorders.

As an example, cells may be mouse embryonic stem cells, or ES cells from another model animal. The labeling of such cells may be useful in tracking the fate of such cells administered to mice, optionally as part of a preclinical research program for developing embryonic stem cell therapeutics. Examples of mouse embryonic stem cells include: the JMI ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers; Arcos Bioscience, Inc., Foster City, Calif., CyThera, Inc., San Diego, Calif., BresaGen, Inc., Athens, Ga., ES cell International, Melbourne, Australia, Geron Corporation, Menlo Park, Calif., Goteborg University, Goteborg, Sweden, Karolinska Institute, Stockholm, Sweden, Maria Biotech Co. Ltd.— Maria infertility Hospital Medical Institute, Seoul, Korea, MizMedi Hospital—Seoul National University, Seoul, Korea, National Centre for Biological; Sciences/Tata Institute of Fundamental Research, Bangalore, India, Pochon CHA University, Seoul, Korea, Reliance Life Sciences, Mumbai, India, ReNeuron, Surrey, United Kingdom, StemCells, Inc., Palo Alto, Calif., Technion University, Haifa, Israel, University of California, San Francisco, Calif., and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 9,351,406; 6,090,622; 5,843,780: 20020045259; 20020068045; all of which are incorporated by reference herein in their entireties. In some embodiments, the human ES cells are selected from the list of approved cell lines provided by the National Institutes of Health (NIH) and accessible at the NIH embryonic Stem Cell Registry. In certain embodiments, an embryonic stem cell line is selected from the group comprising: the WA09 line obtained from Dr. J. Thomson (Univ. of Wisconsin) and the UCO1 and UC06 lines, both on the current NIH registry.

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example. US Patent Publication Nos. 2003/0003579; 2002/0123143; 2002/0016002 and Gritti et al. 2002 J Neurosci 22 (2):437-45), the spinal cord (see, for example, U.S. Pat. Nos. 6,361,996, 5,851,832) or a neuroendocrine lineage, such as the adrenal gland, pituitary gland or certain portions of the gut (see, for example, U.S. Pat. No. 6,171,610 and PC12 cells as described in Kimura et al., 1994, J. Biol. Chem. 269: 1896-67). In some embodiments, a neural stem cell is obtained from a peripheral tissue or an easily healed tissue, thereby providing art autologous population of cells for transplant.

Hematopoietic or mesenchymal stem cells may be employed in certain disclosed methods. Recent studies suggest that bone marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et ah, 2001, Cell 105: 360-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,703,197; 5,750,397; 5,716,827; 5,643,741; 5,061,620. Examples of mesenchymal stem cells include those described in U.S. Pat. Nos. 5,486,350; 5,327,735, 5,942,235; 5,972,703, those described in PCT publication nos. WO 00/53705, WO 00/02654; WO 98/20907, and those described in Pittenger et al. and Zhao et al., supra.

Stem cell lines are preferably derived from mammals, such as rodents (e.g., mouse or rat), primates (e.g., monkeys, chimpanzees or humans), pigs, and ruminants (e.g., cows, sheep and goats), and particularly from humans. In certain embodiments, stem cells are derived from an autologous source or an HLA-type matched source. For example, stem cells may be obtained from a subject in need of pancreatic hormone-producing cells (e.g., diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some embodiments, cells for administration to a human should be compliant with good tissue practice guidelines set by the U.S. Food and Drug Administration (FDA) or equivalent regulatory agency in another country. Methods to develop such a cell line may include donor testing, and avoidance of exposure to non-human cells and products.

Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, inmmnoaffinity chromatography), or by utilizing a magnetic field to collect the cells which are bound to magnetic droplets via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although it is expected that methods disclosed herein will be frequently used for in vivo monitoring of cells, it should be noted that the methodologies are equally effective for the monitoring of cells in culture (i.e., in vitro), in a tissue sample or other ex vivo cellular material. For therapeutic uses, cells may be labeled at a desired step during the preparation for administration to the patient.

A variety of methods may be used to label cells with imaging reagent. In general, cells will be placed in contact with imaging reagent such that the imaging reagent becomes associated with the cell. Conditions will often be standard cell culture conditions designed to maintain, cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fibrocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, the fluorocarbon imaging reagent comprises perfluoro-15-crown ether.

Cellular labeling with fluorocarbons emulsions can also be facilitated using transfection agents to aid in cell delivery. Often transfection agents consist of cationic lipids, cationic liposomes, poly-cations, and the like. The transfection agent is pre-mixed with the fluorocarbon emulsion labeling agent, whereby it becomes associated with, or coats, the emulsion droplets. The transfection agent-treated emulsion droplets are then added to the cultured cells and incubated so that the cells become labeled. Common transaction agents include Lipofectamine (Invitrogen, Inc) FuGene, DOTAP (Roche Diagnostics, Inc.), and poly-L-lysine. Small proteins can also be used as transfection agents, such as many types of protamines. Protamines, the major DNA-landing proteins in the nucleus of sperm in most vertebrates, package the DNA in a volume less than 5% of a somatic cell nucleus. Protamines are simple proteins of low molecular weight that are rich in arginine and strongly basic. Commercially available protamines come from the sperm of salmon and certain other species of fish. The term "protamine" as used herein, refers to a low molecular weight cationic, arginine-rich polypeptide. The protamine molecule typically comprises about 20 to about 200 amino acids and is generally characterized by containing at least 20%, 50% or 70% arginine. Protamines are often formulated as salts, with one or more counter ions such as sulfate, phosphate and chloride.

Data provided in this application show that protamines (e.g., protamine sulfate) are highly effective in delivering PFPE fluorocarbon emulsion droplets to cultured cells. Suitable protamine sulfates can come from a variety of sources (e.g., salmon, herring, trout, etc.) and be of various grades and forms (e.g., USP, grades II, III, X, etc.), with and without histones or any recombinant derivative. Examples of other protamine solutions that may be used as transfection agents include protamine phosphate, protamine chloride, protamine sulfate-2, protamine sulfate-3, protamine sulfate-10, and protamine free base.

Data provided in this application shows self deliverable nanoemulsions prepared with fluorocarbon imaging reagents (e.g., perfluoro-15-crown-5 ether or PFPE oxide) and incorporate a Plutonic™ surfactant, optionally with Protamine Sulfate, or Cremophor EL® with an emulsifier and an additive. Simple co-incubation of cells with certain self-deliverable nanoemulsions provides sufficient cell labeling for imaging, without the need for transfection reagents.

Where cells are to be used in a therapeutic regimen, various methods have been used for delivery of cells including injections and use of special devices to implant cells in various organs. The present invention is not tied to any particular delivery method. Labeled cells may be monitored regardless of whether the cells are delivered directly to a particular site or delivered systemically. For example, labeled dendritic cells were successfully imaged following either a focal implantation directly into tissues or an intravenous injection, and T-cells were imaged following intraperitoneal injection. Cells may be inserted into a delivery device which facilitates introduction by injection or implantation into the subjects. Such delivery devices may include tubes, e.g., catheters, for injecting cells and fluids into the body of a recipient subject. In some embodiments, the tubes additionally have a needle, e.g., a syringe, through which the cells of the disclosure can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such earners and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the disclosure may be prepared by Incorporating cells as described herein in a pharmaceutically acceptable carrier or diluent and, as required, other ingredients enumerated above, followed by filtered sterilization.

Additional descriptions of useful cells and methods of labeling said cells can be found, for example, in U.S. Pat. No. 9,352,057, the contents of which is herein incorporated by reference in its entirety.

Nuclear Magnetic Resonance Imaging Techniques

As described herein, also referred to herein as a type of imaging modality, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of such cells. In many instances, the labeled cells may be administered to a living subject. Following administration of the cells, some portion of the subject, or the entire subject, may be examined by MRI to generate an MRI data set. In other instances, the emulsion is injected directly iv, and the subject is subsequently imaged at one or more time points. A "data set", as the term is used herein, is intended to include raw data gathered during magnetic resonance probing of the subject material, the acquisition parameters, as well as information processed, transformed or extracted from the raw data. The raw data includes transient signals obtained by MRI (magentic resonance imaging)/MRS (magnetic resonance spectroscopy), including the free-induction decays, spin-echoes, stimulated-echoes, and/or gradient echoes. Examples of processed information include two-dimensional or three-dimensional pictorial representations of the subject material. The processed information may also include magnitude images, the real and imaginary image components, as well as the associated phase map images. Another example of extracted information is a score representing the amount or concentration of imaging reagent or $^{19}F$ signal in the subject material. By using the amount of $^{19}F$ signal in the subject material, and a calibration of the mean amount of imaging reagent per cell pre-implantation (m the case of ex vivo labeling), one can estimate the absolute number of cells in the subject material. The amount of $^{19}F$ signal present in a subject material can be represented or calculated in many ways; for example, the average signal-to-noise-ratio (SNR) of the $^{19}F$ signal for a region of interest (ROI) may be measured and used to calculate the abundance of labeled cells. In certain embodiments, the average intensity, or pixel- or voxel-wise summation of the $^{19}F$ signal may be used to calculate the abundance of labeled cells. This type of data may be gathered at a single region of the subject, such as, for example, the spleen or another organ of particular relevance to the labeled cells. Labeled cells may be examined in contexts other than in the subject. It may be desirable to examine labeled cells in culture. In certain embodiments, labeled cells may be applied to or generated within a tissue sample or tissue culture, and labeled cells may therefore be imaged in those contexts as well. For example, an organ, tissue or other cellular material to be transplanted may be contacted with an imaging reagent to generate labeled cells prior to implantation of such transplant in a subject.

In general, labeling agents of the disclosure are designed for use in conventional MRI detection systems. In the most common implementation of MRI, one observes the hydrogen nucleus (proton, $^{1}H$) in molecules of mobile water contained in subject materials. To detect labels disclosed herein, an alternate nucleus is detected, $^{19}F$. $^{19}F$ MRI has only slightly less intrinsic sensitivity compared to $^{1}H$; the relative sensitivity is approximately 0.83. Both have a nuclear spin of +½. The natural isotopic abundance of $^{19}F$ is 100%, which is comparable to 99.985% for $_{1}H$. The physical principles behind the detection and image formation are the same for both $^{1}H$ and $^{19}F$ MRI. The subject material is placed in a large static magnetic field. The field tends to align the magnetic moment associated with the $^{1}H$ or $^{19}F$ nuclei along the field direction. The nuclei are perturbed from equilibrium by pulsed radio-frequency (RF) radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

At constant magnetic field strength, the Larmor frequency of $^{19}F$ is only slightly lower (about 6%) compared to $^{1}H$. Thus, it is straightforward to adapt conventional MRI scanners, both hardware and software, to acquire $^{19}F$ data. The $^{19}$F detection may be coupled with different types of magnetic resonance scans, such as MRI, MRS or other techniques. Typically, it will be desirable to obtain a $^1$H MRI image to compare against the $^{19}$F image. In a living organism or other biological tissue, the proton MRI will provide an image of the subject material and allow one to define the anatomical context of the labeled cells detected in the $^{19}$F image. In some embodiments, data is collected for both $^{19}$F and $^1$H during the same session; the subject is not moved during these acquisitions to better ensure that the two data sets are in spatial registration. Normally, $^{19}$F and $^1$H data sets are acquired sequentially, in either order. An RF coil (i.e., antenna) can be constructed that can be electrically tuned from the $^{19}$F and $^1$H Larmor frequency. Tuning between these two frequencies can be performed manually (e.g. via an electro-mechanical variable capacitor or inductor), or electrically, via active electronic circuitry. Alternatively, with appropriate modifications to the hardware and/or software of the MRI instrument, both data sets can be acquired simultaneously, for example, to conserve imaging time. Simultaneous acquisition of the $^{19}$F and $^1$H data sets require an RF coil or antenna that can be electrically tuned simultaneously to the $^{19}$F and $^1$H Larmor frequency (i.e., a double-tuned coil). Alternatively the RF coil can be "broadband," with one broadly-tuned electrical resonance that covers both Larmor frequencies (i.e., $^{19}$F and $^1$H). Other imaging techniques, such as fluorescence detection may be coupled with $^{19}$F MRI. This will be particularly desirable where a fluorocarbon imaging reagent has been derivatized with a fluorescent moiety. In other embodiments, the $^{19}$F MRI scan may be combined with a PET scan in the same subject or patient by using dual-model radioactive $^{18}$F/$^{19}$F fluorocarbon labeling reagents as described herein.

MRI examination may be conducted according to any suitable methodology known in the art. Many different types of MRI pulse sequences, or the set of instructions used by the MRI apparatus to orchestrate data collection, and signal processing techniques (e.g., Fourier transform and projection reconstruction) have been developed over the years for collecting and processing image data (for example, see Magnetic Resonance Imaging, Third Edition, editors D. D. Stark and W. G. Bradley, Mosby, Inc., St. Louis Mo. 1999). The reagents and methods of this disclosure are not tied to any particular imaging pulse sequence or processing method of the raw NMR signals. For example, MRI methods that can be applied to this disclosure broadly encompasses spin-echo, stimulated-echo, gradient-echo, free-induction decay based imaging, and any combination thereof. Fast imaging techniques, where more than one line in k-space or large segments of k-space are acquired from each excited signal, are also highly suitable to acquire the $^{19}$F (or $^1$H) data. Examples of fast imaging techniques include fast spin-echo approaches (e.g., FSE, turbo SE, TSE, RARE, or HASTE), echo-planar imaging (EPI), combined gradient-echo and spin-echo techniques (e.g., GRASE), spiral imaging, and burst imaging. The development of new and improved pulse sequence and signal processing methods is a continuously evolving field, and persons skilled in the art can devise multiple ways to image the $^{19}$F labeled cells in their anatomical context.

As another example of a nuclear magnetic resonance technique, MRS can be used to detect the presence of fluorocarbon-labeled cells in localised tissues or organs. Normally MRS methods are implemented on a conventional MRI scanner. Often the localized volume of interest (VOI) is defined within a conventional anatomical $^1$H MRI scan. Subsequently, the magnitude of the $^{19}$F NMR signal observed within the VOI is directly related to the number of labeled cells, and/or the mean concentration of PFPE per cell present in the tissue or organ. Methods for isolating a VOI within a much larger subject are well known the art (for example, Magnetic Resonance Imaging, Third Edition, Chapter 9, Editors D. D. Stark and W. G. Bradley, Mosby, Inc., St Louis Mo. 1999). Examples include using a localised RF surface coil near the VOI, surface spoiling, surface coil $B_1$-gradient methods, slice-selective $B_0$-gradient techniques, STEAM, PRESS, image selective in vivo spectroscopy (ISIS), and magnetic resonance spectroscopic imaging (MRSI).

The development of new and improved pulse sequence and signal processing methods is continuously evolving for MRS, and persons skilled in the art can devise multiple ways to detect the $^{19}$F NMR signals emanating from the fluorocarbon labeled cells in VOIs.

In some embodiments, the subject material is a fixed or otherwise preserved specimen of tissue that has been biopsied or necropsied from the animal or human. The subject material is then subjected to conventional high-resolution, one or multi-dimensional, liquid state $^{19}$F NMR to determine the amount of fluorine present in the sample. The fluorine content is directly related to the number of labeled cells in the subject material specimen. In the case of in situ labeling of resident phagocytes (e.g., monocytes, macrophage, neutrophil, cells of the liver) with fluorine emulsion as described above (e.g., using nanoemulsion 3), the amount of $^{19}$F measured in the sample is directly proportional to the number of these phagocytes present in the tissue. In this way one can assay the relative amount of inflammation in the intact tissues without having to use histology or any other destructive and time-consuming techniques. In certain embodiments, to analyze the $^{19}$F content of the tissue, one uses one-dimension $^{19}$F NMR. In certain embodiments, a $^{19}$F reference compound will be added to the sample of known number of $^{19}$F spins that has a chemical shift that is different than the composition of the cell labeling emulsion (see below). In certain embodiments, the relative integrated areas under the emulsion peak and reference peak can be used to calculate the absolute number of fluorines present in the tissue sample. In certain embodiments, the weight of the tissue sample can also be incorporated into the calculation to extract the mean fluorine density of the tissue sample, and this parameter can be considered a quantitative index of inflammation or "inflammation index".

In certain embodiments the disclosure provides a method of quantifying the numbers of labeled cells in vivo or in subject materials within an ROI. An ROI may include all labeled cells in a subject or labeled cells in specific organs such as the pancreas, specific tissues such as lymph nodes, or any region or of one or more voxels showing detectable MRI/MRS $^{19}$F signal. A ROI can be an otherwise undefined area beyond a particular experiment. There are a number of ways that labeled cells may be quantified in the subject materials or in vivo, as described herein.

In the case or ex vivo labeling, calibrating the mean "cellular dose" of $^{19}$F labeling agent pre-implantation of a particular cell population is often a pre-requisite for quantitative cell determinations in subject materials or the patient. It is anticipated that different cell types have different inmate abilities to take up the labeling agents in vitro, and thus the cellular dose of the labeling agent will also vary. Furthermore, different cells of the same type acquired from different sources (e.g., different patients) may have different affinities for the labeling agent. Thus a cellular dose calibration may be required. This calibration may be used, initially, to modify the labeling protocol (i.e., incubation conditions, duration of time that cells are incubated with labeling fluorocarbon emulsion, concentration of fluorocarbon emulsion in culture medium during labeling, etc.) to achieve a certain range of cellular dose before labeled cells are actually used in a subject to be imaged. Alternatively, one can fix the labeling conditions and protocol and measure the mean value $^{19}$F labeled per cell, as is, for subsequent quantification in the subject to be imaged. In certain embodiments the mean number of $^{19}$F molecules (F's) per cell of a labeled cell population is measured (i.e., calibrated) in vitro prior to administration of the cells to the subject or patient. In certain embodiments the mean number of $^{19}$F molecules (F's) per cell of a labeled cell population is calibrated in a test population of cells of a particular type, not necessarily destined for a patient, but used to calibrate cellular dose of labeling agent as a consequence of a particular labeling protocol or set of conditions; optionally, the value of cellular dose is then used for future labeling and in vivo imaging experiments in the same population type of cells with the same labeling protocol.

A variety of methods may be used to label cells with imaging reagent. In general, cells will be placed in contact with imaging reagent such that the imaging reagent becomes associated with the cell. Conditions will often be standard cell culture conditions designed to maintain, cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fibrocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, the fluorocarbon imaging reagent comprises perfluoro-15-crown ether.

The cellular dose of labeling agent can be assayed in vitro using a variety of quantitative techniques. For example, one can use a one-dimensional (1D)$^{19}$F NMR spectrum obtained from a cell pellet, cell suspension, or cell lysate, of a known number of labeled cells. From this spectrum, one can calculate the integrated area of the $^{19}$F spectrum or a portion thereof, originating from the labeling reagent associated with the cells. The integrated area of the $^{19}$F spectrum, denoted $S_{cells}$, is directly proportional to the total amount of $^{19}$F in the cell pellet, suspension, or lysate. To measure the absolute number of $^{19}$F nuclei, the measured S.sub.cells may be normalized to a $^{19}$F standard. A $^{19}$F standard can be, for example, a solution of a known volume and concentration of a fluoro-chemical, where one can calculate the total number of $^{19}$F nuclei in the standard, denoted $F_{scan}$. A suitable fluoro-chemical reference ideally has a simple $^{19}$F NMR spectrum, preferable with a single narrow resonance (e.g. trifluoroacetic acid or TFA) and optionally a $^{19}$F chemical shift that is significantly different than the labeling fluorocarbon. The $^{19}$F standard can be placed in the same NMR tube as the labeled cell material being measured, in a separate tube, or optionally can be measured in a separate experiment using the same NMR instrument. The integrated area of the spectrum from the $^{19}$F standard, denoted $S_{stan}$, can then be measured. Subsequently, the mean number of $^{19}$F per labeled cell, denoted $F_c$, can be calculated, for example using the following formula:

$$F_c = \frac{S_{cells}}{S_{stan}} F_{stan} \frac{1}{N_{cells}}$$

where $N_{cells}$ is the number of labeled cells contained in the in vitro test sample. Quantitative NMR methods for $^{19}$F and other nuclei are well known in the art, and those skilled can devise many variations to the cellular dose calibration procedure described above. Besides $^{19}$F NMR, there are other quantitative methods that can be used to assay the cellular dose of the labeling reagent. For example, a reagent may be labeled fluorescently, luminescently, optically, or radioactively (see, U.S. Patent Publication Nos. 2007/0258886 and 2013/0343999, herein incorporated by reference in their entireties).

Similarly, in the case of in situ cell labeling of circulating phagocytes following iv injection of emulsion, to measure the effective cell labeling, one can extravasate a portion of peripheral blood from the subject and measure the effective cell loading of leukocytes using the methods described above. Furthermore, one or more of the various cell sorting or enrichment techniques can be used to sort out phagocytic cells (e.g., macrophages) prior to the loading measurement (above) to better define which cell population has been labeled in situ. The measured cell labeling parameter can then be used to calculate the apparent number of inflammatory cells present in tissue using the magnetic resonance methods described herein.

In order to extract accurate quantification of labeled cells and/or relative inflammation score from the $^{19}$F MRI/MRS data sets, additional calibrations and standards may be employed. For example, one can use a calibrated external $^{19}$F reference (i.e., phantom) during the actual $^{19}$F MRI/MRS scan of the subject material containing labeled cells. The image intensity of the calibrated phantom is used, tor examples, when analyzing the $^{19}$F MRI/MRS data set to prove an absolute standard for the number of $^{19}$F nuclei when examining the subject material or patient. The calibrated phantom is used to normalize the sensitivity of the particular MRI/MRS system that has been loaded with a particular subject to be imaged. The $^{19}$F reference may be, for example, one or more vessels containing a solution of a known concentration of $^{19}$F nuclei. In some embodiments, the solution contains a dilute concentration of the emulsified fluorocarbon labeling reagent. Optionally, the solution contains non-emulsified fluorocarbon labeling reagent, a gel, or liquid, for example that has been diluted in a suitable solvent. Optionally, the solution can be composed of another fluoro-chemical, ideally wish a simple $^{19}$F NMR spectrum, preferably with a single narrow NMR resonance (e.g. trifluoroacetic acid (TFA) or trifluoroacetamide (TFM) and other fluorinated acids, trifluorotoluene or trifluoroethanol). In some embodiments, the T1 and T2 values of the reference solution are similar to those of the labeling reagent. Optionally, the solution can contain perfluorocarbon-labeled cells, or lysines of the same. The non-cellular reference has the advantage of longer storage times. Optionally, the solution can take the form of a gel. The vessel containing the solution can be sealable, and can take a variety of geometries; vessel geometries including ellipsoidal, cylindrical, spherical, and parallel piped shapes. One or more vessels containing $^{19}$F reference solution can be used during the $^{19}$F MRI/MRS of the subject material if multiple $^{19}$F references (i.e., vessels) are used they can contain the same $^{19}$F concentration or different concentrations, and in the case of the latter, they ideally contain graded concentrations of fluorochemical. The placement of the calibrated $^{19}$F reference vessel(s) can in some embodiments, be placed externally or alongside, or optionally inside, the imaged subject or patient prior to data acquisition. In some embodiments, the reference is imaged using $^{19}$F MRI along with the subject in the same image field of view (FOV). Optionally, $^{19}$F MRS data is acquired in the reference either sequentially or in parallel with the subject data set. Optionally, data from the reference can be acquired using MRI/MRS acquired in a separate scan. Optionally, the external reference is not scanned along with a subject in every $^{19}$F MRI/MRS examination, but rather, values of the reference $^{19}$F signal intensity acquired using MRI/MRS is used from a scan of a comparable subject or a simulated-subject. In a given $^{19}$F MRI/MRS scan, the calibrated $^{19}$F standard may be sampled by one or more voxels. The observable $^{19}$F intensity produced by a voxel may be proportional to the concentration of the fluorochemical in the solution for gel and the voxel volume. Often in a $^{19}$F MRI scan the reference standard is comprised of many voxels. Often one calculates the mean intensity of one, several, or all voxels in the reference standard. Optionally, the mean image intensity is calculated over an ROI defined with in the $^{19}$F image of the reference standard. Optionally, the physical geometry of the reference standard vessel contributes to defining the observed $^{19}$F signal intensity, for example, the volume compartment(s) containing the $^{19}$F reference solution is smaller than the voxel volume. In other embodiments, the calibrated external reference relies on a solution with a $^{1}$H signal intensity of a known number of detectable $^{1}$H; in this case the sensitivity of the $^{19}$F signal in the subject material is reference to a $^{1}$H calibrated standard. Ideally the solution or gel in the $^{1}$H calibrated reference (contained in a vessel as described above) yields a simple $^{1}$H NMR spectrum, preferably with a single narrow NMR resonance (e.g., H$_{2}$O, or mixtures of H$_{2}$O-D$_{2}$O). Other than a different nuclei, the use of the $^{1}$H standard reference is the same in many other respects as described above for the $^{19}$F reference. Optionally, the calibrated reference standard contains any other MRI/MRS-active nuclei. In some embodiment, the reference is an internal organ or tissue detected via $^{1}$H MRI/MRS, where the data may be raw or normalized. In other embodiments, the reference is a standard that is not scanned with the subject, but is calibrated by relevant factors such as the weight of the patient or the size of the body cavity.

By computationally manipulating or combining two or more key parameters from the $^{19}$F MRI/MRS data set, one can calculate the number of labeled cells and/or relative amount of inflammation present in an ROI as described herein. For example, a fey set of parameters may include: (i) the cellular dose of labeling agent (i.e., F$_c$) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see Magnetic Resonance Imaging, Third Edition, chapter 4, editors D. D. Stark and W. G. Bradley, Mosby, Inc., St, Louis Mo. 1999). Those skilled in the art can derive other parameters, combinations of the above set, or derivations thereof, particularly from the $^{19}$MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters, (i-x, above), any subsets of these, or any of their combinations or approximations, to estimate the effective number of labeled cells seen by $^{19}$F MRI in the subject material, denoted by N$_c$. For example, one can use an equation of the following form:

$$N_c = \frac{[F_R]v}{I_R} \frac{1}{F_c} \sum_{F_c}^{N_{ROI}} I_c^{(i)}$$

where: N$_c$=total number of labeled cells in the ROI; [F$_R$]=concentration of $^{19}$F in the calibrated $^{19}$F reference solution (or gel); v=voxel volume; I$_R$=mean intensify of the calibrated $^{19}$F reference taken with the MRI/MRS scan, averaged over one or more voxels, F$_c$=average $^{19}$F cellular dose of the labeling agent measured in vitro; N$_{ROI}$=number of voxels in the ROI containing labeled cells; I$_c^{(i)}$=image intensify of the i$^{th}$ voxel in the ROI containing labeled cells; i=unitless index for voxels in the ROI containing labeled cells. See, U.S. Patent Publication No. 2013/0343999, herein incorporated by reference in its entirety.

There are also many ways to approximate N$_c$ from the $^{19}$F data set. For example, one could use the following expression.

$$N_c \approx \frac{I_c^{avg}}{I_R} [F_R] v \frac{1}{F_c} N_{ROI}$$

where I$_c^{avg}$ is the average intensity of the ROI containing the labeled cells, (i.e. the average intensity of the N$_{ROI}$ voxels).

As another example, one could use the following expression.

$$N_c \approx \frac{I_c^{avg}}{I_R} V_c \frac{1}{F_c} [F_R]$$

where $V_c$ is the total volume of the ROI containing the labeled cells.

As a further example, one could use the following expression.

$$N_c \approx \frac{I_c^{avg}}{I_R} \frac{V_c}{V_{rc}} \frac{1}{F_c} N_R$$

where $V_R$ is the effective volume of the reference in the $^{19}F$ MRI/MRS and $N_R$ is the number $^{19}F$ nuclei in $V_R$. Note that in all of the above formulas the various intensities (i.e., $I_R$, $I_c^{avg}$, $I_c^{(i)}$) can be normalized to the image noise, and thus the above formulas can be equivalently expressed in terms of the appropriate SNR values for the particular regions. Thus, there are many ways to estimate the number of labeled cells, $N_c$, and many similar forms of these basic expressions can be derived by basic mathematical manipulations, however, all rely on the same basic content contained within the input parameters described by (i-x). Furthermore, quantification of labeled cells in an ROI need not be expressed in terms of absolute numbers or effective cell numbers. Other quantitative indices can be derived that are indicative of the amount of cells in an ROI. For example, one can calculate the ratio $I_c^{avg}/I_R$, or the ratio of the average SNR values observed in the ROI and the reference; all of these fall within subsets of the above expressions and/or the parameters. See, U.S. Patent Publication No. 2013/0343999, herein incorporated by reference in its entirety.

It is noted that the above analysis of cell numbers and related indices assume that the $^{19}F$ NMR relaxation times (i.e., particularly T1 and/or T2) of the fluorocarbon label is approximately the same as material in the calibrated $^{19}F$ reference standard. In the case that the relaxation times are not comparable, one of skill in the art can readily correct for this by employing the known MRI intensity equations of the particular imaging protocol being used, expressed in terms of T1 and T2.

Optionally, the $^{19}F$ MRI data set of the subject material can undergo post-processing before the actual cell quantification calculation is performed (as described above). For example, post-processing algorithms may include "de-noising" the $^{19}F$ data set. This can be accomplished by, for example, by thresholding the image to cut off low-intensity noise; this involves rescaling the image intensity so that low values are set to zero. In magnitude MRI images, random Johnson noise is often apparent and uniformly distributed across the image FOV. It is well known in the art that one can threshold out the low-level image intensity so that regions known to contain no true signal (i.e. devoid of $^{19}F$ and/or $^1H$ nuclei) appear to have a null or very near-null intensity. This process can be performed in an ad-hoc fashion (i.e., "manually" or by visual inspection), or by using a computer algorithm. In other embodiments, de-noising of the data set can be achieved by using other algorithms, for example using wavelet analysis, and many methods are known in the art for image de-noising.

The following references are incorporated in their entirety herein: Khare, A., et al., INTERNATIONAL JOURNAL OF WAVELETS MULTIRESOLUTION AND INFORMATION PROCESSING, 3 (4): 477-406 December 2005; Cruz-Enriquez, H., et al., IMAGE ANALYSIS AND RECOGNITION, 3656: 247-254 2005; Awate, S P., et al., INFORMATION PROCESSING IN MEDICAL IMAGING PROCEEDINGS, 3565: 677-688 7005; Ganesan. R.; et al., IE TRANSACTIONS, 36 (9): 787-806 September 2004; Seheunders, P., IEEE TRANSACTIONS ON IMAGE PROCESSING, 13 (4): 475-485 April 2004; Ghugre, N R., MAGNETIC RESONANCE IMAGING, 21 (8): 913-921 October 2003; Bao, P., et al., IEEE TRANSACTIONS ON MEDICAL IMAGING, 22 (9): 1089-199 September 2003; Wu, Z Q., et al., ELECTRONICS LETTERS, 39 (7): 603-605 Apr. 3, 2003; LaConte, S M., et al., MAGNETIC RESONANCE IN MEDICINE, 44 (5): 746-757 November 2000: Laine, A F., ANNUAL REVIEW OF BIOMEDICAL ENGINEERING, 2: 511-550 2000; Zuroubi, S., et al., MAGNETIC RESONANCE IMAGING, 18 (1): 59-68 January 2000: Nowak, R D., IEEE TRANSACTIONS ON IMAGE PROCESSING, 8 (10): 1408-1419 October 1999; and Healy, D M., et al., ANNALS OF BIOMEDICAL ENGINEERING, 23 (5): 637-665 September-October 1995.

Other types of post-processing algorithms are known in the art that can be applied to the $^{19}F$ MRI data set before or after quantification, such as zero-filing (A Handbook of Nuclear Magnetic Resonance, 2nd Edition, Ray Freeman, Addison Wesley Longman Press 1997) and various image interpolation, de-noising, and image smoothing algorithms (for example, see The Image Processing Handbook, 3rd Edition, John C. Russ, CRC Press/IEEE Press).

In certain embodiments the above set of key parameters (i-x) can be used to derive quantitative or statistical measures of the accuracy or confidence of the measured number of labeled cells or related indices. $^{19}F$ MRI/MRS data sets are often subject to SNR limitations within ROI, and thus if is often useful to calculate a metric of the confidence or accuracy of the measurement. Many methods are known in the art for the statistical analysis of MRI and other biomedical-type images. The embodiments described herein are understood to encompass these known methods.

Additional descriptions of useful MRI techniques and the like can be found, for example, in U.S. Pat. No. 9,352,057, the contents are herein incorporated by reference in its entirety.

Pharmaceutical Formulations and Uses

PFC emulsion nano-particles may be functionalized as a MR molecular imaging by bonding paramagnetic chelates and homing ligands onto an external phospholipid monolayer in MRI field, and many studies of the PFC emulsion nano-particles have been conducted as drug delivery vectors including bioactive agents (US 2004/0115192 A1; U.S. Pat. No. 6,676,963B1; US 2003/0086867; US 2003/0215392 A1; US 2004/0248856 A1). In the MRI, the nuclei are dephased and then rearranged in the direction of a magnetic field. At this time, the process of supplying energy to the lattice of the nuclei to reach a thermal equilibrium is referred to as T1. The PFC emulsion nano-particles are used as T1-weighted ultraparamagnetic contrast agents reflected in particulate or molecular relaxivity.

In some embodiments, the emulsions of this invention are made using conventional means and methods and include components common to the well known emulsions of highly fluorinated organic compounds. Among the surfactants useful in the emulsions of this invention are any of the known anionic, cationic, nonionic and zwitterionic surfactants. Preferred examples include the nonionic surfactants, such as alkyl or aryl compounds, whose hydrophilic part consists of polyoxyethylene chains, sugar molecules, polyalcohol derivatives or other hydrophilic groups, for example, any of the BASF Wyandotte formulations of polyoxyethylene and polyoxypropylene oxides sold under the tradename "Pluronic", for example, Pluronic F-68 or F-108, or zwitterionic surfactants. Fluorinated surfactants, e.g., ATSURF® F-31 (ICI, Wilmington, Del.), may also be used in the emulsions of this invention. See, e.g., Riess et al., "Design, Synthesis And Evaluation Of Fluorocarbons And Surfactants For In Vivo Applications, New Perfluoroalkylated Polyhydroxylated Surfactants", Artif. Cells Artif. Organs, 16, pp. 421-30 (1988). Again, combinations of these surfactants may, of course, be used in the emulsions of this invention. In addition, mixtures of compounds, one or more of which are not surfactants, but which compounds when combined act as surfactants, may also be usefully employed as the surfactant component of the emulsions of this invention. While the compositions may be generally referred to herein as emulsions, it should be understood that they may be considered solutions, micellar solutions, microemulsions, vesicular suspensions, or mixtures of all of these physical states. Accordingly, the term "emulsion" as used herein covers all these states and the novel surfactant or solubilizing agent is employed to enhance stable mixtures of these states and the novel surfactant or solubilizing agent is employed to enhance stable mixtures of these physical states of the oil and water phases.

In some embodiments, the surfactants used in the emulsions of this invention are physiologically acceptable, for example, preferably one or more of the following: egg and soybean phosphatides, lecithin, and alkyl salts of oleic acid, such as sodium oleate. Most preferable is lecithin. While the amount of a particular surfactant used in the emulsions of this invention depends on the amounts and properties of the other components of the emulsion, typically we employ between about 0.5 and 10% (by weight of the total emulsion) of surfactant. More preferably, we use about 1 to about 4% (by weight).

In some embodiments, the emulsions of this invention may also contain an oil that is not substantially surface active and not significantly water soluble. Such oils are, for example, described in EP 231,091, WO 89/10118 and U.S. Pat. No. 4,866,096. They include liquid fatty oils, hydrocarbons, waxes, such as monoesters of a fatty acid and a monohydroxide alcohol, long chain ethers, diglycerides, triglycerides, silicone oils and nitriles. Among the useful oils in these classes are palmitoyl oleate, octyl nitrile, dodecyl nitrile, soybean oil, safflower oil, mineral oil, hexadecane, and diglycerides and triglycerides having a C12-18 carbon chain. Of course, any mixture of triglycerides and or oils that are similar in fatty acid composition to triglycerides may be used. These oils may be used singly or in various combinations in the emulsions and processes of this invention. When our emulsions are to be used medically, the oil or combination of oils must, of course, be physiologically acceptable liquid fatty oils, such as soybean and safflower oils.

In some embodiments, the amount of oil, or oils, if present, in the emulsions of this invention varies over a wide range of concentrations depending on the concentration and properties of the other components of the emulsion, being principally dependent on the characteristics of the PFC ether hydride of the emulsion. The actual oil concentration to produce an acceptable emulsion for any given set of components is easily determined as taught by this invention using the simple techniques of preparing the emulsions at various oil concentrations. Within this teaching, we typically employ between about 0.5 and 20 v/v % of oil or a mixture of oils. Preferably, we employ between about 1 and 5 v/v %.

In some embodiments, the emulsions of this invention are useful as contrast media by various biological imaging modalities, e.g., nuclear magnetic resonance, 19 F-magnetic resonance imaging, ultrasound, x-ray, and computed tomography. In addition, the emulsions are useful as contrast agents and for direct imaging in 19 F-MRI. When used as contrast media, the emulsions of the invention may be administered, for example, by bolus, orally, subcutaneously, intraperitoneally, intrathecally, or other medically approved method of administration, e.g., catheterization, to the degree necessary such that the emulsions are capable of producing clear concise shadows of the desired part or parts of the anatomy.

In some embodiments, the emulsions of this invention may be prepared by conventional mixing of the perfluoroalkyl ether hydrides fluorinated components (discontinuous phase) with an aqueous (continuous) phase and a surfactant. Alternatively, the emulsions of this invention may be prepared by mixing an aqueous phase with any suitable surfactant, and optionally, osmotic agents, buffering agents, electrolytes if desired, other emulsifying agents, additional anti-oxidants, and the like into an aqueous dispersion. The perfluoroalkyl ether hydrides may then be mixed into the aqueous dispersion so as to provide an emulsion of this invention.

In some embodiments, the emulsions of this invention may also be prepared by pre-mixing an aqueous dispersion with any suitable surfactant(s) and, optionally, other conventional components of artificial bloods, e.g., osmotic agents and the like. The oil, if present, may then be mixed into the above-described aqueous dispersion at a predetermined rate. The perfluoroalkyl ether hydrides may then be mixed in at a predetermined rate so as to provide an emulsion of this invention.

In some embodiments, the emulsions may be prepared by the following method comprising: 1) performing surface reforming by allowing optical nano-particles coated with hydrocarbon to be coated with perfluorocarbons; 2) allowing the optical nano-particles surface-reformed at the step 1) to be dispersed into a perfluorocarbon liquid; and 3) emulsifying the liquid at the step 2). However the present invention is not limited thereto.

In some embodiments, a targeting moiety will be selected to facilitate association of the imaging reagent with the cell to be labeled. A targeting moiety may be designed to cause non-specific insertion of the fibrocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. Examples of the targeting moiety include but are not limited to: a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, the fluorocarbon imaging reagent comprises perfluoro-15-crown ether.

In some embodiments, the metal chelates SALTAME are stable in a wide pH range from pH=1 to pH=14. The metal chelates are also stable in the existence of other chelators including but not limited to ethylenediaminetetraacetic acid (EDTA).

Methods of administration of the emulsions of the application are well-known to those of skill in the art. To achieve the desired activity, the emulsions can be administered in a variety of unit dosage forms. The dose will vary according to the particular emulsion. The dose will also vary depending on the manner of administration, the overall health, condition, size, and age of the patient.

In certain embodiments, administration of the emulsions may be performed by an intravascular route, e.g., via intravenous infusion by injection. In certain embodiments, other routes of administration may be used. Formulations suitable for injection are found in Remington's Pharmaceutical Sciences, Mack Publishing Company, Philadelphia, Pa., 17th ed. (1983). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. In certain embodiments suitable buffers for intravenous administration are used to aid in emulsion stability. In certain embodiments glycols are used to aid in emulsion stability.

In certain embodiments, administration of the emulsions may be performed by a parenteral route, typically via injection such as intra-articular or intravascular injection (e.g., intravenous infusion) or intramuscular injection. Other routes of administration, e.g., oral (p.o.), may be used if desired and practicable for the particular emulsion to be administered.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject emulsions are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)).

Formulations of the subject emulsions include those suitable for oral, dietary, topical, parenteral (e.g., intravenous, intraarterial, intramuscular, subcutaneous injection), ophthalmologic (e.g., topical or intraocular), inhalation (e.g., intrabronchial, intranasal or oral inhalation, intranasal drops), rectal, and/or intravaginal administration. Other suitable methods of administration can also include rechargeable or biodegradable devices and controlled release polymeric devices. Stents, in particular, may be coated with a controlled release polymer mixed with an agent of the application. The pharmaceutical compositions of this disclosure can also be administered as part of a combinatorial therapy with other agents (either in the same formulation or in a separate formulation).

The amount of the formulation which will be therapeutically effective can be determined by standard clinical techniques. In addition, in vitro assays may optionally be employed to help identify optimal dosage ranges. The precise dose to be employed in the formulation will also depend on the route of administration. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula: Dose (mL)=[patient weight (kg)×dose level (mg/kg)/drug concentration (mg/mL)]

Therapeutics of the disclosure can be administered in a variety of unit dosage forms and their dosages will vary with the size, potency, and in vivo half-life of the particular therapeutic being administered.

For in situ applications, emulsions may be formulated to have optimal pharmacokinetic properties to enable uptake by phagocytes before clearance of the emulsion.

Doses of therapeutics of the disclosure will also vary depending on the manner of administration, the particular use of the emulsion, the overall health, condition, size, and age of the patient, and the judgment of the prescribing physician.

The formulations of the application can be distributed as articles of manufacture comprising packaging material and a pharmaceutical agent which comprises the emulsion and a pharmaceutically acceptable carrier as appropriate to the mode of administration. The pharmaceutical formulations and uses of the disclosure may be combined with any known compositions for the applications of the application.

Diagnostic Detection Methods

Exemplary applications of the present invention include the diagnostic detection of cells, e.g., immune cells that accumulate at tissue sites as part of an inflammatory response and cells that are grafted into the body in order to treat a disease or condition, i.e., cytotherapy. Cytotherapy can generally include the administration of cells to a subject in need thereof. In some cases, the imaging method described herein is used to diagnose a disease or to determine a prognosis. Cells can be endogenous cells in the body, for example, various immune cells (T cells, B cells, macrophages, NK cells, DCs, etc.), stem cells, progenitor cells, cancer cells, as well as engineered cells, which are often used in cytotherapy in its various forms. An engineered cell can express a heterologous nucleic acid or a recombinant protein.

Non-invasive imaging of cells, e.g., immune cells in the body is useful because it can aid in the diagnosis and monitoring of disease, e.g., inflammation. In the field of cytotherapy, the ability to image the cell graft provides valuable feedback about the persistence of the graft, potential cell migration, and improves safety surveillance. Many experimental cell therapies that are in clinical trials, e.g., stem cells and immunotherapeutic cells, could benefit from the use of this technology.

Computer Methods

Methods for quantifying labeled cells will typically be conducted with the aid of a computer, which may operate software designed for the purpose of such quantification. Such software may be a stand-alone program or it may be incorporated into other software, such as MRI image processing software. See, for example, U.S. Patent Publication No. 2007/0253910, herein incorporated by reference in its entirety.

The disclosure will be more readily understood by reference to the following examples, which are included merely for purposes of illustration, of certain aspects and embodiments of the present application, and are not intended to limit the disclosure.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

EXAMPLES

Example 1: Fluorous-Soluble Metal Chelate for Sensitive Fluorine-19 Magnetic Resonance Imaging Nanoemulsion Probes Description of fluorous-soluble metal chelates for use as sensitive fluorine-10 magnetic resonance imaging nanoemulsion probes can be found in Jahromi et al., *ACS Nano*, 2019 Jan. 22, 13(1):143-151, the disclosure is herein incorporated by reference in its entirety, including the figures, figure legends, and supplementary material.

Abstract

Fluorine-19 MRI is an emerging cellular imaging approach, enabling lucid, quantitative 'hot-spot' imaging with no background signal. The utility of 19F-MRI to detect inflammation and cell therapy products in vivo could be expanded by improving the intrinsic sensitivity of the probe by molecular design. Herein we describe a metal chelate based on a salicylidene-tris(aminomethyl)ethane core, with solubility in perfluorocarbon (PFC) oils, and a potent accelerator of the 19F longitudinal relaxation time (T1). Shortening T1 can increase the 19F image sensitivity per time and decrease the minimum number of detectable cells. We used the condensation between a tripodal ligand tris-1,1,1-(aminomethyl)ethane and salicylaldehyde to form the salicylidene-tris(aminomethyl)ethane chelating agent (SALTAME). We purified four isomers of SALTAME, elucidated structures using x-ray scattering and NMR, and identified a single isomer with high PFC solubility. Mn4+, Fe3+, Co3+, and Ga3+ cations formed stable and separable chelates with SALTAME, but only Fe3+ yielded superior T1 shortening with modest line broadening at 3 and 9.4 Tesla. We mixed Fe3+ chelate with perfluorooctyl-bromide (PFOB) to formulate a stable paramagnetic nanoemulsion imaging probe and assessed its biocompatibility in macrophages in vitro using proliferation, cytotoxicity and phenotypic cell assays. Signal-to-noise modeling of paramagnetic PFOB showed that sensitivity enhancement of nearly 4-fold was feasible at clinical magnetic field strengths using a 19F spin-density weighted gradient-echo pulse sequence. We demonstrated the utility of this paramagnetic nanoemulsion as an in vivo MRI probe for detecting inflammation macrophages in mice. Overall, these paramagnetic PFC compounds represent a platform for the development of sensitive 19F probes.

For decades, metal chelate chemistry has been the centerpiece in efforts to formulate magnetic resonance imaging (MRI) contrast media. A compelling direction is the use of metal chelates to emerging non-proton imaging approaches such as fluorine-19 MRI.[1] 19F MRI enables 'hot-spot' imaging with no background signal and quantification of spin density-weighted images.[2,3] 19F MRI using perfluorocarbon (PFC)nanoemulsion (NE) probes has been used to detect cell therapy products in vivo (e.g., stem cells and immune cells) that were labeled ex vivo prior to delivery to the subject; these methods have recently been translated into human patients.[4] In other uses, PFC probes have been used effectively for imaging leukocyte infiltrates associated with multiple inflammatory diseases.[3,5] In this approach, following intravenous injection, the NE droplets are taken up by monocytes and macrophages in situ, and these cells accumulate at sites of inflammation yielding 19F MRI hot-spots. The utility of this nascent technology could be expanded by improving the sensitivity of 19F detection via molecular design. 19F MRI is limited by the total amount and distribution of fluorine atoms introduced into the subject's tissue, as well as the amount of PFC that can be safely internalized into cells of interest. Thus, one must improve the intrinsic sensitivity of the PFC molecule. A key parameter for boosting sensitivity is decreasing the high 19F longitudinal relaxation time (T1) of PFC molecules. The T1 value ultimately limits the rate of 19F MRI data acquisition. Generally, 19F imaging requires summation of multiple acquisitions (i.e., signal averaging) to yield a sufficient signal-to-noise ratio (SNR) to gain statistical confidence. A high 19F T1 value generally requires a longer repetition time, thus limiting the number of acquisitions and amount of signal averaging attainable during a fixed total imaging time. Shortening T1 allows more signal averages and thus increases SNR, sensitivity, and decreases the minimum number of detectable cells per voxel in the same total scan time.

The intermolecular paramagnetic relaxation enhancement (PRE) mechanism[6] can be used to decrease T1 by incorporating paramagnetic centers such as Gd3+ and Fe3+ into or near the fluorous phase.[1,7] The strength of the PRE dipole-dipole interaction is inversely proportional to the sixth power (1/r6) of the fluorine-metal distance. Thus, paramagnetic centers bound to the NE surface can be inefficient, due to the long distance between the relaxation agent and the bulk PFC molecules inside the NE droplet. To yield the optimal T1 and T2 (spin-spin relaxation time) with minimal metal added, the paramagnetic center should be dissolved in PFC. However, dissolving the paramagnetic center is challenging due to PFC's highly hydrophobic and lipophobic nature. Free paramagnetic cations are insoluble in PFC; thus, they must be bound to a fluorous-soluble chelating agent. Previous work has shown than metal-binding β-diketones conjugated to linear perfluoropolyether (PFPE) have solubility in PFC's, and optimal 19F-relaxation occurred when bound to $Fe^{3+}$, whereas Gd3+ yielded severe line broadening.[1]

In this study, we present synthesis and characterization of a fluorophilic chelating agents based on a salicylidene-tris(aminomethyl)ethane core, referred to as SALTAME; these chelates are soluble in PFC and serve as potent PRE agents.

Herein we describe SALTAME structure, physical properties, NMR relaxation times and the impact of different bound metal cations, NE probe formulation, and characterization of probe-labeled macrophages in vitro. We also demonstrate the utility of paramagnetic SALTAME-PFC NE as an in vivo $^{19}$F MRI probe for detecting inflammation-associated macrophages in mouse. Overall, the creation of paramagnetic NE probes is a chemical synthesis avenue for advancing the field of $^{19}$F MRI.

Results/Discussion

Molecular Design and Synthesis of SALTAME Complex

Herein we provide a synthesis scheme for fluorophilic metal chelates. At design onset, based on prior work,[1] we assumed transition metals, and Fe3+ in particular, were the best T1 accelerator for PFCs, while paramagnetic lanthanides (e.g., Gd3+) caused severe line broadening, essentially becoming $^{19}$F T2 agents.[1] Moreover, perfluorooctylbromide (PFOB) is the preferred $^{19}$F-rich MRI signal media for metal chelate dissolution due to its rapid clearance from the body and well-characterized clinical safety profile.[8-10]

Figure 8:
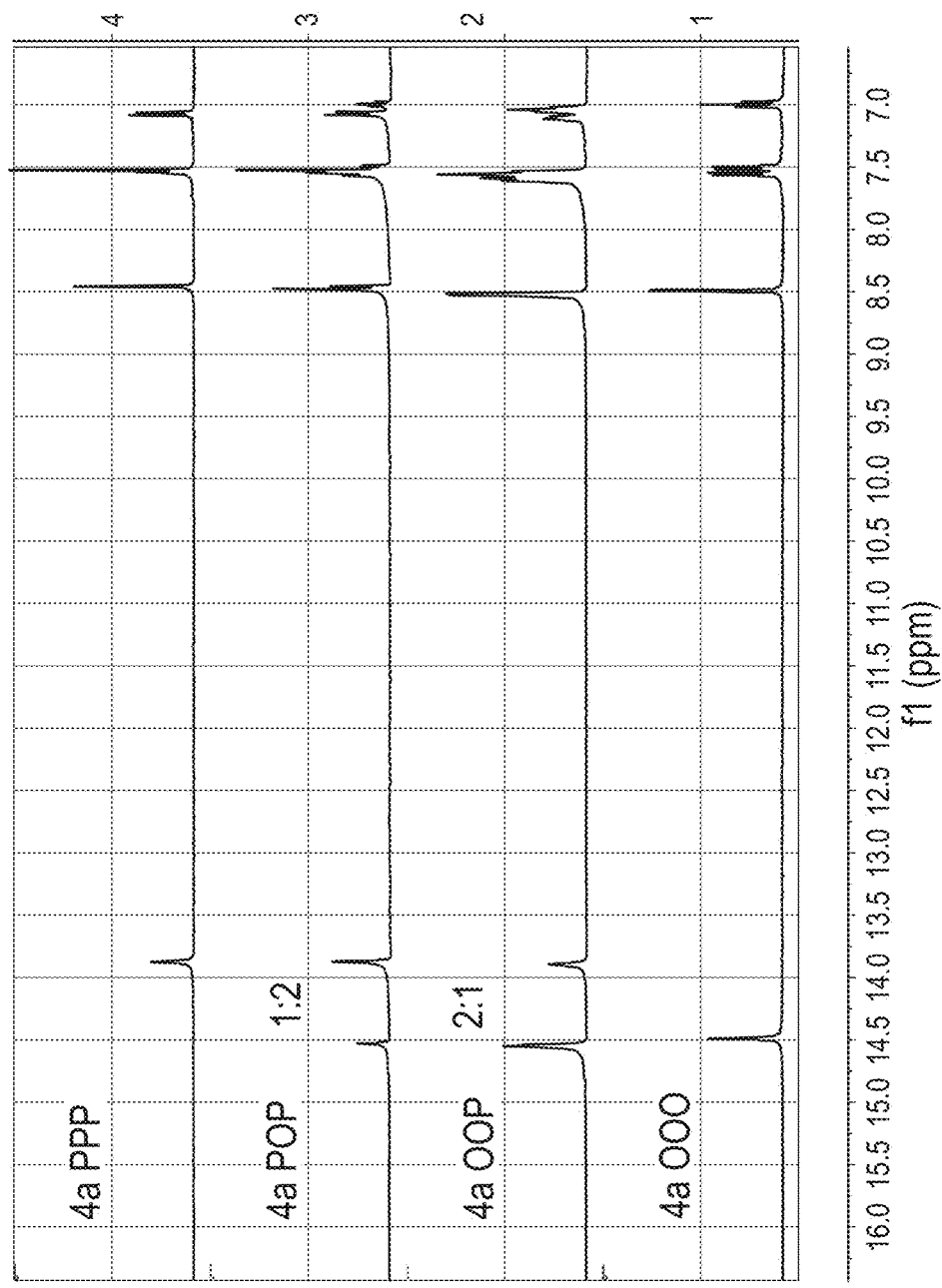
FIG. 8. A comparison of $^1$H NMR spectra of 4a isomers in the aromatic region.
Figure 9:
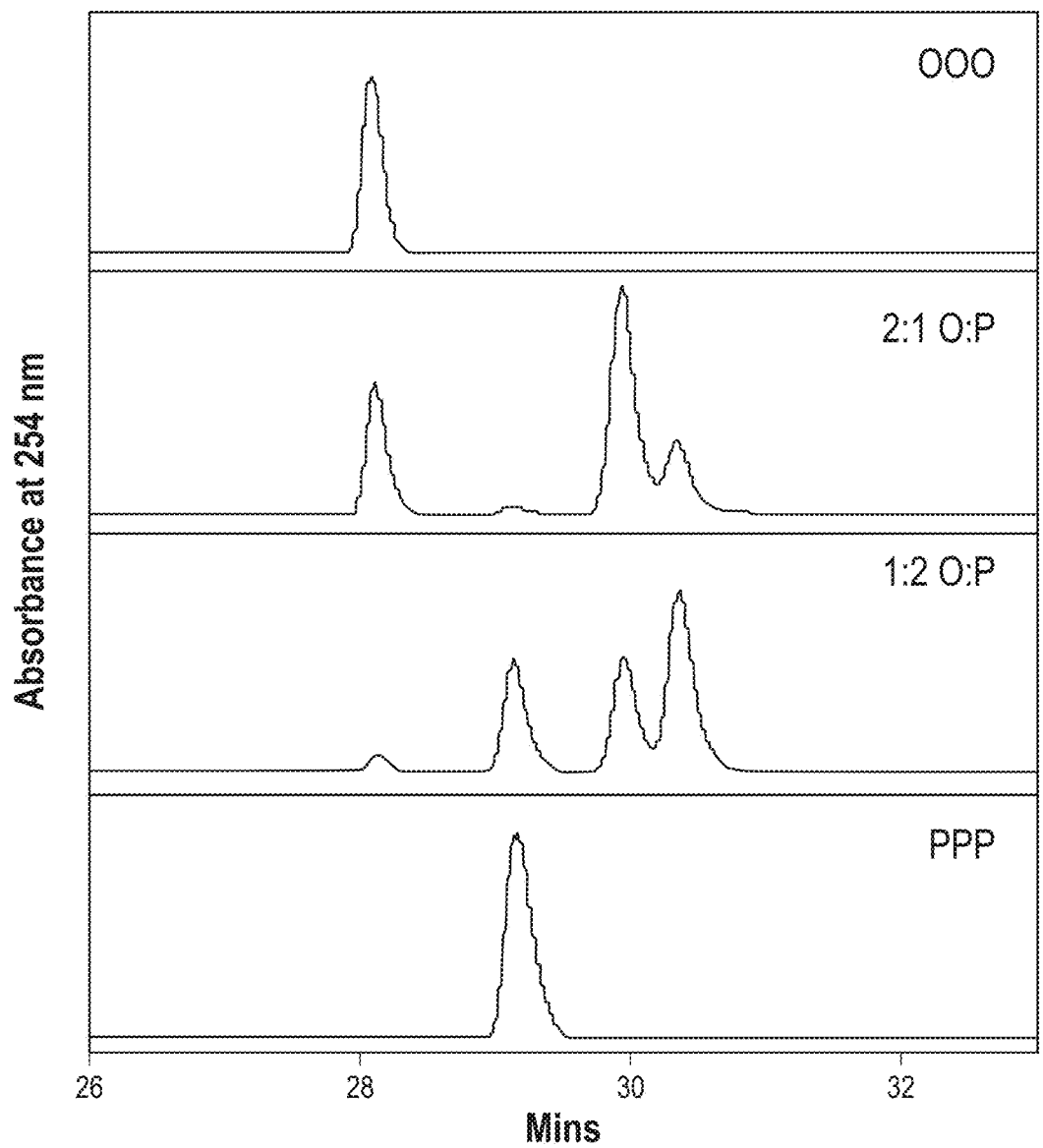
FIG. 9. Identification of 5a Fe OP isomers from HPLC product profiles of reactions using either 3a (0), 2:1 3a:3b, 1:2 3a:3b, or 3b (P).
Figure 10:
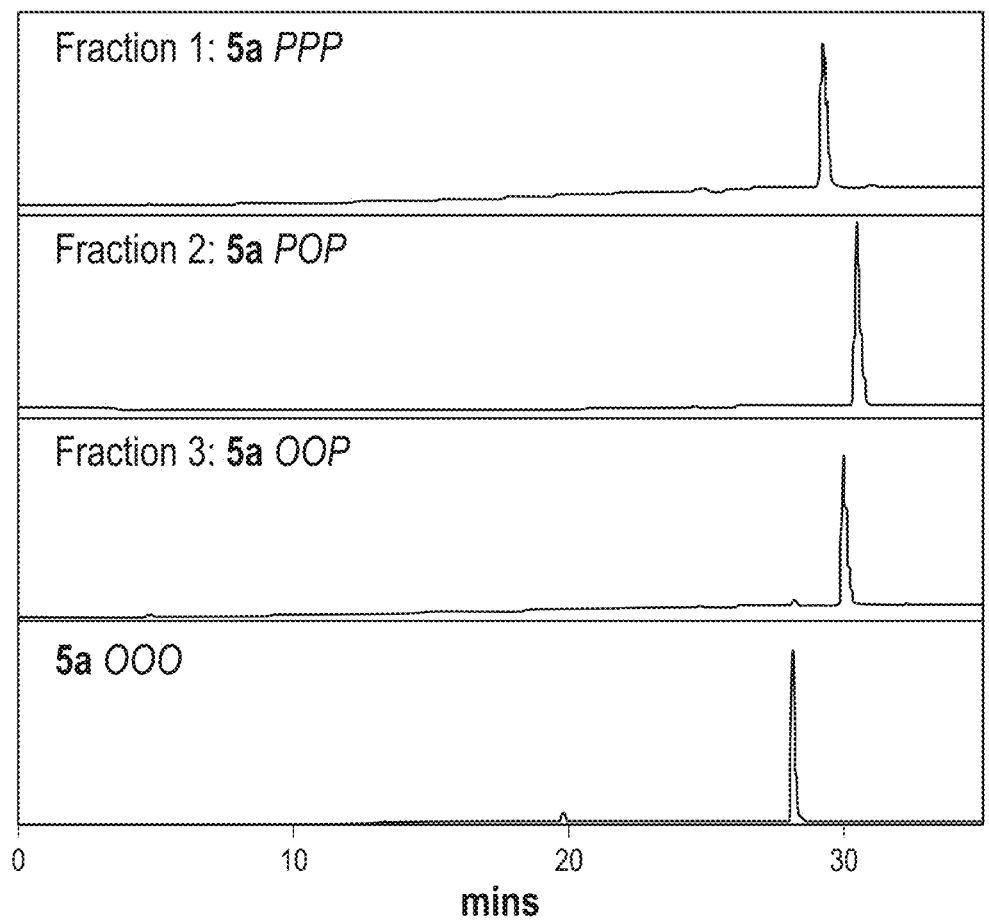
FIG. 10. Purity of column fractions (1-3) in separation of 5a Fe isomers by HPLC analysis and comparison with authentic 5a Fe OOO.
Figure 11:
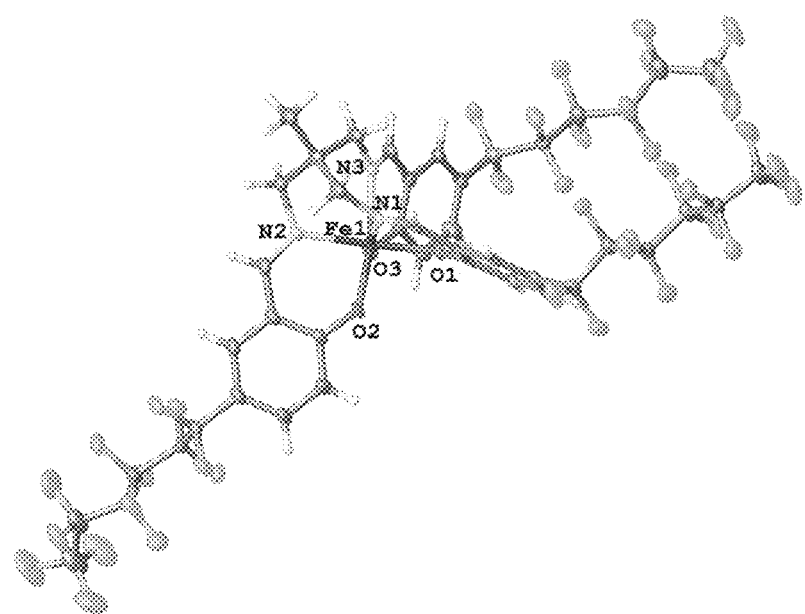
FIG. 11. Structure of 5a PPP.
Figure 12:
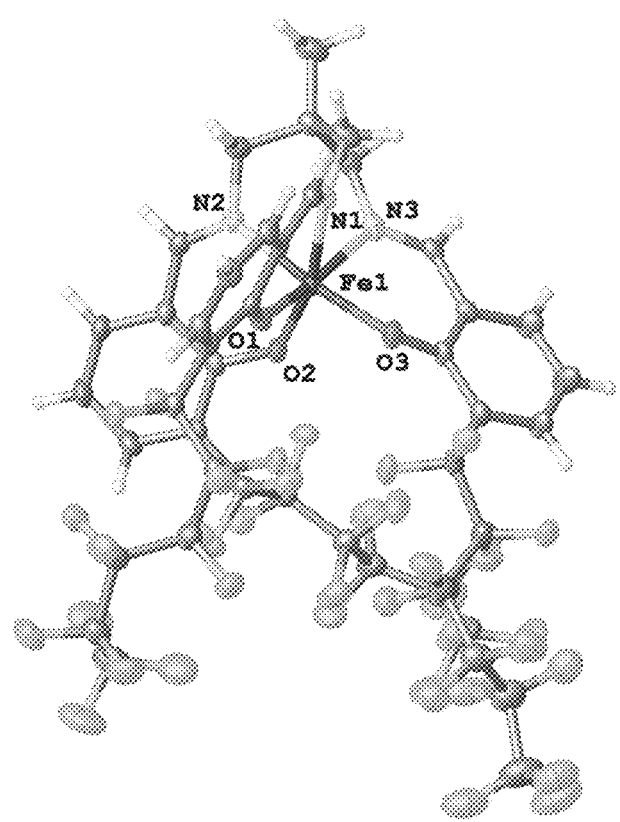
FIG. 12. Structure of 5a OOO.

We used (FIG. 1) the condensation between tris-1,1,1-(aminomethyl)ethane (TAME) and salicylaldehyde (SAL) to form the tripodal salicylidene-tris(aminomethyl)ethane chelating agent (SALTAME), for three reasons: (i) SALTAME is known to be a high affinity hexadentate chelating agent with three N and three O atoms, capable of binding different paramagnetic cations[11]; (ii) with a maximum of three negative charges, a chelated trivalent paramagnetic center (e.g., Fe3+) gives an overall neutral charge that favors solubility in PFCs; (iii) the geometry of the chelate stabilizes the high spin-state of cations, such as S=5/2 for Fe3+, which maximizes PRE effect.[11] However, unsubstituted SALTAME chelate (FIG. 1, 5 R1-R6=H) is insoluble in PFCs due to the simultaneous hydrophobic and lipophobic nature of all PFCs. As PFCs only dissolve highly fluorinated compounds, we sought to append perfluoroalkyl substituents to SALTAME complex to increase fluorophilicity. We tried the reported photochemical ring alkylation of SA with perfluoroalkyl iodides under basic conditions[12] but it gave a mixture of monoalkylated isomers 3a, 3b and dialkylated isomer 3c that were difficult to isolate (route 1). Instead, alkylation of bromosalicylaldehydes with heating under basic conditions,[13] followed by reductive debromination[14] gave 3a and 3b in much higher yields (route 2). Different isomers of 5a can be obtained by condensation of pure 3a or 3b or their weighed mixtures (1:2 or 2:1 w/w) with TAME and subsequent addition of ferric chloride and separation of the isomers. Though the SALTAME imines tend to dissociate, their iron complexes are very stable and can be readily isolated using chromatographic methods. Confirmation of their structures was achieved by high resolution liquid chromatography-mass spectrometry (LC-MS) of 5a, as well as NMR analysis of the respective SALTAME ligands (FIGS. 8-10). As expected, incorporation of paramagnetic Fe3+ into SALTAME greatly increased the intrinsic longitudinal and transverse relaxation rates for fluorine NMR of the 5a isomers (Table 3) and perturbed their proton and carbon NMR spectra. Definitive structural assignment of three of the four possible 5a isomers (5a POP, OOO and PPP) is shown by x-ray crystallography (FIGS. 2A-2C, FIG. 11, and FIG. 12 respectively).

The four 5a isomers were soluble in various PFC molecules, especially PFOB, and to a lesser extent (<0.5 mM) in perfluoro-15-crown-5-ether (PFCE) and perfluoropolyether (PFPE), which are other PFC compounds previously used for $^{19}$F MRI applications.8 Unexpectedly, the 5a isomers had remarkably different solubility in PFOB, with 5a PPP and 5a POP having the highest solubility (26 mM and 102 mM, respectively) among all the isomers (5a OOP and 5a OOO solubilities are 9.4 and 2.0 mM, respectively). Initial studies indicated that more stable PFOB nanoemulsions with 5a POP were formed with concentrations up to 30 mM of the SALTAME incorporated, thus we explored the properties and applications of this isomer. We also synthesized four additional SALTAME complexes 5c-f to explore the inclusion of other fluorous substituents, but all showed inferior solubility in PFOB.

TABLE 3

Intramolecular fluorine-19 relaxation rates (R1 and R2) at 9.4 T of Fe3+-SALTAME chelates 5a, Ga3+-SALTAME chelate 5a POP, and non-chelated perfluorinated salicylaldehydes 3a and 3b. Chelation with diamagnetic Ga3+ had only a small effect, whereas chelation with paramagnetic Fe3+ caused 2-3 orders of magnitude increase in R1 and R2 values. Relaxation rates correspond to 5 CF2 groups for precursors and Ga3+ chelate and the 5' CF2 group in all Fe3+ chelates. The +/− is standard error of mean (s.e.m.).

|  | ismoer | $R_1$ (s$^{-1}$) | $R_2$ (s$^{-1}$) |
| --- | --- | --- | --- |
| Non-chelated | 3b | 0.87 ± 0.01 | 1.12 ± 0.01 |
| Precursors | 3a | 1.33 ± 0.01 | 1.75 ± 0.01 |
| Ga$^{3+}$-SALTAME | 5a PPP | 2.36 ± 0.06 | 5.18 ± 0.01 |
| Fe$^{3+}$-SALTAME | 5a PPP | 146.7 ± 4.4 | 177.6 ± 3.9 |
| isomers | 5a POP | 176.9 ± 3.9 | 219.2 ± 0.3 |
|  | 5a OOP | 227.5 ± 7.3 | 333.9 ± 12.0 |
|  | 5a OOO | 414.7 ± 13.7 | 653.0 ± 14.5 |

Cation Selection

We screened the impact of various cations bound to SALTAME 5a and dissolved in PFOB via NMR relaxometry and susceptibility shift measurements (Table 4). Of the period-4 cations tested (V3+, Cr3+, Mn2+, Fe3+, Co2+, Cu2+, Ni2+, Zn2+, Ga3+), only Mn4+, Fe3+, Co3+, and Ga3+ formed stable and separable (by column chromatography) chelates with SALTAME. These chelates readily dissolved in PFOB, and their intermolecular $^{19}$F NMR relaxivities and susceptibility shift properties at 9.4 T are displayed in Table 4. The diamagnetic Ga3+ chelate had little relaxation effects or shift for PFOB. Co3+ had a significant effect on the transverse relaxivity (r2) but not on the longitudinal relaxivity (r1), and the shift was not impacted. Mn4+ changed r1, r2 and susceptibility shift, but to a much lesser extent than Fe3+. Gd3+ did not form a stable chelate with SALTAME, presumably because it required eight-to-nine coordination sites, whereas SALTAME had a coordination of six.

The longitudinal and transverse $^{19}$F relaxation rates of the Fe3+ chelate, 5a POP, was further evaluated as a function of iron concentration at the clinically-relevant field strength of 3 T yielding relaxivities r1 and r2 of 0.56 s−1 mM−1 and 1.67 s−1 mM−1, respectively, compared to 0.50 s−1 mM−1 and 1.07 s−1 mM−1 values of r1 and r2 at 9.4 T, respectively. For neat PFOB, R1/R2 values are 0.79 s−1/3.5 s−1 and 1.4 s−1/2.2 s−1 at 3 T and 9.4 T, respectively.

Overall, the 5a POP Fe3+ chelate served as the representative additive and was used to formulate paramagnetic PFOB (P-PFOB) NE which was used for further studies.

TABLE 4

Intermolecular fluorine-19 relaxivities (r1 and r2) and susceptibility shifts of SALTAME 5a POP chelates with Fe3+, Mn4+, Co3+, and Ga3+ at 9.4 T in PFOB. Relaxivities were measured for (CF2)6 fluorine atoms of PFOB, and susceptibility shifts were measured for CF3 representative fluorine atoms of PFOB. Overall, the SALTAME 5a POP Fe3+ chelate had the highest relaxivity and susceptibility.

|  | $Mn^{4+}$ | $Fe^{3+}$ | $Co^{3+}$ | $Ga^{3+}$ |
|---|---|---|---|---|
| $r_1$ (s$^{-1}$ mM$^{-1}$) | 0.03 | 0.50 | 0.001 | 0.002 |
| $r_2$ (s$^{-1}$ mM$^{-1}$) | 0.13 | 1.07 | 0.15 | 0.02 |
| shift change (ppm/mM) | 0.035 | 0.060 | 0.001 | 0.001 |

Structure of Fe3+ SALTAME

Figure 13:
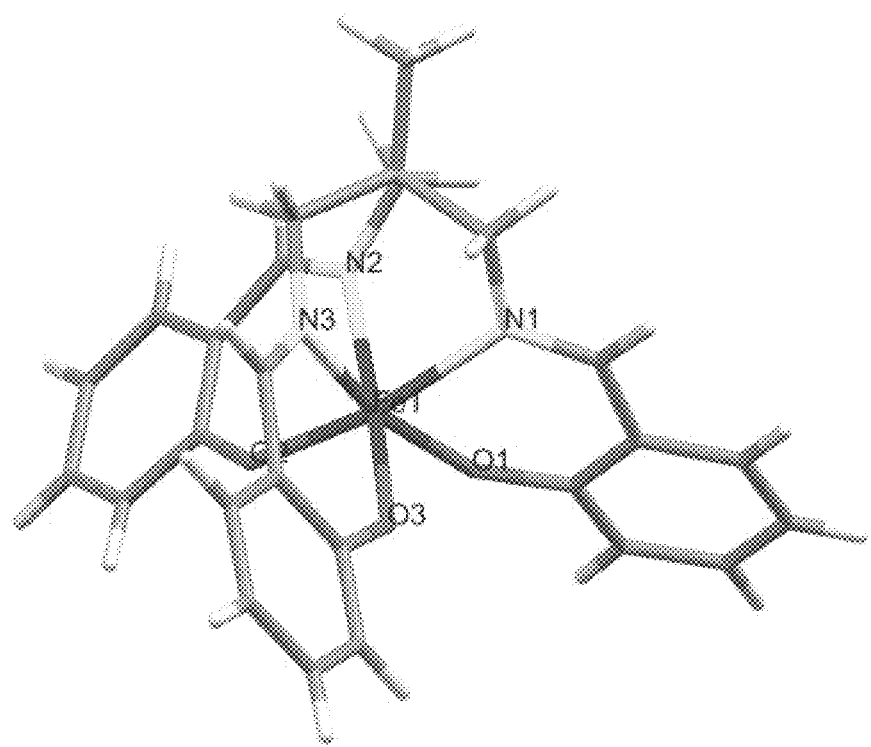
FIG. 13. Structure of unsubstituted Fe SALTAME ((5, $R_1$-$R_6$=H).

To characterize structure and Fe3+ coordination in chelates, data for 5a POP, PPP and OOO were obtained by x-ray crystallography (FIGS. 2A-2C, FIG. 11, FIG. 12) and NMR methods. Comparison of these structures with unsubstituted Fe3+-SALTAME (5, R1-R6=H; FIG. 13) confirmed that the hexadentate coordination of Fe3+ was not affected by appending fluorous substituents to SALTAME with minimal differences in Fe—O or Fe—N bond lengths and angles compared to its non-fluorous parent.[11] From these structures, we speculated that the low solubility of 5a OOO in PFOB (Table 4) may be explained by the observation that all three fluorous substituents were located on one side of 5a OOO yielding less favorable van der Waals interactions between substituents and PFOB. Fluorous substituents are more evenly distributed around the chelate in 5a PPP and POP, yielding higher affinity to PFOB.

Intramolecular $^{19}$F NMR relaxometry measurements of 5a isomers further confirmed the structural analyses. We observed that among Fe3+ chelates, 5a OOO isomer had the highest, and 5a PPP isomer had the lowest, R1 and R2 values (Table 3). Ortho-substitution caused a more drastic intramolecular PRE, by ~3 orders of magnitude, compared to para-substitution due to the closer proximity of the Fe3+ paramagnetic center to the ortho position (6.91 nm) compared to the para position (9.53 nm).

Sensitivity Enhancement of P-PFOB

We modeled potential MRI sensitivity enhancement of P-PFOB compared to undoped PFOB based on measured $^{19}$F NMR relaxivities in these materials. Modeling results (FIG. 3A) show multi-fold sensitivity improvement was possible using a gradient-echo (GRE) based MRI pulse sequence with echo time (TE)<0.8 ms. Model details are given in the Supplementary Information section below.

To support these findings, experimental data were acquired in an MRI phantom (FIG. 3b) consisting of two NMR tubes containing PFOB and P-PFOB nanoemulsions. The phantoms were imaged twice at 9.4 T using a GRE chemical shift imaging (CSI) pulse sequence with two different repetition time (TR) parameters set according to TR=0.5T1 for PFOB or P-PFOB, respectively, with the optimal Ernst angle condition set for each TR-value; both images were acquired using the same total imaging time. (See Supplementary Information below). Image results (FIG. 3B) show the P-PFOB tube had 2.5 times higher SNR than the PFOB tube when comparing the optimal SNR acquisition for each tube, consistent with the model prediction. This phantom imaging example does not represent the absolute value or upper limit to the possible SNR enhancement achievable with these materials; varying [Fe3+], magnetic field strength, pulse sequences and acquisition parameters may yield different values of SNR enhancement.

Imaging Probe Formulation

Figure 14:
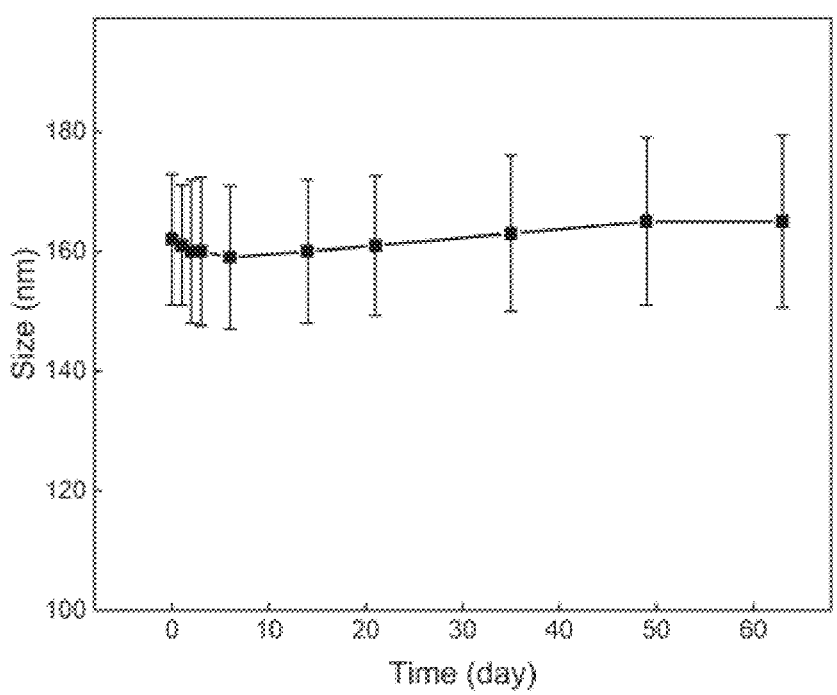
FIG. 14. Dynamic light scattering (DLS) characterization of P-PFOB NE ([Fe$^{3+}$-SALTAME 5a POP]=20 mM in PFOB) at 4° C. Full height of error bars represents polydispersity index (PDI).
Figure 15:
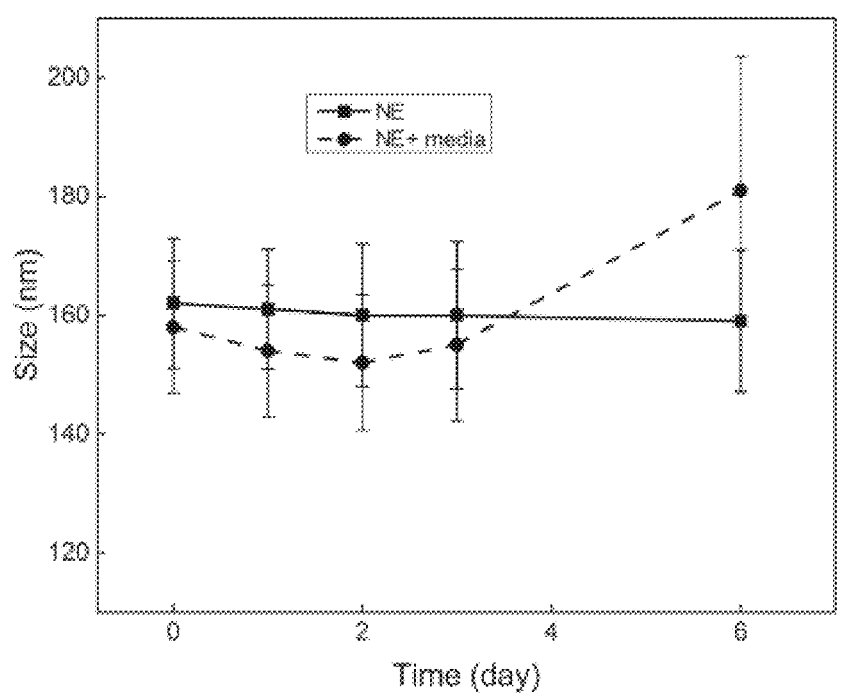
FIG. 15. NE stability in the presence of proteinaceous media. Here, DLS measurements were made with P-PFOB NE ([Fe$^{3+}$-SALTAME 5a POP]=20 mM in PFOB) in PBS solution with or without 10% fetal bovine serum (NE+media and NE, respectively) and stored at 37° C. Full height of error bars represents polydispersity index (PDI).

To create NE-based imaging probes, we formulated colloidal suspensions of P-PFOB. High-shear homogenization of components was used to form NE.[15] To stabilize the NE, egg yolk phospholipids (EYP) was used as a surfactant; P—PFOB has a slight lipophilic character due to PFOB's single bromine, yielding a cohesive tendency between PFOB and the fatty acid chains of EYP.[16,17] Minor surfactant components were also added including CH3-(CH2)5-(CF2)5-CF3, which acted as molecular dowels improving the emulsion stability,[18] Cremophor EL (Polyoxyl 35 hydrogenated castor oil) to decrease NE droplet size and increase shelf-life and circulation time, 19 and mannitol as an isotonizer. After homogenization of P-PFOB ([5a POP]=20 mM) with surfactants, average NE particle size was ~162 nm with polydispersity index (PDI) of 0.27, as measured by dynamic light scattering (DLS). Using similar methods, this particle size was comparable to nanoemulsions made without chelate.[15] The final P-PFOB NE had [F]=14.26 M with PFOB:5a POP molar ratio of 192:1. The R1 and R2 parameters were 9.01±0.03 s−1 and 16.66±0.10 s−1 at 9.4 T, respectively. The NE stability was confirmed by longitudinally monitoring of particle size using DLS measurements for emulsion stored at 4° C. over 60 days (FIG. 14). Also, the NE complex was stable for at least 3 days at 37° C. in proteinaceous saline media used to mimic the blood circulation environment (FIG. 15).

Figure 16:
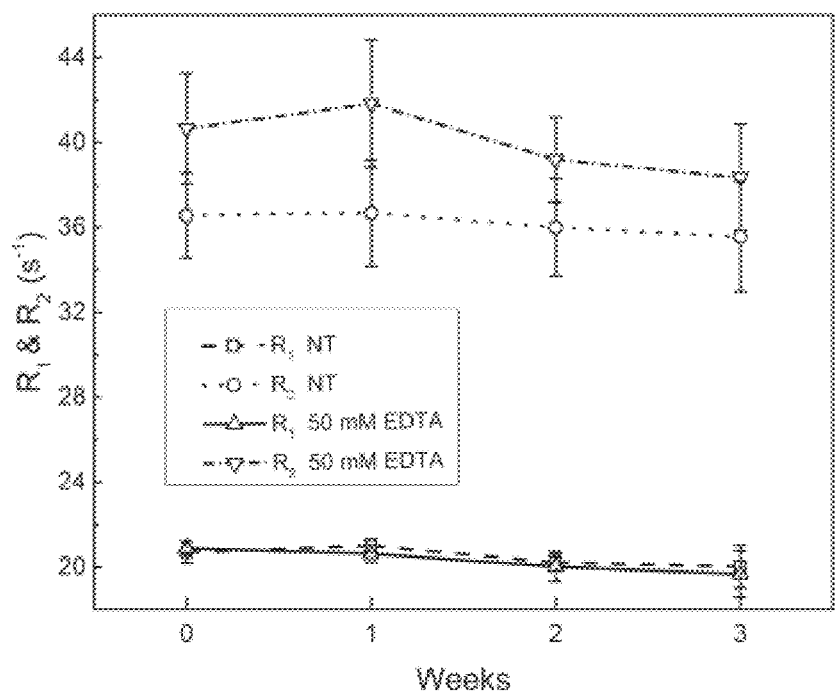
FIG. 16. Stability of P-PFOB NE ([Fe$^{3+}$-SALTAME 5a POP]=20 mM in PFOB) over time in the presence of EDTA, a competing iron chelate in the aqueous phase. The P-PFOB NE was treated with 50 mM EDTA or with no treatment (NT). Shown are $^{19}$F $R_1$=1/$T_1$ and $R_2$=1/$T_2$ values of 6 middle CF2 units of PFOB over a period of 3 weeks. Error bars are standard deviations from three independent replicates. The changes in $R_1$ and $R_2$ values upon addition of EDTA are not statistically significant (p>0.05).

We also evaluated the iron-binding stability of P-PFOB NE ([Fe3+-SALTAME 5a POP]=30 mM in PFOB) following addition of 50 mM ethylenediaminetetraacetate (EDTA), a strong competing Fe3+ chelating agent, to the aqueous phase; P-PFOB NE showed stable relaxometry parameters over 20 days, indicating that iron was tightly bound in the fluorous phase (FIG. 16).

P-PFOB Labeling Macrophages In Vitro

Figure 17:
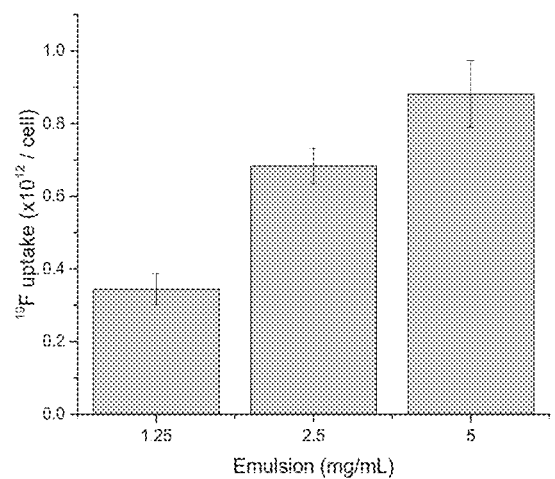
FIG. 17. Cellular uptake of NE, as measured by $^{19}$F NMR. RAW cells were labelled in culture for 16 h, using P-PFOB NE ([Fe$^{3+}$-SALTAME 5a POP]=20 mM in PFOB). Error bars represent standard error of mean from three independent experiments.
Figure 18:
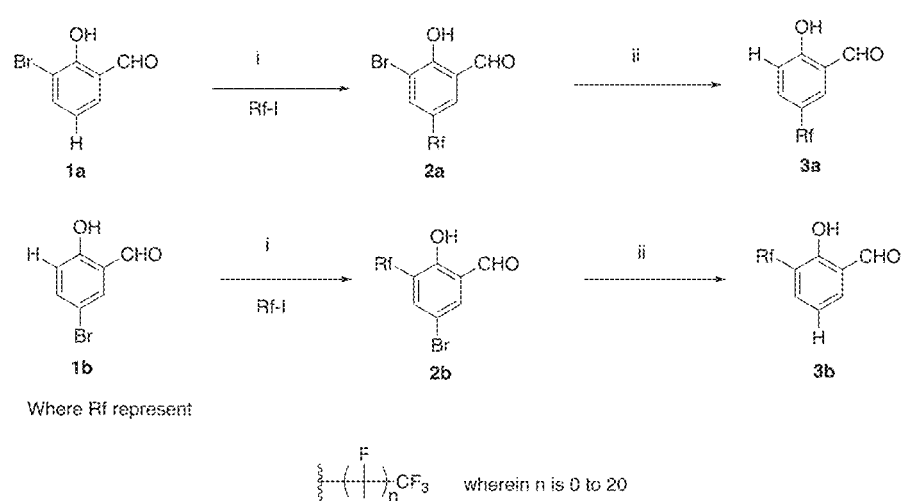
FIG. 18. Synthesis of fluorinated salicylaldehyde derivatives 2a, 2b, 3a and 3b.
Figure 19:
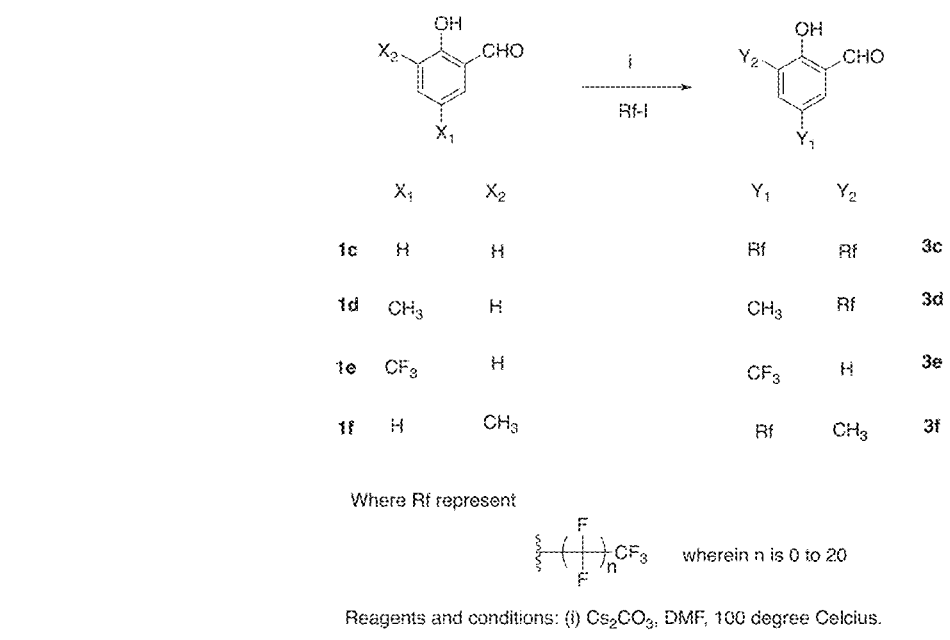
FIG. 19. Synthesis of fluorinated salicylaldehyde derivatives 3c, 3d, 3e and 3f.
Figure 26:
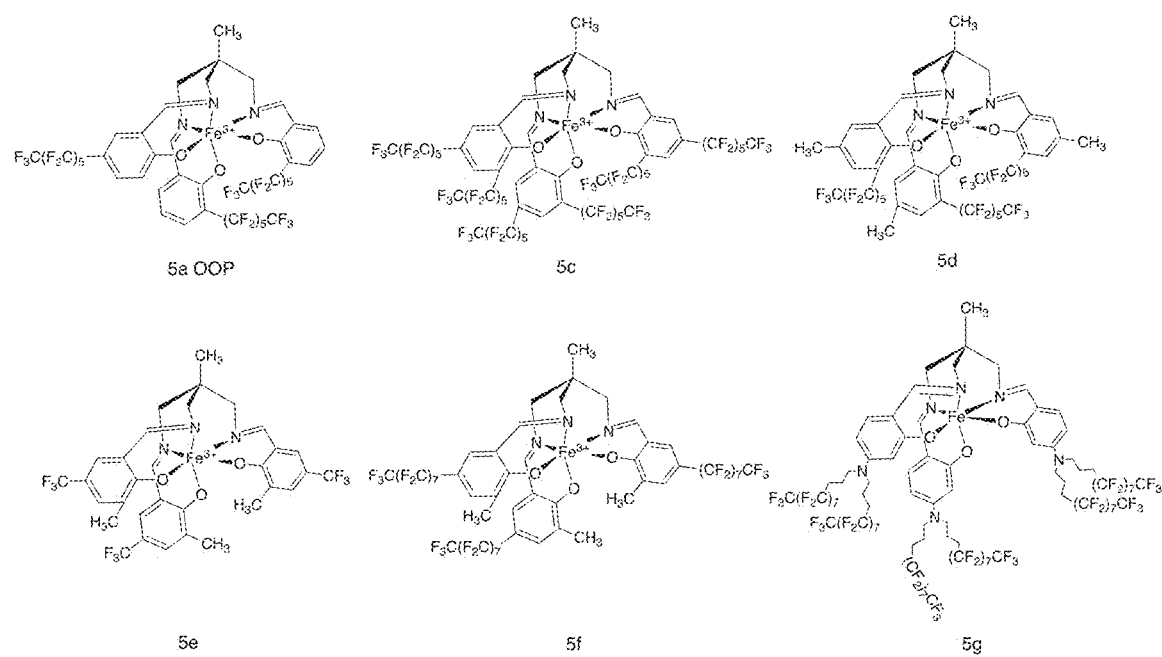
FIG. 26. Structures of fluorinated iron complexes 5a OOP, 5c, 5d, 5e, 5f and 5g.
Figures 27, 27A:
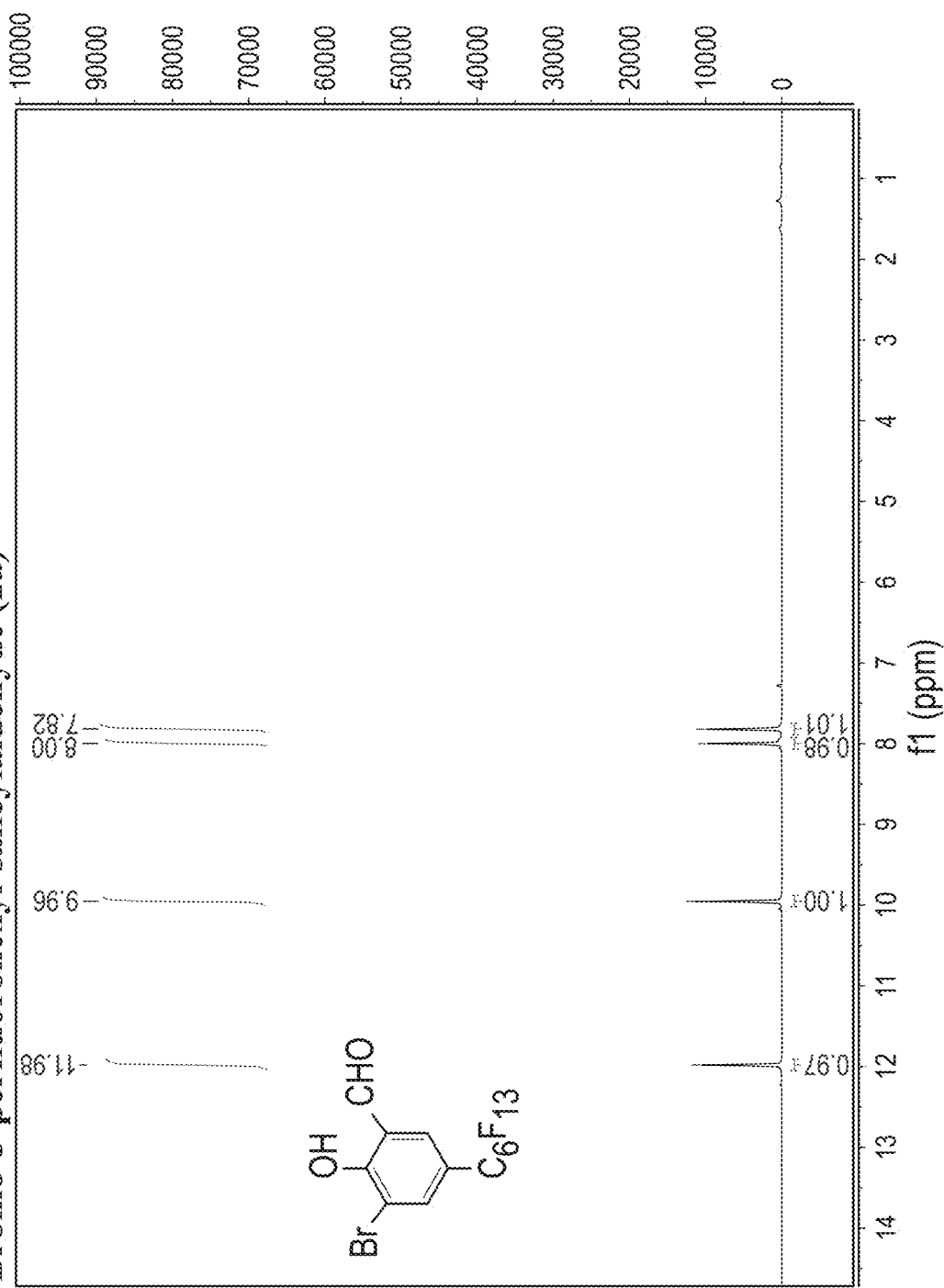
FIG. 27A-FIG. 27AQ. NMR Spectra for the compounds of the invention.
Figure 28:
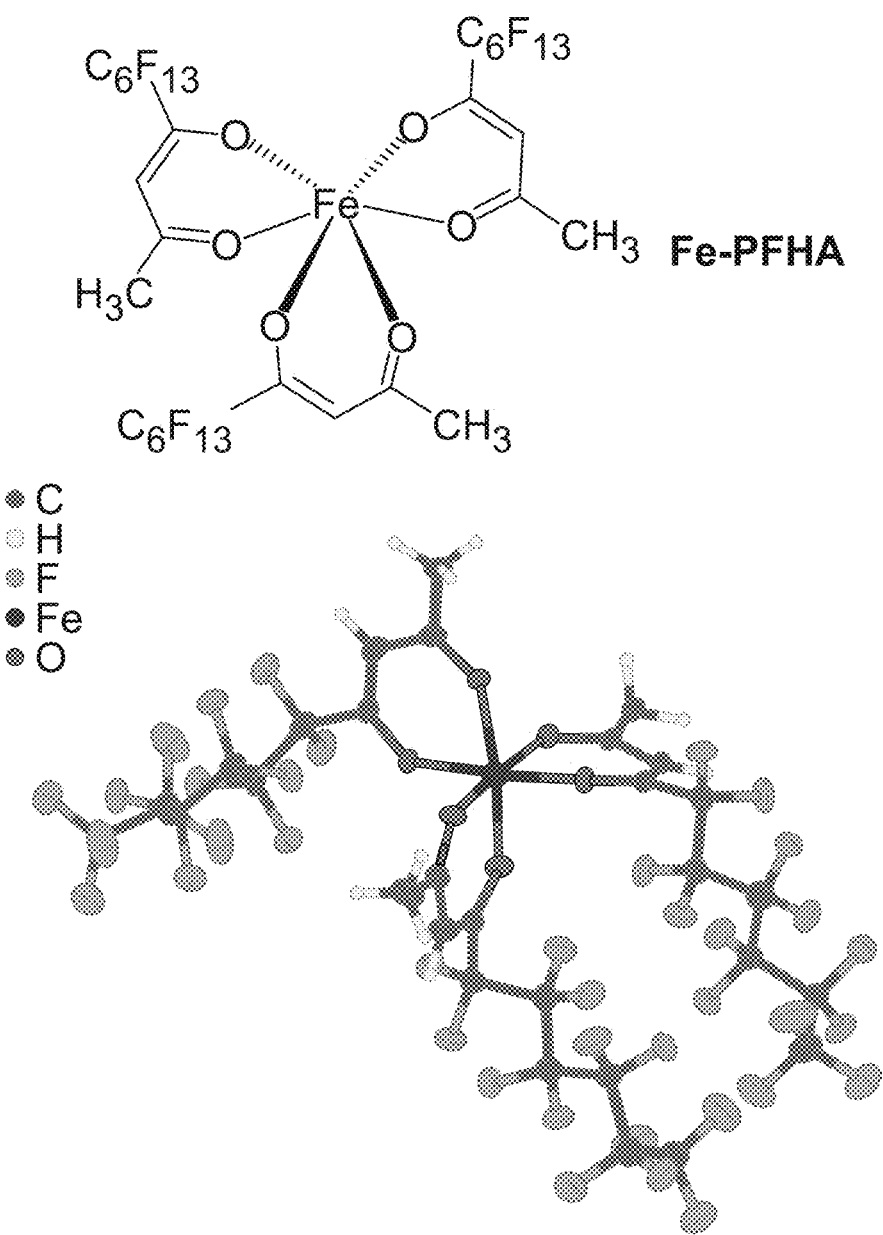
FIG. 28. Top: the structure of the fluorinated iron complex Fe-PFHA. Bottom: X-ray crystal structure of Fe-PFHA. Color code: Grey, carbon; White, hydrogen; Green, fluorine; Red, oxygen; Purple, iron.
Figure 29:
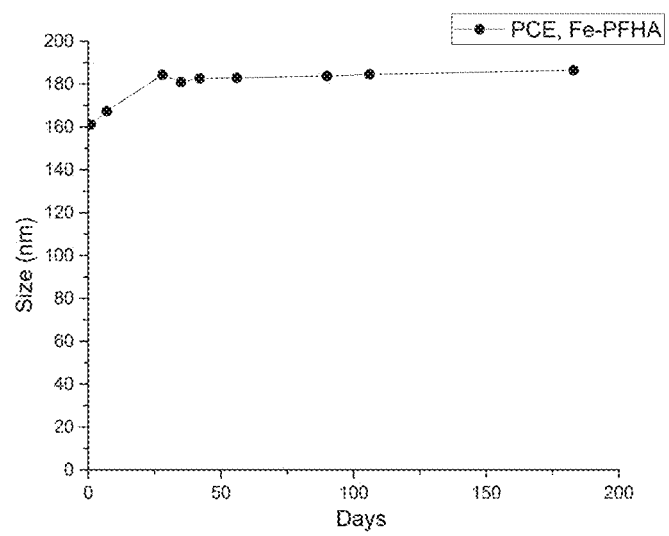
FIG. 29. Particle size of emulsion containing Fe-PFHA, PCE, Pluronic F68 and water stored at 4° C. 200 days.
Figure 32:
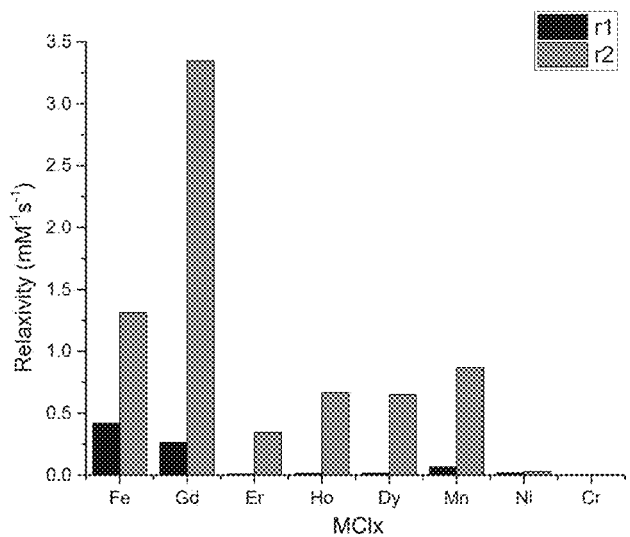
FIG. 32. The effect of metal ions to the relaxivity of fluorine in emulsion containing PFHA, PCE, Pluronic F68 and water (NE-DK).
Figure 33:
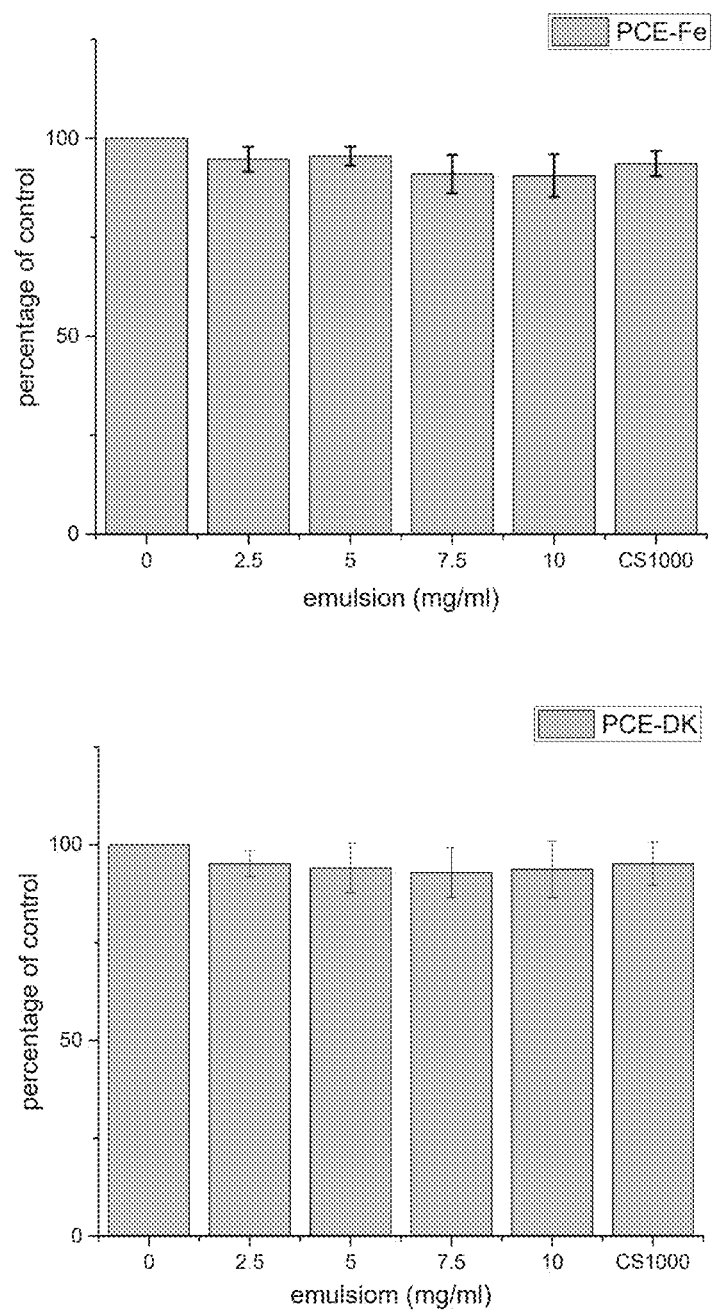
FIG. 33. Viability of RAW 264.7 cells after incubating with various amount of emulsion NE-A or NE-DK overnight. CS1000 represents the commercially available emulsion from CellSense and 5 mg/mL was used. Three independent studies were performed and the average was plotted.
Figure 34:
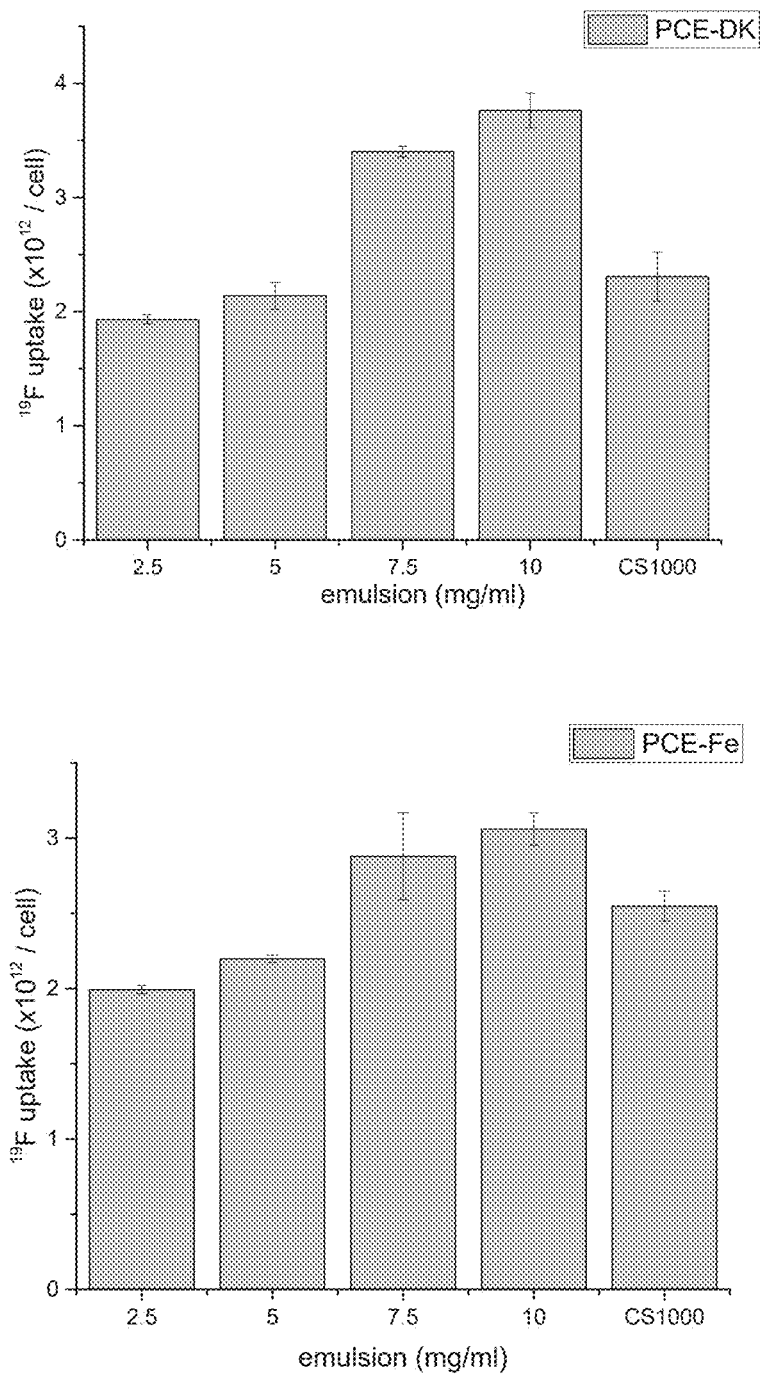
FIG. 34. RAW 264.7 cell uptake of emulsion NE-A and NE-DK at various concentrations. 5 mg/mL CS1000 from CellSense was used as comparison. Three independent studies were performed and the average was plotted.

To test biocompatibility of formulated P-PFOB NE as a cell labeling agent, we performed in vitro assays on a labeled murine macrophage cell line derived from blood (RAW 264.7). This cell is a representative phagocyte that would take up NE in vivo after intravenous delivery. Following a 16 hour incubation of RAW cells with various NE concentrations, the uptake level approached ~10$^{12}$ fluorine atoms per cell, measured by $^{19}$F NMR (FIG. 17).

We investigated the potential effect of P-PFOB labeling on RAW cell viability and phenotype (FIG. 4A-FIG. 4D). To study cytotoxicity, we used a flow cytometry assay for apoptosis (FIGS. 4A-4C) using 10-N-nonyl acridine orange (NAO).[20] As a positive control to induce oxidative stress, 10% ethanol was added to the cell media. No evidence of cytotoxicity was observed in NE-labeled compared to unlabeled cells (FIGS. 4A-4B), whereas ethanol-treated cells displayed cytotoxicity (FIG. 4C) and a characteristic bi-modal appearance described elsewhere.[20] FIG. 4B also shows that the labeled cells had increased side-scatter signal due to light scattering from PFC loaded intracellular vesicles, a common observation. Side-scatter is routinely used in flow cytometry to distinguish cell types by granularity. Labeled cells often display increased granularity with internalization of PFC droplets. To assay cell phenotype, we used flow cytometry to monitor potential changes in cell surface CD86 expression as a marker for macrophage activation, where increased levels indicated a pro-inflammatory response to label. Lipopolysaccharide (LPS) treatment was used as a positive control to induce a pro-inflammatory phenotype. The CD86 expression level in NE-labeled macrophages was comparable to unlabeled cells (FIG. 4D), whereas in LPS-treated cells the level was visibly higher, suggesting that P-PFOB NE did not stimulate a pro-inflammatory phenotype in macrophages.

Visualizing Inflammation In Vivo Using P-PFOB NE

Figure 5:
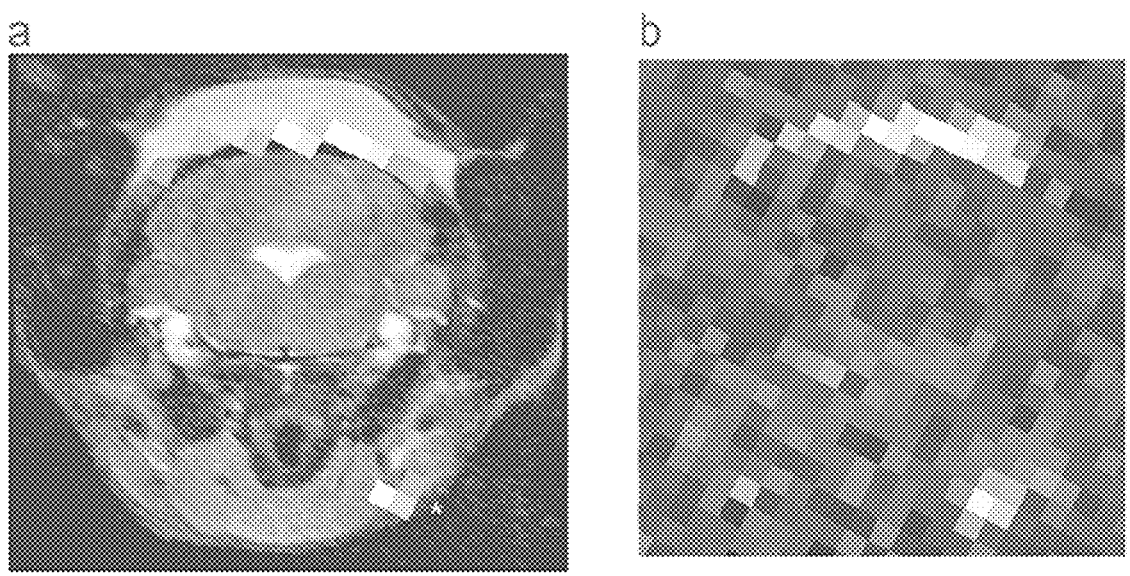
FIG. 5A-FIG. 5B. In vivo 1H/19F MRI using P-PFOB NE to visualize inflammation in mouse. An LPS-doped Matrigel plug implanted in the subcutaneous tissue of the neck was used to induce localized inflammation. One day after intravenous injection of P-PFOB NE ([Fe3+-SALTAME 5a POP]=20 mM in PFOB oil phase, yielding 4.4 mM in inoculant after P-PFOB NE formulation in water)), coronal 1H/19F MRI data of the plug region were acquired. (a) The grayscale 1H shows the hindbrain, cervical spine, and isointense Matrigel in the subcutaneous tissue of the neck. The 19F signal, rendered in pseudo-color, is present in periphery of the Matrigel plug and nearby lymph node (asterisk), consistent with the presence of inflammatory infiltrates. Panel (b) displays the raw, unthresholded 19F image. The peak voxel 19F SNR at Matrigel boundary and lymph node is 17.6 and 16.4, respectively. For 19F, CSI imaging parameters were: 134 averages, TR=13.3 ms, TE=0.53 ms, and matrix size 32×32. For T2*-weighted 1H, TR/TE=550/14 ms and matrix size 128×96. For additional details see Supplementary Information.

Proof of concept in vivo imaging of inflammation was performed using P-PFOB NE in a localized inflammation mouse model. Following established protocols,[5,8,21] localized inflammation was induced using an LPS doped Matrigel solution injected subcutaneously into the posterior neck of a C57BL/6 mouse (N=3). After 2 hours, a single bolus of P-PFOB NE (200 μl, [Fe3+-SALTAME 5a POP]=20 mM in PFOB oil phase), equivalent to 143 mmol F/kg body weight and 0.04 mmol chelated Fe/kg body weight, was injected intravenously. No adverse reactions were observed. Mice were imaged 24 hours after injection to allow for nanoemulsion uptake by monocytes/macrophages in situ. Scans were performed at 11.7 T. The $^{19}$F images were acquired using a two-dimensional CSI pulse sequence along with conventional anatomical 1H images. Representative coronal image in the neck region is displayed in FIGS. 5A-5B, where the Matrigel plug appears as a hyperintense, subcutaneous structure in the dorsal region of the 1H image (FIGS. 5A-5B). Robust $^{19}$F signal signifying macrophage uptake was seen co-registered with the Matrigel plug. $^{19}$F was also found in an area in the anterior neck, presumably at lymph node (asterisk, FIGS. 5A-5B). Overall, these in vivo data showed the feasibility of using P-PFOB NE as an inflammation imaging agent.

Susceptibility Shifts by Fe3+ SALTAME

Figure 6:
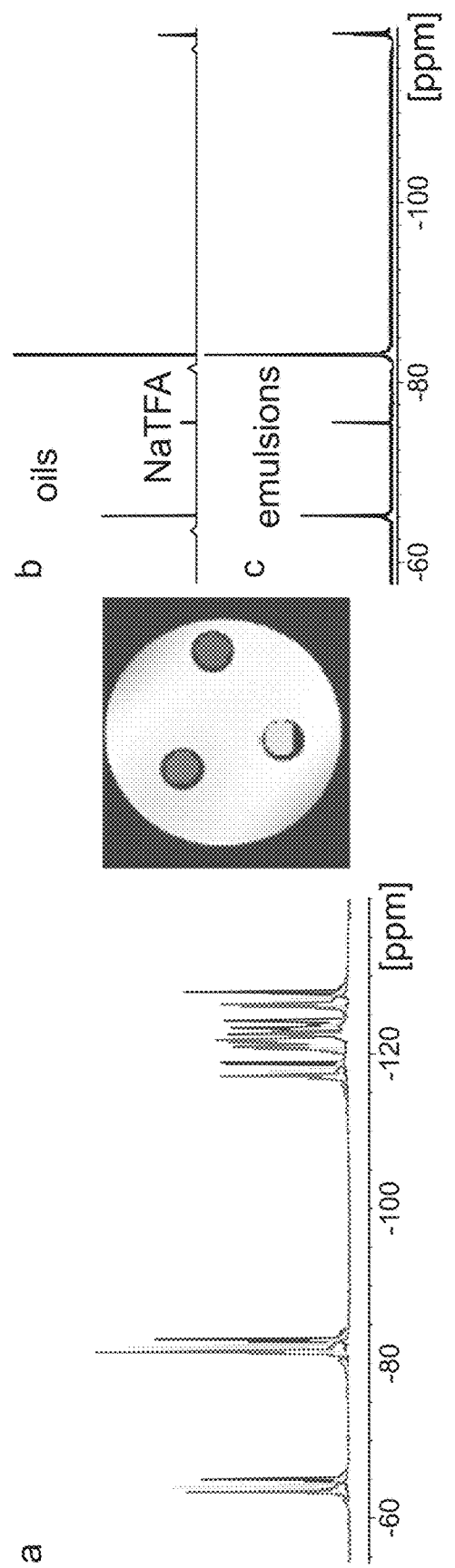
FIG. 6A-FIG. 6C. Bulk magnetic susceptibility (BMS) shifts for P-PFOB. Panel (a, left) shows 19F CSI spectra of NMR tubes containing PFOB with [5a POP]=25 mM (red), PFOB [5a POP]=14.5 mM (green), and pure PFOB (blue) oils. The NMR tubes were embedded in agarose and imaged using the CSI method. Resulting 19F MRI images are shown (a, right), where shifted CF3 peaks are assigned red, green or blue color channels and superimposed along with the 1H grayscale image. Here, red is −81.535 ppm with [5a POP]=25 mM, green is −82.178 ppm with [5a POP]=14.5 mM, and blue is −83.048 ppm for pure PFOB. The CSI data were acquired with TR/TE=26.4/0.53 ms, matrix size 64×64 and 6 averages. (See Supplementary Information for additional details). Panels (b-c) show that P-PFOB emulsification, forming spheroidal oil droplets, eliminates observed BMS shift. Displayed are 19F NMR spectra of PFOB and P-PFOB, prepared with dual capillary NMR samples inside a 5 mm NMR tube, where (b) are oils and (c) formed nanoemulsions. In (b), two sets of peaks are observed, where P-PFOB displays a downfield BMS shift of ~1.6 ppm with peak broadening. After emulsification (c), only one set of peaks is observed. Capillaries are immersed in D2O with 0.1% of NaTFA as an internal standard.
Figure 7:
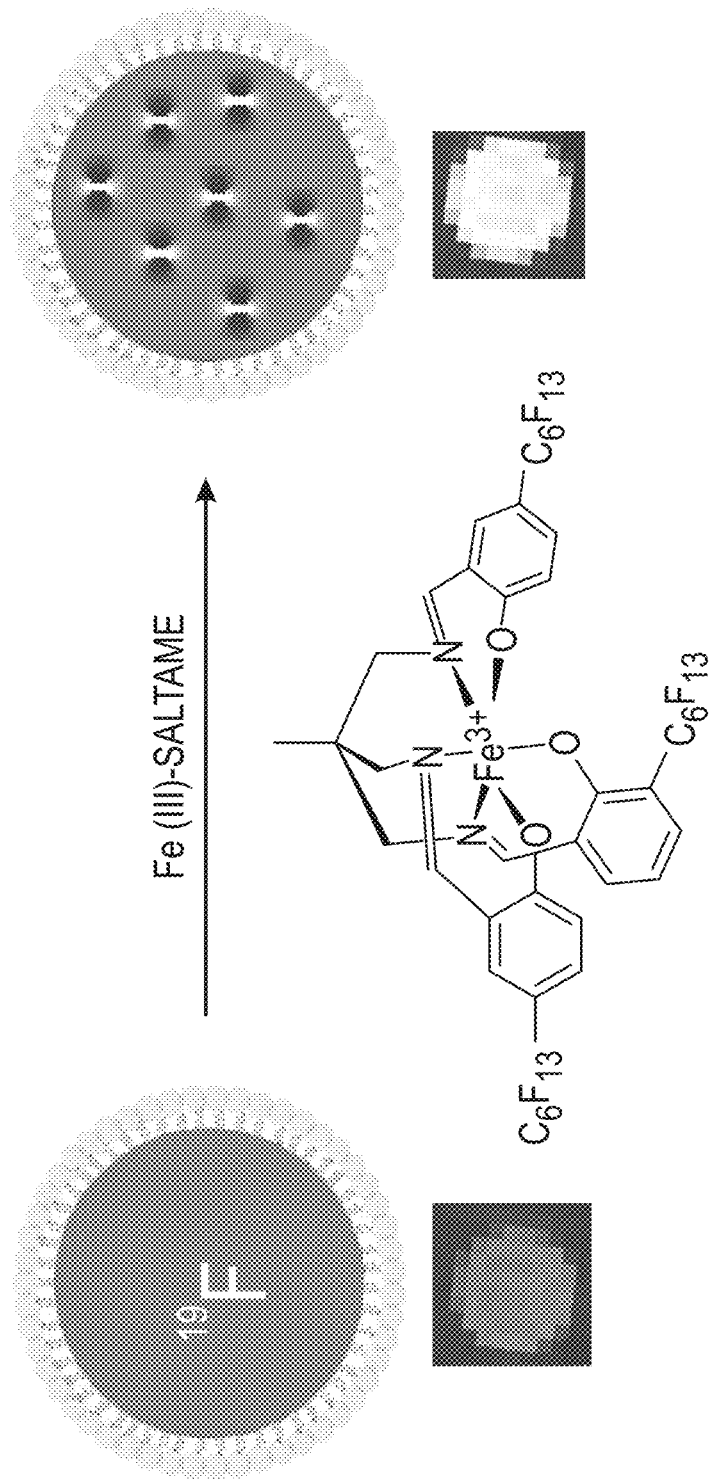
FIG. 7. SALTAME structure.

In unemulsified P-PFOB oil, we observed significant $^{19}$F shifts in all PFOB peaks with the addition of 5a POP Fe3+ chelate (FIG. 6A). This shift was linear with concentration of 5a POP in PFOB, with a slope of −0.060 ppm/mM at 9.4 T. Generally, a $^{19}$F shift reagent can be used for multispectral (color-coded) MRI. To demonstrate multispectral MRI with P-PFOB oil, a phantom was prepared using varying concentrations of 5a POP in three NMR tubes containing PFOB dissolved with [5a POP]=0, 14.5, and 25 mM. It was imaged using a CSI pulse sequence. The red-green-blue overlays (FIG. 6a, right) represent the shift images generated at the characteristic CF3 resonance frequencies of each [5a POP] concentration. The linear relationship between shift change and [5a POP] provides the potential for multiplexed imaging using different amounts of additive 5a POP to achieve $^{19}$F multichromicity.

However, we attributed the observed field shift to bulk magnetic susceptibility (BMS) effects,[22] where shift was dependent on sample geometry (i.e., cylindrical NMR tube). Upon formulating the P-PFOB oil into a colloidal suspension of spherical NE droplets (described above), the P-PFOB shift compared to PFOB was strongly attenuated (FIGS. 6B-6C).

Overall, we describe the design and characterization of SALTAME, a stable hexadentate chelating agent for iron (III). We used this moiety to formulate a nanoemulsion MRI probe that can be used for 'hot-spot' detection in vivo. Incorporation of iron-bound SALTAME into the fluorous phase of NE caused a profound reduction of the $^{19}$F T1 value and only mild line broadening, thus offering improved sensitivity of 19F MRI due to increased signal averaging and/or reduced MRI scan time.

One of the primary challenges in the emerging field of 19F MRI is sensitivity, and improvement of the intrinsic MRI sensitivity of the PFC molecule employed could lower the barriers for wider use in biomedical applications. Generally, PFCs are often employed due to their high F-density and safety profile. PFOB has been shown to be a promising molecular candidate for the translation of $^{19}$F MRI because of its low toxicity and rapid clearance from the body due to its modest lipophilicity.[8,23] In fact, PFOB has already been used in patients as oxygen transporting media.[9,16] Importantly, it has a short half-life (3-8 days), in vivo. By comparison, PFCE, another PFC molecule commonly used for $^{19}$F MRI, has a body half-life of >100 days.[16] Generally, clearance of PFC NE agents from the body occurs via uptake into cells and organs of the reticuloendothelial system, followed by lung exhalation.[24] However, PFOB has some undesirable properties as a $^{19}$F probe; it has a complex multi-peak $^{19}$F spectrum and intrinsically-high T1 values common for many PFC molecules.[25] In fact, among the most common PFCs, PFOB has the highest T1 value of ~1.2 s, compared to ~0.9 ms for PFCE, for example, at 3 T.[26] Generally, $^{19}$F MRI requires signal averaging, and the high T1 value of PFOB limits the rate of $^{19}$F MRI data acquisition within a constrained imaging time. Shortening T1 can increase the SNR per time and decrease the minimum number of detectable cells per voxel.

T1 can be profoundly altered by paramagnetic cations due to PRE. In prior studies, PRE has been used for $^{19}$F probes using lanthanide macrocycles with fluorinated sites.[27-30] These chelates[29] yield a reduction of ~2-3 orders of magnitude in intramolecular T1, similar to Fe3+-SALTAME 5a isomers (Table 2). However, the relatively low $^{19}$F content of macrocyclic chelates makes it challenging to achieve detectable intracellular labeling levels, compared to fluorine-densePFC oils. Gd-macrocyclic chelates tethered to NE surface provides mild $^{19}$F T1 enhancement, but are unstable inside cells.[31]

Fe3+-SALTAME retains the distorted octahedral geometry and presumably, the high-spin state of the previously-reported Fe3+ chelate without fluorous substituents.[11] Its high stability and affinity for Fe3+ permit easy isolation of the complex and formulation into PFOB NE without the requirement of the subsequent iron loading step necessary for prior compounds.[1] We observed that Fe3+ was the most effective cation for intermolecular $^{19}$F T1 acceleration in PFOB, consistent with our prior work[1]. Gd3+ and Fe3+ ions form the basis of T1- and T2-based 1H contrast agents, respectively, but for $^{19}$F MRI, the roles these ions play are reversed.[1]

The in vivo inflammation mouse model results (FIGS. 5A-5B) show in vivo compatibility and MRI detectability of P-PFOB NE. The method of using intravenously delivered $^{19}$F MRI for 'in situ' labeling of macrophages to elucidate inflammation hot-spots is well established and has been used preclinically in a wide range of disease models.[3,23,32] Alternative PFC NE formulations facilitate ex vivo cell uptake in culture,[33] for example during the preparation of stem cell or immunotherapeutic cytotherapies, and following transfer to the patient, these cells were detected in vivo using $^{19}$F MRI.[4] The fluorine inside the cells yielded positive-signal hot-spot images that can be quantified to measure apparent cell numbers at sites of accumulation, thereby enabling 'in vivo cytometry'.[34] The sensitivity limits of detection were on the order of $10^4$-$10^5$ cells/voxel.[3]

The relaxation rates P-PFOB were predictably tuned by varying Fe concentration. Tests were performed using a range of concentrations less than the maximum because these are the most useful for MRI experiments using the conventional (i.e., spin echo or gradient echo) pulse sequences most used in MRI practice (See Supplemental Information). However, advanced MRI pulse sequences, such as zero time to echo (ZTE) and ultra-short time to echo (UTE), which are used by early adoptors in MRI practice,[29] can predictably reap the benefits of the maximum iron concentration when T1 and T2 are very short; a detailed comparison of the performance of P-PFOB with different pulse sequences is beyond the scope of the manuscript.

The total amount of Fe delivered via the P-PFOB injection was miniscule compared to innate Fe levels in mouse. The total dose of SALTAME-bound Fe in the inoculant was approximately 50 μg of chelated Fe. The amount of Fe contained in mouse blood tissue, which represents roughly ⅔ of the total iron stores in body, was approximately 0.75 mg Fe, 15-fold higher. Thus, Fe metabolism of the organism should not be impacted by addition of P-PFOB, which contained small amounts of saturated, SALTAME-bound Fe.

The cell toxicity data presented (FIGS. 4A-4D) showed no overt toxicity induced by intracellular labeling; the flow-based NAO assay was very sensitive, and both positive and negative controls were included in the experimental design. Generally, the cell-safety of PFC cell labeling has been demonstrated exhaustively in numerous studies and cells types,[35-38] including primary immune cells for a human clinical trial[4] using a panel of in vitro cell assays of phenotype and function, including NAO.

We observed significant linear $^{19}$F NMR field shifts in all PFOB peaks with the addition of SALTAME Fe3+ chelate (FIG. 6A) in the unemulsified oil. SALTAME as a 19F shift reagent could be used for multicolor MRI tags comprised of neat P-PFOB oils, for example, to image catheter tips,[39] the gastrointestinal track,[38] or for external $^{19}$F fiduciary capsules.

Conclusions

Here, we describe the design and characterization of SALTAME, a stable hexadentate chelating agent for iron (III). We used this moiety to formulate a nanoemulsion MRI probe that can be used for 'hot-spot' detection in vivo. Incorporation of iron-bound SALTAME into the fluorous phase of NE causes a profound reduction of the $^{19}$F T1 value and only mild line broadening, thus offering improved sensitivity of $^{19}$F MRI due to increased signal averaging and/or reduced MRI scan time. Overall, the use of fluorinated molecules is emerging as an option for cellular imaging probe design. This probe has the potential to enable longitudinal, non-invasive quantification of inflammation and therapeutic cell delivery and aid in the monitoring of therapeutic test articles.

Methods and Materials

Chemicals were purchased from Sigma-Aldrich (St Louis, MO) or other reputable suppliers, and organic solvents (liquid chromatography-grade) were purchased from Fisher Scientific (Pittsburgh, PA) and used as received. Anhydrous dimethylformamide (DMF) and acetonitrile were stored over activated 4 Å molecular sieves. Fluorous solvents were purchased from Perseptive Biosystems (Framingham, MA). Precoated silica gel plates (60 F-254, Merck Millipore, Billerica, MA) were used for thin-layer chromatography (TLC), and silica gel 60 (230-400 mesh) was used for column chromatography.

Analytic Methods

All reactions were carried out under N2 unless otherwise noted. Reactions were monitored by TLC and liquid chromatography mass spectrometry (LC-MS) using an Agilent (Santa Clara, CA) 1100 HPLC with MSD Trap XLT using a Phenomenex Luna C18(2) 100 Å, 5 μm, 4.6 mm×250 column, MeCN/H2O linear gradients with constant 0.05% v/v CF3CO2H additive, 1 mL/min flow, and ESI positive or negative ion mode. Reaction products were purified by flash chromatography on silica gel eluted with ethyl acetate and hexane. High-resolution mass spectrometry was performed by the Molecular Mass Spectrometry Facility at the University of California San Diego. Ultraviolet-visible (UV-Vis) absorption spectra were recorded on a Shimadzu (Kyoto, Japan) spectrophotometer. Solubility of Fe3+-SALTAME compounds in perfluorocarbons were determined by absorbance at 450 nm following dilution in ethyl acetate using experimentally-determined extinction coefficients of 700 M-1 cm$^{-1}$ for the 5a isomers.

NMR Measurements

NMR spectra and relaxation rates were recorded on a Bruker Ascend 400 MHz (9.4 T) spectrometer (Billerica, MA). Additional relaxation rate measurements were performed at 3 T using a GE750 (General Electric, Milwaukee, WI) clinical MRI system equipped with a custom dual-channel $^{19}$F/1H 72 mm diameter volume coil (RAPID Biomedical, Rimpar, Germany). The $^{19}$F NMR spectra were referenced to an internal standard, sodium trifluoroacetate (NaTFA, 0.1 wt %, −76.00 ppm, Sigma-Aldrich, T6508), which was placed in a separate sealed capillary tube within the NMR tube. Relaxation measurements were performed using a standard inversion recovery pulse sequence and a Carr-Purcell-Meiboom-Gill sequence with echo-time (TE) values in 12 linear increments. The T1 and T2 values were obtained by nonlinear fitting using MNova 6.0.2 software (Mestrelab, Escondido, CA). Fit errors were less than 5% of T1 and T2 values. For quantitative peak measurements, spectra were acquired using calibrated 90° pulses, 32,000 complex points, spectral window 0 to −200 ppm, relaxation delay 2.5 s, and 128 averages. Spectra were processed in MNova with manual phase correction and Whittaker smoother baseline correction (filter=1 ppm). Relaxation parameters were measured for six middle CF2 peaks of PFOB, spanning ~10 ppm, which account for 12 out of 17 F atoms in the molecule. To assay nanoemulsion uptake ($^{19}$F/cell) using NMR, an aliquot of 1×10$^6$ cells were pelleted and resuspended in 0.1 mL of lysis solution (0.5% Triton X, 100 mM NaCl, 20 mM Tris, 1 mM EDTA) and reference compound NaTFA (0.745 mg/mL)/D2O was added to 5 mm NMR tube. The integrated ratio of PFOB fluorine peaks to NaTFA singlet fluorine peak at −76.00 ppm determined the amount of $^{19}$F in the cell pellet and the $^{19}$F/cell was calculated.

Phantom MRI

A phantom consisting of two 5 mm NMR tubes containing PFOB and P-PFOB ([5a POP]=20 mM in PFOB oil) nanoemulsions side-by-side. Images were acquired using a 9.4 T Bruker Avance III HD Nanobay spectrometer equipped for microimaging with a double-tuned 10 mm $^1$H/$^{19}$F coil and ParaVision 6 software. Two sets of $^{19}$F images were acquired using a two dimensional chemical shift imaging (CSI) method to yield optimal SNR for each tube. Imaging parameters were TE=0.8 ms (echo time), matrix size 32×32, field of view 9.5×9.5×3 mm3 and acquisition time was 49 min for each. To optimize SNR for each tube, the repetition time (TR) was set to 103 ms with 28 averages, and then TR=721 ms and 4 averages, with the optimal Ernst angle condition set for each TR value.

In Vivo MRI

Live mouse images were acquired using an 11.7 T horizontal-bore Bruker BioSpec MRI system equipped with a double-tuned $^1$H/$^{19}$F mouse volume coil and ParaVision 6 software. Mice were anesthetized using 1.5% isoflurane in O$_2$ and maintained at 37° C. during acquisitions. The $^{19}$F images were acquired using a two dimensional CSI method with TR/TE=13.3/0.53 ms, matrix size 32×32, field of view 20×20×6 mm3, 134 averages and acquisition time ~30 min. For anatomical data, 1H spin-echo images were acquired with TR/TE=550/14 ms, matrix size 128×96, field of view 20×20×1 mm3 and acquisition time ~3 min. CSI visualization was performed using the CSI Visualization Tool inside the ParaVision software. The calculation and display of phantom was performed by selecting all PFOB resonance peaks from −60 to −130 ppm. Notably, examination of the CSI spectral data showed no peaks at −82.8 and −89.9 ppm, corresponding to isoflurane anesthesia.

Shift MRI

Images to demonstrate POP Fe3+ chelate dissolved in PFOB oil induces bulk magnetic susceptibility shifts were acquired using the above 11.7 T MRI system. A CSI pulse sequence was used with TR/TE=26.4/0.53 ms, matrix size 64×64, FOV 30×30×3 mm3, 1,024 complex points, spectrum width 40.8 kHz, 6 averages and an acquisition time 10.8 min. CSI visualization was performed using the CSI Visualization Tool in ParaVision software. The calculation and display of P-PFOB map was performed by selecting the CF3 resonance peak only.

Supporting Information

Provided herein is supporting Information for additional materials and methods associated with chemical synthesis, NMR spectra of compounds and intermediates, MRI sensitivity modeling, and biological cell testing. The crystallization methods are described in the Supporting Information. The crystallographic data have been deposited at the Cambridge Crystallographic Data Centre (CCDC) as CCDC 1572939 (5a POP at 100 K), CCDC 1572845 (5a OOO at 100 K), and CCDC 1572938 (5a PPP at 100 K).

(1) Kislukhin, A. A.; Xu, H. Y.; Adams, S. R.; Narsinh, K. H.; Tsien, R. Y.; Ahrens, E. T. Paramagnetic Fluorinated Nanoemulsions for Sensitive Cellular Fluorine-19 Magnetic Resonance Imaging. Nat Mater 2016, 15, 662.
(2) Ahrens, E. T.; Flores, R.; Xu, H. Y.; Morel, P. A. In Vivo Imaging Platform for Tracking Immunotherapeutic Cells. Nat Biotechnol 2005, 23, 983.
(3) Ahrens, E. T.; Zhong, J. In Vivo MRI Cell Tracking Using Perfluorocarbon Probes and Fluorine-19 Detection. NMR Biomed 2013, 26, 860.
(4) Ahrens, E. T.; Helfer, B. M.; O'Hanlon, C. F.; Schirda, C. Clinical Cell Therapy Imaging Using a Perfluorocarbon Tracer and Fluorine-19 MRI. Magn Reson Med 2014, 72, 1696.
(5) Temme, S.; Bonner, F.; Schrader, J.; Flogel, U. 19F Magnetic Resonance Imaging of Endogenous Macrophages in Inflammation. Wiley Interdiscip Rev Nanomed Nanobiotechnol 2012, 4, 329.
(6) Bloembergen, N.; Morgan, L. O. Proton Relaxation Times in Paramagnetic Solutions. Effects of Electron Spin Relaxation. J Chem Phys 1961, 34, 842.
(7) Neubauer, A. M.; Myerson, J.; Caruthers, S. D.; Hockett, F. D.; Winter, P. M.; Chen, J.; Gaffney, P. J.; Robertson, J. D.; Lanza, G. M.; Wickline, S. A. Gadolinium-Modulated 19F Signals from Perfluorocarbon Nanoparticles as a New Strategy for Molecular Imaging. Magn Reson Med 2008, 60, 1066.
(8) Jacoby, C.; Temme, S.; Mayenfels, F.; Benoit, N.; Krafft, M. P.; Schubert, R.; Schrader, J.; Flogel, U. Probing Different Perfluorocarbons for In Vivo Inflammation Imaging by 19F MRI. Image Reconstruction, Biological Half-Lives and Sensitivity. NMR Biomed 2014, 27, 261.
(9) Riess, J. G.; Weers, J. G. Emulsions for Biomedical Uses. Curr Opin Colloid In 1996, 1, 652.
(10) Klein, D. H.; Jones, R. C.; Keipert, P. E.; Luena, G. A.; Otto, S.; Weers, J. G. Intravascular Behavior of Perflubron Emulsions. Colloid Surface A 1994, 84, 89.
(11) Deeney, F. A.; Harding, C. J.; Morgan, G. G.; McKee, V.; Nelson, J.; Teat, S. J.; Clegg, W. Response to Steric Constraint in Azacryptate and Related Complexes of Iron-(II) and -(III) *. J Chem Soc Dalton 1998, 1837.
(12) Filippini, G.; Nappi, M.; Melchiorre, P. Photochemical Direct Perfluoroalkylation of Phenols. Tetrahedron 2015, 71, 4535.
(13) Matsugi, M.; Hasegawa, M.; Hasebe, S.; Takai, S.; Suyama, R.; Wakita, Y.; Kudo, K.; Imamura, H.; Hayashi, T.; Haga, S. Direct Perfluoroalkylation of Non-Activated Aromatic C—H Bonds of Phenols. Tetrahedron Lett 2008, 49, 4189.
(14) Ramanathan, A.; Jimenez, L. S. Reductive Dehalogenation of Aryl Bromides and Chlorides and Their Use as Aryl Blocking Groups. Synthesis-Stutgart 2010, 2, 217.
(15) Janjic, J. M.; Ahrens, E. T. Fluorine-Containing Nanoemulsions for MRI Cell Tracking. Wiley Interdiscip Rev Nanomed Nanobiotechnol 2009, 1, 492.
(16) Riess, J. G. Oxygen Carriers ("Blood Substitutes") Raison D'etre, Chemistry, and Some Physiology Blut Ist Ein Ganz Besondrer Saft. Chem Rev 2001, 101, 2797.
(17) Weers, J. G.; Liu, J.; Fields, T.; Resch, P.; Cavin, J.; Arlauskas, R. A. Room Temperature Stable Perfluorocarbon Emulsions with Acceptable Half-Lives in the Reticuloendothelial System. Artif Cell Blood Sub 1994, 22, 1175.
(18) Postel, M.; Riess, J. G.; Weers, J. G. Fluorocarbon Emulsions the Stability Issue. Artif Cell Blood Sub 1994, 22, 991.
(19) Ahrens, E. T.; Janjic, J. M. Compositions and Methods for Producing Emulsions for Nuclear Magnetic Resonance Techniques and Other Applications USPTO 9,352, 057.
(20) Lutsenko, G. V. Flow-Cytometry Assay for Apoptosis Using Fluorophor 10-N-nonyl acridine Orange. Biol Membrany 2010, 27, 430.
(21) Temme, S.; Jacoby, C.; Ding, Z.; Bonner, F.; Borg, N.; Schrader, J.; Flogel, U. Technical Advance: Monitoring the Trafficking of Neutrophil Granulocytes and Monocytes During the Course of Tissue Inflammation by Noninvasive 19F MRI. J Leukoc Biol 2014, 95, 689.
(22) Chu, S. C. K.; Xu, Y.; Balschi, J. A.; Springer, C. S. Bulk Magnetic-Susceptibility Shifts in NMR Studies of Compartmentalized Samples—Use of Paramagnetic Reagents. Magn Reson Med 1990, 13, 239.
(23) Bonner, F.; Merx, M. W.; Klingel, K.; Begovatz, P.; Flogel, U.; Sager, M.; Temme, S.; Jacoby, C.; Salehi Ravesh, M.; Grapentin, C.; Schubert, R.; Bunke, J.; Roden, M.; Kelm, M.; Schrader, J. Monocyte Imaging After Myocardial Infarction with 19F MRI at 3 T: A Pilot Study in Explanted Porcine Hearts. Eur Heart J-Card Img 2015, 16, 612.
(24) Flaim, S. F. Pharmacokinetics and Side Effects of Perfluorocarbon-Based Blood Substitutes. Artif Cell Blood Sub 1994, 22, 1043.
(25) Giraudeau, C.; Flament, J.; Marty, B.; Boumezbeur, F.; Meriaux, S.; Robic, C.; Port, M.; Tsapis, N.; Fattal, E.; Giacomini, E.; Lethimonnier, F.; Le Bihan, D.; Valette, J. A New Paradigm for High-Sensitivity 19F Magnetic Resonance Imaging of Perfluorooctylbromide. Magn Reson Med 2010, 63, 1119.
(26) Colotti, R.; Bastiaansen, J. A.; Wilson, A.; Flogel, U.; Gonzales, C.; Schwitter, J.; Stuber, M.; van Heeswijk, R. B. Characterization of Perfluorocarbon Relaxation Times and Their Influence on the Optimization of Fluorine-19 MRI at 3 Tesla. Magn Reson Med 2016 77(6), 2263.
(27) Harvey, P.; Kuprov, I.; Parker, D. Lanthanide Complexes as Paramagnetic Probes for 19F Magnetic Resonance. Eur J Inorg Chem 2012, 2015.

(28) De Luca, E.; Harvey, P.; Chalmers, K. H.; Mishra, A.; Senanayake, P. K.; Wilson, J. I.; Botta, M.; Fekete, M.; Blamire, A. M.; Parker, D. Characterisation and Evaluation of Paramagnetic Fluorine Labelled Glycol Chitosan Conjugates for (19)F and (1)H Magnetic Resonance Imaging. J Biol Inorg Chem 2014, 19, 215.

(29) Schmid, F.; Holtke, C.; Parker, D.; Faber, C. Boosting (19) F MRI-SNR Efficient Detection of Paramagnetic Contrast Agents Using Ultrafast Sequences. Magn Reson Med 2013, 69, 1056.

(30) Funk, A. M.; Fries, P. H.; Harvey, P.; Kenwright, A. M.; Parker, D. Experimental Measurement and Theoretical Assessment of Fast Lanthanide Electronic Relaxation in Solution with Four Series of Isostructural Complexes. J Phys Chem A 2013, 117, 905.

(31) Kok, M. B.; de Vries, A.; Abdurrachim, D.; Prompers, J. J.; Grull, H.; Nicolay, K.; Strijkers, G. J. Quantitative (1)H MRI, (19)F MRI, and (19)F MRS of Cell-Internalized Perfluorocarbon Paramagnetic Nanoparticles. Contrast Media Mol I 2011, 6, 19.

(32) Ratner, A. V.; Hurd, R.; Muller, H. H.; Bradley-Simpson, B.; Pitts, W.; Shibata, J. D.; Sotak, C.; Young, S. W. 19F Magnetic Resonance Imaging of the Reticuloendothelial Systtem. Magn Reson Med 1987, 5, 548.

(33) Janjic, J. M.; Srinivas, M.; Kadayakkara, D. K.; Ahrens, E. T. Self-Delivering Nanoemulsions for Dual Fluorine-19 MRI and Fluorescence Detection. J Am Chem Soc 2008, 130, 2832.

(34) Srinivas, M.; Turner, M. S.; Janjic, J. M.; Morel, P. A.; Laidlaw, D. H.; Ahrens, E. T. In Vivo Cytometry of Antigen-Specific T Cells Using 19F MRI. Magn Reson Med 2009, 62.

(35) Helfer, B. M.; Balducci, A.; Nelson, A. D.; Janjic, J. M.; Gil, R. R.; Kalinski, P.; De Vries, I. J. M.; Ahrens, E. T.; Mailliard, R. B. Functional Assessment of Human Dendritic Cells Labeled for In Vivo F-19 Magnetic Resonance Imaging Cell Tracking. Cytotherapy 2010, 12, 238.

(36) Bouchlaka, M. N.; Ludwig, K. D.; Gordon, J. W.; Kutz, M. P.; Bednarz, B. P.; Fain, S. B.; Capitini, C. M. 19F-MRI for Monitoring Human NK Cells In Vivo. OncoImmunology 2016, 5, e1143996.

(37) Rose, L. C.; Kadayakkara, D. K.; Wang, G.; Bar-Shir, A.; Helfer, B. M.; O'Hanlon, C. F.; Kraitchman, D. L.; Rodriguez, R. L.; Bulte, J. W. M. Fluorine-19 Labeling of Stromal Vascular Fraction Cells for Clinical Imaging Applications. Stem Cells Transl Med 2015, 4, 1472.

(38) Schirra, C. O.; Weiss, S.; Krueger, S.; Pedersen, S. F.; Razavi, R.; Schaeffter, T.; Kozerke, S. Toward True 3D Visualization of Active Catheters Using Compressed Sensing. Magn Reson Med 2009, 62, 341.

(39) Mattrey, R. F.; Hajek, P. C.; Gylys-Morin, V. M.; Baker, L. L.; Martin, J.; Long, D. C.; Long, D. M. Perfluorochemicals as Gastrointestinal Contrast Agents for MR Imaging: Preliminary Studies in Rats and Humans. Am J Roentgen 1987, 148, 1259.

Example 2: $^{19}$F MRI Inflammation Imaging Agent

Abstract

Fluorine-19 MRI is an emerging cellular imaging approach, enabling lucid, quantitative 'hot-spot' imaging with no background signal. The utility of $^{19}$F-MRI to detect inflammation and cell therapy products in vivo could be greatly expanded by improving the intrinsic sensitivity of the probe by molecular design. We describe a metal chelate based on a salicylidene-tris(aminomethyl)ethane core, with solubility in perfluorocarbon (PFC) oils, and a potent accelerator of the $^{19}$F longitudinal relaxation time ($T_1$). Shortening $T_1$ can effectively increase the $^{19}$F image sensitivity per time and decrease the minimum number of detectable cells. We used the condensation between a tripodal ligand tris-1,1,1-(aminomethyl)ethane and salicylaldehyde to form the salicylidene-tris(aminomethyl)ethane chelating agent (SALTAME). We purified four isomers of SALTAME, elucidated structures using x-ray scattering and NMR, and identified a single isomer with high PFC solubility. $Mn^{4+}$, $Fe^{3+}$, $Co^{3+}$, and $Ga^{3+}$ cations formed stable and separable chelates with SALTAME, but only $Fe^{3+}$ yielded superior $T_1$ shortening with modest line broadening at 3 and 9.4 Tesla. We mixed $Fe^{3+}$ chelate with perfluorooctyl-bromide (PFOB) to formulate a stable paramagnetic emulsion imaging probe and assessed its biocompatibility in macrophages in vitro using proliferation, cytotoxicity and phenotypic cell assays. Signal-to-noise modeling of paramagnetic PFOB showed that sensitivity enhancement of nearly 4-fold was feasible at clinical magnetic field strengths using a $^{19}$F spin-density weighted gradient-echo pulse sequence. We demonstrated the utility of this paramagnetic emulsion as an in vivo MRI probe for detecting inflammation-associated macrophages in mice. Overall, these paramagnetic PFC compounds represent a platform for the development of sensitive $^{19}$F MRI probes.

Background

For decades, metal chelate chemistry has been the centerpiece in efforts to formulate magnetic resonance imaging (MRI) contrast media. A compelling direction is the use of metal chelates to emerging non-proton imaging approaches such as fluorine-19 MRI.[1] $^{19}$F MRI enables 'hot-spot' imaging with no background signal and quantification of spin density-weighted images.[2,3] $^{19}$F MRI using perfluorocarbon (PFC) emulsion (NE) probes has been used to detect cell therapy products in vivo (e.g., stem cells and immune cells) that were labeled ex vivo prior to delivery to the subject; these methods have recently been translated into human patients.[4] In other uses, PFC probes have been used effectively for imaging leukocyte infiltrates associated with multiple inflammatory diseases.[3,5] In this approach, following intravenous injection, the NE droplets are taken up by monocytes and macrophages in situ, and these cells accumulate at sites of inflammation yielding $^{19}$F MRI hot-spots.

The utility of this nascent technology could be expanded by improving the sensitivity of $^{19}$F detection via molecular design. $^{19}$F MRI is limited by the total amount and distribution of fluorine atoms introduced into the subject's tissue, as well as the amount of PFC that can be safely internalized into cells of interest. Thus, one must improve the intrinsic sensitivity of the PFC molecule. A key parameter for boosting sensitivity is decreasing the high $^{19}$F longitudinal relaxation time ($T_1$) of PFC molecules. The $T_1$ value ultimately limits the rate of $^{19}$F MRI data acquisition. Generally, $^{19}$F imaging requires summation of multiple acquisitions (i.e., signal averaging) to yield a sufficient signal-to-noise ratio (SNR) to gain statistical confidence. A high $^{19}$F $T_1$ value generally requires a longer repetition time, thus limiting the number of acquisitions and amount of signal averaging attainable during a fixed total imaging time. Shortening $T_1$ allows more signal averages and thus increases SNR, sensitivity, and decreases the minimum number of detectable cells per voxel in the same total scan time.

The intermolecular paramagnetic relaxation enhancement (PRE) mechanism[6] can be used to decrease $T_1$ by incorporating paramagnetic centers such as $Gd^{3+}$ and $Fe^{3+}$ into or near the fluorous phase.[1,7] The strength of the PRE dipole-dipole interaction is inversely proportional to the sixth power ($1/r^6$) of the fluorine-metal distance. Thus, paramagnetic centers bound to the NE surface can be inefficient, due to the long distance between the relaxation agent and the bulk PFC molecules inside the NE droplet. To yield the optimal $T_1$ and $T_2$ (spin-spin relaxation time) with minimal metal added, the paramagnetic center should be dissolved in PFC. However, dissolving the paramagnetic center is challenging due to PFC's highly hydrophobic and lipophobic nature. Free paramagnetic cations are insoluble in PFC; thus, they must be bound to a fluorous-soluble chelating agent.

In this study, we present synthesis and characterization of a fluorophilic chelating agents based on a salicylidene-tris (aminomethyl)ethane core, referred to as SALTAME; these chelates are soluble in PFC and serve as potent PRE agents. We describe herein SALTAME structure, physical properties, NMR relaxation times and the impact of different bound metal cations, NE probe formulation, and characterization of probe-labeled macrophages in vitro. We also demonstrated the utility of paramagnetic SALTAME-PFC NE as an in vivo $^{19}F$ MRI probe for detecting inflammation-associated macrophages in mouse. Overall, the creation of paramagnetic NE probes is a chemical synthesis avenue for advancing the field of $^{19}F$ MRI.

Results

Molecular Design and Synthesis of SALTAME Complex

Described herein is an exemplary synthesis scheme for fluorophilic metal chelates. At design onset, based on prior work,[1] we assumed transition metals, and $Fe^{3+}$ in particular, were the best $T_1$ accelerator for PFCs, while paramagnetic lanthanides (e.g., $Gd^{3+}$) caused severe line broadening, essentially becoming $^{19}F$ $T_2$ agents.[1] Moreover, perfluorooctylbromide (PFOB) is the preferred $^{19}F$-rich MRI signal media for metal chelate dissolution due to its rapid clearance from the body and well-characterized clinical safety profile.[8-10]

We used (FIG. 1) the condensation between tris-1,1,1-(aminomethyl)ethane (TAME) and salicylaldehyde (SAL) to form the tripodal salicylidene-tris(aminomethyl)ethane chelating agent (SALTAME), for three reasons: (i) SALTAME is known to be a high affinity hexadentate chelating agent with three N and three O atoms, capable of binding different paramagnetic cations[11]; (ii) with a maximum of three negative charges, a chelated trivalent paramagnetic center (e.g., $Fe^{3+}$) gives an overall neutral charge that favors solubility in PFCs; (iii) the geometry of the chelate stabilizes the high spin-state of cations, such as S=5/2 for $Fe^{3+}$, which maximizes PRE effect.[11] However, unsubstituted SALTAME chelate (FIG. 1, 5 $R_1$-$R_6$=H) was insoluble in PFCs due to the simultaneous hydrophobic and lipophobic nature of all PFCs. As PFCs only dissolved highly fluorinated compounds, we sought to append perfluoroalkyl substituents to SALTAME complex to increase fluorophilicity. We tried the reported photochemical ring alkylation of SA with perfluoroalkyl iodides under basic conditions[12] but it gave a mixture of monoalkylated isomers 3a, 3b and dialkylated isomer 3c that were difficult to isolate (route 1). Instead, alkylation of bromosalicylaldehydes with heating under basic conditions,[13] followed by reductive debromination[14] gave 3a and 3b in much higher yields (route 2). Different isomers of 5a can be obtained by condensation of pure 3a or 3b or their weighed mixtures (1:2 or 2:1 w/w) with TAME and subsequent addition of ferric chloride and separation of the isomers. Though the SALTAME imines tended to dissociate, their iron complexes were very stable and can be readily isolated using chromatographic methods. Confirmation of their structures was achieved by high resolution liquid chromatography-mass spectrometry (LC-MS) of 5a, as well as NMR analysis of the respective SALTAME ligands (FIGS. 8-10). As expected, incorporation of paramagnetic $Fe^{3+}$ into SALTAME greatly increased the intrinsic longitudinal and transverse relaxation rates for fluorine NMR of the 5a isomers (Table 3) and perturbed their proton and carbon NMR spectra. Definitive structural assignment of three of the four possible 5a isomers (5a POP, OOO and PPP) is shown by x-ray crystallography (FIGS. 2A-2C, 11, and 12, respectively).

The four 5a isomers were soluble in various PFC molecules, especially PFOB, and to a lesser extent (<0.5 mM) in perfluoro-15-crown-5-ether (PFCE) and perfluoropolyether (PFPE), which are other PFC compounds previously used for $^{19}F$ MRI applications.[8] Unexpectedly, the 5a isomers had remarkably different solubility in PFOB, with 5a PPP and 5a POP having the highest solubility (26 mM and 102 mM, respectively) among all the isomers (5a OOP and 5a OOO solubilities are 9.4 and 2.0 mM, respectively). Initial studies indicated that more stable PFOB emulsions with 5a POP were formed with concentrations up to 30 mM of the SALTAME incorporated, thus we explored the properties and applications of this isomer. We also synthesized four additional SALTAME complexes 5c-f to explore the inclusion of other fluorous substituents, but all showed inferior solubility in PFOB.

Cation Selection

We screened the impact of various cations bound to SALTAME 5a and dissolved in PFOB via NMR relaxometry and susceptibility shift measurements (Table 4). Of the period-4 cations tested ($V^{3+}$, $Cr^{3+}$, $Mn^{2+}$, $Fe^{3+}$, $Co^{2+}$, $Cu^{2+}$, $Ni^{2+}$, $Zn^{2+}$, $Ga^{3+}$), only $Mn^{4+}$, $Fe^{3+}$, $Co^{3+}$, and $Ga^{3+}$ formed stable and separable (by column chromatography) chelates with SALTAME. These chelates readily dissolve in PFOB, and their intermolecular $^{19}F$ NMR relaxivities and susceptibility shift properties at 9.4 T are displayed in Table 3. The diamagnetic $Ga^{3+}$ chelate had little relaxation effects or shift for PFOB. $Co^{3+}$ had a significant effect on the transverse relaxivity ($r_2$) but not on the longitudinal relaxivity ($r_1$), and the shift was not impacted. $Mn^{4+}$ changes $r_1$, $r_2$ and susceptibility shift, but to a much lesser extent than $Fe^{3+}$. $Gd^{3+}$ did not form a stable chelate with SALTAME, presumably because it requires eight-to-nine coordination sites, whereas SALTAME has a coordination of six.

The longitudinal and transverse $^{19}F$ relaxation rates of the $Fe^{3+}$ chelate, 5a POP, was further evaluated as a function of iron concentration at the clinically-relevant field strength of 3 T yielding relaxivities $r_1$ and $r_2$ of 0.56 $s^{-1}mM^{-1}$ and 1.67 $s^{-1}mM^{-1}$, respectively, compared to 0.50 $s^{-1}$ $mM^{-1}$ and 1.07 $s^{-1}$ $mM^{-1}$ values of $r_1$ and $r_2$ at 9.4 T, respectively. For neat PFOB, $R_1/R_2$ values were 0.79 $s^{-1}/3.5$ s–1 and 1.4 $s^{-1}/2.2$ $s^{-1}$ at 3 T and 9.4 T, respectively.

Overall, the 5a POP $Fe^{3+}$ chelate served as the representative additive and was used to formulate paramagnetic PFOB (P-PFOB) NE which was used for further studies.

Structure of $Fe^{3+}$ SALTAME

To characterize structure and $Fe^{3+}$ coordination in chelates, data for 5a POP, PPP and OOO were obtained by x-ray crystallography (FIGS. 2A-2C, FIG. 11, FIG. 12) and NMR methods. Comparison of these structures with unsubstituted $Fe^{3+}$-SALTAME (5, $R_1$-$R_6$=H; FIG. 13) confirmed that the hexadentate coordination of $Fe^{3+}$ was not affected by appending fluorous substituents to SALTAME with minimal differences in Fe—O or Fe—N bond lengths and angles compared to its non-fluorous parent.[11] From these structures, we speculated that the low solubility of 5a OOO in PFOB (Table 5) may be explained by the observation that all three fluorous substituents were located on one side of 5a OOO yielding less favorable van der Waals interactions between substituents and PFOB. Fluorous substituents were more evenly distributed around the chelate in 5a PPP and POP, yielding higher affinity to PFOB.

Intramolecular $^{19}F$ NMR relaxometry measurements of 5a isomers further confirmed the structural analyses. We observed that among $Fe^{3+}$ chelates, 5a OOO isomer had the highest, and 5a PPP isomer had the lowest, $R_1$ and $R_2$ values (Table 3). Ortho-substitution caused a more drastic intramolecular PRE, by ~3 orders of magnitude, compared to para-substitution due to the closer proximity of the $Fe^{3+}$ paramagnetic center to the ortho position (6.91 nm) compared to the para position (9.53 nm).

Sensitivity Enhancement of P-PFOB

We modeled potential MRI sensitivity enhancement of P-PFOB compared to undoped PFOB based on measured $^{19}F$ NMR relaxivities in these materials. Modeling results (FIG. 3A) showed multi-fold sensitivity improvement was possible using a gradient-echo (GRE) based MRI pulse sequence with echo time (TE)<0.8 ms. Model details are given in the Supplementary Information section below.

To support these findings, experimental data were acquired in an MRI phantom (FIG. 3b) consisting of two NMR tubes containing PFOB and P-PFOB emulsions. The phantoms were imaged twice at 9.4 T using a GRE chemical shift imaging (CSI) pulse sequence with two different repetition time (TR) parameters set according to TR=$0.5T_1$ for PFOB or P-PFOB, respectively, with the optimal Ernst angle condition set for each TR-value; both images were acquired using the same total imaging time. (Supplementary Information below). Image results (FIG. 3B) show the P-PFOB tube has 2.5 times higher SNR than the PFOB tube when comparing the optimal SNR acquisition for each tube, consistent with the model prediction. This phantom imaging example does not represent the absolute value or upper limit to the possible SNR enhancement achievable with these materials; varying [$Fe^{3+}$], magnetic field strength, pulse sequences and acquisition parameters may yield different values of SNR enhancement.

Imaging Probe Formulation

To create NE-based imaging probes, we formulated colloidal suspensions of P-PFOB. High-shear homogenization of components was used to form NE.[15] To stabilize the NE, egg yolk phospholipids (EYP) was used as a surfactant; P-PFOB had a slight lipophilic character due to PFOB's single bromine, yielding a cohesive tendency between PFOB and the fatty acid chains of EYP.[16,17] Minor surfactant components were also added including $CH_3$—$(CH_2)_5$—$(CF_2)_5$—$CF_3$, which acted as molecular dowels improving the emulsion stability,[18] Cremophor EL (Polyoxyl 35 hydrogenated castor oil) to decrease NE droplet size and increase shelf-life and circulation time,[19] and mannitol as an isotonizer. After homogenization of P-PFOB ([5a POP]=20 mM) with surfactants, average NE particle size was ~162 nm with polydispersity index (PDI) of 0.27, as measured by dynamic light scattering (DLS). Using similar methods, this particle size was comparable to emulsions made without chelate.[15] The final P-PFOB NE had [F]=14.26 M with PFOB:5a POP molar ratio of 192:1. The $R_1$ and $R_2$ parameters were 9.01±0.03 $s^{-1}$ and 16.66±0.10 $s^{-1}$ at 9.4 T, respectively. The NE stability was confirmed by longitudinally monitoring of particle size using DLS measurements for emulsion stored at 4° C. over 60 days (FIG. 14). Also, the NE complex was stable for at least 3 days at 37° C. in proteinaceous saline media used to mimic the blood circulation environment (FIG. 15).

We also evaluated the iron-binding stability of P-PFOB NE ([$Fe^{3+}$-SALTAME 5a POP]=30 mM in PFOB) following addition of 50 mM ethylenediaminetetraacetate (EDTA), a strong competing $Fe^{3+}$ chelating agent, to the aqueous phase; P-PFOB NE showed stable relaxometry parameters over 20 days, indicating that iron was tightly bound in the fluorous phase (FIG. 16).

P-PFOB Labeling Macrophages In Vitro

To test biocompatibility of formulated P-PFOB NE as a cell labeling agent, we performed in vitro assays on a labeled murine macrophage cell line derived from blood (RAW 264.7). This cell is a representative phagocyte that would take up NE in vivo after intravenous delivery. Following a 16 hour incubation of RAW cells with various NE concentrations, the uptake level approached ~$10^{12}$ fluorine atoms per cell, measured by $^{19}F$ NMR (FIG. 17).

We investigated the potential effect of P-PFOB labeling on RAW cell viability and phenotype (FIG. 4A-FIG. 4D). To study cytotoxicity, we used a flow cytometry assay for apoptosis (FIG. 4A-FIG. 4C) using 10-N-nonyl acridine orange (NAO).[20] As a positive control to induce oxidative stress, 10% ethanol was added to the cell media. No evidence of cytotoxicity is observed in NE-labeled compared to unlabeled cells (FIG. 4A-FIG. 4B), whereas ethanol-treated cells display cytotoxicity (FIG. 4C) and a characteristic bi-modal appearance described elsewhere.[20] FIG. 4B also shows that the labeled cells had increased side-scatter signal due to light scattering from PFC loaded intracellular vesicles, a common observation. Side-scatter is routinely used in flow cytometry to distinguish cell types by granularity. Labeled cells often display increased granularity with internalization of PFC droplets. To assay cell phenotype, we used flow cytometry to monitor potential changes in cell surface CD86 expression as a marker for macrophage activation, where increased levels indicate a pro-inflammatory response to label. Lipopolysaccharide (LPS) treatment was used as a positive control to induce a pro-inflammatory phenotype. The CD86 expression level in NE-labeled macrophages was comparable to unlabeled cells (FIG. 4D), whereas in LPS-treated cells the level was visibly higher, suggesting that P-PFOB NE did not stimulate a pro-inflammatory phenotype in macrophages.

Visualizing Inflammation In Vivo Using P-PFOB NE

Proof of concept in vivo imaging of inflammation was performed using P-PFOB NE in a localized inflammation mouse model. Following established protocols,[5,8,21] localized inflammation was induced using an LPS doped Matrigel solution injected subcutaneously into the posterior neck of a C57BL/6 mouse (N=3). After 2 hours, a single bolus of P-PFOB NE (200 µl, [$Fe^{3+}$-SALTAME 5a POP]=20 mM in PFOB oil phase), equivalent to 143 mmol F/kg body weight and 0.04 mmol chelated Fe/kg body weight, was injected intravenously. No adverse reactions were observed. Mice were imaged 24 hours after injection to allow for emulsion uptake by monocytes/macrophages in situ. Scans were performed at 11.7 T. The $^{19}F$ images were acquired using a two-dimensional CSI pulse sequence along with conventional anatomical $^{1}H$ images. Representative coronal image in the neck region is displayed in FIG. 5A-FIG. 5B, where the Matrigel plug appears as a hyperintense, subcutaneous structure in the dorsal region of the $^{1}H$ image (FIG. 5A-FIG. 5B). Robust $^{19}F$ signal signifying macrophage uptake was seen co-registered with the Matrigel plug. $^{19}F$ was also found in an area in the anterior neck, presumably at lymph node (asterisk, FIG. 5A-FIG. 5B). Overall, the in vivo data showed the feasibility of using P-PFOB NE as an inflammation imaging agent.

Susceptibility Shifts by $Fe^{3+}$ SALTAME

In unemulsified P-PFOB, oil we observed significant $^{19}F$ shifts in all PFOB peaks with the addition of 5a POP $Fe^{3+}$ chelate (FIG. 6a). This shift was linear with concentration of 5a POP in PFOB, with a slope of −0.060 ppm/mM at 9.4 T. Generally, a $^{19}F$ shift reagent can be used for multispectral (color-coded) MRI. To demonstrate multispectral MRI with P-PFOB oil, a phantom was prepared using varying concentrations of 5a POP in three NMR tubes containing PFOB dissolved with [5a POP]=0, 14.5, and 25 mM. It was imaged using a CSI pulse sequence. The red-green-blue overlays (FIG. 6A, right) represent the shift images generated at the characteristic $CF_3$ resonance frequencies of each [5a POP] concentration. The linear relationship between shift change and [5a POP] provides the potential for multiplexed imaging using different amounts of additive 5a POP to achieve $^{19}F$ multichromicity.

However, we attributed the observed field shift to bulk magnetic susceptibility (BMS) effects,[22] where shift was dependent on sample geometry (i.e., cylindrical NMR tube). Upon formulating the P-PFOB oil into a colloidal suspension of spherical NE droplets (described above), the P-PFOB shift compared to PFOB is strongly attenuated (FIG. 6B-FIG. 6B).

Discussion

Overall, we describe the design and characterization of SALTAME, a stable hexadentate chelating agent for iron (III). We used this moiety to formulate a emulsion MRI probe that can be used for 'hot-spot' detection in vivo. Incorporation of iron-bound SALTAME into the fluorous phase of NE caused a profound reduction of the $^{19}F$ $T_1$ value and only mild line broadening, thus offering improved sensitivity of $^{19}F$ MRI due to increased signal averaging and/or reduced MRI scan time.

One of the primary challenges in the emerging field of $^{19}F$ MRI is sensitivity, and improvement of the intrinsic MRI sensitivity of the PFC molecule employed could lower the barriers for wider use in biomedical applications. Generally, PFCs are often employed due to their high F-density and safety profile. PFOB has been shown to be a promising molecular candidate for the translation of $^{19}F$ MRI because of its low toxicity and rapid clearance from the body due to its modest lipophilicity.[8,23] In fact, PFOB has already been used in patients as oxygen transporting media.[9,16] Importantly, it has a short half-life (3-8 days), in vivo. By comparison, PFCE, another PFC molecule commonly used for $^{19}F$ MRI, has a body half-life of >100 days.[16] Generally, clearance of PFC NE agents from the body occurs via uptake into cells and organs of the reticuloendothelial system, followed by lung exhalation.[24] However, PFOB has some undesirable properties as a $^{19}F$ probe; it has a complex multi-peak $^{19}F$ spectrum and intrinsically-high $T_1$ values common for many PFC molecules.[25] In fact, among the most common PFCs, PFOB has the highest $T_1$ value of ~1.2 s, compared to ~0.9 ms for PFCE, for example, at 3 T.[26] Generally, $^{19}F$ MRI requires signal averaging, and the high $T_1$ value of PFOB limits the rate of $^{19}F$ MRI data acquisition within a constrained imaging time. Shortening $T_1$ can increase the SNR per time and decrease the minimum number of detectable cells per voxel.

$T_1$ can be profoundly altered by paramagnetic cations due to PRE. In prior studies, PRE has been used for $^{19}F$ probes using lanthanide macrocycles with fluorinated sites.[27-30] These chelates[29] yield a reduction of ~2-3 orders of magnitude in intramolecular T1, similar to $Fe^{3+}$-SALTAME 5a isomers (Table 3). However, the relatively low $^{19}F$ content of macrocyclic chelates makes it challenging to achieve detectable intracellular labeling levels, compared to fluorine-dense PFC oils. Gd-macrocyclic chelates tethered to NE surface provides mild $^{19}F$ $T_1$ enhancement, but are unstable inside cells.[31]

$Fe^{3+}$-SALTAME retains the distorted octahedral geometry and presumably, the high-spin state of the previously-reported $Fe^{3+}$ chelate without fluorous substituents.[11] Its high stability and affinity for $Fe^{3+}$ permit easy isolation of the complex and formulation into PFOB NE without the requirement of the subsequent iron loading step necessary for prior compounds.[1] We observed that $Fe^{3+}$ was the most effective cation for intermolecular $^{19}F$ $T_1$ acceleration in PFOB, consistent with our prior work[1]. $Gd^{3+}$ and $Fe^{3+}$ ions formed the basis of $T_1$- and $T_2$-based $^1H$ contrast agents, respectively, but for $^{19}F$ MRI, the roles these ions played are reversed.

The in vivo inflammation mouse model results (FIG. 5A-FIG. 5B) illustrate in vivo compatibility and MRI detectability of P-PFOB NE. The method of using intravenously delivered $^{19}F$ MRI for 'in situ' labeling of macrophages to elucidate inflammation hot-spots is well established and has been used preclinically in a wide range of disease models.[3,23,32] Alternative PFC NE formulations facilitate ex vivo cell uptake in culture,[33] for example during the preparation of stem cell or immunotherapeutic cytotherapies, and following transfer to the patient, these cells were detected in vivo using $^{19}F$ MRI.[4] The fluorine inside the cells yielded positive-signal hot-spot images that can be quantified to measure apparent cell numbers at sites of accumulation, thereby enabling 'in vivo cytometry'.[34] The sensitivity limits of detection were on the order of $10^4$-$10^5$ cells/voxel.

The relaxation rates P-PFOB were predictably tuned by varying Fe concentration. Tests were performed using a range of concentrations less than the maximum because these are the most useful for MRI experiments using the conventional (i.e., spin echo or gradient echo) pulse sequences most used in MRI practice. However, advanced MRI pulse sequences, such as zero time to echo (ZTE) and ultra-short time to echo (UTE), which are used by early adaptors in MRI practice,[29] can predictably reap the benefits of the maximum iron concentration when $T_1$ and $T_2$ are very short.

The total amount of Fe delivered via the P-PFOB injection was miniscule compared to innate Fe levels in mouse. The total dose of SALTAME-bound Fe in the inoculant was approximately 50 µg of chelated Fe. The amount of Fe contained in mouse blood tissue, which represents roughly ⅔ of the total iron stores in body, was approximately 0.75 mg Fe, 15-fold higher. Thus, Fe metabolism of the organism should not be impacted by addition of P-PFOB, which contained small amounts of saturated, SALTAME-bound Fe.

The cell toxicity data presented (FIG. 4A-FIG. 4D) shows no overt toxicity induced by intracellular labeling; the flow-based NAO assay was very sensitive, and both positive and negative controls were included in the experimental design. Generally, the cell-safety of PFC cell labeling has been demonstrated exhaustively in numerous studies and cells types,[35-38] including primary immune cells for a human clinical trial[4] using a panel of in vitro cell assays of phenotype and function, including NAO.

We observed significant linear $^{19}F$ NMR field shifts in all PFOB peaks with the addition of SALTAME $Fe^{3+}$ chelate (FIG. 6a) in the unemulsified oil. SALTAME as a $^{19}F$ shift reagent could be used for multicolor MRI tags comprised of neat P-PFOB oils, for example, to image catheter tips,[39] the gastrointestinal track,[38] or for external $^{19}F$ fiduciary capsules.

Conclusions

Here, we describe the design and characterization of SALTAME, a stable hexadentate chelating agent for iron (III). We used this moiety to formulate a emulsion MRI probe that can be used for 'hot-spot' detection in vivo. Incorporation of iron-bound SALTAME into the fluorous phase of NE causes a profound reduction of the $^{19}F$ $T_1$ value and only mild line broadening, thus offering improved sensitivity of $^{19}F$ MRI due to increased signal averaging and/or reduced MRI scan time.

Overall, the use of fluorinated molecules is emerging as an option for cellular imaging probe design. This probe has the potential to enable longitudinal, non-invasive quantification of inflammation and therapeutic cell delivery and aid in the monitoring of therapeutic test articles.

(1) Kislukhin, A. A.; Xu, H. Y.; Adams, S. R.; Narsinh, K. H.; Tsien, R. Y.; Ahrens, E. T. Paramagnetic Fluorinated Emulsions for Sensitive Cellular Fluorine-19 Magnetic Resonance Imaging. *Nat Mater* 2016, 15, 662.
(2) Ahrens, E. T.; Flores, R.; Xu, H. Y.; Morel, P. A. In Vivo Imaging Platform for Tracking Immunotherapeutic Cells. *Nat Biotechnol* 2005, 23, 983.
(3) Ahrens, E. T.; Zhong, J. In Vivo MRI Cell Tracking Using Perfluorocarbon Probes and Fluorine-19 Detection. *NMR Biomed* 2013, 26, 860.
(4) Ahrens, E. T.; Helfer, B. M.; O'Hanlon, C. F.; Schirda, C. Clinical Cell Therapy Imaging Using a Perfluorocarbon Tracer and Fluorine-19 MRI. *Magn Reson Med* 2014, 72, 1696.
(5) Temme, S.; Bonner, F.; Schrader, J.; Flogel, U. 19F Magnetic Resonance Imaging of Endogenous Macrophages in Inflammation. *Wiley Interdiscip Rev Nanomed Nanobiotechnol* 2012, 4, 329.
(6) Bloembergen, N.; Morgan, L. O. Proton Relaxation Times in Paramagnetic Solutions. Effects of Electron Spin Relaxation. *J Chem Phys* 1961, 34, 842.
(7) Neubauer, A. M.; Myerson, J.; Caruthers, S. D.; Hockett, F. D.; Winter, P. M.; Chen, J.; Gaffney, P. J.; Robertson, J. D.; Lanza, G. M.; Wickline, S. A. Gadolinium-Modulated 19F Signals from Perfluorocarbon Nanoparticles as a New Strategy for Molecular Imaging. *Magn Reson Med* 2008, 60, 1066.
(8) Jacoby, C.; Temme, S.; Mayenfels, F.; Benoit, N.; Krafft, M. P.; Schubert, R.; Schrader, J.; Flogel, U. Probing Different Perfluorocarbons for In Vivo Inflammation Imaging by 19F MRI. Image Reconstruction, Biological Half-Lives and Sensitivity. *NMR Biomed* 2014, 27, 261.
(9) Riess, J. G.; Weers, J. G. Emulsions for Biomedical Uses. *Curr Opin Colloid In* 1996, 1, 652.
(10) Klein, D. H.; Jones, R. C.; Keipert, P. E.; Luena, G. A.; Otto, S.; Weers, J. G. Intravascular Behavior of Perflubron Emulsions. *Colloid Surface A* 1994, 84, 89.
(11) Deeney, F. A.; Harding, C. J.; Morgan, G. G.; McKee, V.; Nelson, J.; Teat, S. J.; Clegg, W. Response to Steric Constraint in Azacryptate and Related Complexes of Iron-(II) and -(III) *. *J Chem Soc Dalton* 1998, 1837.
(12) Filippini, G.; Nappi, M.; Melchiorre, P. Photochemical Direct Perfluoroalkylation of Phenols. *Tetrahedron* 2015, 71, 4535.
(13) Matsugi, M.; Hasegawa, M.; Hasebe, S.; Takai, S.; Suyama, R.; Wakita, Y.; Kudo, K.; Imamura, H.; Hayashi, T.; Haga, S. Direct Perfluoroalkylation of Non-Activated Aromatic C—H Bonds of Phenols. *Tetrahedron Lett* 2008, 49, 4189.
(14) Ramanathan, A.; Jimenez, L. S. Reductive Dehalogenation of Aryl Bromides and Chlorides and Their Use as Aryl Blocking Groups. *Synthesis-Stutgart* 2010, 2, 217.
(15) Janjic, J. M.; Ahrens, E. T. Fluorine-Containing Emulsions for MRI Cell Tracking. *Wiley Interdiscip Rev Nanomed Nanobiotechnol* 2009, 1, 492.
(16) Riess, J. G. Oxygen Carriers ("Blood Substitutes")— Raison D'etre, Chemistry, and Some Physiology Blut Ist Ein Ganz Besondrer Saft. *Chem Rev* 2001, 101, 2797.
(17) Weers, J. G.; Liu, J.; Fields, T.; Resch, P.; Cavin, J.; Arlauskas, R. A. Room Temperature Stable Perfluorocarbon Emulsions with Acceptable Half-Lives in the Reticuloendothelial System. *Artif Cell Blood Sub* 1994, 22, 1175.
(18) Postel, M.; Riess, J. G.; Weers, J. G. FLUOROCARBON EMULSIONS THE STABILITY ISSUE. *Artif Cell Blood Sub* 1994, 22, 991.
(19) Ahrens, E. T.; Janjic, J. M. Compositions and Methods for Producing Emulsions for Nuclear Magnetic Resonance Techniques and Other Applications USPTO 9,352, 057.
(20) Lutsenko, G. V. Flow-Cytometry Assay for Apoptosis Using Fluorophor 10-N-nonyl acridine Orange. *Biol Membrany* 2010, 27, 430.
(21) Temme, S.; Jacoby, C.; Ding, Z.; Bonner, F.; Borg, N.; Schrader, J.; Flogel, U. Technical Advance: Monitoring the Trafficking of Neutrophil Granulocytes and Monocytes During the Course of Tissue Inflammation by Noninvasive 19F MRI. *J Leukoc Biol* 2014, 95, 689.
(22) Chu, S. C. K.; Xu, Y.; Balschi, J. A.; Springer, C. S. Bulk Magnetic-Susceptibility Shifts in NMR Studies of Compartmentalized Samples—Use of Paramagnetic Reagents. *Magn Reson Med* 1990, 13, 239.
(23) Bonner, F.; Merx, M. W.; Klingel, K.; Begovatz, P.; Flogel, U.; Sager, M.; Temme, S.; Jacoby, C.; Salehi Ravesh, M.; Grapentin, C.; Schubert, R.; Bunke, J.; Roden, M.; Kelm, M.; Schrader, J. Monocyte Imaging After Myocardial Infarction with 19F MRI at 3 T: A Pilot Study in Explanted Porcine Hearts. *Eur Heart J-Card Img* 2015, 16, 612.
(24) Flaim, S. F. Pharmacokinetics and Side Effects of Perfluorocarbon-Based Blood Substitutes. *Artif Cell Blood Sub* 1994, 22, 1043.
(25) Giraudeau, C.; Flament, J.; Marty, B.; Boumezbeur, F.; Meriaux, S.; Robic, C.; Port, M.; Tsapis, N.; Fattal, E.; Giacomini, E.; Lethimonnier, F.; Le Bihan, D.; Valette, J. A New Paradigm for High-Sensitivity 19F Magnetic Resonance Imaging of Perfluorooctylbromide. *Magn Reson Med* 2010, 63, 1119.
(26) Colotti, R.; Bastiaansen, J. A.; Wilson, A.; Flogel, U.; Gonzales, C.; Schwitter, J.; Stuber, M.; van Heeswijk, R. B. Characterization of Perfluorocarbon Relaxation Times and Their Influence on the Optimization of Fluorine-19 MRI at 3 Tesla. *Magn Reson Med* 2016 77(6), 2263.
(27) Harvey, P.; Kuprov, I.; Parker, D. Lanthanide Complexes as Paramagnetic Probes for 19F Magnetic Resonance. *Eur J Inorg Chem* 2012, 2015.
(28) De Luca, E.; Harvey, P.; Chalmers, K. H.; Mishra, A.; Senanayake, P. K.; Wilson, J. I.; Botta, M.; Fekete, M.; Blamire, A. M.; Parker, D. Characterisation and Evaluation of Paramagnetic Fluorine Labelled Glycol Chitosan Conjugates for (19)F and (1)H Magnetic Resonance Imaging. *J Biol Inorg Chem* 2014, 19, 215.
(29) Schmid, F.; Holtke, C.; Parker, D.; Faber, C. Boosting (19) F MRI-SNR Efficient Detection of Paramagnetic Contrast Agents Using Ultrafast Sequences. *Magn Reson Med* 2013, 69, 1056.
(30) Funk, A. M.; Fries, P. H.; Harvey, P.; Kenwright, A. M.; Parker, D. Experimental Measurement and Theoretical Assessment of Fast Lanthanide Electronic Relaxation in Solution with Four Series of Isostructural Complexes. *J Phys Chem A* 2013, 117, 905.

(31) Kok, M. B.; de Vries, A.; Abdurrachim, D.; Prompers, J. J.; Grull, H.; Nicolay, K.; Strijkers, G. J. Quantitative (1)H MRI, (19)F MRI, and (19)F MRS of Cell-Internalized Perfluorocarbon Paramagnetic Nanoparticles. *Contrast Media Mol I* 2011, 6, 19.

(32) Ratner, A. V.; Hurd, R.; Muller, H. H.; Bradley-Simpson, B.; Pitts, W.; Shibata, J. D.; Sotak, C.; Young, S. W. *Magn Reson Med* 1987, 5, 548.

(33) Janjic, J. M.; Srinivas, M.; Kadayakkara, D. K.; Ahrens, E. T. Self-Delivering Emulsions for Dual Fluorine-19 MRI and Fluorescence Detection. *J Am Chem Soc* 2008, 130, 2832.

(34) Srinivas, M.; Turner, M. S.; Janjic, J. M.; Morel, P. A.; Laidlaw, D. H.; Ahrens, E. T. In Vivo Cytometry of Antigen-Specific T Cells Using 19F MRI. *Magn Reson Med* 2009, 62,

(35) Helfer, B. M.; Balducci, A.; Nelson, A. D.; Janjic, J. M.; Gil, R. R.; Kalinski, P.; De Vries, I. J. M.; Ahrens, E. T.; Mailliard, R. B. Functional Assessment of Human Dendritic Cells Labeled for In Vivo F-19 Magnetic Resonance Imaging Cell Tracking. *Cytotherapy* 2010, 12, 238.

(36) Bouchlaka, M. N.; Ludwig, K. D.; Gordon, J. W.; Kutz, M. P.; Bednarz, B. P.; Fain, S. B.; Capitini, C. M. 19F-MRI for Monitoring Human NK Cells In Vivo. *OncoImmunology* 2016, 5, e1143996.

(37) Rose, L. C.; Kadayakkara, D. K.; Wang, G.; Bar-Shir, A.; Helfer, B. M.; O'Hanlon, C. F.; Kraitchman, D. L.; Rodriguez, R. L.; Bulte, J. W. M. Fluorine-19 Labeling of Stromal Vascular Fraction Cells for Clinical Imaging Applications. *Stem Cells Transl Med* 2015, 4, 1472.

(38) Schirra, C. O.; Weiss, S.; Krueger, S.; Pedersen, S. F.; Razavi, R.; Schaeffter, T.; Kozerke, S. Toward True 3D Visualization of Active Catheters Using Compressed Sensing. *Magn Reson Med* 2009, 62, 341.

(39) Mattrey, R. F.; Hajek, P. C.; Gylys-Morin, V. M.; Baker, L. L.; Martin, J.; Long, D. C.; Long, D. M. Perfluorochemicals as Gastrointestinal Contrast Agents for MR Imaging: Preliminary Studies in Rats and Humans. *Am J Roentgen* 1987, 148, 1259.

Supplementary Information for Examples 1 and 2

1. General Information

Materials. Chemicals were purchased from Sigma-Aldrich (St Louis, MO) or other reputable suppliers, and organic solvents (liquid chromatography-grade) were purchased from Fisher Scientific (Pittsburgh, PA) and used as received. Anhydrous dimethylformamide (DMF) and acetonitrile were stored over activated 4 Å molecular sieves. Fluorous solvents were purchased from Perseptive Biosystems (Framingham, MA). Precoated silica gel plates (60 F-254, Merck Millipore, Billerica, MA) were used for thin-layer chromatography (TLC), and silica gel 60 (230-400 mesh) was used for column chromatography.

Methods. All reactions were carried out under $N_2$ unless otherwise noted. Reactions were monitored by TLC and liquid chromatography mass spectrometry (LC-MS) using an Agilent (Santa Clara, CA) 1100 HPLC with MSD Trap XLT using a Phenomenex Luna C18(2) 100 Å, 5 μm, 4.6 mm×250 column, MeCN/$H_2O$ linear gradients with constant 0.05% v/v $CF_3CO_2H$ additive, 1 mL/min flow, and ESI positive or negative ion mode. Reaction products were purified by flash chromatography on silica gel eluted with ethyl acetate and hexane. High-resolution mass spectrometry was performed by the Molecular Mass Spectrometry Facility at the University of California San Diego. Ultraviolet-visible (UV-Vis) absorption spectra were recorded on a Shimadzu (Kyoto, Japan) spectrophotometer. Solubility of $Fe^{3+}$-SALTAME compounds in perfluorocarbons were determined by absorbance at 450 nm following dilution in ethyl acetate using experimentally-determined extinction coefficients of 700 $M^{-1}$ $cm^{-1}$ for the 5a isomers.

NMR measurements. NMR spectra and relaxation rates were recorded on a Bruker Ascend 400 MHz (9.4 T) spectrometer (Billerica, MA). Additional relaxation rate measurements were performed at 3 T using a GE750 (General Electric, Milwaukee, WI) clinical MRI system equipped with a custom dual-channel $^{19}F/^{1}H$ 72 mm diameter volume coil (RAPID Biomedical, Rimpar, Germany). The $^{19}F$ NMR spectra were referenced to an internal standard, sodium trifluoroacetate (NaTFA, 0.1 wt %, -76.00 ppm, Sigma-Aldrich, T6508), which was placed in a separate sealed capillary tube within the NMR tube. Relaxation measurements were performed using a standard inversion recovery pulse sequence and a Carr-Purcell-Meiboom-Gill sequence with echo-time (TE) values in 12 linear increments. The $T_1$ and $T_2$ values were obtained by nonlinear fitting using MNova 6.0.2 software (Mestrelab, Escondido, CA). Fit errors were less than 5% of $T_1$ and $T_2$ values. For quantitative peak measurements, spectra were acquired using calibrated 90° pulses, 32,000 complex points, spectral window 0 to -200 ppm, relaxation delay 2.5 s, and 128 averages. Spectra were processed in MNova with manual phase correction and Whittaker smoother baseline correction (filter=1 ppm). Relaxation parameters were measured for six middle $CF_2$ peaks of PFOB, spanning ~10 ppm, which account for 12 out of 17 F atoms in the molecule. To assay emulsion uptake ($^{19}F$/cell) using NMR, an aliquot of 1×10$^6$ cells were pelleted and resuspended in 0.1 mL of lysis solution (0.5% Triton X, 100 mM NaCl, 20 mM Tris, 1 mM EDTA) and reference compound NaTFA (0.745 mg/mL)/$D_2O$ was added to 5 mm NMR tube. The integrated ratio of PFOB fluorine peaks to NaTFA singlet fluorine peak at -76.00 ppm determined the amount of $^{19}F$ in the cell pellet and the $^{19}F$/cell was calculated.

2. Synthesis and Characterization

General method for perfluoroalkylation of salicylaldehydes. The overall synthetic scheme is displayed in FIG. 1. The salicylaldehyde (10 mM), perfluoroalkyl iodide (20 mM) and anhydrous cesium carbonate (40 mM) were heated in dry DMF (50 mL) at 100° C. overnight with vigorous stirring under a dry $N_2$ atmosphere. The dark reaction mixture was cooled and cautiously poured into ~4M HCl (100 mL), and the crude product was extracted with EtOAc (3×50 mL), dried over $Na_2SO_4$ and evaporated to dryness. The product was purified by silica gel chromatography eluted with EtOAc-hexane (1:50 to 1:10 ratio).

3-Bromo-5-perfluorohexyl-salicylaldehyde, 2a. Prepared from 3-bromosalicylaldehyde (1a) and perfluorohexyl iodide. Purified by silica gel chromatography eluted with 5% EtOAc-hexane to give a white solid. Yield, 63%. $^1H$ NMR (400 MHz, Chloroform-d) δ 11.98 (s, 1H), 9.96 (s, 1H), 8.00 (s, 1H), 7.82 (s, 1H). $^{19}F$ NMR (376 MHz, Chloroform-d) δ -80.94, -110.22--110.71 (m), -121.60 (dt, J=50.9, 15.6 Hz), -122.95, -126.31 (d, J=15.1 Hz). $^{13}C$ NMR (101 MHz, Chloroform-d) δ 195.51, 160.98, 137.77, 131.77, 121.77 (t, J=26.1 Hz), 120.67, 112.49. MS (m/z, ESI-TOF) for [M-H]$^+$ calculated 516.9114, found 516.9110.

5-Bromo-3-perfluorohexyl-salicylaldehyde, 2b. Prepared from 5-bromosalicylaldehyde (1b) and perfluorohexyl iodide. Purified by silica gel chromatography eluted with 5% EtOAc-hexane to give a white solid. Yield, 75%. $^1$H NMR (400 MHz, Chloroform-d) δ 11.74 (s, 1H), 9.90 (s, 1H), 7.90 (s, 1H), 7.85 (s, 1H). $^{19}$F NMR (376 MHz, Chloroform-d) δ −80.95 (d, J=25.4 Hz), −108.48--110.07 (m), −121.46 (d, J=113.9 Hz), −121.94, −122.91, −126.32. $^{13}$C NMR (101 MHz, Chloroform-d) δ 195.33, 159.75, 140.25, 139.00, 122.65, 119.25 (t, J=24.1 Hz), 111.05. MS (m/z, ESI-TOF) for [M−H]$^+$ calculated 516.9114, found 516.9112.

5-Perfluorohexyl-salicylaldehyde, 3a (route 2). 2a, (3.2 g, 6.3 mmol) was dissolved in MeOH (100 ml), sodium acetate (0.57 g, 7 mmol) and Pd—C(5%, 50 mg), and the mixture was hydrogenated at room temperature and pressure until uptake was complete (30 min). The reaction mixture was filtered through Celite and evaporated to dryness, dissolved in EtOAc (50 ml) and washed with water (3×25 ml). The organic layer was dried (Na$_2$SO$_4$) and evaporated to give the product as a white solid. Yield, 2.71 g (98%). $^1$H NMR (400 MHz, Chloroform-d) δ 11.32 (s, 1H), 9.95 (s, 1H), 7.80 (s, 1H), 7.70 (d, J=8.8 Hz, 1H), 7.12 (d, J=8.8 Hz, 1H). $^{19}$F NMR (376 MHz, Chloroform-d) δ −80.75 (t, J=10.2 Hz), −110.24 (t, J=14.0 Hz), −121.64 (d, J=145.9 Hz), −122.83, −126.14. $^{13}$C NMR (101 MHz, Chloroform-d) δ 196.12, 164.36, 134.97, 133.01, 120.34, 118.90, 122-108 (m, weak). MS (m/z, ESI-TOF) for [M−H]$^+$ calculated 439.0009, found 439.0010.

3-Perfluorohexyl-salicylaldehyde, 3b (route 2). Prepared from 2b using the procedure used for 3a to give 3b as a white solid, yield 100%. $^1$H NMR (400 MHz, Chloroform-d) δ 11.83 (s, 1H), 9.94 (s, 1H), 7.76 (dd, J=10.7, 8.0 Hz, 2H), 7.14 (t, J=7.8 Hz, 1H). $^{19}$F NMR (376 MHz, Chloroform-d) δ −80.81 (d, J=8.2 Hz), −109.01 (t, J=14.7 Hz), −121.65 (d, J=144.0 Hz), −122.80, −126.19. $^{13}$C NMR (101 MHz, Chloroform-d) δ 196.55, 160.96, 138.27, 136.58, 121.55, 119.58, 122-108 (m, weak). MS (m/z, ESI-TOF) for [M−H]$^+$ calculated 439.0009, found 439.0008.

3,5-Bis-perfluorohexyl-salicylaldehyde, 3c (route 1). Prepared from salicylaldehyde, 1c and perfluorohexyl iodide (3 equivalent). Purified by silica gel chromatography eluted with 15% EtOAc-hexane producing a white solid. Yield, 68%. $^1$H NMR (400 MHz, Chloroform-d) δ 12.21 (s, 1H), 10.02 (s, 1H), 8.03 (s, 1H), 7.93 (s, 1H). $^{19}$F NMR (376 MHz, Chloroform-d) δ −80.96 (d, J=7.7 Hz), −109.49 (t, J=15.5 Hz), −110.56--111.15 (m), −121.54 (q, J=17.7, 16.6 Hz), −121.94 (t, J=16.8 Hz), −122.93, −126.31 (d, J=14.3 Hz). $^{13}$C NMR (101 MHz, Chloroform-d) δ 195.76, 163.30, 136.71 (t, J=6.9 Hz), 134.61 (t, J=8.4 Hz), 121.31, 120.64 (t, J=24.2 Hz), 118.52 (t, J=22.4 Hz), 120-108 (m, weak). MS (m/z, ESI-TOF) for [M−H]$^+$ calculated 756.9723, found 756.9719.

5-Methyl-3-perfluorohexyl-salicylaldehyde, 3d (route 1). Prepared from 5-methylsalicylaldehyde (1d) and perfluorohexyl iodide. Purified by short pathlength distillation 90-120° C. at 100 mTorr to give a yellow-brown oil. Yield, 75%. $^1$H NMR (400 MHz, Chloroform-d) δ 11.62 (s, 1H), 9.90 (s, 1H), 7.48-7.62 (m, 2H), 2.40 (s, 3H). $^{19}$F NMR (376 MHz, Chloroform-d) δ −80.82 (t, J=10.7 Hz), −108.92 (t, J=15.6 Hz), −121.44 (d, J=16.4 Hz), −121.87 (t, J=14.7 Hz), −122.81 (d, J=15.9 Hz), −126.18 (d, J=16.9 Hz). $^{13}$C NMR (101 MHz, Chloroform-d) δ 196.47, 158.75 (t, J=2.7 Hz), 138.22, 137.07 (t, J=7.9 Hz), 133.56, 129.12, 121.31, 20.32. MS (m/z, ESI-TOF) for [M−H]$^+$ calculated 453.0166, found 453.0164.

3-Methyl-5-perfluorooctyl-salicylaldehyde, 3f (route 1). Prepared from 3-methylsalicylaldehyde (1f) and perfluorooctyl iodide. Purified by short pathlength distillation 135° C. at 100 mTorr to give a yellow-brown oil that slowly solidified. Yield, 78%. $^1$H NMR (400 MHz, Chloroform-d) δ 11.59 (s, 1H), 9.94 (s, 1H), 7.66 (s, 1H), 7.57 (s, 1H), 2.34 (s, 3H). $^{19}$F NMR (376 MHz, Chloroform-d) δ −80.72 (t, J=9.5 Hz), −110.15 (t, J=14.5 Hz), −121.08--121.42 (m), −121.54--122.10 (m), −122.70, −126.11 (t, J=14.3 Hz). $^{13}$C NMR (101 MHz, Chloroform-d) δ 196.27, 162.72, 135.16 (t, J=6.2 Hz), 130.50 (t, J=6.8 Hz), 128.57, 120.11 (t, J=25.2 Hz), 119.52, 15.40. MS (m/z, ESI-TOF) for [M−H]$^+$ calculated 553.0102, found 553.0099.

1,1,1-(Tris(3'(5')-perfluorosalicylidene)methyl)-ethane, 4a. 2-(Aminomethyl)-2-methyl-1,3-propanediamine trihydrochloride (226 mg, 1 mmol) was added to a solution of 3a (0.88 g, 2 mmol), 3b (0.44 g, 1 mmol) and triethylamine (0.46 ml, 3.33 mmol) in absolute EtOH (10 ml). The mixture was refluxed for 4 h until a yellow solution was formed, then cooled and evaporated to dryness. The residue was dissolved in EtOAc/water (1:1 v/v, 100 ml), separated and the EtOAc layer washed with water (2×25 ml). The combined organic layers were dried (Na$_2$SO$_4$) to give the crude product as a mixture of isomers that was used without further purification. For analysis, a small amount these intermediates was separated by HPLC on a C18 reverse-phase column (Luna-2, Phenomenex, Torrance, CA) using isocratic elution with acetonitrile.

1,1,1-(Tris(5'-perfluorohexylsalicylidene)methyl)-ethane, 4a PPP ($R_2$, $R_4$, $R_6$=H; $R_1$, $R_3$, R=perfluorohexyl). $^1$H NMR (400 MHz, Methylene Chloride-d$_2$) δ 13.87 (s, 3H), 8.46 (s, 3H), 7.53 (d, J=7.5 Hz, 6H), 7.07 (d, J=9.3 Hz, 3H), 3.71 (s, 6H), 1.20 (s, 3H). $^{19}$F NMR (376 MHz, Methylene Chloride-d$_2$) δ− 81.16 (d, J=8.6 Hz), −110.04 (t, J=13.7 Hz), −121.74, −122.15, −123.09, −126.43.

1,1,1-(Bis(5'-perfluorohexylsalicylidene)(3'-perfluorohexylsalicylidene) methyl)-ethane, 4a POP ($R_2$, $R_3$, $R_6$=H; $R_1$, $R_4$, R=perfluorohexyl). $^1$H NMR (400 MHz, Methylene Chloride-d$_2$) δ 14.52 (s, 1H, OH of ortho), 13.86 (s, 2H, OH of para), 8.46 (d, J=8.3 Hz, 3H), 7.53 (q, J=8.8, 7.9 Hz, 6H), 7.18-6.92 (m, 3H), 3.71 (d, J=13.7 Hz, 6H), 1.20 (s, 3H). $^{19}$F NMR (376 MHz, Methylene Chloride-d$_2$) δ− 81.18 (t, J=9.8 Hz), −108.82 (t, J=14.5 Hz), −110.06 (t, J=13.4 Hz), −120.24--125.45 (m), −126.45.

1,1,1-(Bis(3'-perfluorohexylsalicylidene)(5'-perfluorohexylsalicylidene) methyl)-ethane, 4a OOP ($R_2$, $R_3$, $R_5$=H; $R_1$, $R_4$, $R_6$=perfluorohexyl). $^1$H NMR (400 MHz, Methylene Chloride-d$_2$) δ 14.55 (s, 2H, OH of ortho), 13.89 (s, 1H, OH of para), 8.52 (d, J=4.7 Hz, 3H), 7.64-7.52 (m, 6H), 7.14-6.99 (m, 3H), 3.75 (s, 6H), 1.23 (s, 3H). $^{19}$F NMR (376 MHz, Methylene Chloride-d$_2$) δ −81.18, −108.81 (t, J=14.3 Hz), −110.07 (t, J=13.1 Hz), −120.31--125.21 (m), −126.43.

1,1,1-(Tris(3'-perfluorohexylsalicylidene)methyl)-ethane, 4a OOO($R_1$, $R_3$, $R_5$=H; $R_2$, $R_4$, $R_6$=perfluorohexyl). $^1$H NMR (400 MHz, Methylene Chloride-d$_2$) δ 14.49 (s, 3H, OH), 8.49 (s, 3H, CH=N), 7.53 (dd, J=19.4, 7.7 Hz, 6H), 7.00 (t, J=7.7 Hz, 3H), 3.72 (s, 6H), 1.19 (s, 3H). $^{19}$F NMR (376 MHz, Methylene Chloride-d$_2$) δ− 81.11 (dt, J=20.6, 10.0 Hz), −108.80 (t, J=14.0 Hz), −120.23--124.17 (m), −126.40.

Preparation of Fe SALTAME isomers (5a PPP, POP, OOP, and OOO). A solution of 3a (0.78 g, 1.77 mmol) in absolute EtOH (5 ml) was added dropwise to a stirred suspension of 2-(aminomethyl)-2-methyl-1,3-propanediamine, trihydrochloride (210 mg, 0.88 mmol) and triethylamine (0.49 ml, 3.52 mmol) in absolute EtOH (10 ml) at 80° C. 3b (387 mg, 0.88 mmol) dissolved in 2.5 ml EtOH was then added and further heated for 30 min, followed by the addition of a solution of anhydrous ferric chloride (162 mg, 1 mmol), then anhydrous sodium acetate (0.24 g, 3 mmol) in absolute EtOH (5 ml). The resulting deep red reaction mixture was cooled, evaporated to dryness, dissolved in EtOAc:water (1:1 v/v, 100 ml) and separated. The aqueous layer was extracted (2×50 ml) with EtOAc; the combined organic layers dried over $Na_2SO_4$ and evaporated to dryness. The products were separated by $SiO_2$ column chromatography eluted with 0-55% EtOAc-hexane. Three distinct, red products were collected:

i. 5a Fe PPP eluted with 20% EtOAc-hexane. Yield, 228 mg (18%). $^{19}F$ NMR (376 MHz, Methanol-$d_4$) δ −82.31, −108.47, −117.87, −123.11, −127.14. MS (m/z, ESI-TOF) for $[M+H]^+$ calculated 1437.0383, found 1437.0405.

ii. 5a Fe POP eluted with 40% EtOAc-hexane. Yield, 346 mg (27%). $^{19}F$ NMR (376 MHz, Methanol-$d_4$) δ− 82.31, −108.92, −114.90-−130.03 (m). MS (m/z, ESI-TOF) for $[M+H]^+$ calculated 1437.0383, found 1437.0400.

iii. 5a Fe OOP eluted with 50% EtOAc-hexane. Yield, 183 mg (14%). $^{19}F$ NMR (376 MHz, Methanol-$d_4$) δ− 82.22 (d, J=98.2 Hz), −117.04-−124.61 (m), −125.89, −127.17. MS (m/z, ESI-TOF) for $[M+H]^+$ calculated 1437.0383, found 1437.0397.

Only trace amount of 5a OOO was observed on TLC. 5a OOO was also prepared by using 3b (1.16 g, 2.65 mmol) without adding 3a.

5a Fe OOO: $^{19}F$ NMR (376 MHz, Methanol-$d_4$) δ− 82.04, −121.06, −125.89. MS (m/z, ESI-TOF) for $[M+H]^+$ calculated 1437.0383, found 1437.0407. Compound 5a Fe PPP can also be obtained using 3a (1.16 g, 2.65 mmol) only. The independent preparation of 5a Fe OOO and 5a Fe PPP help assign the four isomers on TLC.

Preparation of Fe SALTAMEs (5c-f). Perfluoroalkyl-substituted salicylaldehyde 3c-f (3.3 mmol), 2-(aminomethyl)-2-methyl-1,3-propanediamine trihydrochloride (226 mg, 1 mmol) and triethylamine (0.46 ml, 3.3 mmol) in absolute EtOH (10 ml) were heated at 80° C. for 3 h. A solution of anhydrous ferric chloride (243 mg, 1.5 mmol) in absolute EtOH (5 ml) was added, followed by anhydrous sodium acetate (287 mg, 3.5 mmol) to give a red colored solution. The reaction mixture was cooled, evaporated to dryness, dissolved in EtOAc:water (20 ml/20 ml) and separated. The aqueous layer was extracted with EtOAc (3×20 ml); the combined organic layers were dried over anhydrous $Na_2SO_4$ and evaporated to dryness. The products were separated by $SiO_2$ column chromatography eluted with EtOAc-hexane.

5c ($R_1$-$R_6$=perfluorohexyl) was obtained by starting with 3c in a 70% yield. $^{19}F$ NMR (376 MHz, Chloroform-d) δ −80.77, −81.04, −109.32, −117.57, −121.42, −122.48, −126.13. MS (m/z, ESI-TOF) for $[M+H]^+$ calculated 2412.9346, found 2412.9307.

5d ($R_1$, $R_3$, $R_5$=$CH_3$; $R_2$, $R_4$, $R_6$=perfluorohexyl) was obtained by starting with 3d at 69% yield. $^{19}F$ NMR (376 MHz, Chloroform-d) δ −80.82, −120.49, −122.28, −126.36. MS (m/z, ESI-TOF) for $[M+H]^+$ calculated 1479.0853, found 1479.0843.

5e ($R_1$, $R_3$, $R_5$=$CF_3$; $R_2$, $R_4$, $R_6$=H) was obtained by starting with 1e (or 3e) at yield of 65%. $^{19}F$ NMR (376 MHz, Chloroform-d) δ −61.86. MS (m/z, ESI-TOF) for $[M+H]^+$ calculated 687.0862, found 687.0865.

5f ($R_1$, $R_3$, $R_5$=perfluorooctyl; $R_2$, $R_4$, $R_6$=$CH_3$) was obtained by starting with 3f at yield of 49%. $^{19}F$ NMR (376 MHz, Chloroform-d) δ −80.72, −105.82, −116.21, −121.24, −121.82, −122.69, −126.11. MS (m/z, ESI-TOF) for $[M+H]^+$ calculated 1779.0661, found 1779.0644.

Preparation of 5a Mn, Co and Ga SALTAME. Prepared as described above for the Fe complex, except replacing $FeCl_3$ with $MnCl_2$, $CoCl_2$ and $GaCl_3$, to form brown, green and colorless reaction mixtures, respectively, that were isolated as isomer mixtures (predominately POP and OOP in approximately equal amounts for Co and Ga but one major isomer for Mn) by silica gel chromatography. Ga POP and OOP complexes were separated by preparative HPLC. Complexes formed with other Period 4 metals were detected by LC-MS or, if unstable to the acidic LC conditions, by MS only, if not isolatable by silica gel chromatography.

5a Ga OOP $^1H$ NMR (400 MHz, Methylene Chloride-$d_2$) δ 11.92 (s, 1H), 11.39 (s, 1H), 10.00 (s, 1H), 8.32-8.16 (m, 2H), 7.88 (d, J=8.6 Hz, 1H), 7.79 (dd, J=16.6, 8.4 Hz, 1H), 7.52-7.41 (m, 2H), 7.26-7.16 (m, 1H), 6.92-6.66 (m, 2H), 4.26 (dt, J=27.8, 14.2 Hz, 3H), 3.65-3.43 (m, 3H), 1.38-1.08 (m, 3H). $^{19}F$ NMR (376 MHz, Methylene Chloride-$d_2$) δ− 76.34, −79.87-−82.57 (m), −107.68-−111.95 (m), −120.11-−124.32 (m), −126.41. MS (m/z, ESI-TOF) for $[M+H]^+$ calculated 1450.0289, found 1450.0281.

5a Ga POP $^1H$ NMR (400 MHz, Methylene Chloride-$d_2$) δ 8.29-8.06 (m, 3H), 7.56-7.21 (m, 6H), 6.80-6.55 (m, 3H), 4.26-4.07 (m, 3H), 3.48 (t, J=16.5 Hz, 3H), 1.19 (s, 3H). $^{19}F$ NMR (376 MHz, Methylene Chloride-$d_2$) δ− 81.08-−81.66 (m), −107.56-−111.35 (m), −121.14-−123.63 (m), −126.60 (d, J=61.7 Hz). $^{13}C$ NMR (101 MHz, Methylene Chloride-$d_2$) δ 172.02, 169.75, 169.68, 169.56, 168.03, 139.06, 138.10, 135.57, 135.48, 135.21, 133.05, 132.45, 123.88, 120.99, 120.57, 120.32, 118.95, 115.12, 114.60, 114.36, 114.31, 122.55-105.27 (m, weak), 67.27, 66.09, 65.88, 35.47, 23.43. MS (m/z, ESI-TOF) for $[M+H]^+$ calculated 1450.0289, found 1450.0282.

5a $Mn^{4+}$ SALTAME MS (m/z, ESI) for $[M]^+$ calculated 1435.0, found 1435.0.

5a $Co^{3+}$ SALTAME MS (m/z, ESI) for $[M+H]^+$ calculated 1440.0, found 1440.2.

3. X-Ray Crystallography

Crystals of the subject compound were grown by dissolving approximately 20 mg of sample in 1 mL of perfluorooctyl bromide, which was then vapor diffused with pentane over several days. A 0.299×0.283×0.13 mm piece of a dark red crystal was mounted on a Cryoloop with Parabar oil. The single crystal X-ray diffraction data were collected on a Bruker D8 Venture kappa diffractometer equipped with a Photon 100 CMOS detector. An Ips microfocus source provided the Mo Kα radiation (0.71073 Å) that was monochromated with multilayer mirrors. Data were collected in a nitrogen gas stream at 100(2) K. Crystal-to-detector distance was 34 mm and exposure time was 60 seconds per frame using a scan width of 0.50°. Data collection was 99.9% complete to 25.242° in θ. A total of 147,277 reflections were collected covering the indices −22≤h≤22, −25≤k≤25, and −27≤l≤27. A total of 27,918 reflections were found to be symmetry independent, with $R_{int}$=0.0522. Indexing and unit cell refinement indicated a triclinic lattice. The space group was found to be P-1. The data were integrated using the Bruker SAINT software program and scaled using the SADABS software program.[1] Solution by direct methods (SHELXT)[2,3] produced a complete phasing model consistent with the proposed structure.

All nonhydrogen atoms were refined anisotropically by full-matrix, least-squares using SHELXL-2014 software. All hydrogen atoms were placed using a riding model. Their positions were constrained relative to their parent atom using the appropriate HFIX command in SHELXL-2014. Please see additional information in the cif for explanation of disorder and the restraints and constraints that were imposed on the structure model. Crystallographic parameters are summarized in Tables 5-7.

TABLE 5

Crystal data and structure refinement for 5a PPP.

| | |
|---|---|
| Identification code | dd40g1s_sq |
| Empirical formula | C44 H21 F39 Fe N3 O3 |
| Formula weight | 1436.49 |
| Temperature | 100(2) K |
| Wavelength | 0.71073 Å |
| Crystal system | Monoclinic |
| Space group | P2$_1$/n |
| Unit cell dimensions | a = 18.7587(13) Å = 90°. |
| | b = 14.9103(10) Å = 100.778(2)°. |
| | c = 41.473(3) Å = 90°. |
| Volume | 11395.3(13) Å$^3$ |
| Z | 8 |
| Density (calculated) | 1.675 Mg/m$^3$ |
| Absorption coefficient | 0.433 mm$^{-1}$ |
| F(000) | 5.656 |
| Crystal size | 0.476 × 0.186 × 0.066 mm$^3$ |
| Theta range for data collection | 2.121 to 25.403°. |
| Index ranges | −22 ≤ h ≤ 18, −17 ≤ k ≤ 17, −49 ≤ l ≤ 49 |
| Reflections collected | 146,200 |
| Independent reflections | 20,891 [R(int) = 0.0439] |
| Completeness to theta = 25.242° | 99.8% |
| Absorption correction | Semi-empirical from equivalents |
| Max. and min. transmission | 0.7452 and 0.6602 |
| Refinement method | Full-matrix least-squares on F$^2$ |
| Data/restraints/parameters | 20891/3332/2048 |
| Goodness-of-fit on F$^2$ | 1.128 |
| Final R indices [I > 2sigma(I)] | R1 = 0.0699, wR2 = 0.1600 |
| R indices (all data) | R1 = 0.0844, wR2 = 0.1677 |
| Extinction coefficient | n/a |
| Largest diff. peak and hole | 1.441 and −0.912 e · Å$^{-3}$ |

TABLE 6

Crystal data and structure refinement for 5a POP.

| | |
|---|---|
| Identification code | dd39g1s |
| Empirical formula | C44 H21 F39 Fe N3 O3 |
| Formula weight | 1436.49 |
| Temperature | 100(2) K |
| Wavelength | 0.71073 Å |
| Crystal system | Triclinic |
| Space group | P-1 |
| Unit cell dimensions | a = 18.9287(12) Å = 69.132(2)°. |
| | b = 20.9323(13) Å = 67.049(2)°. |
| | c = 22.6097(13) Å = 72.740(2)°. |
| Volume | 7,577.4(8) Å$^3$ |
| Z | 6 |
| Density (calculated) | 1.889 Mg/m$^3$ |
| Absorption coefficient | 0.489 mm$^{-1}$ |
| F(000) | 4.242 |
| Crystal size | 0.299 × 0.283 × 0.13 mm$^3$ |
| Theta range for data collection | 2.268 to 25.443°. |
| Index ranges | −22 ≤ h ≤ 22, −25 < k ≤ 25, −27 ≤ l ≤ 27 |
| Reflections collected | 147,277 |
| Independent reflections | 27,918 [R(int) = 0.0522] |
| Completeness to theta = 25.242° | 99.9% |
| Absorption correction | Semi-empirical from equivalents |
| Max. and min. transmission | 0.7452 and 0.6127 |
| Refinement method | Full-matrix least-squares on F$^2$ |
| Data/restraints/parameters | 27,918/882/2,590 |
| Goodness-of-fit on F$^2$ | 1.123 |
| Final R indices [I > 2sigma(I)] | R1 = 0.0703, wR2 = 0.1882 |
| R indices (all data) | R1 = 0.0860, wR2 = 0.2052 |
| Extinction coefficient | 0.00211(15) |
| Largest diff. peak and hole | 1.637 and −0.788 e · Å$^{-3}$ |

TABLE 7

Crystal data and structure refinement for 5a OOO.

| | |
|---|---|
| Identification code | ooo |
| Empirical formula | C44.33 H21.67 C10.67 F39 Fe N3 O3 |
| Formula weight | 1,464.80 |
| Temperature | 100.0 K |
| Wavelength | 0.71073 Å |
| Crystal system | Trigonal |
| Space group | R-3 |
| Unit cell dimensions | a = 21.9360(10) Å = 90°. |
| | b = 21.9360(10) Å = 90°. |
| | c = 55.501(3) Å = 120°. |
| Volume | 23128(2) Å$^3$ |
| Z | 18 |
| Density (calculated) | 1.893 Mg/m$^3$ |
| Absorption coefficient | 0.516 mm$^{-1}$ |
| F(000) | 12978 |
| Crystal size | 0.317 × 0.255 × 0.176 mm$^3$ |
| Theta range for data collection | 1.299 to 26.382°. |
| Index ranges | −27 ≤ h ≤ 27, −27 ≤ k ≤ 17, −69 ≤ l ≤ 68 |
| Reflections collected | 61,788 |
| Independent reflections | 10,520 [R(int) = 0.0442] |
| Completeness to theta = 25.000° | 99.9% |
| Absorption correction | Semi-empirical from equivalents |
| Max. and min. transmission | 0.1495 and 0.1220 |
| Refinement method | Full-matrix least-squares on F$^2$ |
| Data/restraints/parameters | 10,520/465/1,068 |
| Goodness-of-fit on F$^2$ | 1.041 |
| Final R indices [I > 2sigma(I)] | R1 = 0.0395, wR2 = 0.0887 |
| R indices (all data) | R1 = 0.0629, wR2 = 0.1010 |
| Extinction coefficient | n/a |

4. Sensitivity Modeling

Numerical simulation was used to predict the approximate $^{19}$F MRI sensitivity gain using P-PFOB NE agents. With repetitive signal averaging ($N_{av}$ was the number of acquisitions) signal was additive, whereas noise tended to diminish, thereby increasing overall image signal-to-noise ratio (SNR) by SNR=SNR$_1 \sqrt{N_{av}}$, where SNR$_1$ was the SNR for $N_{av}$=1. We assumed a conventional spoiled gradient-echo (GRE) imaging sequence,[4] where the signal S$_1$ acquired per acquisition was given by $$S_1 = \frac{(1 - e^{-n})e^{\frac{-TE}{T_2}} \sin \alpha}{1 - e^{-n} \cos \alpha} \quad (1)$$

where n=TR/T$_1$, TR was the repetition time, TE was the echo time, T$_1$ and T$_2$ were longitudinal and transverse relaxation times, and a was the flip angle set at the optimal Ernst angle value given by a=cos$^{-1}$(e$^{-n}$). The total imaging time t≈N$_{av}$TR. We assumed t=1, T$_2$*~T$_2$, and TR<T$_1$ with a value fixed such that TR∝T1. For two different materials designated a and b with differing T$_1$ and T$_2$ values (e.g., a=P-PFOB NE and b=PFOB) and using (Eq. 1), the model defined sensitivity gain G as $$G = \frac{SNR_a}{SNR_b} = \sqrt{\frac{T_{1b}}{T_{1a}}} \frac{e^{\frac{-TE}{T_{2a}}}}{e^{\frac{-TE}{T_{2b}}}} \quad (2)$$

Figure 3:
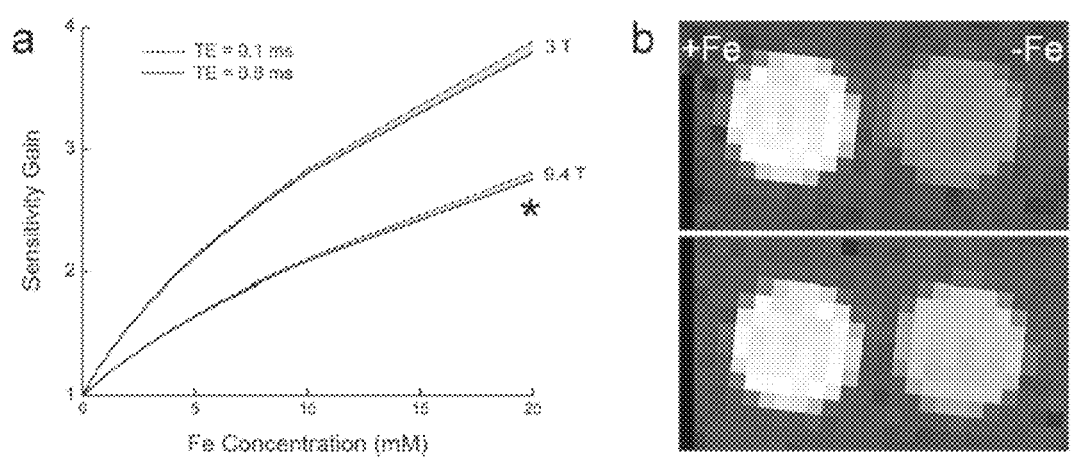
FIG. 3A-FIG. 3B. P-PFOB 19F MRI signal intensity enhancement. Panel (a) shows simulated sensitivity gain of P-PFOB versus PFOB at 3 T and 9.4 T as a function of nanoemulsion-bound iron. Sensitivity gain is defined as SNR(P-PFOB)/SNR(PFOB) for constant time imaging. The model uses the empirically measured r1 and r2 relaxivities. The shaded regions represent a 0.1-0.8 ms TE parameter range. See Supplementary Information Section 4 for model details. (b) Displays phantom 19F images (9.4 T) for P-PFOB (+Fe) and PFOB (—Fe). The top and bottom panels show the tubes optimized separately for P-PFOB ([5a POP]=20 mM in oil) and PFOB SNR, respectively. From these images P-PFOB displays a 2.5-fold increase in SNR over PFOB when both are imaged optimally, and the asterisk in panel (a) shows approximate experimental agreement (~7.5% error) with the model. CSI parameters for (b) were 28 averages, TR=103 ms, and TE=0.8 ms for top panel P-PFOB and 4 averages, TR=721 ms, and TE=0.8 ms for bottom panel PFOB.
Figure 4:
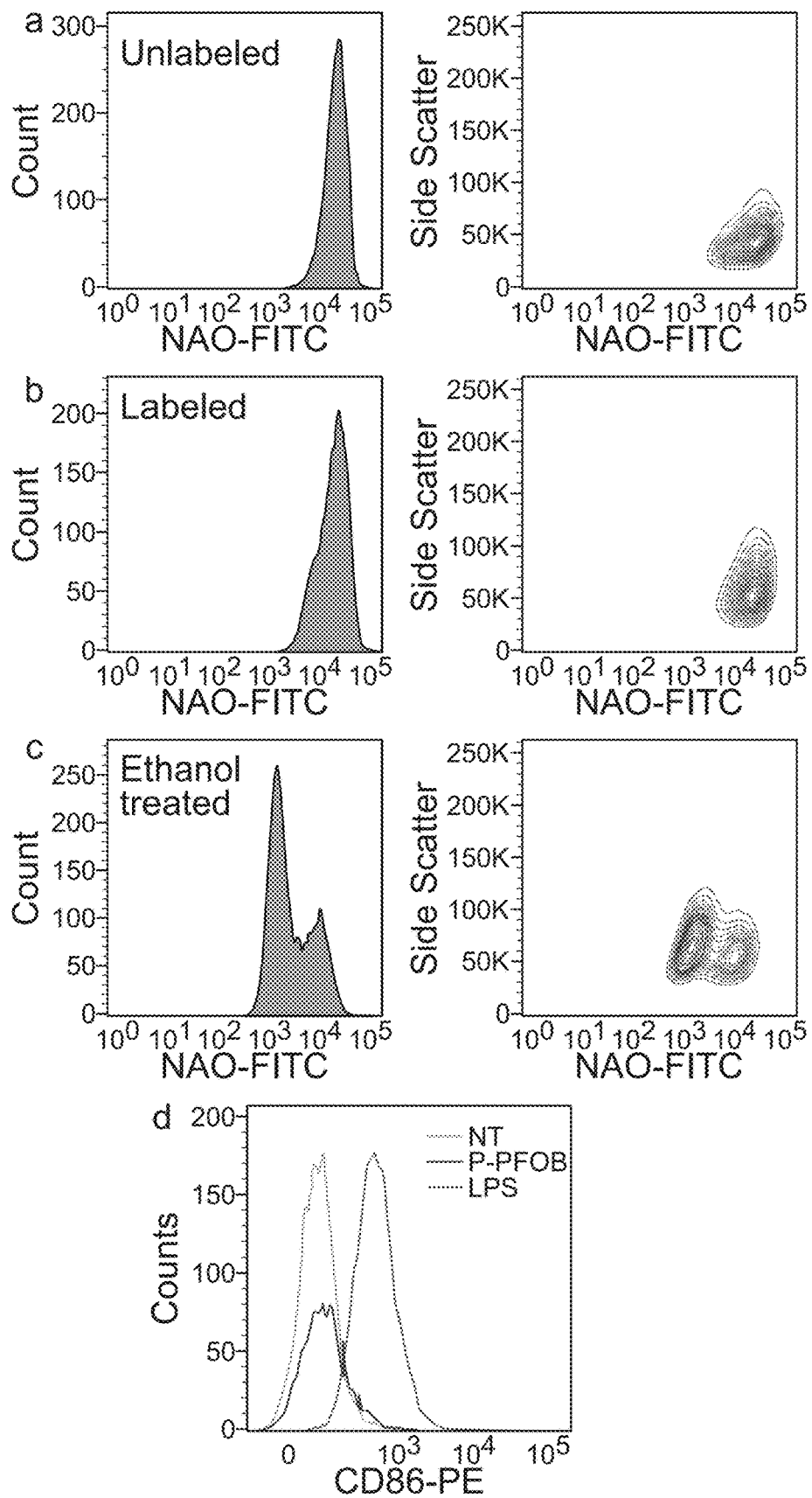
FIG. 4A-FIG. 4D. In vitro cytotoxicity and cell phenotype in P-PFOB labeled RAW cells. Cells were incubated with P-PFOB NE ([Fe3+-SALTAME 5a POP]=20 mM in PFOB) in culture for 16 h. The NAO flow cytometry assay was used to measure cytotoxicity (apoptosis). Panels (a) show unlabeled (negative) control cells, (b) labeled cells, and (c) with 10% ethanol treated cells as positive control. (d) Displays flow cytometry results for CD86 expression in P-PFOB labeled RAW cells. LPS treated cells serve as a positive control.

Simulated results are displayed in FIG. 3a using empirical, magnetic field dependent relaxivities measured at 3 T and 9.4 T.

5. Emulsion and Biological Studies

Emulsion preparation. The fluorous phase consisted of a solution of 36 mg of Fe 5a POP and 102 mg of 1-(perfluoro-n-hexyl)decane (Fluoryx) in 2.4 g PFOB (Acros, Geel, Belgium). The aqueous phase consisted of lipids, mannitol and water. A lipid solution of 139 mg egg yolk phospholipids (EYP, Sigma-Aldrich), 28 mg cholesterol (Avanti Polar Lipids, Alabaster, AL) and 3 mg 1,2-dihexadecanoyl-sn-glycero-3-phospho-L-serine, sodium salt (DPPS, Avanti) was prepared in chloroform, from which a lipid film was made and dried under high vacuum overnight. The lipid film was hydrated with 3.07 g $H_2O$ and 90 mg mannitol was added. The aqueous phase was vortexed for 1 min and sonicated for 2 mins (Omni Ruptor 250 W, 30% power, 2 min, Omni International, Kennesaw, GA). The fluorous phase and 132 mg Cremophor (Sigma-Aldrich) were added subsequently, followed by ultrasonication for 2 mins. The crude emulsion was passed 5 times through a LV1 microfluidizer (Microfluidics, Newton, MA) operating at 20,000 psi and then filtered through a 0.2 m Supor membrane (no. 4187, Pall, Port Washington, NY) into sterile glass vials. Emulsion size characterizations (FIGS. 15-16) were performed using a dynamic light scattering (DLS) instrument (Malvern Zetasizer ZS, Malvern, PA).

In vitro cell labeling. The murine macrophage cell line RAW 267.4 (TIB-71, ATCC, Manassas, VA) were maintained in Dulbecco's modified eagle media containing 10% fetal bovine serum (FBS), 100 μg/mL streptomycin and 100 U/mL penicillin at 37° C. in 5% $Co_2$ atmosphere. Cells were plated in 10 cm dishes in media supplemented with 10% (v/v) FBS, and PFOB-5a POP NE, [F]=5 mg/mL, was added. After 24 h incubation at 37° C., cells were washed three times in phosphate-buffered saline (PBS) and resuspension in 1 mL of PBS. A portion of the cell suspension was used for cell number estimates using Cell Titer Glo assay (Promega, Madison, WI) using vendor instructions, as well as $^{19}F$ uptake measurements in cell pellets (FIG. S11).

Phenotype assay. Phycoerythrin conjugated Rat anti-mouse CD86 (CD86-PE) antibody was purchased from BD Bioscience (#553692, San Jose, CA). The NE-labeled and control cells were incubated with anti-CD86 antibody for 30 minutes, followed by three washes. Samples were analyzed using flow cytometry (BD™ LSR Fortessa) and 10,000 events were recorded. As a pro-inflammatory positive control, bacterial lipopolysaccharide (LPS, *Salmonella enterica*, #L7770, Sigma-Aldrich) was added to RAW cells (200 ng/mL for 16 h).

Viability assay. 10-N-nonyl acridine orange (NAO) was obtained from Invitrogen (A1372, Carlsbad, CA). NE labeled and control RAW cells were stained with 100 ng/ml of NAO for 15 minutes followed by washes according to manufacturer's instructions. As a positive control, cells were stressed by incubation with 10% ethanol at 37° C. containing 5% $CO_2$ for 90 minutes before NAO staining. Green fluorescence from NAO dye (emission max at 520 nm) was detected using flow cytometry (LSR Fortessa, BD Biosciences).

Inflammation mouse model. Animal experiments were performed in accordance with the guidelines provided by the UCSD Institutional Animal Care and Use Committee (IACUC) and the National Institute of Health Guide for the Care and Use of Laboratory Animals. C57BL/6 mice (N=3, female, 6-8 weeks, Jackson Laboratory, Bar Harbor, ME) were anesthetized with 1.5% isoflurane and the neck was shaved. Local inflammation was induced with a 0.3 ml injection of a LPS and Matrigel (Corning, Oneonta, NY) mixture containing 800 μg LPS subcutaneously into the posterior neck area. Two hours after Matrigel implantation, a single bolus of P-PFOB NE (200 μl of 0.6% w/w emulsion, [F]=271 mg/ml, [SALTAME]=5.5 mM, 54.2 mg total F), was injected intravenously. $^1H/^{19}F$ MRI scans were performed 24 h after.

Phantom MRI. A phantom consisting of two 5 mm NMR tubes containing PFOB and P-PFOB ([5a POP]=20 mM in PFOB oil) emulsions side-by-side. Images were acquired using a 9.4 T Bruker Avance III HD Nanobay spectrometer equipped for microimaging with a double-tuned 10 mm $^1H/^{19}F$ coil and ParaVision 6 software. Two sets of $^{19}F$ images were acquired using a two dimensional chemical shift imaging (CSI) method to yield optimal SNR for each tube. Imaging parameters were TE=0.8 ms (echo time), matrix size 32×32, field of view 9.5×9.5×3 $mm^3$ and acquisition time was 49 min for each. To optimize SNR for each tube, the repetition time (TR) was set to 103 ms with 28 averages, and then TR=721 ms and 4 averages, with the optimal Ernst angle condition set for each TR value.

In vivo MRI. Live mouse images were acquired using an 11.7 T horizontal-bore Bruker BioSpec MRI system equipped with a double-tuned $^1H/^{19}F$ mouse volume coil and ParaVision 6 software. Mice were anesthetized using 1.5% isoflurane in $O_2$ and maintained at 37° C. during acquisitions. The $^{19}F$ images were acquired using a two dimensional CSI method with TR/TE=13.3/0.53 ms, matrix size 32×32, field of view 20×20×6 $mm^3$, 134 averages and acquisition time ~30 min. For anatomical data, $^1H$ spin-echo images were acquired with TR/TE=550/14 ms, matrix size 128×96, field of view 20×20×1 $mm^3$ and acquisition time ~3 min. CSI visualization was performed using the CSI Visualization Tool inside the ParaVision software. The calculation and display of phantom was performed by selecting all PFOB resonance peaks from −60 to −130 ppm. Notably, examination of the CSI spectral data showed no peaks at −82.8 and −89.9 ppm, corresponding to isoflurane anesthesia.

Shift MRI. Images to demonstrate POP $Fe^{3+}$ chelate dissolved in PFOB oil induced bulk magnetic susceptibility shifts were acquired using the above 11.7 T MRI system. A CSI pulse sequence was used with TR/TE=26.4/0.53 ms, matrix size 64×64, FOV 30×30×3 $mm^3$, 1,024 complex points, spectrum width 40.8 kHz, 6 averages and an acquisition time 10.8 min. CSI visualization was performed using the CSI Visualization Tool in ParaVision software. The calculation and display of P-PFOB map was performed by selecting the $CF_3$ resonance peak only.

Additional figures in support of Examples 1 and 2 include FIG. 18-FIG. 34.

6. Supplemental References

1. Krause, L.; Herbst-Irmer, R.; Sheldrick, G. M.; Stalke, D., Comparison of Silver and Molybdenum Microfocus X-ray Sources for Single-Crystal Structure Determination. J Appl Crystallogr 2015, 48, 3-10.
2. Sheldrick, G. M., SHELXT—Integrated Space-Group and Crystal-Structure Determination. Acta Crystallogr A 2015, 71, 3-8.
3. Sheldrick, G. M., Crystal Structure Refinement with SHELXL. Acta Crystallogr C 2015, 71, 3-8.
4. Haase, A.; Frahm, J.; Matthaei, D., FLASH Imaging: Rapid NMR Imaging Using Low Flip-Angle Pulses. J Magn Reson 1986, 67, 258-263.
5. Deeney, F. A.; Harding, C. J.; Morgan, G. G.; McKee, V.; Nelson, J.; Teat, S. J.; Clegg, W., Response to Steric Constraint in Azacryptate and Related Complexes of Iron-(II) and -(III) *. J Chem Soc Dalton 1998, 11, 1837-1844.

Example 3: Compound Synthesis

Methods

The following example is described as to provide those with ordinary skill in the art with a complete disclosure of how the compounds and compositions described herein were prepared and characterized, and are purely intended to be exemplary of the invention and are not intended to limit the scope of the invention.

Unless otherwise noted, chemicals and reagents were obtained from commercial resources and used without further purification. Anhydrous dimethylformamide (DMF) and acetonitrile were stored over activated 4 Å molecular sieves. Fluorous solvents were purchased from Perseptive Biosystems (Framingham, MA). Precoated silica gel plates (60 F-254, Merck Millipore, Billerica, MA) were used for thin-layer chromatography (TLC) and silica gel 60 (230-400 mesh) was used for column chromatography. All reactions were carried out under N2 unless otherwise noted. Reactions were monitored by TLC and liquid chromatography mass spectrometry (LC-MS) using an Agilent (Santa Clara, CA) 1100 HPLC with MSD Trap XLT using a Phenomenex Luna C18(2) 100 Å, 5 μm, 4.6 mm×250 column, MeCN/H2O linear gradients with constant 0.05% v/v CF3CO2H additive, 1 mL/min flow, and ESI positive or negative ion mode. Reaction products were purified by flash chromatography on silica gel eluted with ethyl acetate and hexane. High-resolution mass spectrometry was performed by the Molecular Mass Spectrometry Facility at the University of California San Diego. Ultraviolet-visible (UV-Vis) absorption spectra were recorded on a Shimadzu (Kyoto, Japan) spectrophotometer.

NMR spectra and relaxation rates were recorded on a Bruker Ascend 400 MHz (9.4 T) spectrometer (Billerica, MA). Additional relaxation rate measurements were performed at 3 T using a GE750 (General Electric, Milwaukee, WI) clinical MRI system equipped with a custom dual-channel 19F/1H 72 mm diameter volume coil (RAPID Biomedical, Rimpar, Germany). The 19F NMR spectra were referenced to an internal standard, sodium trifluoroacetate (NaTFA, 0.1 wt %, −76.00 ppm, Sigma-Aldrich), which was placed in a separate sealed capillary tube within the NMR tube. Relaxation measurements were performed using a standard inversion recovery pulse sequence and a Carr-Purcell-Meiboom-Gill sequence with echo-time (TE) values in 12 linear increments. The T1 and T2 values were obtained by nonlinear fitting using MNova 6.0.2 software (Mestrelab, Escondido, CA). Fit errors were less than 5% of T1 and T2 values. For quantitative peak measurements, spectra were acquired using calibrated 90° pulses, 32,000 complex points, spectral window 0 to −200 ppm, relaxation delay 2.5 s, and 128 averages. Spectra were processed in MNova with manual phase correction, and Whittaker smoother baseline correction (filter=1 ppm). Relaxation parameters were measured for six middle CF2 peaks of PFOB, spanning ~10 ppm, which account for 12 out of 17 F atoms in the molecule. To assay emulsion uptake (19F/cell) using NMR, an aliquot of 1×106 cells were pelleted and resuspended in 0.1 mL of lysis solution (0.5% Triton X, 100 mM NaCl, 20 mM Tris, 1 mM EDTA) and reference compound NaTFA (0.745 mg/mL)/D20 was added to 5 mm NMR tube. The integrated ratio of PFOB fluorine peaks to NaTFA singlet fluorine peak at −76.00 ppm determined the amount of 19F in the cell pellet and the 19F/cell was calculated.

Synthesis of 3-Bromo-5-perfluorohexyl-salicylaldehyde (2a)

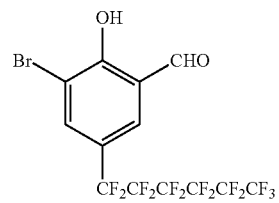

The 3-Bromo-2-hydroxybenzaldehyde (10 mM), perfluorohexyl iodide (20 mM) and anhydrous cesium carbonate (40 mM) were heated in dry DMF (50 mL) at 100° C. overnight with vigorous stirring under a dry N2 atmosphere. The dark reaction mixture was cooled and cautiously poured into ~4M HCl (100 mL), and the crude product was extracted with EtOAc (3×50 mL), dried over Na2SO4 and evaporated to dryness. The product was purified by silica gel chromatography eluted with 5% of EtOAc-hexane in a yield of 63%. $^1$H NMR (400 MHz, Chloroform-d) δ 11.98 (s, 1H), 9.96 (s, 1H), 8.00 (s, 1H), 7.82 (s, 1H). $^{19}$F NMR (376 MHz, Chloroform-d) δ −80.94, −110.22--110.71 (m), −121.60 (dt, J=50.9, 15.6 Hz), −122.95, −126.31 (d, J=15.1 Hz). $^{13}$C NMR (101 MHz, Chloroform-d) δ 195.51, 160.98, 137.77, 131.77, 121.77 (t, J=26.1 Hz), 120.67, 112.49. MS (m/z, ESI-TOF) for [M−H]$^+$: calculated 516.9114, found 516.9110.

Synthesis of 5-Bromo-3-perfluorohexyl-salicylaldehyde (2b)

F3CF2CF2CF2CF2CF2C — (structure with OH, CHO, Br substituents on benzene ring)

The 5-bromosalicylaldehyde (10 mM), perfluorohexyl iodide (20 mM) and anhydrous cesium carbonate (40 mM) were heated in dry DMF (50 mL) at 100° C. overnight with vigorous stirring under a dry N2 atmosphere. The dark reaction mixture was cooled and cautiously poured into ~4M HCl (100 mL), and the crude product was extracted with EtOAc (3×50 mL), dried over Na2SO4 and evaporated to dryness. The product was purified by silica gel chromatography eluted with 5% EtOAc-hexane (1:50 to 1:10 ratio) in a yield of 75% as a white solid. $^1$H NMR (400 MHz, Chloroform-d) δ 11.74 (s, 1H), 9.90 (s, 1H), 7.90 (s, 1H), 7.85 (s, 1H). $^{19}$F NMR (376 MHz, Chloroform-d) δ −80.95 (d, J=25.4 Hz), −108.48--110.07 (m), −121.46 (d, J=113.9 Hz), −121.94, −122.91, −126.32. $^{13}$C NMR (101 MHz, Chloroform-d) δ 195.33, 159.75, 140.25, 139.00, 122.65, 119.25 (t, J=24.1 Hz), 111.05. MS (m/z, ESI-TOF) for [M−H]$^+$: calculated 516.9114, found 516.9112.

Synthesis of 5-Perfluorohexyl-salicylaldehyde (3a)

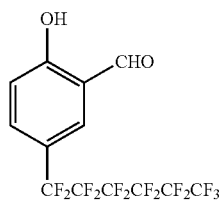

3-Bromo-5-perfluorohexyl-salicylaldehyde (2a, 3.2 g, 6.3 mmol) was dissolved in MeOH (100 ml), sodium acetate (0.57 g, 7 mmol) and Pd—C(5%, 50 mg), and the mixture was hydrogenated at room temperature and 1 atm pressure until uptake was complete (30 min). The reaction mixture was filtered through Celite and evaporated to dryness, dissolved in EtOAc (50 ml) and washed with water (3×25 ml). The organic layer was dried ($Na_2SO_4$) and evaporated to give the product as a white solid. Yield, 2.71 g (98%). $^1$H NMR (400 MHz, Chloroform-d) δ 11.32 (s, 1H), 9.95 (s, 1H), 7.80 (s, 1H), 7.70 (d, J=8.8 Hz, 1H), 7.12 (d, J=8.8 Hz, 1H). $^{19}$F NMR (376 MHz, Chloroform-d) δ −80.75 (t, J=10.2 Hz), −110.24 (t, J=14.0 Hz), −121.64 (d, J=145.9 Hz), −122.83, −126.14. $^{13}$C NMR (101 MHz, Chloroform-d) δ 196.12, 164.36, 134.97, 133.01, 120.34, 118.90, 122-108 (m, weak). MS (m/z, ESI-TOF) for [M−H]$^+$: calculated 439.0009, found 439.0010.

Synthesis of 3-Perfluorohexyl-salicylaldehyde (3b)

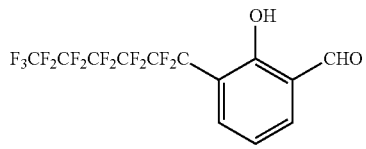

5-Bromo-3-perfluorohexyl-salicylaldehyde (2b, 3.2 g, 6.3 mmol) was dissolved in MeOH (100 ml), sodium acetate (0.57 g, 7 mmol) and Pd—C(5%, 50 mg), and the mixture was hydrogenated at room temperature and 1 atm pressure until uptake was complete (30 min). The reaction mixture was filtered through Celite and evaporated to dryness, dissolved in EtOAc (50 ml) and washed with water (3×25 ml). The organic layer was dried ($Na_2SO_4$) and evaporated to give the product as a white solid in a yield of 100%. $^1$H NMR (400 MHz, Chloroform-d) δ 11.83 (s, 1H), 9.94 (s, 1H), 7.76 (dd, J=10.7, 8.0 Hz, 2H), 7.14 (t, J=7.8 Hz, 1H). $^{19}$F NMR (376 MHz, Chloroform-d) δ −80.81 (d, J=8.2 Hz), −109.01 (t, J=14.7 Hz), −121.65 (d, J=144.0 Hz), −122.80, −126.19. $^{13}$C NMR (101 MHz, Chloroform-d) δ 196.55, 160.96, 138.27, 136.58, 121.55, 119.58, 122-108 (m, weak). MS (m/z, ESI-TOF) for [M−H]$^+$: calculated 439.0009, found 439.0008.

Synthesis of 3,5-Bis-perfluorohexyl-salicylaldehyde (3c)

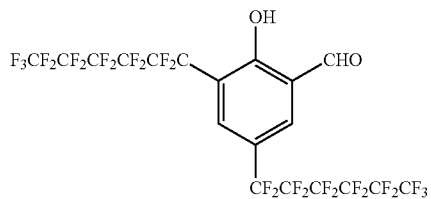

The salicylaldehyde (10 mM), perfluorohexyl iodide (60 mM) and anhydrous cesium carbonate (40 mM) were heated in dry DMF (50 mL) at 100° C. overnight with vigorous stirring under a dry $N_2$ atmosphere. The dark reaction mixture was cooled and cautiously poured into ~4M HCl (100 mL), and the crude product was extracted with EtOAc (3×50 mL), dried over $Na_2SO_4$ and evaporated to dryness. The product was purified by silica gel chromatography eluted with 15% of EtOAc-hexane as a white solid in a yield of 63%. $^1$H NMR (400 MHz, Chloroform-d) δ 12.21 (s, 1H), 10.02 (s, 1H), 8.03 (s, 1H), 7.93 (s, 1H). $^{19}$F NMR (376 MHz, Chloroform-d) δ −80.96 (d, J=7.7 Hz), −109.49 (t, J=15.5 Hz), −110.56--111.15 (m), −121.54 (q, J=17.7, 16.6 Hz), −121.94 (t, J=16.8 Hz), −122.93, −126.31 (d, J=14.3 Hz). $^{13}$C NMR (101 MHz, Chloroform-d) δ 195.76, 163.30, 136.71 (t, J=6.9 Hz), 134.61 (t, J=8.4 Hz), 121.31, 120.64 (t, J=24.2 Hz), 118.52 (t, J=22.4 Hz), 120-108 (m, weak). MS (m/z, ESI-TOF) for [M−H]: calculated 756.9723, found 756.9719.

Synthesis of 5-Methyl-3-perfluorohexyl-salicylaldehyde (3d)

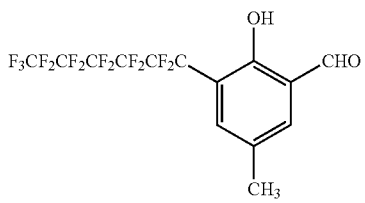

The 5-methylsalicylaldehyde (10 mM), perfluorohexyl iodide (20 mM) and anhydrous cesium carbonate (40 mM) were heated in dry DMF (50 mL) at 100° C. overnight with vigorous stirring under a dry $N_2$ atmosphere. The dark reaction mixture was cooled and cautiously poured into ~4M HCl (100 mL), and the crude product was extracted with EtOAc (3×50 mL), dried over $Na_2SO_4$ and evaporated to dryness. The product was purified by short pathlength distillation 90-120° C. at 100 mTorr to give a yellow-brown oil in a yield of 75%. $^1$H NMR (400 MHz, Chloroform-d) δ 11.62 (s, 1H), 9.90 (s, 1H), 7.48-7.62 (m, 2H), 2.40 (s, 3H). $^{19}$F NMR (376 MHz, Chloroform-d) δ −80.82 (t, J=10.7 Hz), −108.92 (t, J=15.6 Hz), −121.44 (d, J=16.4 Hz), −121.87 (t, J=14.7 Hz), −122.81 (d, J=15.9 Hz), −126.18 (d, J=16.9 Hz). $^{13}$C NMR (101 MHz, Chloroform-d) δ 196.47, 158.75 (t, J=2.7 Hz), 138.22, 137.07 (t, J=7.9 Hz), 133.56, 129.12, 121.31, 20.32. MS (m/z, ESI-TOF) for [M−H]$^+$: calculated 453.0166, found 453.0164.

Synthesis of 3-Methyl-5-perfluorooctyl-salicylaldehyde (3f)

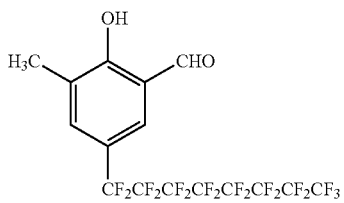

The 3-methylsalicylaldehyde (10 mM), perfluorooctyl iodide (20 mM) and anhydrous cesium carbonate (40 mM) were heated in dry DMF (50 mL) at 100° C. overnight with vigorous stirring under a dry $N_2$ atmosphere. The dark reaction mixture was cooled and cautiously poured into ~4M HCl (100 mL), and the crude product was extracted with EtOAc (3×50 mL), dried over $Na_2SO_4$ and evaporated to dryness. The product was purified by short pathlength distillation 135° C. at 100 mTorr to give a yellow-brown oil that slowly solidified in a yield of 78%. $^1H$ NMR (400 MHz, Chloroform-d) δ 11.59 (s, 1H), 9.94 (s, 1H), 7.66 (s, 1H), 7.57 (s, 1H), 2.34 (s, 3H). $^{19}F$ NMR (376 MHz, Chloroform-d) δ −80.72 (t, J=9.5 Hz), −110.15 (t, J=14.5 Hz), −121.08-−121.42 (m), −121.54-−122.10 (m), −122.70, −126.11 (t, J=14.3 Hz). $^{13}C$ NMR (101 MHz, Chloroform-d) δ 196.27, 162.72, 135.16 (t, J=6.2 Hz), 130.50 (t, J=6.8 Hz), 128.57, 120.11 (t, J=25.2 Hz), 119.52, 15.40. MS (m/z, ESI-TOF) for [M−H]$^+$: calculated 553.0102, found 553.0099.

Synthesis of 1,1,1-(Tris(3'(5')-perfluorosalicylidene) methyl)-ethane (4a PPP)

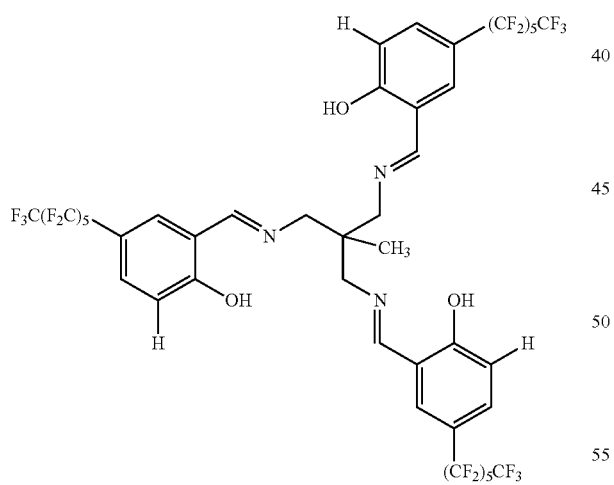

2-(Aminomethyl)-2-methyl-1,3-propanediamine trihydrochloride (226 mg, 1 mmol) was added to a solution of 5-Perfluorohexyl-salicylaldehyde (3a, 1.32 g, 2 mmol) and triethylamine (0.46 ml, 3.33 mmol) in absolute EtOH (10 ml). The mixture was refluxed for 4 h until a yellow solution was formed, then cooled and evaporated to dryness. The residue was dissolved in EtOAc/water (1:1 v/v, 100 ml), separated and the EtOAc layer washed with water (2×25 ml). The combined organic layers were dried ($Na_2SO_4$) and evaporated to give the crude product that was used without further purification. For analysis, a small amount these intermediates was separated by HPLC on a C18 reverse-phase column (Luna-2, Phenomenex, Torrance, CA) using isocratic elution with acetonitrile. $^1H$ NMR (400 MHz, Methylene Chloride-d$_2$) δ 13.87 (s, 3H), 8.46 (s, 3H), 7.53 (d, J=7.5 Hz, 6H), 7.07 (d, J=9.3 Hz, 3H), 3.71 (s, 6H), 1.20 (s, 3H). $^{19}F$ NMR (376 MHz, Methylene Chloride-d$_2$) δ− 81.16 (d, J=8.6 Hz), −110.04 (t, J=13.7 Hz), −121.74, −122.15, −123.09, −126.43.

Synthesis of 1,1,1-(Bis(5'-perfluorohexylsalicylidene)(3'-perfluorohexylsalicylidene) methyl)-ethane (4a POP)

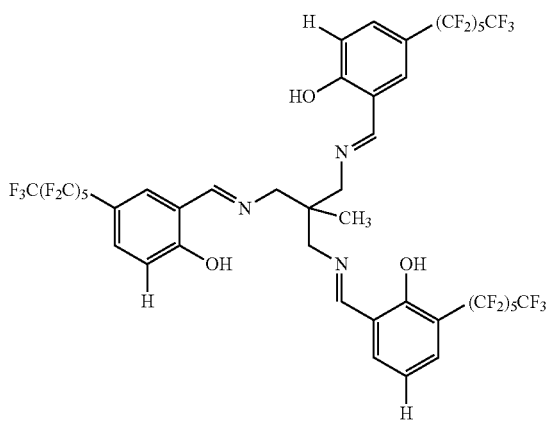

2-(Aminomethyl)-2-methyl-1,3-propanediamine trihydrochloride (226 mg, 1 mmol) was added to a solution of 5-Perfluorohexyl-salicylaldehyde (3a, 0.88 g, 2 mmol), 3-Perfluorohexyl-salicylaldehyde (3b, 0.44 g, 1 mmol) and triethylamine (0.46 ml, 3.33 mmol) in absolute EtOH (10 ml). The mixture was refluxed for 4 h until a yellow solution was formed, then cooled and evaporated to dryness. The residue was dissolved in EtOAc/water (1:1 v/v, 100 ml), separated and the EtOAc layer washed with water (2×25 ml). The combined organic layers were dried ($Na_2SO_4$) and evaporated to give the crude product that was used without further purification. For analysis, a small amount these intermediates was separated by HPLC on a C18 reverse-phase column (Luna-2, Phenomenex, Torrance, CA) using isocratic elution with acetonitrile. $^1H$ NMR (400 MHz, Methylene Chloride-d$_2$) δ 14.52 (s, 1H, OH of ortho), 13.86 (s, 2H, OH of para), 8.46 (d, J=8.3 Hz, 3H), 7.53 (q, J=8.8, 7.9 Hz, 6H), 7.18-6.92 (m, 3H), 3.71 (d, J=13.7 Hz, 6H), 1.20 (s, 3H). $^{19}F$ NMR (376 MHz, Methylene Chloride-d$_2$) δ− 81.18 (t, J=9.8 Hz), −108.82 (t, J=14.5 Hz), −110.06 (t, J=13.4 Hz), −120.24-−125.45 (m), −126.45.

Synthesis of 1,1,1-(Bis(3'-perfluorohexylsalicylidene)(5'-perfluorohexylsalicylidene) methyl)-ethane (4a OOP)

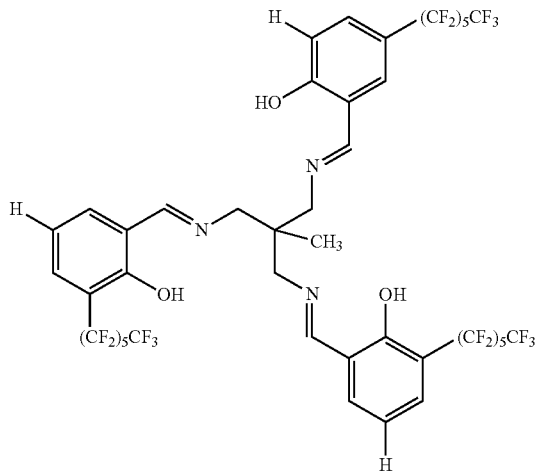

2-(Aminomethyl)-2-methyl-1,3-propanediamine trihydrochloride (226 mg, 1 mmol) was added to a solution of 5-Perfluorohexyl-salicylaldehyde (3a, 0.44 g, 1 mmol), 3-Perfluorohexyl-salicylaldehyde (3b, 0.88 g, 2 mmol) and triethylamine (0.46 ml, 3.33 mmol) in absolute EtOH (10 ml). The mixture was refluxed for 4 h until a yellow solution was formed, then cooled and evaporated to dryness. The residue was dissolved in EtOAc/water (1:1 v/v, 100 ml), separated and the EtOAc layer washed with water (2×25 ml). The combined organic layers were dried ($Na_2SO_4$) and evaporated to give the crude product that was used without further purification. For analysis, a small amount these intermediates was separated by HPLC on a C18 reverse-phase column (Luna-2, Phenomenex, Torrance, CA) using isocratic elution with acetonitrile. $^1$H NMR (400 MHz, Methylene Chloride-$d_2$) δ 14.55 (s, 2H, OH of ortho), 13.89 (s, 1H, OH of para), 8.52 (d, J=4.7 Hz, 3H), 7.64-7.52 (m, 6H), 7.14-6.99 (m, 3H), 3.75 (s, 6H), 1.23 (s, 3H). $^{19}$F NMR (376 MHz, Methylene Chloride-$d_2$) δ− 81.18, −108.81 (t, J=14.3 Hz), −110.07 (t, J=13.1 Hz), −120.31-−125.21 (m), −126.43.

Synthesis of 1,1,1-(Tris(3'-perfluorohexylsalicylidene)methyl)-ethane (4a OOO)

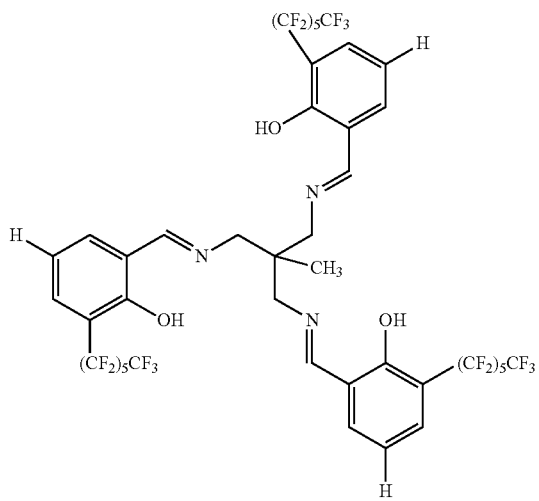

2-(Aminomethyl)-2-methyl-1,3-propanediamine trihydrochloride (226 mg, 1 mmol) was added to a solution of 3-Perfluorohexyl-salicylaldehyde (3b, 1.32 g, 3 mmol) and triethylamine (0.46 ml, 3.33 mmol) in absolute EtOH (10 ml). The mixture was refluxed for 4 h until a yellow solution was formed, then cooled and evaporated to dryness. The residue was dissolved in EtOAc/water (1:1 v/v, 100 ml), separated and the EtOAc layer washed with water (2×25 ml). The combined organic layers were dried ($Na_2SO_4$) and evaporated to give the crude product that was used without further purification. For analysis, a small amount these intermediates was separated by HPLC on a C18 reverse-phase column (Luna-2, Phenomenex, Torrance, CA) using isocratic elution with acetonitrile. $^1$H NMR (400 MHz, Methylene Chloride-$d_2$) δ 14.49 (s, 3H, OH), 8.49 (s, 3H, CH=N), 7.53 (dd, J=19.4, 7.7 Hz, 6H), 7.00 (t, J=7.7 Hz, 3H), 3.72 (s, 6H), 1.19 (s, 3H). $^{19}$F NMR (376 MHz, Methylene Chloride-$d_2$) δ− 81.11 (dt, J=20.6, 10.0 Hz), −108.80 (t, J=14.0 Hz), −120.23-−124.17 (m), −126.40.

Synthesis of Iron Complex 5a PPP, 5a POP, 5a OOP, and 5a OOO

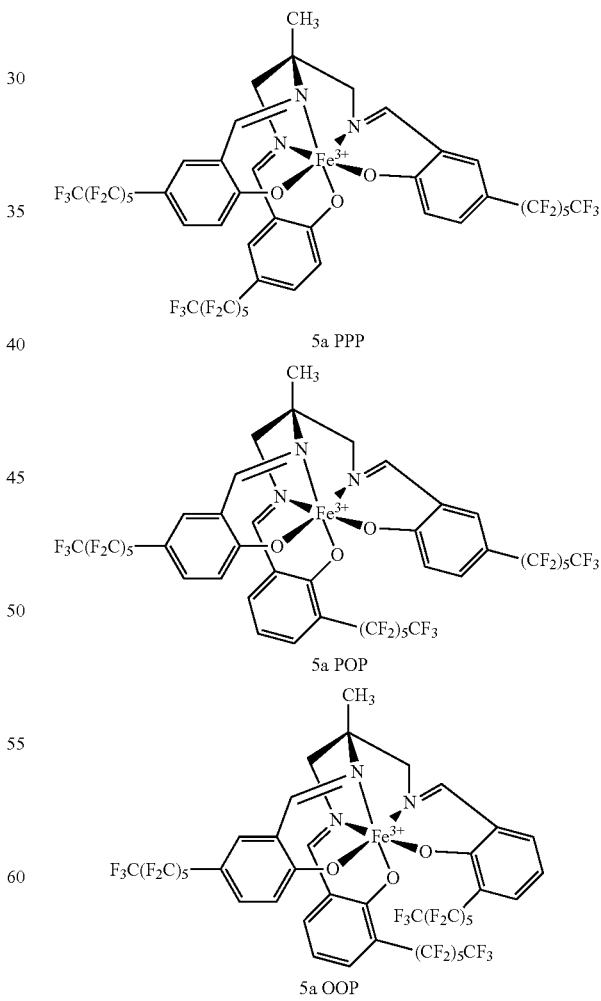

5a PPP

5a POP

5a OOP

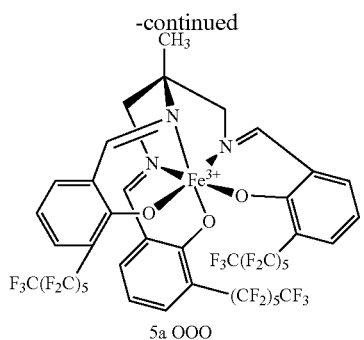

5a OOO

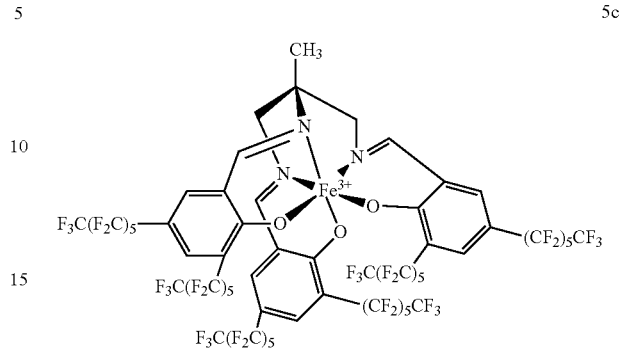

Synthesis of Iron Complex 5c

A solution of 5-Perfluorohexyl-salicylaldehyde (3a, 0.78 g, 1.77 mmol) in absolute EtOH (5 ml) was added dropwise to a stirred suspension of 2-(aminomethyl)-2-methyl-1,3-propanediamine, trihydrochloride (210 mg, 0.88 mmol) and triethylamine (0.49 ml, 3.52 mmol) in absolute EtOH (10 mL) at 80° C. Compound 3-Perfluorohexyl-salicylaldehyde (3b, 387 mg, 0.88 mmol) dissolved in 2.5 ml EtOH was then added and further heated for 30 min, followed by the addition of a solution of anhydrous ferric chloride (162 mg, 1 mmol), then anhydrous sodium acetate (0.24 g, 3 mmol) in absolute EtOH (5 ml). The resulting deep red reaction mixture was cooled, evaporated to dryness, dissolved in EtOAc:water (1:1 v/v, 100 ml) and separated. The aqueous layer was extracted (2×50 ml) with EtOAc; the combined organic layers dried over $Na_2SO_4$ and evaporated to dryness. The products were separated by $SiO_2$ column chromatography eluted with 0-55% EtOAc-hexane. Three distinct, red products were collected:

i. 5a PPP eluted with 20% EtOAc-hexane. Yield, 228 mg (18%). $^{19}F$ NMR (376 MHz, Methanol-$d_4$) δ− 82.31, −108.47, −117.87, −123.11, −127.14. MS (m/z, ESI-TOF) for [M+H]$^+$: calculated 1437.0383, found 1437.0405.

ii. 5a POP eluted with 40% EtOAc-hexane. Yield, 346 mg (27%). $^{19}F$ NMR (376 MHz, Methanol-$d_4$) δ− 82.31, −108.92, −114.90−−130.03 (m). MS (m/z, ESI-TOF) for [M+H]$^+$: calculated 1437.0383, found 1437.0400.

iii. 5a OOP eluted with 50% EtOAc-hexane. Yield, 183 mg (14%). $^{19}F$ NMR (376 MHz, Methanol-$d_4$) δ− 82.22 (d, J=98.2 Hz), −117.04−−124.61 (m), −125.89, −127.17. MS (m/z, ESI-TOF) for [M+H]$^+$: calculated 1437.0383, found 1437.0397.

Iron complex 5a OOO was prepared by using 3-Perfluorohexyl-salicylaldehyde (3b, 1.16 g, 2.65 mmol) without adding 5-Perfluorohexyl-salicylaldehyde (3a) in the procedure described above. 5a OOO: $^{19}F$ NMR (376 MHz, Methanol-$d_4$) δ− 82.04, −121.06, −125.89. MS (m/z, ESI-TOF) for [M+H]$^+$: calculated 1437.0383, found 1437.0407. Iron complex 5a PPP can also be obtained by using 5-Perfluorohexyl-salicylaldehyde (3a, 1.16 g, 2.65 mmol) without adding 3-Perfluorohexyl-salicylaldehyde (3b). The independent preparation of 5a OOO and 5a Fe PPP helps assign the four isomers (5a PPP, 5a POP, 5a OOP, and 5a OOO) on TLC and HPLC.

Compound 3,5-Bis-perfluorohexyl-salicylaldehyde (3c, 3.3 mmol), 2-(aminomethyl)-2-methyl-1,3-propanediamine trihydrochloride (226 mg, 1 mmol) and triethylamine (0.46 ml, 3.3 mmol) in absolute EtOH (10 ml) were heated at 80° C. for 3 h. A solution of anhydrous ferric chloride (243 mg, 1.5 mmol) in absolute EtOH (5 ml) was added, followed by anhydrous sodium acetate (287 mg, 3.5 mmol) to give a red colored solution. The reaction mixture was cooled, evaporated to dryness, dissolved in EtOAc:water (20 ml/20 ml) and separated. The aqueous layer was extracted with EtOAc (3×20 ml); the combined organic layers were dried over anhydrous $Na_2SO_4$ and evaporated to dryness. The products were separated by $SiO_2$ column chromatography eluted with EtOAc-hexane. Iron complex 5c was obtained by starting with 3c in a 70% yield. $^{19}F$ NMR (376 MHz, Chloroform-d) δ −80.77, −81.04, −109.32, −117.57, −121.42, −122.48, −126.13. MS (m/z, ESI-TOF) for [M+H]$^+$: calculated 2412.9346, found 2412.9307.

Synthesis of iron complex 5d

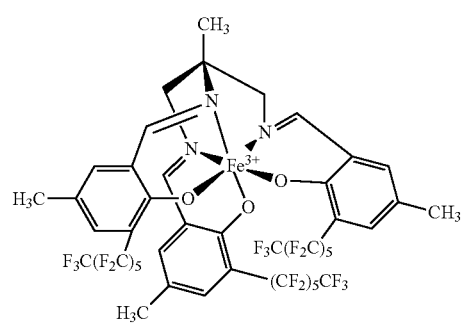

Compound 5-Methyl-3-perfluorohexyl-salicylaldehyde (3d, 3.3 mmol), 2-(aminomethyl)-2-methyl-1,3-propanediamine trihydrochloride (226 mg, 1 mmol) and triethylamine (0.46 ml, 3.3 mmol) in absolute EtOH (10 ml) were heated at 80° C. for 3 h. A solution of anhydrous ferric chloride (243 mg, 1.5 mmol) in absolute EtOH (5 ml) was added, followed by anhydrous sodium acetate (287 mg, 3.5 mmol) to give a red colored solution. The reaction mixture was cooled, evaporated to dryness, dissolved in EtOAc:water (20 ml /20 ml) and separated. The aqueous layer was extracted with EtOAc (3×20 ml); the combined organic layers were dried over anhydrous $Na_2SO_4$ and evaporated to dryness. The products were separated by $SiO_2$ column chromatography eluted with EtOAc-hexane in a yield of 69%. $^{19}$F NMR (376 MHz, Chloroform-d) δ −80.82, −120.49, −122.28, −126.36. MS (m/z, ESI-TOF) for [M+H]$^+$: calculated 1479.0853, found 1479.0843.

Synthesis of Iron Complex 5e

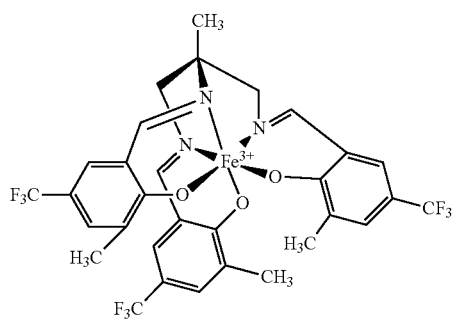

5e

Compound 5-(trifluoromethyl)salicylaldehyde (3e, 3.3 mmol, commercially available), 2-(aminomethyl)-2-methyl-1,3-propanediamine trihydrochloride (226 mg, 1 mmol) and triethylamine (0.46 ml, 3.3 mmol) in absolute EtOH (10 ml) were heated at 80° C. for 3 h. A solution of anhydrous ferric chloride (243 mg, 1.5 mmol) in absolute EtOH (5 ml) was added, followed by anhydrous sodium acetate (287 mg, 3.5 mmol) to give a red colored solution. The reaction mixture was cooled, evaporated to dryness, dissolved in EtOAc: water (20 ml/20 ml) and separated. The aqueous layer was extracted with EtOAc (3×20 ml); the combined organic layers were dried over anhydrous Na$_2$SO$_4$ and evaporated to dryness. The products were separated by SiO$_2$ column chromatography eluted with EtOAc-hexane in a yield of 65%. $^{19}$F NMR (376 MHz, Chloroform-d) δ −61.86. MS (m/z, ESI-TOF) for [M+H]$^+$: calculated 687.0862, found 687.0865.

Synthesis of Iron Complex 5f

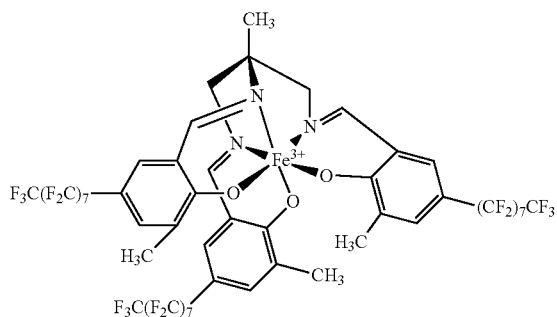

5f

Compound 3-Methyl-5-perfluorooctyl-salicylaldehyde (3f, 3.3 mmol), 2-(aminomethyl)-2-methyl-1,3-propanediamine trihydrochloride (226 mg, 1 mmol) and triethylamine (0.46 ml, 3.3 mmol) in absolute EtOH (10 ml) were heated at 80° C. for 3 h. A solution of anhydrous ferric chloride (243 mg, 1.5 mmol) in absolute EtOH (5 ml) was added, followed by anhydrous sodium acetate (287 mg, 3.5 mmol) to give a red colored solution. The reaction mixture was cooled, evaporated to dryness, dissolved in EtOAc:water (20 ml /20 ml) and separated. The aqueous layer was extracted with EtOAc (3×20 ml); the combined organic layers were dried over anhydrous Na$_2$SO$_4$ and evaporated to dryness. The products were separated by SiO$_2$ column chromatography eluted with EtOAc-hexane in a yield of 49%. $^{19}$F NMR (376 MHz, Chloroform-d) δ −80.72, −105.82, −116.21, −121.24, −121.82, −122.69, −126.11. MS (m/z, ESI-TOF) for [M+H]$^+$: calculated 1779.0661, found 1779.0644.

Synthesis of 5a Ga OOP and 5a Ga POP

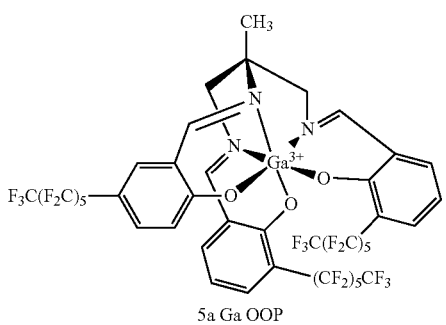

5a Ga OOP

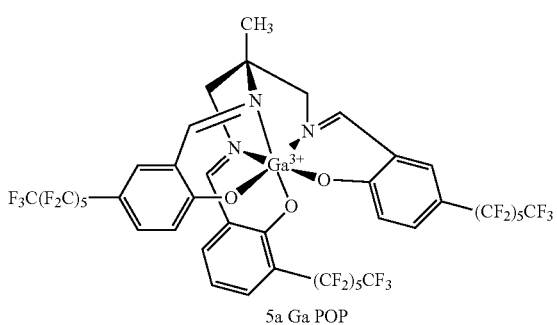

5a Ga POP

A solution of 5-Perfluorohexyl-salicylaldehyde (3a, 0.78 g, 1.77 mmol) in absolute EtOH (5 ml) was added dropwise to a stirred suspension of 2-(aminomethyl)-2-methyl-1,3-propanediamine, trihydrochloride (210 mg, 0.88 mmol) and triethylamine (0.49 ml, 3.52 mmol) in absolute EtOH (10 mL) at 80° C. Compound 3-Perfluorohexyl-salicylaldehyde (3b, 387 mg, 0.88 mmol) dissolved in 2.5 ml EtOH was then added and further heated for 30 min, followed by the addition of a solution of anhydrous Gallium chloride (176 mg, 1 mmol), then anhydrous sodium acetate (0.24 g, 3 mmol) in absolute EtOH (5 ml). The resulting deep red reaction mixture was cooled, evaporated to dryness, dissolved in EtOAc:water (1:1 v/v, 100 ml) and separated. The aqueous layer was extracted (2×50 ml) with EtOAc; the combined organic layers dried over Na$_2$SO$_4$ and evaporated to dryness. The Gallium complex 5a Ga POP and 5a Ga OOP were separated by preparative HPLC. 5a Ga POP $^1$H NMR (400 MHz, Methylene Chloride-d$_2$) δ 8.29-8.06 (m, 3H), 7.56-7.21 (m, 6H), 6.80-6.55 (m, 3H), 4.26-4.07 (m, 3H), 3.48 (t, J=16.5 Hz, 3H), 1.19 (s, 3H). $^{19}$F NMR (376 MHz, Methylene Chloride-d$_2$) δ− 81.08--81.66 (m), −107.56--111.35 (m), −121.14--123.63 (m), −126.60 (d, J=61.7 Hz). $^{13}$C NMR (101 MHz, Methylene Chloride-d$_2$) δ 172.02, 169.75, 169.68, 169.56, 168.03, 139.06, 138.10, 135.57, 135.48, 135.21, 133.05, 132.45, 123.88, 120.99, 120.57, 120.32, 118.95, 115.12, 114.60, 114.36, 114.31, 122.55-105.27 (m, weak), 67.27, 66.09, 65.88, 35.47, 23.43. MS (m/z, ESI-TOF) for [M+H]$^+$: calculated 1450.0289, found 1450.0282.

5a Ga OOP $^1$H NMR (400 MHz, Methylene Chloride-d$_2$) δ 11.92 (s, 1H), 11.39 (s, 1H), 10.00 (s, 1H), 8.32-8.16 (m, 2H), 7.88 (d, J=8.6 Hz, 1H), 7.79 (dd, J=16.6, 8.4 Hz, 1H), 7.52-7.41 (m, 2H), 7.26-7.16 (m, 1H), 6.92-6.66 (m, 2H), 4.26 (dt, J=27.8, 14.2 Hz, 3H), 3.65-3.43 (m, 3H), 1.38-1.08 (m, 3H). $^{19}$F NMR (376 MHz, Methylene Chloride-d$_2$) δ-76.34, −79.87--82.57 (m), −107.68--111.95 (m), −120.11--124.32 (m), −126.41. MS (m/z, ESI-TOF) for [M+H]$^+$: calculated 1450.0289, found 1450.0281.

Synthesis of 4-(2,2-difluoro-2-(1,1,2,2-tetrafluoro-2-(1,1,2,2-tetrafluoro-2-(trifluoromethoxy)ethoxy)ethoxy)ethoxy)-2-hydroxybenzaldehyde (3g-1)

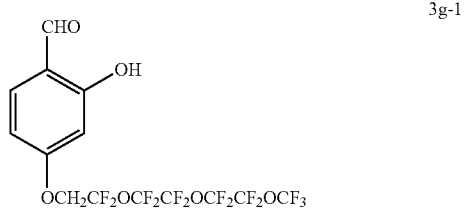

3g-1

To a solution of 1.1 mL (5 mmol) of 1H, 1H-Perfluoro-3, 6, 9-trioxadecan-1-ol (CAS #147492-57-7) in dichloromethane (15 mL), anhydrous pyridine (5.5 mmol, 0.485 mL) was added under nitrogen. The mixture was stirred at room temperature for 30 min and then cooled to 0° C. A solution of triflate anhydride (1 mL) in dichloromethane (10 mL) was added dropwise using a dropping funnel over 1 hour. The reaction was stirred at room temperature overnight and TLC (using PMA stain) showed complete conversion. After evaporation of solvents, the intermediate, which had the following structure:

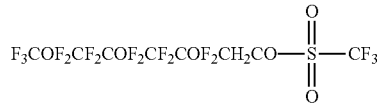

was isolated by silica gel chromatography eluted with 10% ethyl acetate-hexane in a yield of 85% as colorless oil. To the intermediate (0.5 mmol, 265 mg) was added 2,4-dihydroxybenzaldehyde (0.55 mmol, 76 mg), potassium bicarbonate (0.75 mmol, 75 mg) and anhydrous acetonitrile (8 mL). The mixture was heated at 60° C. overnight, and then cooled to room temperature. The solvent was evaporated, and the mixture was dissolved in ethyl acetate (15 mL) and then poured into H$_2$O (15 mL). The organic phase was collected, and the aqueous phase was washed with ethyl acetate (15 mL×2). The combined organic phase was washed with brine, dried over anhydrous sodium sulfate, and the solvent was evaporated. The product 3g-1 was isolated by silica gel chromatography eluted with 10% ethyl acetate-hexane in a yield of 70%. The structure was confirmed by NMR and LC-MS.

Synthesis of Iron Complex 3g-2

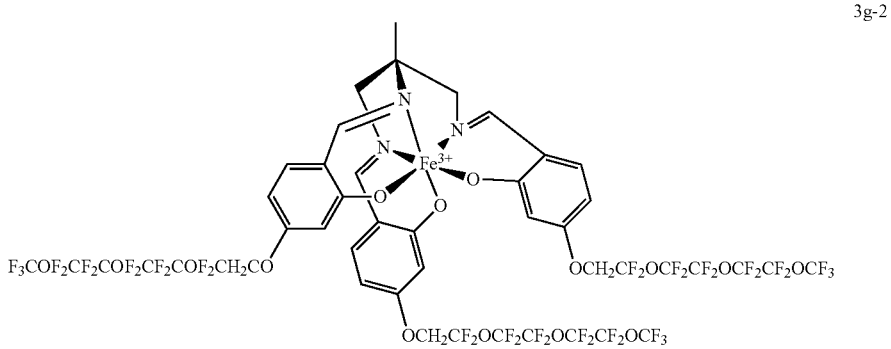

3g-2

A solution of 3g-1 (101 mg, 0.195 mmol) in absolute EtOH (2 ml) was added dropwise to a stirred suspension of 2-(aminomethyl)-2-methyl-1,3-propanediamine, trihydrochloride (14.5 mg, 0.064 mmol) and triethylamine (0.036 ml, 0.256 mmol) in absolute EtOH (2 mL) at 80° C. and heated for 4 hours, followed by the addition of a solution of anhydrous ferric chloride (10.5 mg, 0.065 mmol), then anhydrous sodium acetate (15.6 mg, 0.195 mmol) in absolute EtOH (2 ml). The resulting deep red reaction mixture was cooled, evaporated to dryness, dissolved in EtOAc: water (1:1 v/v, 10 ml) and separated. The aqueous layer was extracted (2×10 ml) with EtOAc; the combined organic layers dried over Na$_2$SO$_4$ and evaporated to dryness. The products were separated by silica gel column chromatography eluted with 60% EtOAc-hexane in a yield of 80% as a red powder. The structure of 3g-1 was confirmed by LC-MS.

Synthesis of 2-hydroxy-4-((2,2,3,3,4,4,5,5,6,6,7,7,7-tridecafluoroheptyl)oxy)benzaldehyde (3g-3)

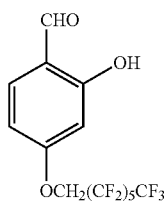

3g-3

To a solution of 1.75g (5 mmol) of 1H, 1H-Perfluoro-1-heptanol (CAS #375-82-6) in dichloromethane (15 mL), anhydrous pyridine (5.5 mmol, 0.485 mL) was added under nitrogen. The mixture was stirred at room temperature for 30 min and then cooled to 0° C. A solution of triflate anhydride (1 mL) in dichloromethane (10 mL) was added dropwise using a dropping funnel over 1 hour. The reaction was stirred at room temperature overnight and TLC (using PMA stain) shows complete conversion. After evaporation of solvents, the intermediate, which had the following structure:

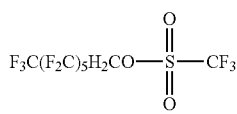

was isolated by silica gel chromatography eluted with 10% ethyl acetate-hexane in a yield of 85% as colorless oil. To the intermediate (1 mmol, 482 mg) was added 2,4-dihydroxybenzaldehyde (1.2 mmol, 165.7 mg), potassium bicarbonate (1.2 mmol, 120 mg) and anhydrous acetonitrile (10 mL). The mixture was heated at 60° C. overnight, and then cooled to room temperature. The solvent was evaporated, and the mixture was dissolved in ethyl acetate (15 mL) and then poured into $H_2O$(15 mL). The organic phase was collected, and the aqueous phase was washed with ethyl acetate (15 mL×2). The combined organic phase was washed with brine, dried over anhydrous sodium sulfate, and the solvent was evaporated. The product 3g-3 was isolated by silica gel chromatography eluted with 2-6% ethyl acetate-hexane in a yield of 39%. The structure was confirmed by NMR and LC-MS.

Synthesis of Iron Complex 3g-4

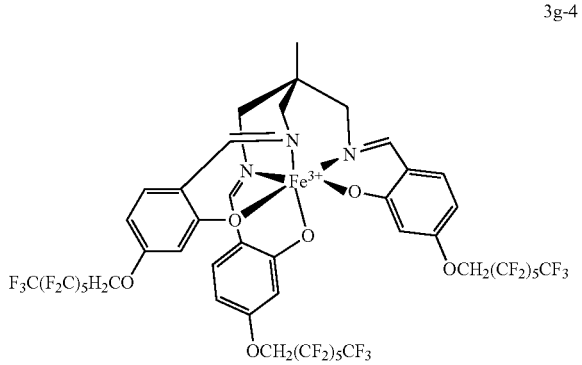

3g-4

A solution of 3g-3 (175 mg, 0.372 mmol) in absolute EtOH (3 ml) was added dropwise to a stirred suspension of 2-(aminomethyl)-2-methyl-1,3-propanediamine, trihydrochloride (29.6 mg, 0.124 mmol) and triethylamine (0.07 ml, 0.496 mmol) in absolute EtOH (3 mL) at 80° C. and heated for 4 hours, followed by the addition of a solution of anhydrous ferric chloride (20.3 mg, 0.125 mmol), then anhydrous sodium acetate (30 mg, 0.375 mmol) in absolute EtOH (4 ml). The resulting deep red reaction mixture was cooled, evaporated to dryness, dissolved in EtOAc:water (1:1 v/v, 10 ml) and separated. The aqueous layer was extracted (2×10 ml) with EtOAc; the combined organic layers dried over $Na_2SO_4$ and evaporated to dryness. The products were separated by silica gel column chromatography eluted with 50% EtOAc-hexane in a yield of 76% as a red powder. The structure of 3g-4 was confirmed by LC-MS.

Synthesis of 3-(bis(4,4,5,5,6,6,7,7,8,8,9,9,10,10,11,11,11-heptadecafluoroundecyl)amino)phenol (6)

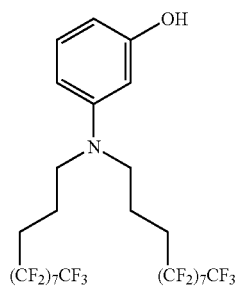

6

Under nitrogen, a mixture of 3-aminophenol (378 mg, 3.5 mmol), 3-(Perfluorooctyl)propyl iodide (4.515 g, 7.7 mmol), and diisopropylethylamine (0.74 mL) was dissolved in anhydrous DMF (8 mL), and heated at 120° C. overnight. The mixture was cooled to room temperature and loaded directly to silica gel column chromatography eluted with 20% ethyl acetate-hexane. The product 6 was isolated in a yield of 75% as a white solid. The structure of 6 was confirmed by NMR and LC-MS.

Synthesis of 4-(bis(4,4,5,5,6,6,7,7,8,8,9,9,10,10,11,11,11-heptadecafluoroundecyl)amino)-2-hydroxybenzaldehyde (7)

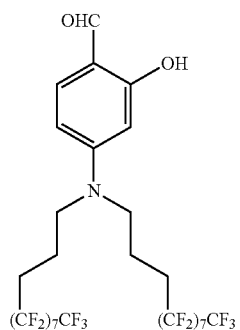

7

Under nitrogen, to a solution of compound 6 (205.8 mg, 0.2 mmol) in DMF (5 mL) was added phosphoryl chloride (0.075 mL, 0.8 mmol) at 0° C. The mixture was stirred at 0° C. for 5 min and then warmed to room temperature. The mixture was then heated at 80° C. for 2 h and a yellow colored homogenous solution appeared. The mixture was allowed to cool to room temperature, and a saturated aqueous solution of NaHCO$_3$ was added dropwise until no bubble formation was observed. The mixture was extracted by ethyl acetate (20 mL×5) and the organic phase was collected. The combined organic phase was washed with brine (50 mL) and dried over anhydrous sodium sulfate. The solvent was evaporated the residual was loaded to silica gel column chromatography eluted with 10% ethyl acetate-hexane. Compound 7 was isolated as an off-white powder in a yield of 72%. The structure of 7 was confirmed by NMR and LC-MS.

Synthesis of Compound 8

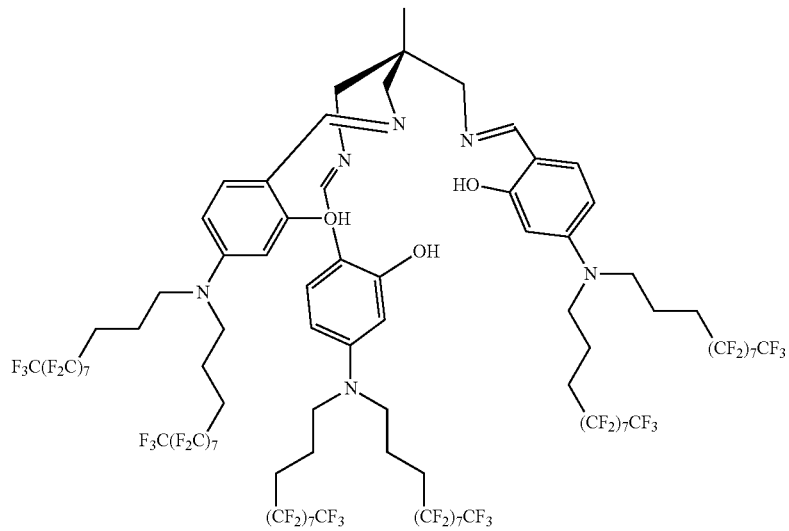

8

A solution of compound 7 (695.8 mg, 0.658 mmol) in 2,2,2-Trifluoroethanol (TFE, 5 ml) was added dropwise to a stirred suspension of 2-(aminomethyl)-2-methyl-1,3-propanediamine, trihydrochloride (49.6 mg, 0.219 mmol) and triethylamine (0.123 ml, 0.876 mmol) in TFE (5 mL). The mixture was heated reflux overnight, The resulting yellow-colored solution was cooled and evaporated to dryness, dissolved in trifluorotoluene (10 mL) and washed with water (10 mL). The aqueous layer was extracted (2×10 mL) with trifluorotoluene, and the combined trifluorotoluene layers was dried over Na$_2$SO$_4$ and concentrated to around 1 mL. The products were separated by silica gel column chromatography eluted with 0-50% EtOAc-hexane in a yield of 35%. The structure of compound 8 was confirmed by NMR and LC-MS.

Synthesis of Iron Complex 9

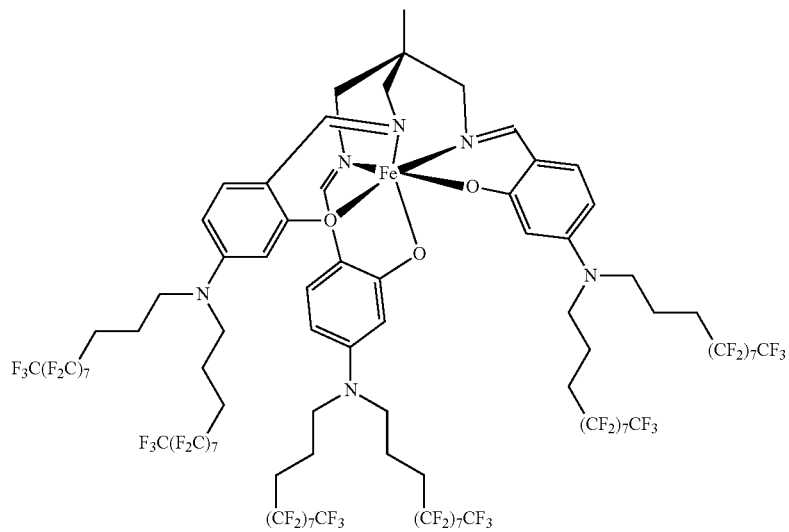

To a stirred solution was compound 8 (360 mg, 0.111 mmol) in TFE (5 mL) was added anhydrous ferric chloride (20 mg, 0.122 mmol) and sodium acetate (36 mg, 0.444 mmol). The solution turned into dark black immediately. The solution was evaporated and dried under vacuum to remove solvents. The product was purified by washing with water 3 times and dried under high vacuum in quantitative yield. Higher purity of the product can be obtained by passing through a silica gel column eluted with ethyl acetate containing 0-20% of TFE. Compound 9 was confirmed by LC-MS.

Emulsification of Iron Complex with Perfluorocarbon:

The fluorous phase consisted of a solution of 36 mg of 5a POP and 102 mg of 1-(perfluoro-n-hexyl)decane (Fluoryx) in 2.4 g PFOB (Acros, Geel, Belgium). The aqueous phase consisted of lipids, mannitol and water. A lipid solution of 139 mg egg yolk phospholipids (EYP, Sigma-Aldrich), 28 mg cholesterol (Avanti Polar Lipids, Alabaster, AL) and 3 mg 1,2-dihexadecanoyl-sn-glycero-3-phospho-L-serine, sodium salt (DPPS, Avanti) was prepared in chloroform, from which a lipid film was made and dried under high vacuum overnight. The lipid film was hydrated with 3.07 g $H_2O$ and 90 mg mannitol was added. The aqueous phase was vortexed for 1 min and sonicated for 2 mins (Omni Ruptor 250 W, 30% power, 2 min, Omni International, Kennesaw, GA). The fluorous phase and 132 mg Cremophor (Sigma-Aldrich) were added subsequently, followed by ultrasonication for 2 mins. The crude emulsion thus obtained was passed 5 times through a LV1 microfluidizer (Microfluidics, Newton, MA) operating at 20,000 psi and filtered through a 0.2 m Supor membrane (no. 4187, Pall, Port Washington, NY) into sterile glass vials. Emulsion size characterizations were performed using a dynamic light scattering (DLS) instrument (Malvern Zetasizer ZS, Malvern, PA)

Use of Metal-Diketonate as T1 Accelerator of Fluorine in PCE.

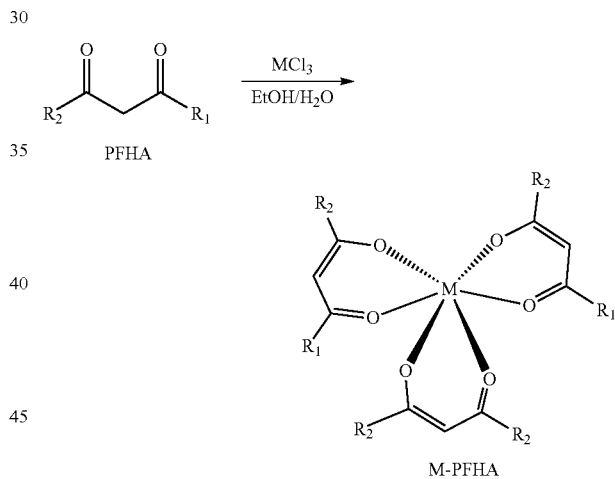

Where $R_1$ represents

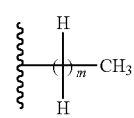

wherein m is 0 to 20
$R_2$ represents

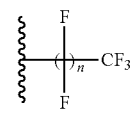

wherein n is 0 to 20
M represents
$Fe^{3+}$, $Fe^{2+}$, $Ga^{3+}$, $Mn^{2+}$, $Mn^{3+}$, $Mn^{4+}$, $Co^{2+}$, $Co^{3+}$, $Cr^{3+}$, $Gd^{3+}$, $Er^{3+}$, $Ho^{3+}$ or $Dy^{3+}$.

Schematic Preparation of the metal complex formed between metal ions (M) and fluorinated diketones (PFHA).

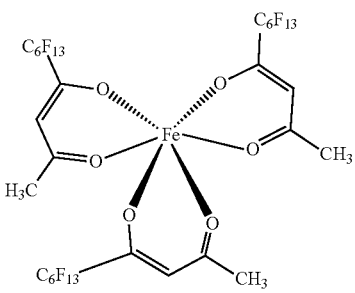

Fe-PFHA

Methods:

Synthesis of Compound Fe-PFHA

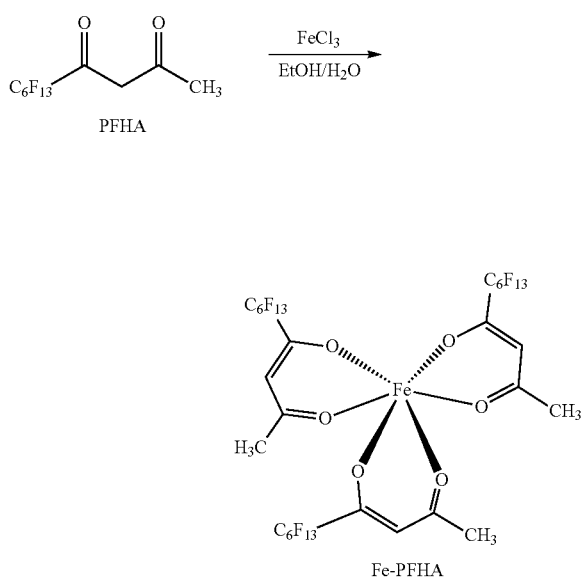

To a stirred solution of diketone PFHA (2.4 mmol, 0.97 g) in ethanol (5 mL) in a 10 mL vial was added an aqueous solution of ferric chloride (0.8 mmol, 0.13 mg in 1 mL water). A dark reddish layer was formed immediately at the bottom. The resulting mixture was heated at 60° C. for 1 h while stirring, cooled to room temperature and then 0° C. The solvents were decanted, and the residual was washed 5 times with hot water/ethanol (1/1, 60°) to remove any remaining starting materials. The red oil obtained was dried under vacuum pump, which turns into red powder after 24 h in a yield of 94%. The product was used directly without further purification. To obtain Fe-PFHA suitable for X-ray crystallography, an oversaturated solution of Fe-PFHA was prepared in hot methanol and placed at 0° C. overnight. The red precipitates were collected by filtration and dried under vacuum pump. High resolution MS (m/z, ESI-TOF) for $[M+NH_4]^+$: calculated 1282.9699, found 1282.9725. Microanalyses, including ICP, CHN and halide analysis, were performed to assure the purity of Fe-PFHA.

TABLE 8

| Microanalysis | Fe (ICP) | C (CHN) | H (CHN) | F (Halide) |
|---|---|---|---|---|
| Theoretical | 4.41%, | 28.48% | 0.96% | 58.56% |
| Found | 4.36% | 27.77% | 0.87% | 60.28% |
| Difference | −0.05% | −0.71% | +0.09% | 1.72% |

X-Ray Crystallography of Fe-PFHA

The single crystal X-ray diffraction studies were carried out on a Bruker Kappa APEX-II CCD diffractometer equipped with Mo Kα radiation (λ=0.71073 Å). Crystals of Fe-PFHA were grown by dissolving approximately 1 mg of sample in 350 μL of Dichloroethane, which was then vapor diffused with Pentane over several days, followed by slow evaporation of the resulting solution for 5 days. A 0.317× 0.025×0.021 mm piece of an orange needle was mounted on a Cryoloop with Paratone oil. Data were collected in a nitrogen gas stream at 100(2) K using φ and ω scans. Crystal-to-detector distance was 40 mm and exposure time was 30 seconds per frame using a scan width of 0.75°. Data collection was 100% complete to 25.00° in θ. A total of 107048 reflections were collected covering the indices, $-18<=h<=18, -19<=k<=19, -23<=l<=23$. 15618 reflections were found to be symmetry independent, with a Rint of 0.0741. Indexing and unit cell refinement indicated a primitive, triclinic lattice. The space group was found to be P-1. The data were integrated using the Bruker SAINT software program and scaled using the SADABS software program. Solution by direct methods (SHELXT) produced a complete phasing model consistent with the proposed structure. All nonhydrogen atoms were refined anisotropically by full-matrix least-squares (SHELXL-2014). All hydrogen atoms were placed using a riding model. Their positions were constrained relative to their parent atom using the appropriate HFIX command in SHELXL-2014.

Preparation of emulsion comprising Fe-PFHA, PCE, Pluoronic F68 and water (NE-A) Compound Fe-PFHA (25.3 mg, 0.02 mmol) was added to PCE (1 mL, 1.79 g) and was fully dissolved by vortex and bath sonication. To this solution was added an aqueous solution of Pluoronic F68 (1.43 mL, 0.1 g/mL). The mixture was vortexed at high for 1 min, followed by an addition of 3.57 mL of Milli-Q water. The final mixture was vortexed at high for 1 min, followed by ultrasonication for 2 mins (Omni Ruptor 250 W, 30% power, 2 min, Omni International). The orange colored pre-emulsion obtained was passed 5 times through a LV1 microfluidizer (Microfluidics) operating at 20,000 psi and filtered through a 0.8/0.2 m Supor membrane (Pall Corp. no. 4187) into sterile glass vials.

Preparation of emulsion comprising Fe-PFHA, PFOB, EYP and water (NE-B). NE-B was prepared as follows: A solution of Fe-PFHA in 1g PFOB was prepared in a concentration of 6.37 mM (4.6 mg), 15.81 mM (11.4 mg) and, 28.15 mM (20.3 mg). They were emulsified with EYP layer (0.16 g) and water (4 g) by vortex, ultrasonication, microfluidization (4 passages) and filtration using the same procedure for the preparation of NE-A.

Preparation of emulsion comprising PFHA, PCE, Pluoronic F68 and water (NE-DK). Emulsion NE-DK was prepared using the same method as of NE-A: The diketone PFHA (24.24 mg, 0.06 mmol) was added to PCE (1 mL, 1.79 g) and was mixed by vortexing. To this solution was added an aqueous solution of Pluoronic F68 (1.43 mL, 0.1 g/mL). The mixture was vortexed at high for 1 min, followed by an addition of 3.57 mL of Milli-Q water. The final mixture was vortexed at high for 1 min, followed by ultrasonication for 2 mins (Omni Ruptor 250 W, 30% power, 2 min, Omni International). The pre-emulsion obtained was passed 5 times through a LV1 microfluidizer (Microfluidics) operating at 20,000 psi and filtered through a 0.8/0.2 m Supor membrane (Pall Corp. no. 4187) into sterile glass vials.

REFERENCES

Paul J. Toscano, Claudia Dettelbacher, John Waechter, Neville P. Pavri, Daniel H. Hunt, Eric T. Eisenbraun, Bo Zheng & Alain E. Kaloyeros (1996) SYNTHESIS AND CHARACTERIZATION OF POLYFLUORINATED β-DIKETONATE TRANSITION METAL COMPLEXES Journal of Coordination Chemistry, 38:4, 319-335.

Sievers, R. (1970). Tris(1,1,1,2,2,3,3-heptafluoro-7,7-dimethyl-4,6-octanedionato)iron(III) and related complexes. Inorganic Syntheses, 12, 72-77.

Belcher, R. (1970). Preparative gas chromatography of volatile metal compounds—I Separation of aluminium, chromium and iron β-diketonates. Talanta (Oxford), 17(6), 455-463.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A compound comprising an salicylidene-tris(aminomethyl) ethane (SALTAME) core comprising a metal-binding moiety capable of binding metal ions, wherein the compound comprises at least one fluorine-19 ($^{19}$F) and the compound is selected from:

Formula (A)

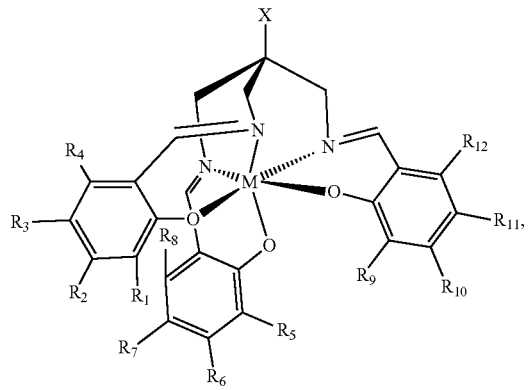

wherein

X is $^{18}$F, or

X is selected from —$(CH_2)_mCH_3$, —$O(CH_2)$ $CH_3$, —$(CH_2)OH$, —$(CH_2)_mNH_2$,

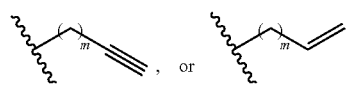

wherein X comprises one or more of $^{11}$C, $^{13}$N, or $^{15}$O and m is an integer from 0 to 20, M is a metal ion selected from $Fe^{3+}$, $Fe^{2+}$, $Ga^{3+}$, $Mn^{2+}$, $Mn^{3+}$, $Mn^{4+}$, $Ni^{2+}$, $Cu^{2+}$, $Zn^{2+}$, $Co^{3+}$, or $Cr^{3+}$, and $R_1$ to $R_{12}$ are each independently selected from: H, $CH_3$, perfluorohexyl (PFH), perfluorooctyl (PFO), Me, $CF_3$, O—$(CF_2)_m$—$CF_3$, $(CF_2)_n$—$CF_3$, and O—$CF_2$—$(OCF_2CF_2)_n$—O—Y, wherein n is 0 to 20, and Y is $CF_3$, $CF_2$—$CF_3$ or $CF_2$—$CF_2$—$CF_3$;

or

Formula (B)

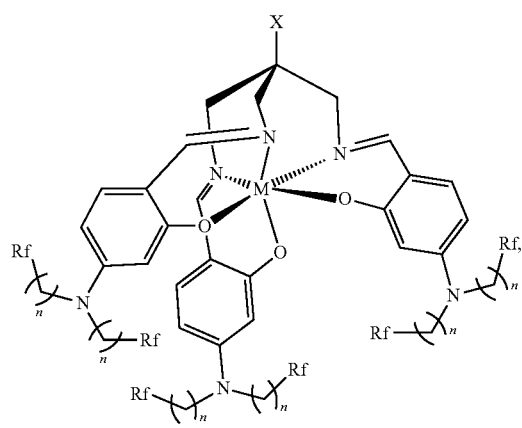

wherein

X is $^{18}$F, or

X is selected from —$(CH_2)_mCH_3$, —$O(CH_2)_mCH_3$, —$(CH_2)_mOH$, —$(CH_2)_mNH_2$,

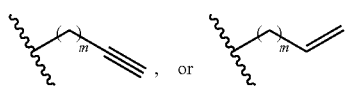
wherein X comprises one or more of $^{11}C$, $^{13}N$, or $^{15}O$ and m is an integer from 0 to 20,
Rf is $(CF_2)$—$CF_3$ or O—$(CF_2)$—$CF_3$,
j is an integer from 0 to 20,
M is a metal ion, and
n is an integer from 0 to 20.
2. The compound of claim 1, wherein the compound is selected from:
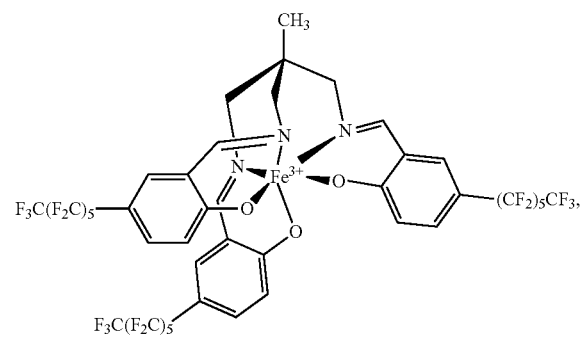
5a PPP
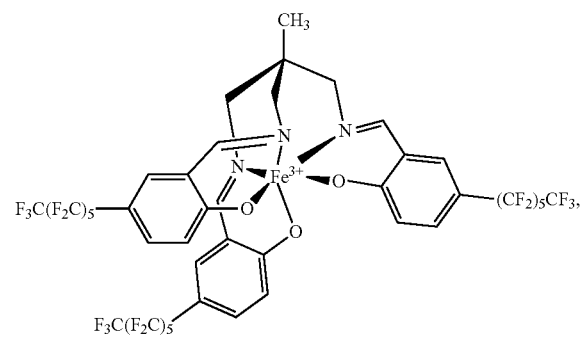
5a POP
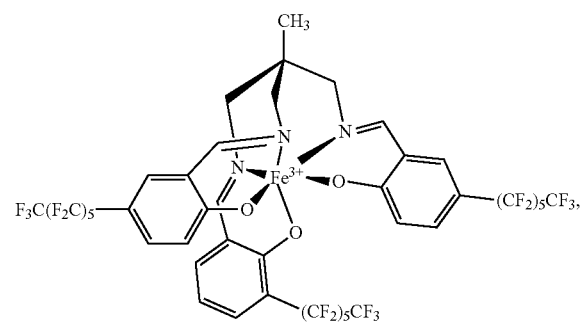
5a OOP
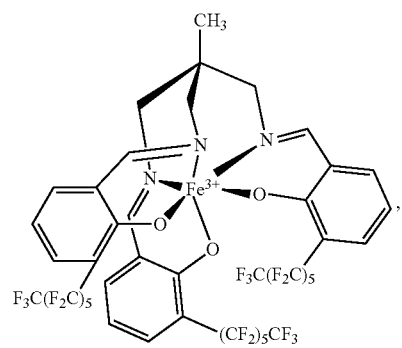
5a OOO
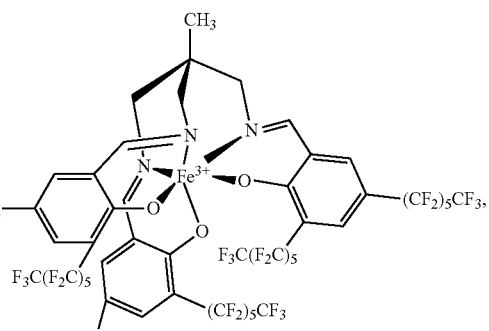
5c
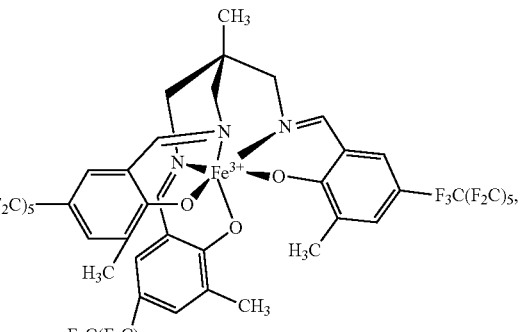
5d
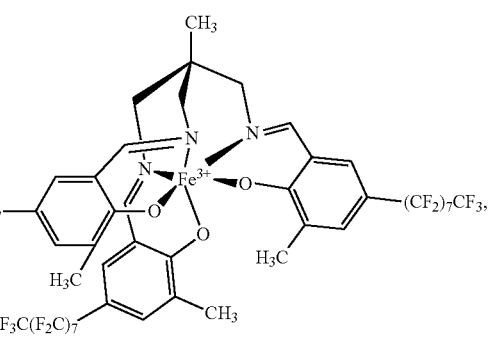
5f -continued

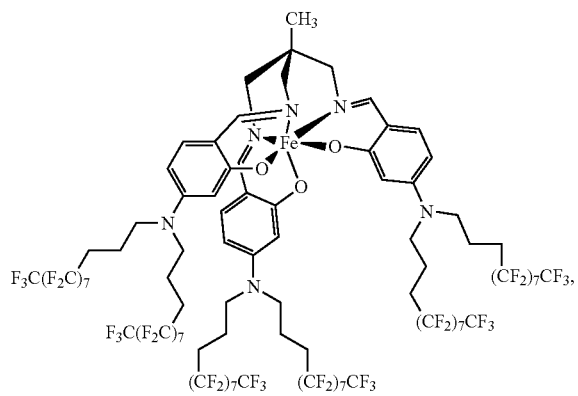

5g

GA OOP

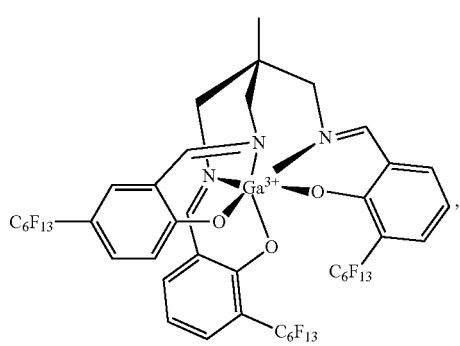

GA POP

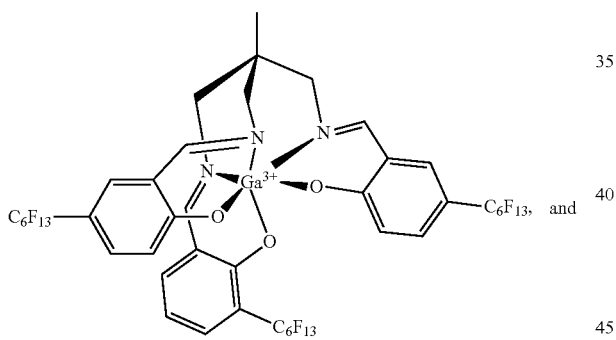
and

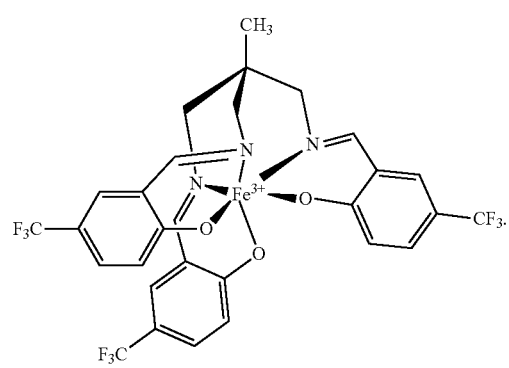

5e

3. The compound of claim 1, wherein at least one of (i)-(iv) applies:
(i) the compound is a perfluorinated compound,
(ii) the compound has a solubility greater than 0.005 mol/L in perfluorocarbons selected from the group consisting of perfluorooctylbromide (PFOB), perfluoro-15-crown-5-ether (PFCE), and perfluoro (polyethylene glycol) (PFPE),
(iii) the compound is stable in pH from 1 to 14, and
(iv) the compound is formulated as a nanoemulsion.

4. The compound of claim 1, wherein at least one of (a)-(d) applies:
(a) the compound comprises a compound of Formula (B) and M is selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$, and $^{177}Lu^{3+}$,
(b) binding of one or more of the metal ions to the metal-binding moiety of the SALTAME core changes the chemical shift of the SALTAME core in 19F nuclear magnetic resonance (19F-NMR),
(c) binding of one or more of the metal ions to the metal-binding moiety of the SALTAME reduces the T1 relaxivity of fluorine-19 ($^{19}F$) in the SALTAME core, and
(d) the compound comprises a compound of Formula (A) and M is selected from the group consisting of $Mn^{4+}$, $Fe^{3+}$, $Co^{3+}$, and $Ga^{3+}$.

5. A non-invasive imaging method comprising:
a) administering to a subject a cellular labelling composition comprising a compound of claim 1, wherein the compound associates with one or more cells; and
b) detecting the association using an imaging modality, wherein the association can include cellular binding and/or cellular uptake.

6. The non-invasive imaging method of claim 5, wherein the compound is selected from the group consisting of:

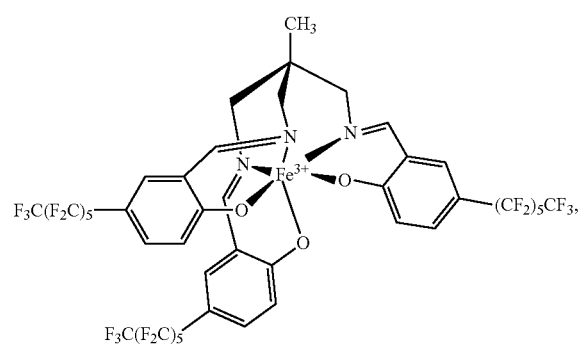

5a PPP

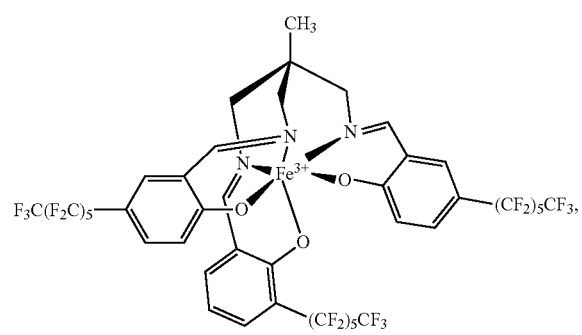

5a POP

5a OOP
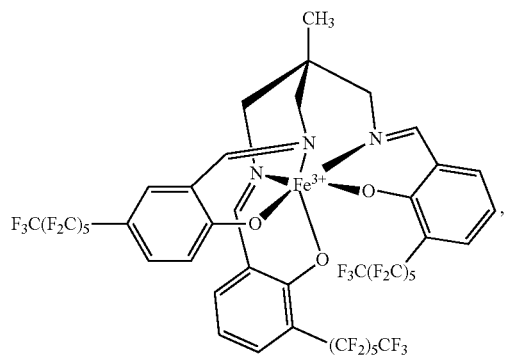
5a OOO
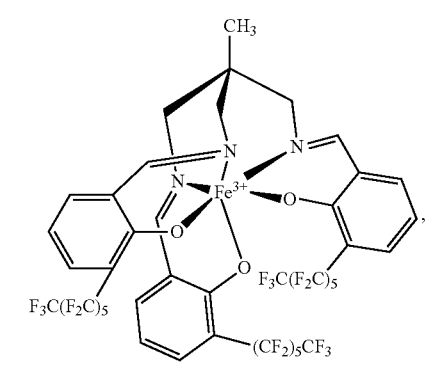
5c
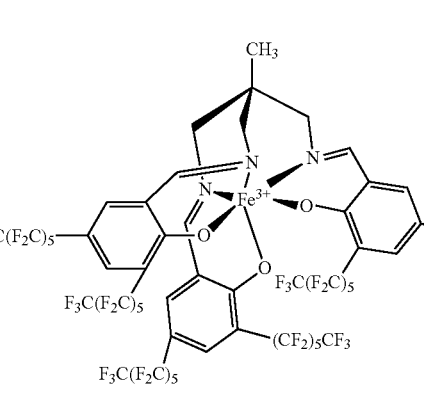
5d
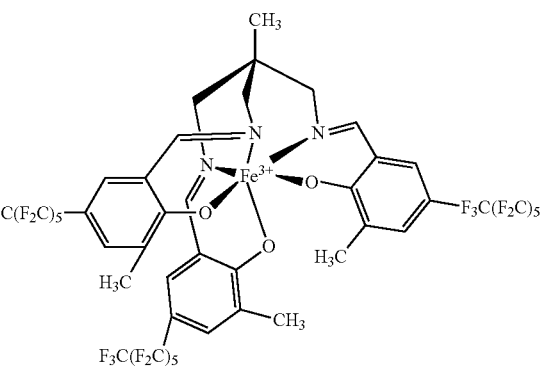
5f
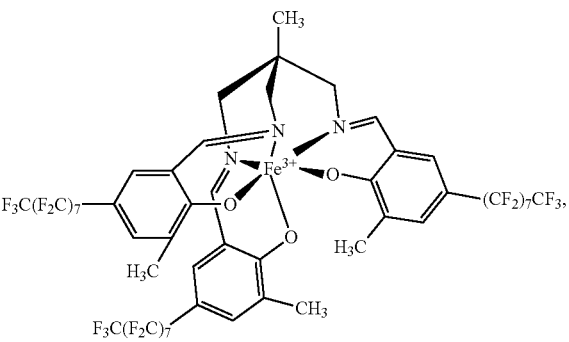
5g
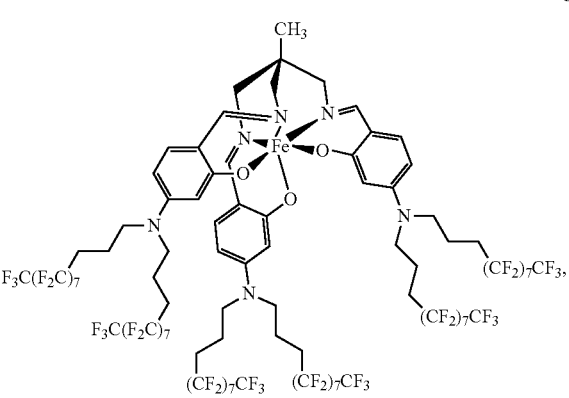
Ga OOP
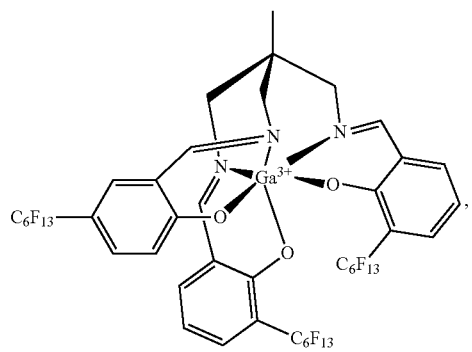
Ga POP
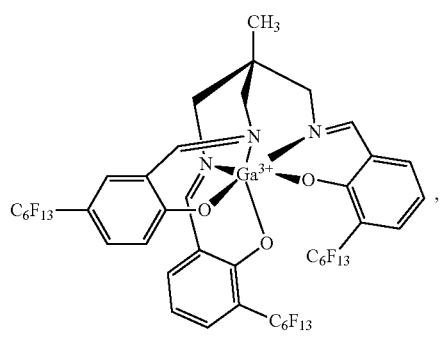
and

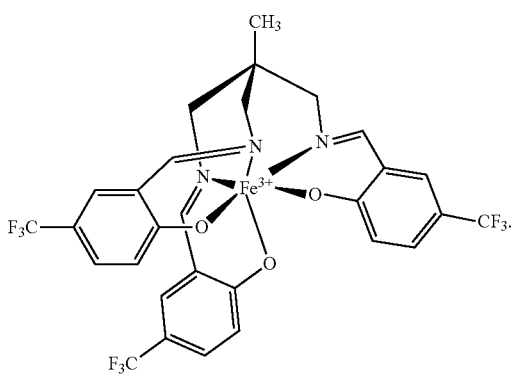

7. The method of claim 5, wherein the imaging modality is selected from the group consisting of magnetic resonance imaging (MRI), positron emission tomography (PET), single-photon emission coherent tomography (SPECT), ultrasonography (US), and computed tomography (CT).

8. The method of claim 5, wherein at least one of (i)-(iv) applies:
   (i) the compound is a perfluorinated compound,
   (ii) the compound has a solubility greater than 0.005 mol/L in perfluorocarbons selected from the group consisting of perfluorooctylbromide (PFOB), perfluoro-13-crown-5-ether (PFCE), and perfluoro (polyethylene glycol) (PFPE),
   (iii) the compound is stable in pH from 1 to 14, and
   (iv) the compound is formulated as a nanoemulsion.

9. The method of claim 8, wherein at least one of (a)-(e) applies:
   (a) the compound comprises a compound of Formula (B) and M is selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$ and $^{177}Lu^{3+}$,
   (b) binding of one or more of the metal ions of to the metal-binding moiety of the SALTAME core changes the chemical shift of the SALTAME core in $^{19}F$ nuclear magnetic resonance (19F-NMR),
   (c) binding of one or more of the metal ions to the metal-binding moiety of the SALTAME reduces the T1 relaxivity of fluorine-19 in the SALTAME core,
   (d) the nanoemulsion of (iv) further comprises a perflorocarbon, and
   (e) the nanoemulsion of (iv) further comprises one or more targeting moieties, wherein the targeting moieties are selected from the group consisting of peptides, binding proteins, antibodies, antibody fragment thereof, and aptamers.

10. The method of claim 5, wherein the composition allows tracking cells by MRI, wherein the method comprises detecting the cells associated with at least one component of the composition comprising fluorine-19 ($^{19}F$).

11. The method of claim 5, wherein at least one of (i)-(v) applies:
    (i) the one or more cells are immune cells that accumulate at tissue sites as part of an inflammatory response,
    (ii) the one or more cells are cells that are grafted into the body in order to treat a disease or condition,
    (iii) the one or more cells are endogenous cells in body of said subject,
    (iv) the one or more cells are selected from the group consisting of T cells, B cells, macrophages, natural killer (NK) cells, dendritic cells (DCs), stem cells, progenitor cells, and cancer cells, and
    (v) the one or more cells comprise engineered cells.

12. The method of claim 5, wherein the method is a diagnostic detection method or cytotherapy.

13. The method of claim 5, wherein the compound is a dual-mode agent and is capable of being detected by more than one imaging modality.

14. An in vivo imaging method, comprising
    a) ex vivo labeling cells with a cellular labelling composition comprising a compound of claim 1 under such conditions that the compound is bound to the cells and/or internalized by the cells;
    b) administering the labeled cells to a subject,
    c) detecting the labeled cells in the subject using an imaging modality, and
    d) assaying for the degree of cell accumulation in one or more tissues in the subject.

15. The method of claim 14, wherein the assaying comprises quantitating the average total intracellular probe mass at sites of accumulation of said labeled cells, and/or the imaging modality is selected from the group consisting of magnetic resonance imaging (MRI), positron emission tomography (PET), single-photon emission coherent tomography (SPECT), ultrasonography (US), and computed tomography (CT).

16. The method of claim 14, wherein at least one of (i)-(iv) applies:
    (i) the cells are autologous cells,
    (ii) the cells are allogeneic cells,
    (iii) the cells are selected from the group consisting of T cells, B cells, macrophages, natural killer (NK) cells, dendritic cells (DCs), stem cells, progenitor cells, and cancer cells, and
    (iv) the cells are engineered cells.

17. The method of claim 14, wherein at least one of (i)-(iv) applies:
    (i) the compound is a perfluorinated compound,
    (ii) the compound has a solubility greater than 0.005 mol/L in perfluorocarbons selected from the group consisting of perfluorooctylbromide (PFOB), perfluoro-13-crown-5-ether (PFCE), and perfluoro (polyethylene glycol) (PFPE),
    (iii) the compound is stable in pH from 1 to 14, and
    (iv) the compound is formulated as a nanoemulsion.

18. The method of claim 17, wherein at least one of (a)-(f) applies:
    (a) the compound comprises a compound of Formula (B) and M is selected from the group consisting of $Co^{3+}$, $VO^{2+}$, $Cr^{3+}$, $Mn^{2+}$, $Mn^{3+}$, $Mn^{4+}$, $Fe^{2+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $Zn^{2+}$, $^{66}Ga^{3+}$, $^{68}Ga^{3+}$, $^{82}Rb$, $^{86}Y^{3+}$, $^{89}Zr^{4+}$, $^{67}Ga^{3+}$, $^{99m}Tc^{4+}$, $^{111}In^{3+}$ and $^{177}Lu^{3+}$,
    (b) binding of one or more of the metal ions of to the metal-binding moiety of the SALTAME core changes the chemical shift of the SALTAME core in $^{19}F$ nuclear magnetic resonance (19F-NMR),
    (c) binding of one or more of the metal ions to the metal-binding moiety of the SALTAME reduces the T1 relaxivity of fluorine-19 in the SALTAME core,
    (d) the nanoemulsion of (iv) further comprises a perflorocarbon, and (e) the nanoemulsion of (iv) further comprises one or more targeting moieties, wherein the targeting moieties are selected from the group consisting of peptides, binding proteins, antibodies, antibody fragment thereof, and aptamers, and (f) the nanoemulsion of (iv) comprises the compound in an oil-in-water colloidal suspension or emulsion.

19. The compound of claim 3, wherein the nanoemulsion of (iv) further comprises a perfluorocarbon.

* * * * *